United States Patent
Nabutovsky et al.

(10) Patent No.: US 12,183,458 B2
(45) Date of Patent: Dec. 31, 2024

(54) SYSTEMS, DEVICES, AND METHODS FOR ANALYTE MONITORING AND BENEFITS THEREOF

(71) Applicant: Abbott Diabetes Care Inc., Alameda, CA (US)

(72) Inventors: Yelena Nabutovsky, Mountain View, CA (US); Matthew S. D. Kerr, Issaquah, WA (US); Gregory J. Roberts, Alameda, CA (US); Jennifer M. Joseph, Mountain View, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 360 days.

(21) Appl. No.: 17/329,101

(22) Filed: May 24, 2021

(65) Prior Publication Data

US 2021/0366609 A1 Nov. 25, 2021

Related U.S. Application Data

(60) Provisional application No. 63/104,282, filed on Oct. 22, 2020, provisional application No. 63/029,339, filed on May 22, 2020.

(51) Int. Cl.
*G16H 40/67* (2018.01)
*A61B 5/00* (2006.01)
(Continued)

(52) U.S. Cl.
CPC ......... *G16H 40/67* (2018.01); *A61B 5/14532* (2013.01); *A61B 5/4839* (2013.01); *G16H 20/17* (2018.01)

(58) Field of Classification Search
CPC ........ G16H 40/67; G16H 20/17; G16H 10/20; A61B 5/14532; A61B 5/4839;
(Continued)

(56) References Cited

U.S. PATENT DOCUMENTS 6,605,200 B1 8/2003 Mao et al.
6,932,894 B2 8/2005 Mao et al.
(Continued)

FOREIGN PATENT DOCUMENTS

WO WO 2018/136898 A1 7/2018
WO WO 2019/236850 A1 12/2019

OTHER PUBLICATIONS

"The frequency of FreeStyle Libre glucose sensor scans performed by the diabetic patient on a daily basis is associated with better parameters for monitoring his glucose profile: Analysis of 312 million hours of monitoring in real life in France," Medecine des Maladies Metaboliques, vol. 14, Issue 7 in Nov. 2020 and can be accessed at the website https://www.sciencedirect.com/science/article/pii/S1957255720002163 [with English translations of Summary, Method, Results and Conclusion].
(Continued)

*Primary Examiner* — David J. McCrosky
*Assistant Examiner* — Meghan R Kumar
(74) *Attorney, Agent, or Firm* — Baker Botts L.L.P.

(57) ABSTRACT

A method of treatment of a type 2 diabetic patient includes selecting a type 2 diabetic patient having a predetermined comorbidity for treatment, initiating a continuous glucose monitor regimen for the selected type 2 diabetic patient, wherein after six months of initiation of the continuous glucose monitor regimen, a rate of hospitalization for a predetermined diagnostic category of the selected patient having the predetermined comorbidity is reduced by at least 12% relative to an average rate of hospitalization for the predetermined diagnostic category of selected patients having the predetermined comorbidity without the continuous glucose monitor regimen.

21 Claims, 145 Drawing Sheets

(51) Int. Cl.
  *A61B 5/145* (2006.01)
  *G16H 20/17* (2018.01)
(58) Field of Classification Search
  CPC ....... A61B 5/742; A61B 5/002; A61B 5/7275; A61B 2560/0271
  See application file for complete search history.

(56) References Cited

U.S. PATENT DOCUMENTS

| | | | |
|---|---|---|---|
| 8,280,474 | B2 | 10/2012 | Liu et al. |
| 9,913,600 | B2 | 3/2018 | Taub et al. |
| 10,856,785 | B2 | 12/2020 | Taub et al. |
| 2008/0071580 | A1 | 3/2008 | Marcus et al. |
| 2008/0154513 | A1 | 6/2008 | Kovatchev et al. |
| 2010/0240079 | A1 | 9/2010 | Jackson |
| 2011/0319322 | A1* | 12/2011 | Bashan ................ G16H 20/17 514/5.9 |
| 2012/0232368 | A1* | 9/2012 | Jin ..................... A61B 5/14532 600/365 |
| 2014/0200426 | A1 | 7/2014 | Taub et al. |
| 2015/0289821 | A1 | 10/2015 | Rack-Gomer et al. |
| 2016/0038077 | A1 | 2/2016 | Otto |
| 2016/0042154 | A1 | 2/2016 | Goldberg et al. |
| 2017/0112421 | A1 | 4/2017 | Taub et al. |
| 2017/0347971 | A1 | 12/2017 | Davis et al. |
| 2018/0192927 | A1 | 7/2018 | Taub et al. |
| 2018/0228408 | A1* | 8/2018 | Raisoni ............. A61B 5/14532 |
| 2020/0196919 | A1 | 6/2020 | Rao et al. |

OTHER PUBLICATIONS

U.S. Appl. No. 17/329,065, filed May 24, 2021.
Bailey et al., "The Performance and Usability of a Factory-Calibrated Flash Glucose Monitoring System," Diabetes Tech. Ther., 17(11):787-794 (2015).
Bergenstal et al., "Flash CGM is Associated with Reduced Diabetes Events and Hospitalizations in Insulin-Treated Type 2 Diabetes," Journal of the Endocrine Society, vol. 5, Issue 4, pp. 1-9, 2021 https://academic.oup.com/jes/article/5/4/bvab013/6126709.
Bolinder et al., "Novel glucose-sensing technology and hypoglycaemia in type 1 diabetes: a multicentre, non-masked, randomized controlled trial," Lancet, 388(10057):2254-2263 (2016).
Deshmukh et al., "Effect of Flash Glucose Monitoring on Glycemic Control, Hypoglycemia, Diabetes-Related Distress, and Resource Utilization in the Association of British Clinical Diabetologists (ABCD) Nationwide Audit," J Diabetes Care, 43(9):2153- 2160 (2020).
Dunn et al., "Real-world flash glucose monitoring patterns and associations between self-monitoring frequency and glycaemic measures: A European analysis of over 60 million glucose tests," Diabetes Res. & Clinical Practice, 137:37-46 (2018).
Evans et al., "The Impact of Flash Glucose Monitoring on Glycaemic Control as Measured by HbA1c: A Meta-analysis of Clinical Trials and Real-World Observational Studies," Diabetes Therapy, 11(1):83-95 (2020).
Fokkert et al., "Improved well-being and decreased disease burden after 1-year use of flash glucose monitoring (FLARE-NL4)," BMJ Open Diabetes Research & Care, 7:e000809 (2019) 10 pgs.
Haak et al., "Use of Flash Glucose-Sensing Technology for 12 months as a Replacement for Blood Glucose Monitoring in Insulin-treated Type 2 Diabetes," Diabetes Therapy 8(3):573-586 (2017).
Heller et al., "Severe Hypoglycaemia in adults with insulin-treated diabetes: impact on healthcare resources," J Diabetic Medicine 33(4):471-477 (2016).
Ida et al., Effects of Flash Glucose Monitoring on Dietary Variety, Physical Activity, and Self-Care Behaviors in Patients with Diabetes, J. Diabetes Res., 2020.
Krakauer et al., "A review of flash glucose monitoring in type 2 diabetes," Diabetology & Metabolic Syndrome, vol. 13:42 (2021) 10 pgs. https://dmsjournal.biomedcentral.com/articles/10.1186/s13098-021-00654-3.
Kroger et al., "Three European Retrospective Real-World Chart Review Studies to Determine the Effectiveness of Flash Glucose Monitoring on HbA1c in Adults with Type 2 Diabetes," Diabetes Therapy 11:279-291 (2020).
Nathan et al., "Translating the A1C Assay into Estimated Average Glucose Values," Dia-betes Care 31:1473-1478 (2008).
Ogawa et al., "Effect of the Freestyle Libre Flash Glucose Monitoring System on Glycemic Control in individuals with Type 2 Diabetes Treated with Basal-Bolus Insulin Therapy: An Open Label, Prospective, Multicenter Trial in Japan," J. Diabetes Investigation 12(1):82-90 (2021).
Rose et al., "Improving HbA1c Control in Type 1 or Type 2 Diabetes Using Flash Glucose Monitoring: A Retrospective Observational Analysis in Two German Centres," Diabetes Therapy, vol. 12, pp. 363-372, 2021 https://link.springer.com/article/10.1007/s13300-020-00978-9.
Wada et al., "Flash glucose monitoring Helps achieve better glycemic control than conventional self-monitoring of blood glucose in non-insulin treated type 2 diabetes: a randomized controlled trial," BMJ Open Diabetes Res. Care, 8:e001115 (2020).
Xu et al., "Accurate prediction of HbA 1c by continuous glucose monitoring using a kinetic model with patient-specific parameters for red blood cell lifespan and glucose uptake," Diabetes and Vascular Disease Research, vol. 18, Issue 3, 2021 https://journals.sagepub.com/doi/full/10.1177/14791641211013734.
Yaron et al., "Effect of Flash Glucose Monitoring Technology on Glycemic Control and Treatment Satisfaction in Patients with Type 2 Diabetes," Diabetes Care, 42:1178-1184 (2019).
Costa et al., "Clinical Performance of Flash Glucose Monitoring System in Patients with Liver Cirrhosis and Diabetes Mellitus," Scientific Reports 10:7460 (2020).
International Search Report and Written Opinion mailed Sep. 28, 2021 in International Application No. PCT/US21/33947.
International Search Report and Written Opinion mailed Sep. 30, 2021 in International Application No. PCT/US21/33946.
Kompala et al., "A New Era: Increasing Continuous Glucose Monitoring Use in Type 2 Diabetes," Evidence-Based Diabetes Management 25(4):4 pgs. (2019).
Sato et al., "Glucose Variability Based on Continuous Glucose Monitoring Assessment is Associated with Postoperative Complications after Cardiovascular Surgerv," Annals of and Cardiovascular Surgery 23:239-247 (2017).
Shi et al., "Cost Comparison of Flash Continuous Glucose Monitoring with Self-monitoring of Blood Glucose in Adults with Type 1 or Type 2 Diabetes Using Intensive Insulin—From a US Private Payer Perspective," US Endocrinology 16(1):24-30 (2020).
International Search Report and Written Opinion dated Oct. 29, 2021 in International Application No. PCT/US21/35500.

* cited by examiner

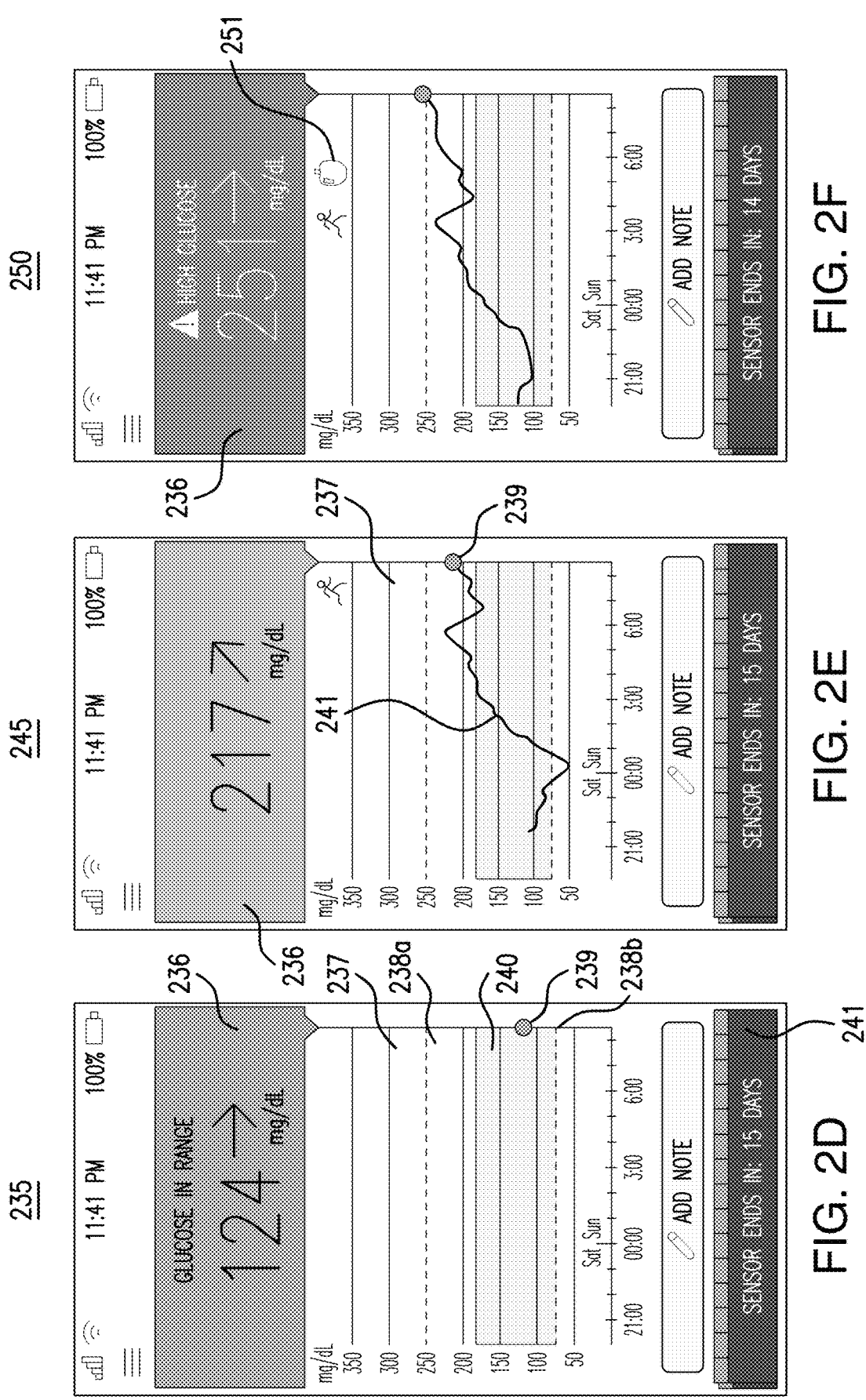

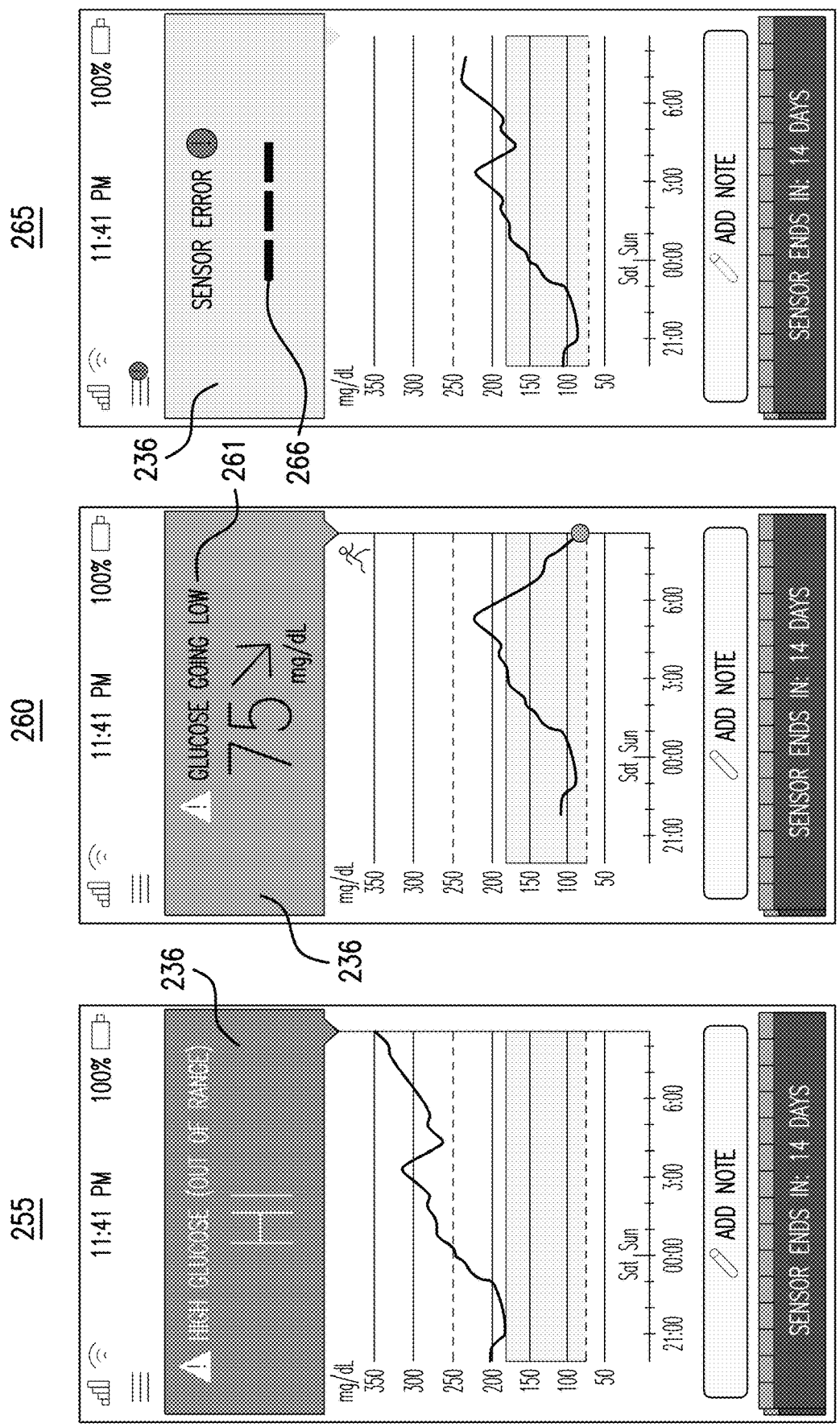

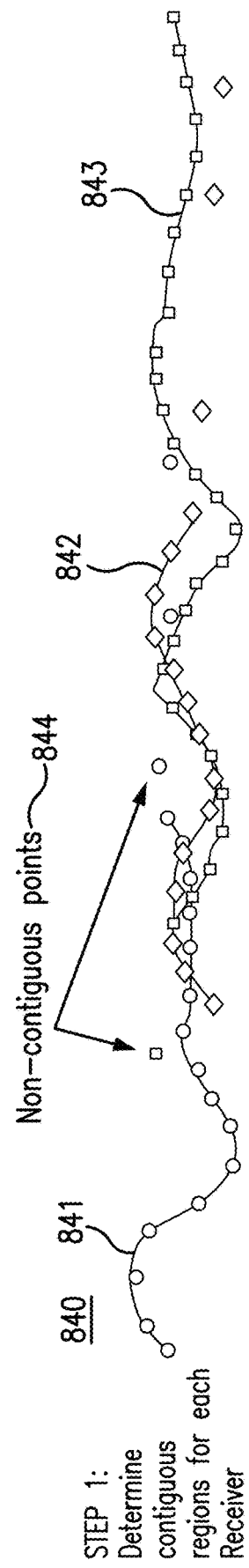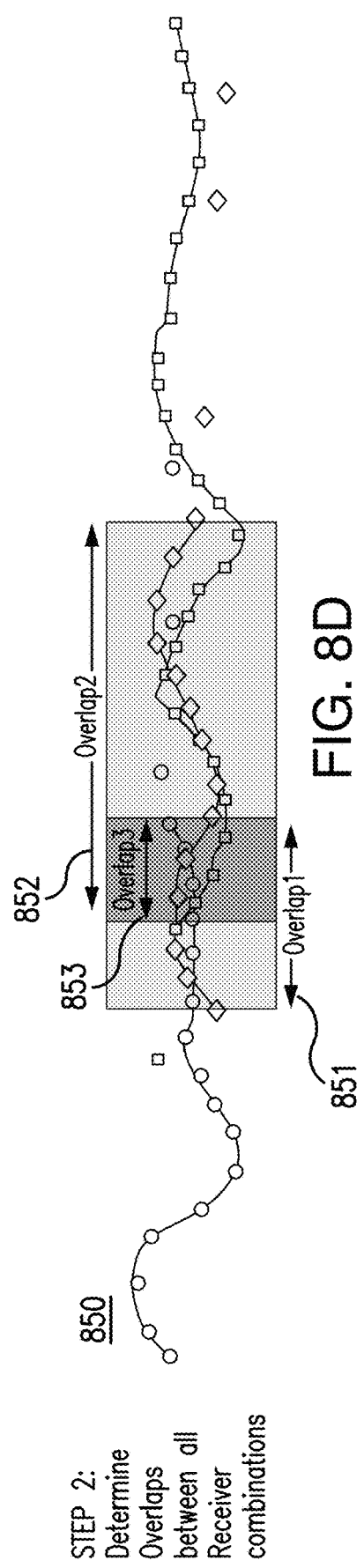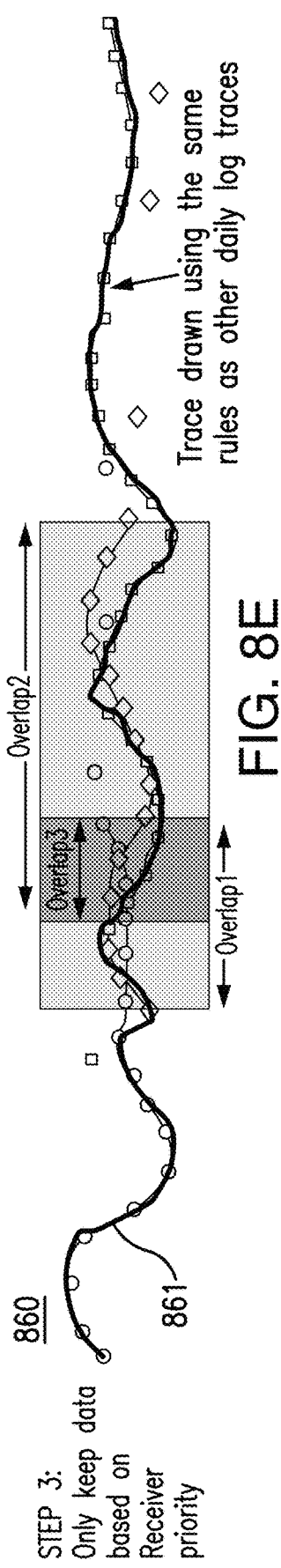

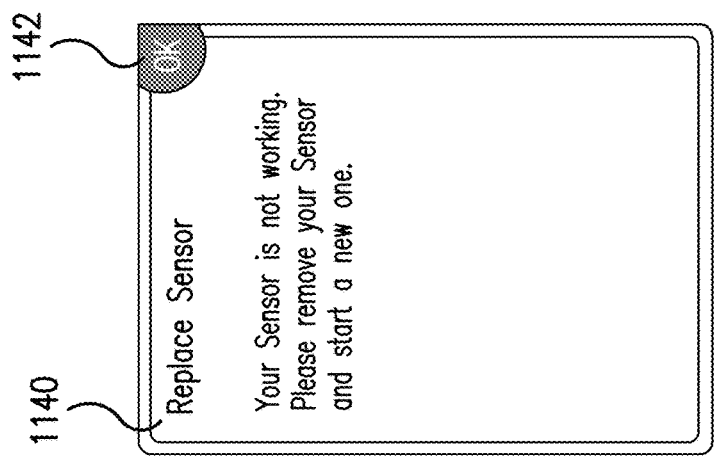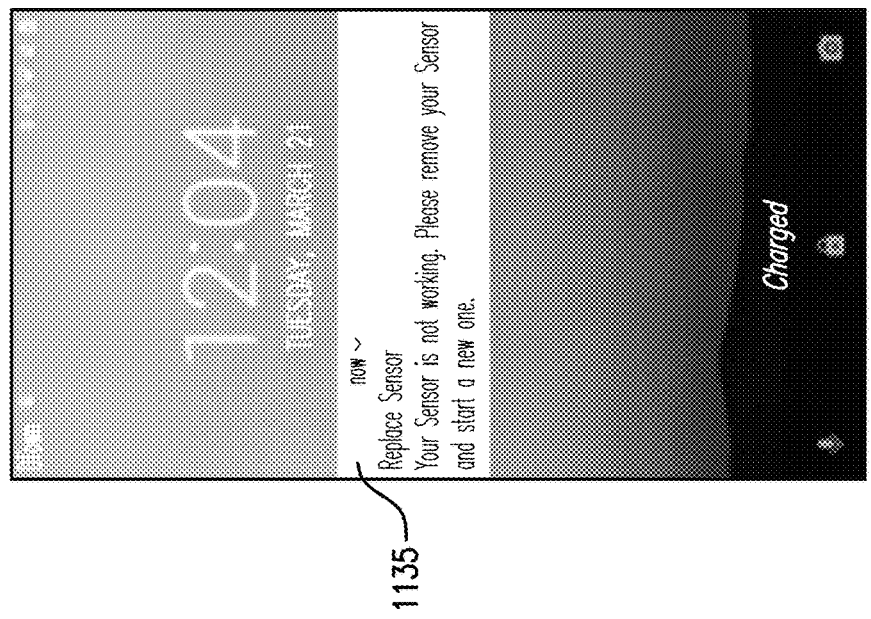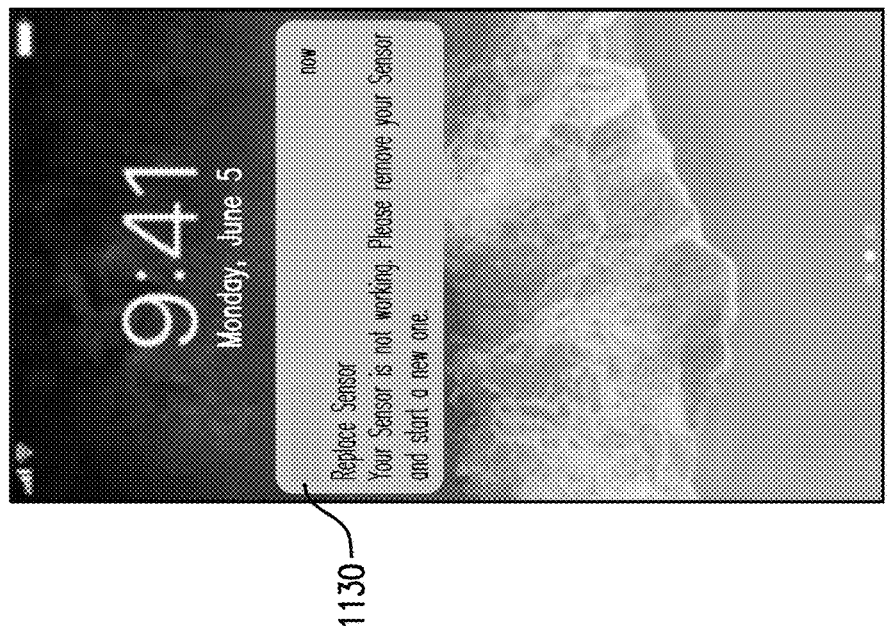
FIG. 11D
FIG. 11C
FIG. 11B

| | |
|---|---|
| Mean Age, years (mean ± SD) | 54.2±9.6 |
| Male Gender, % (n) | 52.9% (1,304) |
| Comorbidities, % (n) | |
| Lipid Disorder | 89.7% (2,210) |
| Hypertension | 87.5% (2,155) |
| Obesity | 60.0% (1,479) |
| Neuropathy | 48.1% (1,185) |
| Retinopathy | 31.2% (768) |
| Depression | 29.4% (724) |
| Pulmonary Disease | 28.8% (709) |
| Hypothyroid | 26.2% (646) |
| Anemia | 25.8% (635) |
| Myocardial Infarction or Coronary Artery Disease | 24.6% (606) |
| Liver Disease | 20.8% (513) |
| Renal Disease | 19.5% (480) |
| Peripheral Vascular Disease | 17.4% (429) |
| Heart Failure | 13.1% (323) |

FIG. 12A

| Event Type | 6-months Pre-Acquisition # events (# affected) | 6-months Post-Acquisition # events (# affected) |
|---|---|---|
| All-cause inpatient hospitalizations (ACH) | 516 (357) | 331 (239) |
| Acute Diabetes Events (ADE) | 221 (181) | 84 (73) |
| Hypoglycemic ADE | 24 (21) | 17 (16) |
| Hyperglycemic ADE | 199 (166) | 69 (62) |

FIG. 12C

| Characteristic | |
|---|---|
| N | 10,282 |
| Follow-up, days [10%, 90% deciles] | 171 [152, 182] |
| Age, yrs (SD±) | 53.1±9.6 |
| Age 18 – 49 | 32.3% |
| Age 50 – 64 | 62.5% |
| Age 65+ | 5.2% |
| Gender (Male) | 51.9% |
| Comorbidities | |
| Hypertension | 80.6% |
| Obesity | 55.6% |
| Pulmonary Disease | 24.5% |
| Depression | 24.2% |
| Hypothyroid Disease | 21.5% |
| Anemia | 19.2% |
| Liver Disease | 18.5% |
| MI or Coronary Artery Disease | 15.8% |
| Peripheral Vascular Disease | 10.8% |
| Renal Disease | 9.6% |
| Heart Failure | 6.9% |
| Insulin Usage Status | |
| Insulin (short- or rapid-acting) | 38.7% |
| Non-insulin therapy | 61.3% |
| Non-Insulin Diabetes Medications | |
| Biguanide | 71.2% |
| Sulfonylurea | 30.4% |
| GLP1a | 30.3% |
| SGLT2i | 26.2% |
| DPP4i | 20.6% |
| TZD | 7.4% |
| Meglitinides | 1.6% |
| Alpha-Glucosidase Inhibitor | 0.4% |

FIG. 13A

| Event Type | 6-months Pre-Acquisition<br># events (# affected) | 6-months Post-Acquisition<br># events (# affected) |
|---|---|---|
| All-cause inpatient hospitalizations (ACH) | 905 (688) | 726 (558) |
| Overall Acute Diabetes Events (ADE)* | 391 (324) | 252 (211) |
| Inpatient ADE | 68 (61) | 20 (18) |
| Outpatient ADE | 324 (274) | 234 (195) |

FIG. 13B

| Before flash CGM | | After flash CGM | | |
| --- | --- | --- | --- | --- |
| Hospitalizations (Events/100 pt-yr) | Major Diagnostic Category | Hospitalizations (Events/100 pt-yr) | Major Diagnostic Category | % reduction from Before Flash CGM |
| 3.4 | Circulatory System | 3.0 | Circulatory System | 12% |
| 2.3 | Endocrine, Nutritional and Metabolic System | 1.7 | Endocrine, Nutritional and Metabolic System | 26% |
| 1.9 | Nervous System | 1.7 | Musculoskeletal System and Connective Tissue | -13% |
| 1.8 | Infectious and Parasitic | 1.5 | Digestive System | -15% |
| 1.5 | Musculoskeletal System and Connective Tissue | 1.4 | Nervous System | 26% |
| 1.3 | Kidney and Urinary Tract | 1.2 | Infectious and Parasitic | 33% |
| 1.3 | Digestive System | 0.9 | Kidney and Urinary Tract | 31% |

FIG. 13C

| Type of new incident FreeStyle Libre user* | 2016 | 2017 | 2018 | 2019 | Total |
|---|---|---|---|---|---|
| Type 1 diabetes | | | | | |
|     Truly naïve | 463 | 3,404 | 3,980 | 1,634 | 9,481 |
|     New with unknown prior status | 10,366 | 9,877 | 3,908 | 1,389 | 25,540 |
|     New with prior use of CGM | NA | 417 | 604 | 307 | 1,328 |
|     Prevalent user, with index date in previous years† | NA | 8,128 | 15,781 | 19,716 | NA |
| Type 2 diabetes | | | | | |
|     Truly naïve | 20 | 164 | 320 | 323 | 827 |
|     New with unknown prior status | 387 | 471 | 219 | 1,166 | 2,243 |
|     New with prior use of CGM | NA | 16 | 28 | 16 | 60 |
|     Prevalent user, with index date in previous years† | NA | 354 | 808 | 1,246 | NA |

FIG. 14A

| Status of FreeStyle Libre users registered in NDR | 6 months | 12 months |
|---|---|---|
| Type 1 diabetes | | |
| Truly naïve users | 3827 | 3220 |
| New to FreeStyle Libre system but prior use of CGM | 730 | 599 |
| New to FreeStyle Libre system with unknown prior status | 4630 | 4497 |
| Total incident users T1DM | 9187 | 8316 |
| Type 2 diabetes | | |
| Truly naïve users | 261 | 203 |
| New to FreeStyle Libre system but prior use of CGM | 45 | 37 |
| New to FreeStyle Libre system with unknown prior status | 405 | 298 |
| Total incident users T2DM | 711 | 538 |

FIG. 14B

|  |  | Incident users | Mean change in % HbA1c (%, 95% CI) | Group size (n) | p-value* |
|---|---|---|---|---|---|
| Mean HbA1c range at baseline | <8.0% | Total incident users | 0.00 (-0.01, 0.22) | 4676 | 1.000 |
|  |  | Truly naïve | -0.05 (-0.08, -0.02) | 1930 | 0.0017 |
|  |  | Prior use unknown | 0.02 (0.00, 0.5) | 2372 | 0.0901 |
|  |  | Prior use of CGM | 0.10 (0.030, 0.17) | 374 | 0.0061 |
|  | 8.0 - <9.0% | Total incident users | -0.42 (-0.45, -0.39) | 2599 | < 0.0001 |
|  |  | Truly naïve | -0.51 (-0.56, -0.46) | 1105 | < 0.0001 |
|  |  | Prior use unknown | -0.37 (-0.41, -0.33) | 1318 | < 0.0001 |
|  |  | Prior use of CGM | -0.24 (-0.37, -0.12) | 176 | 0.0002 |
|  | 9.0 - <12.0% | Total incident users | -0.98 (-1.00, -0.92) | 1771 | < 0.0001 |
|  |  | Truly naïve | -1.20 (-1.3, -1.1) | 733 | < 0.0001 |
|  |  | Prior use unknown | -0.90 (-0.99, -0.81) | 871 | < 0.0001 |
|  |  | Prior use of CGM | -0.63 (-0.84, -0.42) | 167 | < 0.0001 |
|  | ≥12.0% | Total incident users | -3.1 (-3.5, -2.7) | 141 | < 0.0001 |
|  |  | Truly naïve | -2.8 (-3.3, -2.2) | 59 | < 0.0001 |
|  |  | Prior use unknown | -3.5 (- 4.2, -2.9) | 69 | < 0.0001 |
|  |  | Prior use of CGM | -2.2 (-3.4, -1.0) | 13 | 0.0016 |

FIG. 14C

|  |  | Incident users | Mean change in % HbA1c (%, 95% CI) | Group size (n) | p-value* |
|---|---|---|---|---|---|
| Mean HbA1c range at baseline | <8.0% | Total incident users | 0.10 (-0.01, 0.22) | 281 | 0.0779 |
|  |  | Truly naïve | 0.00 (-0.16, 0.15) | 86 | 0.9782 |
|  |  | Prior use unknown | 0.15 (-0.01, 0.31) | 174 | 0.0674 |
|  |  | Prior use of CGM | 0.13 (-0.29, 0.55) | 21 | 0.5213 |
|  | 8.0 - <9.0% | Total incident users | -0.33 (-0.47, -0.18) | 189 | < 0.0001 |
|  |  | Truly naïve | -0.41 (-0.63, -0.20) | 77 | 0.0002 |
|  |  | Prior use unknown | -0.30 (-0.50, -0.90) | 101 | 0.0045 |
|  |  | Prior use of CGM | 0.01 (-1.00, 1.00) | 11 | 0.9857 |
|  | 9.0 - <12.0% | Total incident users | -1.10 (-1.3, -0.90) | 214 | < 0.0001 |
|  |  | Truly naïve | -1.30 (-1.6, -1.0) | 88 | < 0.0001 |
|  |  | Prior use unknown | -0.99 (-1.30, -0.73) | 117 | < 0.0001 |
|  |  | Prior use of CGM | NA | <10 | NA |
|  | ≥12.0% | Total incident users | -3.4 (-4.4, -2.5) | 27 | < 0.0001 |
|  |  | Truly naïve | -2.7 (-4.2, -1.2) | 10 | 0.0028 |
|  |  | Prior use unknown | -4.2 (-5.8, -2.6) | 13 | < 0.0001 |
|  |  | Prior use of CGM | NA | <10 | NA |

FIG. 14D

| Incident users by age range (years) | Mean change in % HbA1c (95% CI) | HbA1c baseline mean (%) | Group size (n) | p-value* |
|---|---|---|---|---|
| Type 1 diabetes | | | | |
| All ages | -0.36 (-0.38, -0.33) | 8.1 | 9187 | < 0.0001 |
| 18-24 | -0.37 (-0.45, -0.30) | 8.3 | 1172 | < 0.0001 |
| 25-65 | -0.39 (-0.42, -0.37) | 8.1 | 6322 | < 0.0001 |
| 66-74 | -0.20 (-0.25, -0.16) | 7.8 | 1230 | < 0.0001 |
| >74 | -0.19 (-0.27, -0.11) | 8.1 | 463 | < 0.0001 |
| Type 2 diabetes | | | | |
| All ages | -0.50 (-0.61, -0.40) | 8.6 | 711 | < 0.0001 |
| 18-24 | -0.44 (-1.70, 0.84) | 8.8 | 12 | 0.464 |
| 25-65 | -0.70 (-0.85, -0.54) | 8.8 | 413 | < 0.0001 |
| 66-74 | -0.34 (-0.49, -0.19) | 8.2 | 196 | < 0.0001 |
| >74 | 0.00 (-0.22, 0.22) | 8.0 | 90 | 0.986 |

FIG. 14E

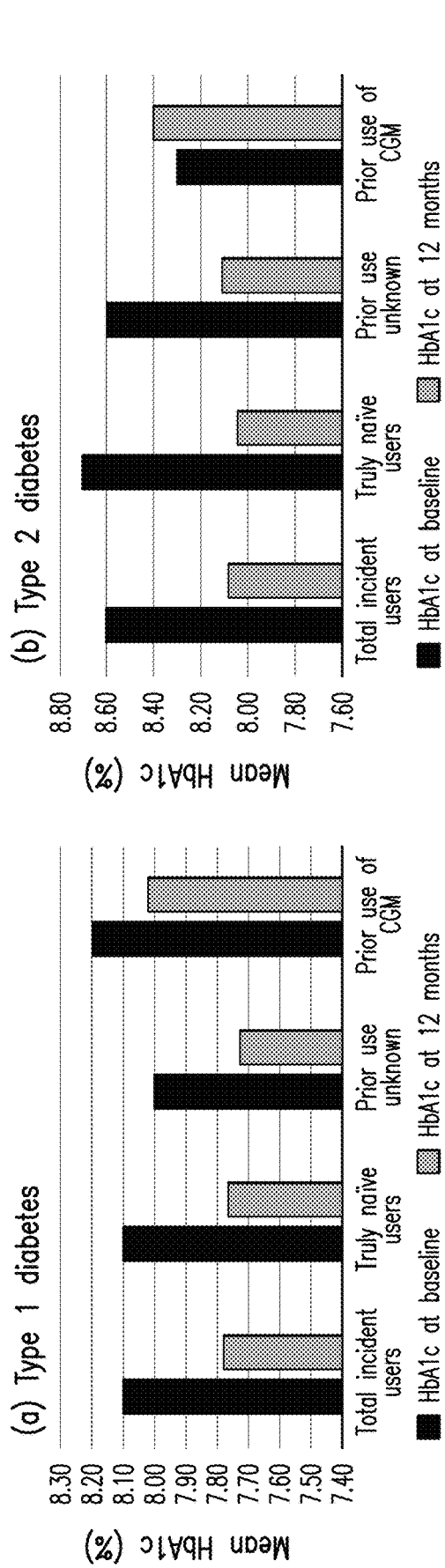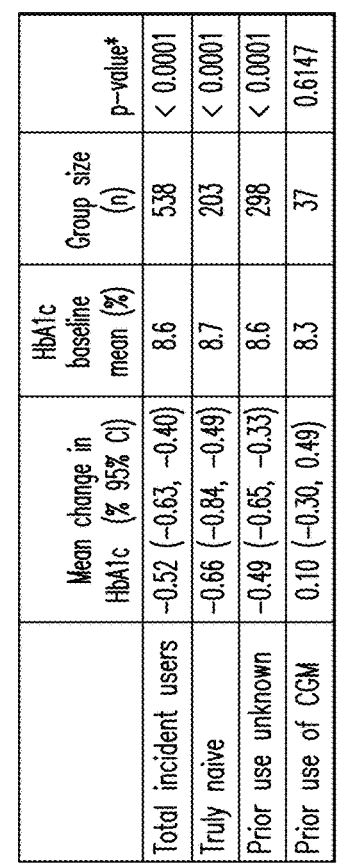
FIG. 14G

|  | T1DM | T2DM |
|---|---|---|
| Number of new incident users identified* | 36,352 | 3,202 |
| Glucose lowering medication registered in NDR, number of subjects (%) | | |
| Insulin | 35,924 (98.8) | 2,523 (78.8) |
| - injection | 27,855 (77.5) | 1,853 (73.4) |
| - pump | 7,043 (19.6) | 69 (2.7) |
| - route of administration unknown | 1,026 (2.9) | 601 (23.8) |
| Other glucose lowering medication | 38 (0.1) | 567 (17.7) |
| No medication registered in NDR | 7 (0) | 60 (1.9) |
| Information missing | 383 (1.1) | 52 (1.6) |

FIG. 14H

|  | Type 1 diabetes (n=131) | Type 2 diabetes (n=176) |
| --- | --- | --- |
| Age (years) | 42.37 ± 16.81 [11, 81] | 62.82 ± 11.31 [34, 92] |
| Duration of diabetes | 16.34 ± 13.31 [1, 60] | 14.20 ± 8.55 [1, 52] |
| HbA1c (% ± SE) | 8.15 ± 0.15 | 7.76 ± 0.12 |
| Insulin therapy (% of patients) |  |  |
| CSII | 12.2% | 0% |
| MDI* | 87.8% | 100% |

FIG. 16A

| Subject count | 51 |
|---|---|
| Gender M/F | 14/37 |
| Age (years): median [IQR] [range] | 42 [37-55] [6-73] |
| CGM usage per subject (days): median [IQR] [range] | 440 [176-489] [112-541] |
| Data section count per subject: median [IQR] [range] | 13 [6-15] [3-17] |
| Ending HbA1c (%) — median [IQR] | 6.9 [6.6-7.5] |
| Ending HbA1c (%) — mean (STD) | 7.1 (0.96) |
| Ending 14-day Average Glucose (mg/dL) — median [IQR] | 143 [127 - 160] |
| Ending 14-day Average Glucose (mg/dL) — mean (STD) | 145 (27) |

FIG. 17B

| | Method | | cHbA1c | eHbA1c(AG) | GMI(AG) |
|---|---|---|---|---|---|
| Comparing estimated HbA1c against Lab HbA1c | Absolute deviation (%) | Mean (STD) | 0.11 (0.06) | 0.54 (0.47) | 0.47 (0.46) |
| | | Median [IQR] | 0.10 [0.07, 0.13] | 0.42 [0.21, 0.81] | 0.36 [0.18, 0.62] |
| | Absolute deviation (mmol/mol) | Mean (STD) | 1.2 (0.7) | 5.9 (5.1) | 5.1 (5.0) |
| | | Median [IQR] | 1.1 [0.8, 1.4] | 4.6 [2.3, 8.9] | 3.9 [2.0, 6.8] |
| | MARD | | 3.1% | 7.5% | 6.3% |
| | Fraction of AD<0.5% (AD<5.5 mmol/mol) | | 92.3% | 65.4% | 73.1% |
| | Average bias (%) | | 0 | -0.4 | -0.3 |
| | Average bias (mmol/mol) | | 0 | -4.4 | -3.3 |
| | Fraction within ARD | 5% | 79% | 57% | 49% |
| | | 10% | 94% | 68% | 82% |
| | | 15% | 100% | 96% | 96% |
| | Linear regression | $R^2$ | 0.91 | 0.65 | 0.65 |
| | | slope | 0.94 | 0.84 | 1.22 |
| | | intercept | 0.49 | 1.5 | -1.17 |

FIG. 17C

| Inclusion Criteria | Source |
|---|---|
| Prescription of FreeStyle Libre CGM (Nov 2017-Feb 2020) | NDC, text search |
| Type 2 Diabetes | ICD-9/-10; SNOMED |
| Age <65 | Patient data |
| Not treated with short- or rapid-acting insulin (bolus insulin) | NDC |
| Necessary HbA1c data | Patient lab values |
| Baseline HbA1c ≥8 | Patient lab values |
| At least 6-months pre-prescription database enrollment | Enrollment data |

| Exclusion Criteria | Source |
|---|---|
| History of any CGM purchase | NDC; HCPCS; SNOMED |
| Gestational Diabetes | ICD-9/-10; SNOMED |
| Both Type 1 and Type 2 code on latest encounter | ICD-9/-10; SNOMED |

NDC: national drug code
ICD: international classification of disease
HCPCS: healthcare common procedure coding system
SNOMED: systematized nomenclature of medicine

FIG. 19A

| Model Parameters | Input | OSWA Range | Source |
|---|---|---|---|
| Clinical parameters | | | |
| SHE admissions (per year) | | | |
| Pre-FreeStyle Libre system | 294 | | n = 4,250<br>ABCD audit |
| Prorated post-FreeStyle Libre system | 149* | | n = 4,250<br>87 events in 7 months of follow up<br>ABCD audit* |
| SMBG admissions per 100 person years | 6.9 | 5.5, 8.3 | Pre-FreeStyle Libre System events / n * 100 |
| FreeStyle Libre System admission per 100 person years | 3.5 | 2.8, 4.2 | Prorated post-FreeStyle Libre system events / n * 100 |
| SHE paramedic callouts (per year) | | | |
| Pre-FreeStyle Libre system | 556 | | n = 4,250<br>ABCD audit |
| Prorated post-FreeStyle Libre system | 99 | | n = 4,250<br>58 admissions in 7 months of follow up<br>ABCD audit |
| SMBG paramedic callouts per 100 person years | 13.1 | 10.47, 15.70 | Pre-FreeStyle Libre System events / n * 100 |
| FreeStyle Libre paramedic callouts per 100 person years | 2.3 | 1.87, 2.81 | Prorated post-FreeStyle Libre system events / n * 100 |
| DKA and hyperglycaemic admissions (per year) | | | |
| Pre-FreeStyle Libre system | 410 | | n = 4,250<br>ABCD audit |
| Prorated post-FreeStyle Libre system | 133 | | n = 4,250<br>86 admissions in 7.5 months of follow up<br>ABCD audit |
| SMBG admissions per 100 person years | 9.6 | 7.71, 11.58 | Pre-FreeStyle Libre System events / n * 100 |
| FreeStyle Libre system admissions per 1000 person years | 5.4 | 4.28, 6.44 | Prorated post-FreeStyle Libre system events / n * 100 |
| HbA1c change after FreeStyle Libre system initiation | | | |
| Reduction in HbA1c (overall population) | 0.5% | 0.3%, 0.5% | ABCD audit |
| Reduction in HbA1c (> 8.5% at baseline) | 1.2% | 1.0%, 1.4% | ABCD audit |
| Cost parameters | | | |
| FreeStyle Libre sensor unit cost | £35 | £28, £42 | NHS BSA Drug Tariff listing price [7] |
| FreeStyle Libre sensor lifetime (days) | 14 | 11.2, 16.8 | Manufacturer instructions |
| FreeStyle Libre additional SMBG tests per day | 0.5 | 0.25, 0.329 | IMPACT, [5] |
| SMBG lancet unit cost | £0.04 | £0.03, £0.05 | IQVIA, average price of 10 units<br>(data held by Abbott Diabetes Care Ltd) |
| SMBG test strip unit cost | £0.23 | £0.18, £0.28 | IQVIA, average price of 10 strips<br>(data held by Abbott Diabetes Care Ltd) |
| SMBG tests per day | 5.60 | 4.48, 6.72 | IMPACT, [5] |
| Cost of ambulance call out | £243 | £194, £291 | NHS reference costs 2018-2019 weighted average of ASS01/ASS02 [17] |
| Cost of hypoglycaemic admission | £2,118 | £1,694, £2,541 | Weighted average of KB02J -G codes from 2019/2020 NHS tariff [18] |
| Cost of DKA admission** | £1,843 | £1,474, £2,211 | Weighted average of KB01C-F codes from 2019/2020 NHS tariff** [18] |
| Annual cost diff per % HbA1c decrease | | | |
| HbA1c <7.5% at baseline | £33 | £26, £40 | Baxter et al. 2016 [19] - derived by assuming linear relationship between 0.4 and 1% |
| HbA1c 7.5 to 8% at baseline | £45 | £36, £53 | |
| HbA1c 8 to 9% at baseline | £52 | £41, £62 | |
| HbA1c >9% at baseline | £92 | £74, £110 | |

FIG. 21A

| Utility Parameters | | | |
|---|---|---|---|
| | Input | OWSA Range | Source |
| Utility increment FreeStyle Libre system vs SMBG | 0.030 | 0.024, 0.036 | Matza et al. 2017 [21] |
| Utility gain per % decrease in HbA1c | 0.027 | 0.022, 0.033 | McQueen et al. 2014 [22] |
| Utility decrement per SHE | 0.047 | 0.038, 0.056 | Currie et al. 2006 [23] |
| Utility decrement per DKA | 0.009 | 0.007, 0.011 | Peasgood 2016 [24] |

FIG. 21B

| Per patient cost analysis | FreeStyle Libre System | SMBG |
|---|---|---|
| Acquisition costs | £937 | £552 |
| Healthcare resource use costs* | £200 | £396 |
| Costs avoided due to HbA1c | -£21 | - |
| Annual Total | £1,116 | £948 |
| Annual Difference | | £168 |

FIG. 21C

| Budget impact analysis of increasing FreeStyle Libre System uptake | | | |
|---|---|---|---|
|  | Year 1 | Year 2 | Year 3 |
| FreeStyle Libre System users | 537 | 895 | 1,253 |
| SMBG users | 1,253 | 895 | 1,253 |
| FreeStyle Libre System Costs | £599,490 | £1,847,618 | £1,907,890 |
|    Cost of acquisition | £502,959 | £838,265 | £1,173,570 |
|    Healthcare resource use costs* | £107,593 | £179,593 | £251,050 |
|    Cost offset due to improved HbA1c | -£11,062 | -£18,437 | -£25,812 |
| SMBG Costs | £1,187,856 | £1,847,618 | £1,907,890 |
|    Cost of acquisition | £691,506 | £493,933 | £296,360 |
|    Cost of SHE/DKA and hyperglycaemia events | £496,350 | £354,536 | £212,721 |
| Total cost for local health economy | £1,787,345 | £1,847,618 | £1,907,890 |
| Cost increase relative to year 1 per T1DM person | - | £33.67 | £67.34 |

FIG. 21D

| Cost Utility Analysis | | | |
|---|---|---|---|
| | FreeStyle libre System | SMBG | Difference |
| Base-case 1: FreeStyle Libre system and SMBG | | | |
| Cost per person in Year 1 | £1,116 | £948 | £168 |
| Incremental QALYs | | | |
|     Increment due to device | 0.030 | | 0.030 |
|     Increment due to HbA1c reduction | 0.011 | | 0.011 |
|     Increment due to reduction in hypoglycaemia | 0.007 | | 0.007 |
|     Increment due to reduction in DKA | <0.001 | | 0.000 |
| Total incremental QALYs | 0.048 | | 0.048 |
| Incremental cost effectiveness ratio | | | £3,516 |

FIG. 21E

| Sub-Group Analysis | | | | | | |
|---|---|---|---|---|---|---|
| | Overall Population | | | High HbA1c baseline | | |
| | FreeStyle Libre system | SMBG | Difference | FreeStyle Libre system | SMBG | Difference |
| Acquisition costs | £937 | £552 | £385 | £937 | £552 | £385 |
| Healthcare resource use costs | £200 | £396 | -£196 | £200 | £396 | -£196 |
| Costs avoided due to HbA1c | -£21 | £0 | -£21 | -£110 | £0 | -£110 |
| Total Cost per patient | £1,116 | £948 | £168 | £1,027 | £948 | £79 |
| Total QALYs gained | 0.048 | 0.00 | 0.048 | 0.07 | 0.000 | 0.07 |
| Incremental cost effectiveness ratio | | | £3,516 | | | £1,129 |

FIG. 21I

| Randomized controlled trial | Outcome (FGMS vs. SMBG) [N=149 vs. N=75] | | P value |
|---|---|---|---|
| Overall population (6 months) | Mean change from baseline in HbA1c: | −0.29 ± 0.07 vs. −0.31 ± 0.09% | P=0.8222 |
| Subgroup analyses (6 months) | | | |
| Age | | | |
| <65 years | Mean change from baseline in HbA1c: | −0.53 ± 0.09 vs. −0.20 ± 0.12% | P=0.0301 |
| ≥65 years | | −0.05 ± 0.10 vs. −0.49 ± 0.13% | P=0.0081 |
| Time spent in hypoglycemia [hours/day]: mean change from baseline | | | |
| Glucose <70 mg/dL | Between-group difference: | −43% [mean ± SE −0.47 ± 0.13] | P=0.0006 |
| Glucose <55 mg/dL | | −53% [−0.22 ± 0.07] | P=0.0014 |
| Glucose <45 mg/dL | | −64% [−0.14 ± 0.04] | P=0.0013 |
| Frequency of hypoglycemic events [per day]: mean change from baseline | | | |
| Glucose <70 mg/dL | Between-group difference: | −28% [mean ± SE −0.16 ± 0.07] | P=0.0164 |
| Glucose <55 mg/dL | | −44% [−0.12 ± 0.04] | P=0.0017 |
| Glucose <45 mg/dL | | −49% [−0.06 ± 0.02] | P=0.0098 |
| AUC [hours/day × mg/dL] | | | |
| Glucose <70 mg/dL | Between-group difference: | −51% [mean ± SE −7.80 ± 2.20] | P=0.0005 |
| Glucose <55 mg/dL | | −60% [−2.51 ± 0.76] | P=0.0012 |
| Glucose <45 mg/dL | | −67% [−0.70 ± 0.22] | P=0.0015 |
| Extension phase | Outcome (FGMS vs. baseline) [N=139] | | |
| Subgroup analyses (12 months) | | | |
| Time spent in hypoglycemia [hours/day] | | | |
| Glucose <70 mg/dL | Mean change from baseline (start of treatment phase): | −50% [mean ± SD −0.70 ± 1.85] | P=0.0002 |
| Glucose <55 mg/dL | | −62% [−0.40 ± 1.09] | P=0.0002 |
| Glucose <45 mg/dL | | −67% [−0.23 ± 0.73] | P=0.0013 |
| Frequency of hypoglycemic events [per day] | | | |
| Glucose <70 mg/dL | Mean change from baseline (start of treatment phase): | −41% [mean ± SD −0.27 ± 0.67] | P<0.0001 |
| Glucose <55 mg/dL | | −56% [−0.20 ± 0.49] | P<0.0001 |
| Glucose <45 mg/dL | | −62% [−0.13 ± 0.35] | P=0.0002 |
| AUC [hours/day × mg/dL] | | | |
| Glucose <70 mg/dL | Mean change from baseline (start of treatment phase): | −58% (mean ± SD −12.73 ± 34.53] | P=0.0002 |
| Glucose <55 mg/dL | | −65% [−4.28 ± 12.76] | P=0.0007 |
| Glucose <45 mg/dL | | −69% [−1.12 ± 3.67] | P=0.0021 |
| BG levels are presented as mg/dL, which can be converted to mmol/L by multiplying values by 0.05551. | | | |
| AUC, area under the concentration-time curve; FGMS, flash glucose monitoring system; HbA1c, glycosylated hemoglobin; SMBG, self-monitoring of blood glucose. | | | |

FIG. 22A

| Study (population) | Effect of: | HbA1c (%) |
|---|---|---|
| Fokkert et al. 2019 [20]<br>T1D, n=1054; T2D, n=223; Other, n=88 | Before vs. after FGMS use on estimated HbA1c | At baseline: 8.0% (95% CI 7.9–8.1)<br>At 6 months: 7.6% (95% CI 7.5–7.7); $P<0.001$ vs. baseline<br>At 12 months: 7.6% (95% CI 7.6–7.7); $P<0.001$ vs. baseline |
| Eeg-Olofsson et al. 2020 [21]<br>T1D, n=8316; T2D, n=538 | Before vs. after FGMS use on HbA1c (method of measurement not specified) | T1D: 8.1% at baseline. Mean change −0.33% (95% CI −0.36 to −0.31); $P<0.0001$<br>T2D: 8.6% at baseline. Mean change −0.52% (95% CI −0.63 to −0.40); $P<0.0001$ |
| Evans et al. 2020 [22]<br>Meta-analysis of 29 studies; n=1723 with T1D or T2D | FGMS use on laboratory HbA1c | In adults at 2–4 months: mean change −0.56% (95% CI −0.76 to −0.36)<br>In children and adolescents at 2–4 months: mean change −0.54% (95% CI −0.84 to −0.23) |
| Ish-Shalom et al. 2016 [23]<br>T1D, n=6; T2D, n=25 | FGMS use on HbA1c (method of measurement not specified) | In patients with HbA1c ≥ 7.5%<br>At 8 weeks: mean change −1.33 ± 0.29%; $P<0.0001$<br>At 24 weeks: mean change −1.21 ± 0.42%; $P=0.009$ |
| Dunn et al. 2018 [24]<br>n>50,000 | ↑ Scanning frequency on estimated HbA1c | Highest (48.1 scans/day) vs. lowest (4.4 scans/day) scan rate group:<br>6.7% (95% CI 6.7–6.8) vs. 8.0% (95% CI 7.9–8.0; $P<0.001$ |
| Gomez-Peralta et al. 2020 [26]<br>n=22,949 | ↑ Scanning frequency on estimated HbA1c | Highest (39.6 scans/day) vs. lowest (3.9 scans/day) scan rate group:<br>6.9% (95% CI 6.9–7.0) vs. 8.0% (95% CI 8.0–8.1); $P<0.001$ |
| Calliari et al. 2020 [27]<br>Brazil: 17,691 readers and 147,166 sensors<br>Worldwide: 688,640 readers and 7,329,052 sensors | ↑ Scanning frequency on estimated HbA1c | Brazil: Highest (43.1 scans/day) vs. lowest (3.6 scans/day) scan rate group:<br>6.7% (95% CI 6.6–6.8) vs. 7.6% (95% CI 7.4–7.7); $P<0.01$<br>Worldwide: Highest (37.8 scans/day) vs. lowest (3.4 scans/day) scan rate group:<br>6.7% (95% CI 6.7–6.7) vs. 8.1% (95% CI 8.1–8.2); $P<0.01$ |

BG levels are presented as mg/dL, which can be converted to mmol/L by multiplying values by 0.05551.

BG, blood glucose; FGMS, flash glucose monitoring system; HbA1c, glycosylated hemoglobin; T1D, type 1 diabetes; T2D, type 2 diabetes; ↑ indicates increased.

FIG. 22B

| Study | Effect of | Time spent in hypoglycemia | Time spent in hyperglycemia | Time in range |
|---|---|---|---|---|
| Dunn et al. 2018 [24] n>50,000 | ↑ Scanning frequency: 48.1 highest and 4.4 lowest scans/day (mean 16.3 scans/day) | Highest vs. lowest scan rate group:<br>BG <70 mg/dL: ↓ 15%; 79.3 vs. 93.4 min/day; $P<0.001$<br>BG <56 mg/dL: ↓ 40%; 26.2 vs. 43.4 min/day; $P<0.001$<br>BG <45 mg/dL: ↓ 49%; 11.9 vs. 23.4 min/day; $P<0.001$ | Highest vs. lowest scan rate group:<br>BG >180 mg/dL: ↓ 44%; 5.9 vs. 10.5 hours/day; $P<0.001$ | Highest vs. lowest scan rate group:<br>BG 70–180 mg/dL: ↑ 40%; 16.8 vs. 12.0 hours/day; $P<0.001$ |
| Jangam et al. 2019 [25] Hypoglycemia n=2,268 or hyperglycemia n=2,268 | Comparison between first and last 14-day periods of sensor wear[a], after stratification of results based on risk of hypoglycemia or hyperglycemia and scanning frequency[b] | High-risk hypoglycemia group (BG ≤ 70 mg/dL):<br>↓ 19.5% from 200 ± 3 to 161 ± 5 min/day in higher-frequency scanners (mean 20.3 scans/day); $P<0.0001$<br>↓ 24.5% from 196 ± 3 to 148 ± 4 min/day in medium-frequency scanners (mean 11.6 scans/day); $P<0.0001$<br>↓ 24.5% from 204 ± 3 to 154 ± 4 min/day in low-frequency scanners (mean 7 scans/day); $P<0.0001$ | High-risk hyperglycemia group (BG >240 mg/dL):<br>↓ 14.2% from 5.7 ± 0.10 to 4.9 ± 0.14 hours/day in higher-frequency scanners (mean 18.1 scans/day); $P<0.0001$<br>↓ 6.3% from 5.8 ± 0.09 to 5.5 ± 0.13 hours/day in medium-frequency scanners (mean 10.5 scans/day); $P=0.02$<br>No effect in low-frequency scanners (mean 6.2 scans/day) | |
| Gomez-Peralta et al. 2020 [26] n=22,949 | ↑ Scanning frequency: 39.6 highest and 3.9 lowest scans/day (mean 13 scans/day) | Highest vs. lowest scan rate group:<br>BG <70 mg/dL: ↓ 14%; 85.3 (95% CI 79.3–91.2) vs. 99.2 (95% CI 93.9–104.4) min/day; $P<0.001$<br>BG <54 mg/dL: ↓ 37%; 29.7 (95% CI 26.6–32.8) vs. 46.8 (95% CI 43.6–49.9) min/day; $P<0.001$ | Highest vs. lowest scan rate group:<br>BG >180 mg/dL: ↓ 37%; 6.9 (95% CI 6.7–7.2) vs. 10.9 (95% CI 10.6–11.2) hours/day; $P<0.001$ | Highest vs. lowest scan rate group:<br>BG 70–180 mg/dL: ↑ 36%; 15.6 (95% CI 15.4–15.9) vs. 11.5 (95% CI 11.2–11.7) hours/day; $P<0.001$ |
| Calliari et al. 2020 [27] Brazil: 17,691 readers and 147,166 sensors Worldwide: 688,640 readers and 7,329,052 sensors | ↑ Scanning frequency Brazil: 43.1 highest and 3.6 lowest scans/day (average 14 scans/day) Worldwide: 37.8 highest and 3.4 lowest scans/day (average 12 scans/day) | Highest vs. lowest scan rate group (BG <54 mg/dL):<br>Brazil: 27.1 (95% CI 23.8–30.5) vs. 28.3 (95% CI 25.0–31.5) min/day; $P=0.64$<br>Worldwide: 22.9 (95% CI 22.5–23.4) vs. 31.1 (95% CI 30.6–31.6) min/day; $P<0.01$ | Highest vs. lowest scan rate group (BG >180 mg/dL):<br>Brazil: 6.0 (95% CI 5.7–6.3) vs. 8.7 (95% CI 8.3–9.1) hours/day; $P<0.01$<br>Worldwide: 5.8 (95% CI 5.8–5.9) vs. 10.8 (95% CI 10.7–10.8) hours/day; $P<0.01$ | Highest vs. lowest scan rate group (BG 70–180 mg/dL):<br>Brazil:16.6 vs. 14.2 hours/day; $P<0.01$<br>Worldwide: 17.0 vs. 12.1 hours/day; $P<0.01$ |

BG levels are presented as mg/dL, which can be converted to mmol/L by multiplying values by 0.05551.
[a] Scanning frequency decreased gradually from >18 scans/day during first sensor use to ≈ 15 scans/day at 2 months, and was maintained at the lower level for the remainder of the 6-month analysis period.
[b] Glucose results were analyzed after being divided into high, medium and low-risk groups based on tertiles of time spent in hypoglycemia (min/day <70 mg/dL) or hyperglycemia (hours/day >240 mg/dL), and further subdivision into tertiles of glucose scanning frequency (high, medium, low).
BG, blood glucose; CI, confidence interval; ↑ indicates increased; ↓ indicates decreased/reduced.

FIG. 22C

| Study title or author | Year | Study design | Sample size Disease/treatment | Observation period | Outcome measures* | Country/race |
|---|---|---|---|---|---|---|
| IMPACT | 2016 | RCT | Type 1 diabetes Multiple injections and CSII Flash glucose monitoring group: 119 patients SMBG group: 120 patients | 6 months | Time in hypoglycemia TIR, HbA1c SMBG frequency, DTSQ, DQoL, etc. | Sweden, Austria, Germany, Spain, Netherlands/ white, black |
| REPLACE 6 months | 2017 | RCT | Type 2 diabetes Multiple injections and CSII Flash glucose monitoring group: 149 patients SMBG group: 75 patients | 6 months | HbA1c Time in hypoglycemia SMBG frequency, DTSQ, DQoL, etc. | France, Germany, UK/ white, black, Asian, Pacific Islander, other |
| REPLACE 12 months | 2017 | Prospective observational study | Type 2 diabetes Multiple injections and CSII 139 patients | 6 months | Changes in sensor-derived glycemic measures Time in hypoglycemia, SMBG frequency, etc. | France, Germany, UK/ white, black, Asian, Pacific Islander, other |
| Dunn et al. | 2018 | RWD study | 50,831 patients with type 1 and type 2 diabetes | At least 5 days | Scan frequency, eA1c Time in hypoglycemia, etc. | N/A |
| SELFY | 2018 | Prospective (single arm) study | Type 1 diabetes Using insulin (administered by injections or CSII) 76 children and teenagers with T1D | 18 weeks | TIR Time in hyperglycemia, frequency and duration of hyperglycemia/hypoglycemia, HbA1c etc. | UK, Ireland, Germany/not described |

FIG. 23A

| | | | | SMBG | | | |
|---|---|---|---|---|---|---|---|
| Yaron et al. | 2019 | RCT | Type 2 diabetes Multiple injections Flash glucose monitoring group: 53 patients SMBG group: 48 patients | | 10 weeks | DTSQ, HbA1c, etc. | Israel/not described |
| FLARE-NL4 | 2019 | Prospective registry study | Using insulin 1,054 patients with type 1 diabetes 223 patients with type 2 diabetes | | 12 months | HbA1c SF-12$^2$, EQ-5D-3L, diabetes-related hospital admission rate, work absenteeism rate, etc. | Netherlands/not described |
| Evans et al. | 2019 | Meta-analysis | 25 studies 1,496 patients with type 1 diabetes 227 patients with type 2 diabetes | | 1–12 months | HbA1c | N/A |
| Kröger et al. | 2019 | Chart review | Type 2 diabetes Multiple injections and CSII 363 patients | | 3–6 months | HbA1c | France, Austria, Germany/not described |

FIG. 23A Continued

| Study title or author | Year | Study design | Sample size Disease/treatment | Observation period | Outcome measures* | Country/race |
|---|---|---|---|---|---|---|
| Overend et al. (ABCD manuscript) | 2019 | Prospective observational study | Type 1 diabetes 40 patients with T1D | 6 months | DQoL HbA1c, hypoglycaemia | UK/ not described |

FIG. 23B

| | | | | | |
|---|---|---|---|---|---|
| FUTURE (Charleer et al.) | 2019 | Prospective observational RWD study | Type 1 diabetes 1,913 patients with T1D | 12 months | DQoL HbA1c, time in hyperglycemia/hypoglycemia, ketoacidosis, work absenteeism | Belgium/not described |
| Tyndall et al. (Tyndall from 2019) | 2019 | Prospective observational study | Type 1 diabetes 900 patients with T1D | 2 months | HbA1c hypoglycaemia, DQoL, flash monitoring data and hospital admissions | UK/ not described |
| Gomez-Peralta et al. | 2020 | RWD study | 22,949 readers 207,386 sensors | 52 months | Scan frequency, eA1c, TIR, time in hyperglycemia, time in hypoglycemia, etc. | N/A |
| Calliari et al. | 2020 | RWD study | 17,691 readers 147,166 sensors | 52 months | Scan frequency, eA1c, TIR, time in hyperglycemia, time in hypoglycemia, etc. | N/A |
| Wada et al. | 2020 | RCT | Type 2 diabetes Oral agents 100 patients | 24 weeks | HbA1c Changes in BMI, blood pressure, fasting plasma glucose, triglycerides, HDL cholesterol, LDL cholesterol, uric acid, urinary albumin, DTSQ score, antidiabetic drugs, glucose variability measures, etc. | Japan/not described |
| Ida et al. | 2020 | Observational study | Multiple injections 42 patients with type 1 diabetes | 12 weeks | HbA1c, SD, MAGE, CV, MODD, AAC, AUC, self-administered questionnaires (DVS, IPAQ, SDSCA, DTSQ), etc. | Japan/not described |

FIG. 23B Continued

| | | | | | |
|---|---|---|---|---|---|
| | | | 48 patients with type 2 diabetes | | |
| SHIFT | 2020 | Prospective (single-arm) study | Type 2 diabetes 94 patients using insulin | 11 weeks | Time in hypoglycemia TIR, frequency and duration of hyperglycemia/hypoglycemia, eA1c, AUC, SD, LBGI, HBGI, SD of glucose rate of change, CONGA, etc. | Japan/not described |
| Al Hayek et al. | 2020 | Prospective observational study | Type 1 diabetes Multiple injections 67 patients with T1D | 6 months | HbA1c Standard questionnaire for acceptability measures | Saudi Arabia/not described |
| Tsur et al. | 2020 | RWD study | Type 1 diabetes 3490 patients with T1D | 14 months | HbA1c Internal medicine hospitalizations, Rate of glucose test strip purchases, etc. | Israel/not described |

FIG. 23B Continued

| | N | Baseline Mean ± SD | Final phase Mean ± SD | Change Mean ± SD | 95% CI for change | p value |
|---|---|---|---|---|---|---|
| Austria | | | | | | |
| HbA1c (%) | 92 | 8.8 ± 0.8 | 7.9 ± 1.0 | −0.9 ± 0.8 | (−1.0, −0.7) | <0.0001 |
| HbA1c (mmol/mol) | 92 | 72.2 ± 8.9 | 62.6 ± 10.5 | −9.6 ± 8.8 | (−11.4, −7.7) | <0.0001 |
| France | | | | | | |
| HbA1c (%) | 88 | 9.0 ± 0.9 | 8.2 ± 1.1 | −0.8 ± 1.1 | (−1.1, −0.6) | <0.0001 |
| HbA1c (mmol/mol) | 88 | 74.7 ± 9.7 | 65.9 ± 12.5 | −8.9 ± 12.5 | (−11.5, −6.2) | <0.0001 |
| Germany | | | | | | |
| HbA1c (%) | 183 | 8.9 ± 0.9 | 7.9 ± 0.9 | −0.9 ± 1.1 | (1.1, −0.8) | <0.0001 |
| HbA1c (mmol/mol) | 183 | 73.1 ± 10.3 | 63.0 ± 9.6 | −10.1 ± 12.2 | (−11.9, −8.3) | <0.0001 |

FIG. 23D

Table 5 Changes in indices of disease burden

| | | Baseline | 6months | 12months | Difference (12months) |
|---|---|---|---|---|---|
| SF-12-o | | | | | |
| PCS | Observed | 50.6 (44.7 to 54.1) | 51.6 (45.9 to 54.7)" | 51.2 (45.8 to 54.7)' | |
| | Number | 1380 | 10es | 680 | |
| | Estimated | 48.8 (48.4 to 40.2) | 40.6 (40.2 to 50.1) | 40.4 (48.8 to 49.9) | 0.6 (−0.3 to 1.5) |
| MCS | Observed | 40.6 (40.6 to 56.4) | 51.2 (43.4 to 57.8)' | 52.6 (45.1 to 58.6)" | |
| | Number | 1380 | 10es | 68s | |
| | Estimated | 48.0 (47.5 to 48.6) | 50.0 (40.4 to 50.7) | 51.3 (50.5 to 52.1) | 3.3 (2.1 to 4.4) |
| EQ-5D-3L | | | | | |
| Dutch Tariff | Observed | 0.84 (0.77 to 1.00) | 0.90 (0.78 to 1.00)' | 0.90 (0.78 to 1.00)" | |
| | Number | 1380 | 10e6 | 68s | |
| | Estimated | 0.83 (0.82 to 0.4) | 0.86 (0.8s to 0.8t) | 0.86 (0.84 to 0.87) | 0.03 (0.01 to 0.0e) |
| EQ-VAS | Observed | 72 (81 to 81) | 78 (87 to 82)' | 77 (69 to 8e) | |
| | Number | 1381 | 10e6 | 68s | |
| | Estimated | 68.2 (67.1 to 60.2) | 71s (70.3 to 72.8) | 72.8 (71.1 to 74.2) | 4.4 (2.1 to 6.7) |
| Hypoglycemic events | | | | | |
| Presence of any hypoglycomic events in past 6months, yes/no, n (%) | | 1271 yes (13.5) n=1380 | 78 yes (92.4)' n=10e6 | 624 yes (91.0)' n=686 | |
| Number of Hypoglycomic events in past 6months, n (%) | Observed | 30 (10 to 72) | 30 (12 to 72) | 26 (11 to 70)' | |
| | Number | 1266 | 972 | 623 | |

FIG. 23K

| | | | | | |
|---|---|---|---|---|---|
| | Estimated | 54.0 (50.1 to 58.0) | 54.8 (50.4 to 50.3) | 54.4 (51.9 to 63.0) | 3.4 (-4.9 to 11.7) |
| Use of strips | | | | | |
| Strips per day, n (%) | Observed | 6 (4 to 8) | 5 (1 to 7)* | 3 (0 to 6)* | |
| | Number | 1350 | 1040 | 68s | |
| | Estimated | 6.1 (5.9 to 6.3) | 5.0 (4.8 to 5.3) | 4.0 (3.7 to 4.3) | -2.2 (-2.6 to -1.7) |
| Hospital admissions | | | | | |
| Hospital admissions in past 12months, yes, n (%) | | 187 (13.7) | 97 (7.1)** | 32 (4.7)** | |
| | Number | 1385 | 1040 | 681 | |
| Number of hospital admissions, n | Observed | 1.0 (1.0 to 2.0) | 1.0 (1.0 to 2.5) | 1.0 (1.0 to 2.0) | |
| | Number | 187 | 97 | 32 | |
| | Estimated | 0.33 (0.24 to 0.42) | 0.30 (0.19 to 0.40) | 0.09 (-0.03 to 0.22) | -0.24 (-0.43 to -0.04) |
| Loss of working days | | | | | |
| Absenteeism rate in past 6months, yes, n (%) | | 2e1 (18.5) | 104 (9.8)* | 53 (7.7)* | |
| | Number | 1380 | 10e6 | 686 | |
| Number of working days lost in last 6months | Observed | 7 (3 to 25) | 9 (3 to 35) | 10 (3 to 44) | |
| | Number | 247 | 9s | 50 | |
| | Estimated | 34.6 (27.2 to 42.0) | 38.2 (26.5 to 50.0) | 44.4 (28.1 to 60.8) | 9.8 (-12.1 to 31.8) |

Values are presented as numbers (%), median path, 75th percentile and intimated means (difference) (psx Cl). Data are presented as observed data and intimated data using this linear mized model. 
*p<0.05 as compared with baseline; **p<0.001 as compared with baseline.
EQ-sD-eL, s-level version of EuroCd sD; EQ-VAS, EQ-visual analogus scales; MCS, Mental Component Score, PCS, Physical Component Score; SF=12", 12-Item Short Form Health Survey".

FIG. 23K Continued

| | | Sample size, N | Total ADE | | Hypoglycemic ADE | | Hyperglycemic ADE | |
|---|---|---|---|---|---|---|---|---|
| | | | Before flash CGM # events (# affected) | After flash CGM # events (# affected) | Before flash CGM # events (# affected) | After flash CGM # events (# affected) | Before flash CGM # events (# affected) | After flash CGM # events (# affected) |
| | Full Cohort | 10282 | 391 (324) | 252 (211) | 35 (33) | 44 (39) | 359 (298) | 212 (181) |
| Age | Age 18 – 49 | 3321 | 173 (138) | 103 (86) | 11 (10) | 15 (15) | 164 (131) | 89 (74) |
| | Age 50 – 64 | 6425 | 197 (167) | 131 (111) | 20 (20) | 21 (18) | 178 (150) | 112 (97) |
| | Age 65+ | 536 | 21 (19) | 18 (14) | 4 (3) | 8 (6) | 17 (17) | 11 (10) |
| Gender | Male | 5341 | 184 (150) | 125 (101) | 15 (15) | 26 (22) | 169 (137) | 101 (84) |
| | Female | 4941 | 207 (174) | 127 (110) | 20 (18) | 18 (17) | 190 (161) | 111 (97) |
| Comorbidities | Hypertension | 8286 | 321 (268) | 212 (174) | 32 (31) | 35 (30) | 292 (244) | 180 (152) |
| | Obesity | 5713 | 235 (191) | 157 (138) | 17 (16) | 23 (23) | 219 (179) | 135 (119) |
| | Pulmonary Disease | 2520 | 122 (92) | 87 (70) | 14 (13) | 18 (17) | 108 (83) | 71 (58) |
| | Depression | 2488 | 142 (109) | 108 (83) | 16 (16) | 20 (16) | 127 (98) | 91 (74) |
| | Hypothyroid Disease | 2210 | 69 (62) | 47 (44) | 7 (7) | 10 (9) | 65 (59) | 37 (35) |
| | Anemia | 1975 | 111 (88) | 69 (53) | 21 (19) | 20 (16) | 91 (73) | 52 (43) |
| | Liver Disease | 1905 | 125 (91) | 79 (61) | 10 (10) | 14 (10) | 115 (84) | 66 (53) |
| | MI or Coronary Artery Disease | 1628 | 79 (59) | 76 (58) | 14 (13) | 15 (10) | 65 (48) | 63 (51) |
| | Peripheral Vascular Disease | 1113 | 64 (45) | 46 (35) | 11 (10) | 15 (11) | 53 (37) | 32 (27) |
| | Renal Disease | 985 | 51 (43) | 37 (34) | 8 (7) | 14 (13) | 43 (39) | 24 (23) |
| | Heart Failure | 706 | 50 (37) | 41 (29) | 9 (8) | 11 (7) | 41 (31) | 32 (25) |
| | Alcohol | 238 | 40 (26) | 10 (10) | 3 (3) | 3 (3) | 37 (23) | 7 (7) |
| | Rheumatic | 856 | 38 (34) | 42 (36) | 7 (7) | 7 (7) | 32 (28) | 35 (31) |
| | Blood Loss | 275 | 18 (16) | 11 (10) | 5 (5) | 1 (1) | 14 (13) | 10 (10) |
| | Coagulopathy | 341 | 16 (15) | 16 (16) | 3 (2) | 1 (1) | 13 (13) | 15 (15) |
| | Lymphoma | 92 | 4 (3) | 7 (2) | 0 (0) | 1 (1) | 4 (3) | 6 (2) |
| | Fluids Lytes | 1885 | 186 (142) | 100 (82) | 17 (16) | 20 (17) | 170 (130) | 84 (70) |
| | Mets | 133 | 7 (5) | 7 (6) | 0 (0) | 3 (2) | 7 (5) | 4 (4) |
| | Neuro Other | 971 | 105 (75) | 67 (46) | 13 (13) | 19 (14) | 93 (65) | 49 (36) |
| | Paralysis | 167 | 13 (11) | 10 (6) | 1 (1) | 2 (2) | 12 (11) | 9 (6) |
| | Psychoses | 552 | 48 (38) | 33 (22) | 10 (9) | 9 (8) | 39 (32) | 25 (19) |
| | PulmCircD | 213 | 12 (10) | 5 (5) | 1 (1) | 1 (1) | 11 (9) | 4 (4) |
| | Tumor | 704 | 19 (15) | 23 (20) | 1 (1) | 5 (4) | 18 (14) | 19 (17) |
| | PepticUlcer | 202 | 32 (16) | 12 (11) | 1 (1) | 3 (2) | 31 (15) | 9 (9) |
| | Valvular | 1061 | 67 (57) | 40 (30) | 10 (9) | 9 (7) | 57 (48) | 31 (26) |
| | WeightLoss | 501 | 49 (36) | 39 (26) | 7 (6) | 12 (7) | 42 (31) | 29 (22) |
| Insulin Usage | Insulin (short- or rapid-acting) | 3984 | 219 (176) | 130 (105) | 16 (15) | 24 (20) | 205 (164) | 108 (89) |
| Status | Non-insulin therapy | 6298 | 172 (148) | 122 (106) | 19 (18) | 20 (19) | 154 (134) | 104 (92) |
| Non-Insulin Diabetes Medications | Biguanide | 7321 | 233 (206) | 126 (114) | 16 (16) | 13 (13) | 219 (193) | 114 (102) |
| | Sulfonylurea | 3127 | 107 (90) | 70 (62) | 11 (11) | 9 (9) | 97 (81) | 62 (55) |
| | GLP1a | 3116 | 81 (67) | 51 (43) | 5 (5) | 12 (11) | 78 (64) | 39 (32) |
| | SGLT2i | 2691 | 78 (66) | 43 (39) | 5 (5) | 11 (11) | 74 (63) | 32 (29) |
| | DPP4i | 2121 | 73 (61) | 30 (26) | 10 (10) | 5 (4) | 63 (52) | 25 (22) |
| | TZD | 761 | 25 (20) | 17 (17) | 4 (3) | 3 (3) | 21 (18) | 14 (14) |
| | Meglitinides | 161 | 4 (4) | 0 (0) | 1 (1) | 0 (0) | 4 (4) | 0 (0) |
| | Alpha-Glucosidase Inhibitor | 41 | 3 (3) | 1 (1) | 1 (1) | 1 (1) | 2 (2) | 0 (0) |

FIG. 24A

|  |  | Sample size, N | Total ACH | | | | 
|---|---|---|---|---|---|---|
|  |  |  | Before flash CGM # events (# affected) | After flash CGM # events (# affected) | Before flash CGM Hospitalizations (Events/100 pt-yr) | After flash CGM Hospitalizations (Events/100 pt-yr) (% reduction) |
| Age | Full Cohort | 10282 | 905 (688) | 726 (558) | 905 (17.7) | 726 (15.1) (15%) |
|  | Age 18 – 49 | 3321 | 227 (171) | 204 (154) | 227 (13.7) | 204 (13) (5%) |
|  | Age 50 – 64 | 6425 | 593 (463) | 456 (352) | 593 (18.5) | 456 (15.1) (18%) |
|  | Age 65+ | 536 | 85 (54) | 66 (52) | 85 (31.8) | 66 (28.6) (10%) |
| Gender | Male | 5341 | 508 (370) | 386 (288) | 508 (19.1) | 386 (15.4) (19%) |
|  | Female | 4941 | 397 (318) | 340 (270) | 397 (16.1) | 340 (14.7) (9%) |
| Comorbidities | Hypertension | 8286 | 843 (634) | 643 (495) | 843 (20.4) | 643 (16.6) (19%) |
|  | Obesity | 5713 | 570 (428) | 437 (343) | 570 (20) | 437 (16.3) (18%) |
|  | Pulmonary Disease | 2530 | 322 (238) | 247 (191) | 322 (25.6) | 247 (20.9) (18%) |
|  | Depression | 2488 | 362 (253) | 258 (190) | 362 (29.2) | 258 (22.2) (24%) |
|  | Hypothyroid Disease | 2210 | 251 (186) | 181 (134) | 251 (22.8) | 181 (17.5) (23%) |
|  | Anemia | 1975 | 440 (290) | 300 (203) | 440 (44.7) | 300 (32.6) (27%) |
|  | Liver Disease | 1905 | 289 (205) | 212 (157) | 289 (30.4) | 212 (23.8) (22%) |
|  | MI or Coronary Artery Disease | 1628 | 386 (266) | 232 (172) | 386 (47.6) | 232 (30.8) (35%) |
|  | Peripheral Vascular Disease | 1113 | 258 (169) | 182 (130) | 258 (46.5) | 182 (35.7) (23%) |
|  | Renal Disease | 985 | 271 (179) | 209 (137) | 271 (55.2) | 209 (46.2) (16%) |
|  | Heart Failure | 706 | 299 (190) | 174 (115) | 299 (85) | 174 (53.7) (37%) |
|  | Alcohol | 238 | 82 (53) | 41 (30) | 82 (69.1) | 41 (37.2) (46%) |
|  | Rheumatic | 856 | 127 (98) | 102 (80) | 127 (29.8) | 102 (25.6) (14%) |
|  | Blood Loss | 275 | 59 (38) | 37 (24) | 59 (43.1) | 37 (29.2) (32%) |
|  | Coagulopathy | 341 | 115 (76) | 80 (53) | 115 (67.7) | 80 (50.4) (26%) |
|  | Lymphoma | 92 | 25 (17) | 13 (10) | 25 (54.5) | 13 (30.4) (44%) |
|  | Fluids Lytes | 1885 | 572 (387) | 310 (211) | 572 (60.9) | 310 (35.5) (42%) |
|  | Mets | 133 | 40 (27) | 44 (29) | 40 (60.4) | 44 (73.6) (-22%) |
|  | Neuro Other | 971 | 300 (191) | 177 (127) | 300 (62) | 177 (39.1) (37%) |
|  | Paralysis | 167 | 96 (54) | 32 (27) | 96 (115.4) | 32 (41.7) (64%) |
|  | Psychoses | 552 | 112 (67) | 59 (45) | 112 (40.7) | 59 (23) (43%) |
|  | PulmCircD | 213 | 75 (50) | 43 (34) | 75 (70.7) | 43 (43.2) (39%) |
|  | Tumor | 704 | 118 (85) | 100 (72) | 118 (33.6) | 100 (30.9) (8%) |
|  | PepticUlcer | 202 | 69 (47) | 38 (26) | 69 (68.6) | 38 (42.5) (38%) |
|  | Valvular | 1061 | 268 (182) | 160 (113) | 268 (50.7) | 160 (32.6) (36%) |
|  | WeightLoss | 501 | 146 (91) | 98 (61) | 146 (58.5) | 98 (42.7) (27%) |
| Insulin Usage | Insulin (short -or rapid-acting) | 3984 | 461 (346) | 351 (262) | 461 (23.2) | 351 (18.8) (19%) |
| Status | Non-insulin therapy | 6298 | 444 (342) | 375 (296) | 444 (14.1) | 375 (12.7) (10%) |
| Non-Insulin Diabetes Medications | Biguanide | 7321 | 506 (405) | 405 (326) | 506 (13.9) | 405 (11.8) (15%) |
|  | Sulfonylurea | 3127 | 256 (201) | 182 (145) | 256 (16.4) | 182 (12.4) (24%) |
|  | GLP1a | 3116 | 164 (137) | 168 (138) | 164 (10.6) | 168 (11.5) (-8%) |
|  | SGLT2i | 2691 | 164 (131) | 123 (95) | 164 (12.2) | 123 (9.6) (21%) |
|  | DPP4i | 2121 | 162 (124) | 132 (102) | 162 (15.3) | 132 (13.3) (13%) |
|  | TZD | 761 | 36 (35) | 60 (43) | 36 (9.5) | 60 (16.8) (-77%) |
|  | Meglitinides | 161 | 24 (19) | 7 (7) | 24 (29.9) | 7 (9.6) (68%) |
|  | Alpha-Glucosidase Inhibitor | 41 | 9 (5) | 3 (3) | 9 (44.1) | 3 (15.5) (65%) |

FIG. 24B

|  |  |  | Circulatory System | | | Endocrine, Nutritional and Metabolic System | |
|---|---|---|---|---|---|---|---|
|  |  | Sample size, N | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
|  | Full Cohort | 10282 | 175 (3.4) | 143 (3) (12%) | 118 (2.3) | 81 (1.7) (26%) |
| Age | Age 18 – 49 | 3321 | 44 (2.7) | 27 (1.7) (37%) | 29 (1.8) | 32 (2) (-11%) |
|  | Age 50 – 64 | 6425 | 117 (3.7) | 99 (3.3) (11%) | 81 (2.5) | 44 (1.5) (40%) |
|  | Age 65+ | 536 | 14 (5.2) | 17 (7.4) (-42%) | 8 (3) | 5 (2.2) (27%) |
| Gender | Male | 5341 | 97 (3.6) | 90 (3.6) (0%) | 75 (2.8) | 44 (1.8) (36%) |
|  | Female | 4941 | 78 (3.2) | 53 (2.3) (28%) | 43 (1.7) | 37 (1.6) (6%) |
| Comorbidities | Hypertension | 8286 | 165 (4) | 140 (3.6) (10%) | 110 (2.7) | 66 (1.7) (37%) |
|  | Obesity | 5713 | 123 (4.3) | 93 (3.5) (19%) | 71 (2.5) | 47 (1.8) (28%) |
|  | Pulmonary Disease | 2530 | 70 (5.6) | 58 (4.9) (12%) | 27 (2.2) | 20 (1.7) (23%) |
|  | Depression | 2488 | 69 (5.6) | 35 (3) (46%) | 46 (3.7) | 30 (2.6) (30%) |
|  | Hypothyroid Disease | 2210 | 54 (4.9) | 29 (2.8) (43%) | 24 (2.2) | 23 (2.2) (0%) |
|  | Anemia | 1975 | 86 (8.7) | 52 (5.7) (34%) | 57 (5.8) | 36 (3.9) (33%) |
|  | Liver Disease | 1905 | 41 (4.3) | 33 (3.7) (14%) | 32 (3.4) | 24 (2.7) (21%) |
|  | MI or Coronary Artery Disease | 1628 | 135 (16.6) | 82 (10.9) (34%) | 34 (4.2) | 15 (2) (52%) |
|  | Peripheral Vascular Disease | 1113 | 63 (11.4) | 52 (10.2) (11%) | 35 (6.3) | 21 (4.1) (35%) |
|  | Renal Disease | 985 | 63 (12.8) | 58 (12.8) (0%) | 31 (6.3) | 15 (3.3) (48%) |
|  | Heart Failure | 706 | 92 (26.2) | 58 (17.9) (32%) | 35 (9.9) | 16 (4.9) (51%) |
|  | Alcohol | 238 | 12 (10.1) | 3 (2.7) (73%) | 19 (16) | 8 (7.3) (54%) |
|  | Rheumatic | 856 | 28 (6.6) | 12 (3) (55%) | 15 (3.5) | 10 (2.5) (29%) |
|  | Blood Loss | 275 | 11 (8) | 4 (3.2) (60%) | 5 (3.6) | 1 (0.8) (78%) |
|  | Coagulopathy | 341 | 17 (10) | 17 (10.7) (-7%) | 7 (4.1) | 4 (2.5) (39%) |
|  | Lymphoma | 92 | 2 (4.4) | 3 (7) (-59%) | 2 (4.4) | 2 (4.7) (-7%) |
|  | Fluids Lytes | 1885 | 98 (10.4) | 73 (8.4) (19%) | 87 (9.3) | 33 (3.8) (59%) |
|  | Mets | 133 | 4 (6) | 8 (13.4) (-123%) | 1 (1.5) | 3 (5) (-233%) |
|  | Neuro Other | 971 | 48 (9.9) | 26 (5.8) (41%) | 44 (9.1) | 22 (4.9) (46%) |
|  | Paralysis | 167 | 12 (14.4) | 6 (7.8) (46%) | 6 (7.2) | 6 (7.8) (-8%) |
|  | Psychoses | 552 | 23 (8.4) | 9 (3.5) (58%) | 14 (5.1) | 8 (3.1) (39%) |
|  | PulmCircD | 213 | 30 (28.3) | 13 (13.1) (54%) | 6 (5.7) | 3 (3) (47%) |
|  | Tumor | 704 | 15 (4.3) | 19 (5.9) (-37%) | 5 (1.4) | 7 (2.2) (-57%) |
|  | PepticUlcer | 202 | 10 (9.9) | 5 (5.6) (43%) | 9 (8.9) | 1 (1.1) (88%) |
|  | Valvular | 1061 | 68 (12.9) | 44 (9) (30%) | 29 (5.5) | 12 (2.4) (56%) |
|  | WeightLoss | 501 | 17 (6.8) | 12 (5.2) (24%) | 23 (9.2) | 16 (7) (24%) |
| Insulin Usage Status | Insulin (short -or rapid-acting) | 3984 | 87 (4.4) | 71 (3.8) (14%) | 75 (3.8) | 35 (1.9) (50%) |
| Non-Insulin Diabetes Medications | Non-insulin therapy | 6398 | 88 (2.8) | 72 (2.4) (14%) | 43 (1.4) | 46 (1.6) (-14%) |
|  | Biguanide | 7321 | 98 (2.7) | 73 (2.1) (22%) | 64 (1.8) | 46 (1.3) (28%) |
|  | Sulfonylurea | 3127 | 56 (3.6) | 31 (2.1) (42%) | 23 (1.5) | 23 (1.6) (-7%) |
|  | GLP1a | 3116 | 35 (2.3) | 26 (1.8) (22%) | 17 (1.1) | 23 (1.6) (-45%) |
|  | SGLT2i | 2691 | 33 (2.5) | 22 (1.7) (32%) | 24 (1.8) | 15 (1.2) (33%) |
|  | DPP4i | 2121 | 30 (2.8) | 28 (2.8) (0%) | 20 (1.9) | 12 (1.2) (37%) |
|  | TZD | 761 | 12 (3.2) | 11 (3.1) (3%) | 6 (1.6) | 6 (1.7) (-6%) |
|  | Meglitinides | 161 | 8 (10) | 3 (4.1) (59%) | 0 (0) | 0 (0) (NaN%) |
|  | Alpha-Glucosidase Inhibitor | 41 | 1 (4.9) | 0 (0) (100%) | 4 (19.6) | 1 (5.2) (73%) |

FIG. 24C

|  |  | Sample size, N | Infectious and Parasitic DDs (Systemic or unspecified sites) | | Respiratory System | |
|---|---|---|---|---|---|---|
|  |  |  | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
|  | Full Cohort | 10282 | 94 (1.8) | 60 (1.2) (33%) | 59 (1.2) | 38 (0.8) (33%) |
| Age | Age 18 – 49 | 3321 | 21 (1.3) | 18 (1.1) (15%) | 16 (1) | 13 (0.8) (20%) |
|  | Age 50 – 64 | 6425 | 62 (1.9) | 37 (1.2) (37%) | 37 (1.2) | 21 (0.7) (42%) |
|  | Age 65+ | 536 | 11 (4.1) | 5 (2.2) (46%) | 6 (2.2) | 4 (1.7) (23%) |
| Gender | Male | 5341 | 51 (1.9) | 32 (1.3) (32%) | 31 (1.2) | 22 (0.9) (25%) |
|  | Female | 4941 | 43 (1.7) | 28 (1.2) (29%) | 28 (1.1) | 16 (0.7) (36%) |
| Comorbidities | Hypertension | 8286 | 88 (2.1) | 50 (1.3) (38%) | 55 (1.3) | 35 (0.9) (31%) |
|  | Obesity | 5713 | 57 (2) | 36 (1.3) (35%) | 40 (1.4) | 22 (0.8) (43%) |
|  | Pulmonary Disease | 2520 | 34 (2.7) | 21 (1.8) (33%) | 40 (3.2) | 18 (1.5) (53%) |
|  | Depression | 2488 | 38 (3.1) | 18 (1.5) (52%) | 28 (2.3) | 15 (1.3) (43%) |
|  | Hypothyroid Disease | 2210 | 20 (1.8) | 16 (1.5) (17%) | 15 (1.4) | 9 (0.9) (36%) |
|  | Anemia | 1975 | 51 (5.2) | 25 (2.7) (48%) | 36 (3.7) | 14 (1.5) (59%) |
|  | Liver Disease | 1905 | 37 (3.9) | 16 (1.8) (54%) | 18 (1.9) | 10 (1.1) (42%) |
|  | MI or Coronary Artery Disease | 1628 | 32 (3.9) | 11 (1.5) (62%) | 38 (4.7) | 14 (1.9) (60%) |
|  | Peripheral Vascular Disease | 1113 | 24 (4.3) | 13 (2.6) (40%) | 22 (4) | 12 (2.4) (40%) |
|  | Renal Disease | 985 | 36 (7.3) | 15 (3.3) (55%) | 22 (4.5) | 13 (2.9) (36%) |
|  | Heart Failure | 706 | 34 (9.7) | 17 (5.3) (45%) | 27 (7.7) | 13 (4) (48%) |
|  | Alcohol | 238 | 6 (5.1) | 2 (1.8) (65%) | 5 (4.2) | 0 (0) (100%) |
|  | Rheumatic | 856 | 14 (3.3) | 5 (1.3) (61%) | 9 (2.1) | 6 (1.5) (29%) |
|  | Blood Loss | 275 | 8 (5.8) | 4 (3.2) (45%) | 10 (7.3) | 4 (3.2) (56%) |
|  | Coagulopathy | 341 | 17 (10) | 9 (5.7) (43%) | 6 (3.5) | 6 (3.8) (-9%) |
|  | Lymphoma | 92 | 0 (0) | 0 (0) (NaN%) | 4 (8.7) | 1 (2.3) (74%) |
|  | Fluids Lytes | 1885 | 70 (7.5) | 21 (2.4) (68%) | 45 (4.8) | 16 (1.8) (62%) |
|  | Mets | 133 | 5 (7.5) | 4 (6.7) (11%) | 4 (6) | 4 (6.7) (-12%) |
|  | Neuro Other | 971 | 31 (6.4) | 7 (1.5) (77%) | 19 (3.9) | 4 (0.9) (77%) |
|  | Paralysis | 167 | 3 (3.6) | 3 (3.9) (-8%) | 2 (2.4) | 1 (1.3) (46%) |
|  | Psychoses | 552 | 11 (4) | 3 (1.2) (70%) | 9 (3.3) | 4 (1.6) (52%) |
|  | PulmCircD | 213 | 5 (4.7) | 3 (3) (36%) | 14 (13.2) | 5 (5) (62%) |
|  | Tumor | 704 | 13 (3.7) | 10 (3.1) (16%) | 9 (2.6) | 5 (1.5) (42%) |
|  | PepticUlcer | 202 | 8 (7.9) | 3 (3.4) (57%) | 0 (0) | 2 (2.2) (-Inf%) |
|  | Valvular | 1061 | 25 (4.7) | 11 (2.2) (53%) | 25 (4.7) | 15 (3.1) (34%) |
|  | WeightLoss | 501 | 23 (9.2) | 7 (3) (67%) | 14 (5.6) | 3 (1.3) (77%) |
| Insulin Usage Status | Insulin (short -or rapid-acting) | 3984 | 46 (2.3) | 24 (1.3) (43%) | 28 (1.4) | 21 (1.1) (21%) |
| Non-Insulin Diabetes Medications | Non-insulin therapy | 6298 | 48 (1.5) | 36 (1.2) (20%) | 31 (1) | 17 (0.6) (40%) |
|  | Biguande | 7321 | 55 (1.5) | 34 (1) (33%) | 27 (0.7) | 16 (0.5) (29%) |
|  | Sulfonylurea | 3127 | 28 (1.8) | 23 (1.6) (11%) | 17 (1.1) | 8 (0.5) (55%) |
|  | GLP1a | 3116 | 14 (0.9) | 10 (0.7) (22%) | 7 (0.5) | 10 (0.7) (-40%) |
|  | SGLT2i | 2691 | 19 (1.4) | 11 (0.9) (36%) | 8 (0.6) | 3 (0.2) (67%) |
|  | DPP4i | 2121 | 14 (1.3) | 9 (0.9) (31%) | 7 (0.7) | 5 (0.5) (29%) |
|  | TZD | 761 | 2 (0.5) | 9 (2.5) (-400%) | 2 (0.5) | 3 (0.8) (-60%) |
|  | Meglitinides | (6) | 2 (2.5) | 0 (0) (100%) | 2 (2.5) | 0 (0) (100%) |
|  | Alpha-Glucosidase Inhibitor | 41 | 1 (4.9) | 0 (0) (100%) | 0 (0) | 1 (5.2) (-Inf%) |

FIG. 24D

| | | Sample size, N | Kidney and Urinary Tract | | Musculoskeletal System and Connective Tissue | | Digestive System | |
|---|---|---|---|---|---|---|---|---|
| | | | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
| | Full Cohort | 10282 | 68 (1.3) | 44 (0.9) (31%) | 75 (1.5) | 81 (1.7) (-13%) | 67 (1.3) | 71 (1.5) (-15%) |
| Age | Age 18 – 49 | 3321 | 18 (1.1) | 11 (0.7) (36%) | 10 (0.6) | 15 (1) (-67%) | 23 (1.4) | 25 (1.6) (-14%) |
| | Age 50 – 64 | 6425 | 41 (1.3) | 27 (0.9) (31%) | 58 (1.8) | 61 (2) (-11%) | 42 (1.3) | 41 (1.4) (-8%) |
| | Age 65+ | 536 | 8 (3) | 6 (2.6) (13%) | 7 (2.6) | 5 (2.2) (15%) | 2 (0.7) | 5 (2.2) (-214%) |
| Gender | Male | 5341 | 34 (1.3) | 18 (0.7) (46%) | 35 (1.3) | 43 (1.7) (-31%) | 42 (1.6) | 37 (1.5) (6%) |
| | Female | 4941 | 33 (1.3) | 26 (1.1) (15%) | 40 (1.6) | 38 (1.6) (0%) | 25 (1) | 34 (1.5) (-50%) |
| Comorbidities | Hypertension | 8286 | 61 (1.5) | 38 (1) (33%) | 72 (1.7) | 77 (2) (-18%) | 60 (1.5) | 66 (1.7) (-13%) |
| | Obesity | 5713 | 42 (1.5) | 25 (0.9) (40%) | 51 (1.8) | 53 (2) (-11%) | 46 (1.6) | 39 (1.5) (6%) |
| | Pulmonary Disease | 2520 | 26 (2.1) | 18 (1.5) (29%) | 32 (2.5) | 18 (1.5) (40%) | 27 (2.2) | 24 (2) (9%) |
| | Depression | 2488 | 16 (1.3) | 12 (1) (23%) | 33 (2.7) | 42 (3.6) (-33%) | 22 (1.8) | 28 (2.4) (-33%) |
| | Hypothyroid Disease | 2210 | 16 (1.5) | 14 (1.4) (7%) | 27 (2.5) | 20 (1.9) (24%) | 22 (2) | 12 (1.2) (40%) |
| | Anemia | 1975 | 40 (4.1) | 18 (2) (51%) | 24 (2.4) | 29 (3.2) (-33%) | 31 (3.3) | 35 (3.8) (-19%) |
| | Liver Disease | 1905 | 16 (1.7) | 14 (1.6) (6%) | 22 (2.3) | 22 (2.5) (-9%) | 31 (3.3) | 28 (3.1) (6%) |
| | MI or Coronary Artery Disease | 1628 | 24 (3) | 12 (1.6) (47%) | 20 (2.5) | 16 (2.1) (16%) | 25 (3.1) | 22 (2.9) (6%) |
| | Peripheral Vascular Disease | 1113 | 11 (2) | 15 (2.9) (-45%) | 23 (4.1) | 16 (3.1) (24%) | 16 (2.9) | 11 (2.2) (24%) |
| | Renal Disease | 985 | 36 (7.3) | 20 (4.4) (40%) | 13 (2.6) | 14 (3.1) (-19%) | 14 (2.9) | 24 (5.3) (-83%) |
| | Heart Failure | 706 | 16 (4.5) | 14 (4.3) (4%) | 16 (4.5) | 10 (3.1) (31%) | 12 (3.4) | 13 (4) (-18%) |
| | Alcohol | 238 | 5 (4.2) | 1 (0.9) (79%) | 3 (2.5) | 3 (2.7) (-8%) | 5 (4.2) | 7 (6.4) (-52%) |
| | Rheumatic | 856 | 9 (2.1) | 9 (2.1) (-10%) | 13 (3) | 19 (4.8) (-60%) | 10 (2.3) | 6 (1.5) (35%) |
| | Blood Loss | 275 | 4 (2.9) | 2 (1.6) (45%) | 1 (0.7) | 2 (1.6) (-129%) | 6 (4.4) | 7 (5.5) (-25%) |
| | Coagulopathy | 341 | 11 (6.5) | 9 (5.7) (12%) | 8 (4.7) | 3 (1.9) (60%) | 5 (2.9) | 4 (2.5) (14%) |
| | Lymphoma | 92 | 3 (6.5) | 1 (2.3) (65%) | 5 (10.9) | 1 (2.3) (79%) | 1 (2.2) | 2 (2.3) (-5%) |
| | Fluids Lytes | 1885 | 49 (5.2) | 21 (2.4) (54%) | 31 (3.3) | 20 (2.5) (36%) | 39 (4.2) | 38 (4.4) (-5%) |
| | Mets | 133 | 0 (0) | 2 (3.3) (-Inf%) | 1 (1.5) | 1 (1.7) (-13%) | 4 (6) | 5 (8.4) (-40%) |
| | Neuro Other | 971 | 16 (3.3) | 13 (2.9) (12%) | 27 (5.6) | 14 (3.1) (45%) | 11 (2.3) | 20 (4.4) (-91%) |
| | Paralysis | 167 | 5 (6) | 3 (3.9) (35%) | 5 (6) | 1 (1.3) (78%) | 2 (2.4) | 1 (1.3) (46%) |
| | Psychoses | 552 | 6 (2.2) | 3 (1.2) (45%) | 7 (2.5) | 2 (0.8) (68%) | 8 (2.9) | 8 (3.1) (-7%) |
| | PulmCircD | 213 | 2 (1.9) | 5 (5) (-163%) | 2 (1.9) | 3 (3) (-58%) | 4 (3.8) | 4 (4) (-5%) |
| | Tumor | 704 | 11 (3.1) | 9 (2.8) (10%) | 15 (4.3) | 4 (1.2) (72%) | 15 (4.3) | 10 (3.1) (28%) |
| | PepticUlcer | 202 | 4 (4) | 1 (1.1) (72%) | 3 (3) | 4 (4.5) (-50%) | 16 (15.9) | 14 (15.7) (1%) |
| | Valvular | 1061 | 15 (2.8) | 9 (1.8) (36%) | 17 (3.2) | 9 (1.8) (44%) | 16 (1.2) | 13 (2.6) (-13%) |
| | WeightLoss | 501 | 8 (3.2) | 8 (0.8) (47%) | 18 (1.3) | 13 (1.3) (7%) | 9 (0.9) | 21 (2.1) (-133%) |
| Insulin Usage Status | Insulin (short- or rapid-acting) | 3984 | 35 (1.8) | 25 (1.3) (28%) | 35 (1.8) | 39 (2.1) (-17%) | 30 (1.5) | 44 (2.4) (-60%) |
| Non-Insulin Diabetes Medications | Non-insulin therapy | 6298 | 32 (1) | 19 (0.6) (40%) | 40 (1.3) | 42 (1.4) (-8%) | 37 (1.2) | 27 (0.9) (25%) |
| | Biguanide | 7321 | 28 (0.8) | 19 (0.6) (25%) | 49 (1.3) | 51 (1.5) (-15%) | 44 (1.2) | 34 (1) (17%) |
| | Sulfonylurea | 3127 | 13 (0.8) | 12 (0.8) (0%) | 18 (1.2) | 24 (1.6) (-33%) | 18 (1.2) | 17 (1.2) (0%) |
| | GLP1a | 3116 | 12 (0.8) | 8 (0.5) (38%) | 17 (1.1) | 24 (1.6) (-45%) | 19 (1.2) | 23 (1.6) (-33%) |
| | SGLT2i | 2691 | 9 (0.7) | 6 (0.5) (29%) | 18 (1.3) | 18 (1.3) (-8%) | 16 (1.2) | 15 (1.2) (0%) |
| | DPP4i | 2121 | 16 (1.5) | 8 (0.8) (47%) | 15 (1.4) | 13 (1.3) (7%) | 9 (0.9) | 21 (2.1) (-133%) |
| | TZD | 761 | 2 (0.5) | 2 (0.6) (-20%) | 3 (0.8) | 13 (3.6) (-350%) | 1 (0.3) | 6 (1.7) (-467%) |
| | Meglitinides | 161 | 1 (1.2) | 0 (0) (100%) | 2 (2.5) | 1 (1.4) (44%) | 3 (3.7) | 0 (0) (100%) |
| | Alpha-Glucosidase Inhibitor | 41 | 2 (9.8) | 0 (0) (100%) | 0 (0) | 0 (0) (NaN%) | 1 (4.9) | 0 (0) (100%) |

FIG. 24E

|  |  | Sample size, N | Nervous System | | | Hepatobiliary System and Pancreas | | | Skin, Subcutaneous Tissue and Breast | | |
|---|---|---|---|---|---|---|---|---|---|---|---|
|  |  |  | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | |
|  | Full Cohort | 10282 | 99 (1.9) | 67 (1.4) (26%) | | 48 (0.9) | 32 (0.7) (22%) | | 21 (0.4) | 27 (0.6) (-50%) | |
| Age | Age 18 – 49 | 3321 | 11 (0.7) | 13 (0.8) (-14%) | | 17 (1) | 7 (0.4) (60%) | | 9 (0.5) | 6 (0.4) (20%) | |
|  | Age 50 – 64 | 6425 | 69 (2.2) | 44 (1.5) (32%) | | 29 (0.9) | 23 (0.8) (11%) | | 10 (0.3) | 17 (0.6) (-100%) | |
|  | Age 65+ | 536 | 19 (7.1) | 10 (4.3) (39%) | | 2 (0.7) | 2 (0.9) (-29%) | | 2 (0.7) | 4 (1.7) (-143%) | |
| Gender | Male | 5341 | 50 (1.9) | 40 (1.6) (16%) | | 32 (1.2) | 14 (0.6) (50%) | | 15 (0.6) | 14 (0.6) (0%) | |
|  | Female | 4941 | 49 (2) | 27 (1.2) (40%) | | 16 (0.6) | 18 (0.8) (-33%) | | 6 (0.2) | 13 (0.6) (-200%) | |
| Comorbidities | Hypertension | 8286 | 97 (2.3) | 65 (1.7) (26%) | | 44 (1.1) | 25 (0.6) (45%) | | 17 (0.4) | 26 (0.7) (-75%) | |
|  | Obesity | 5713 | 52 (1.8) | 31 (1.2) (33%) | | 25 (0.9) | 17 (0.6) (33%) | | 13 (0.5) | 18 (0.7) (-40%) | |
|  | Pulmonary Disease | 2520 | 22 (1.8) | 21 (1.8) (0%) | | 12 (1) | 8 (0.7) (30%) | | 3 (0.2) | 10 (0.8) (-300%) | |
|  | Depression | 2488 | 42 (3.4) | 21 (1.8) (47%) | | 13 (1) | 13 (1.1) (-10%) | | 6 (0.5) | 9 (0.8) (-60%) | |
|  | Hypothyroid Disease | 2210 | 31 (2.8) | 17 (1.6) (43%) | | 10 (0.9) | 5 (0.5) (44%) | | 7 (0.6) | 8 (0.8) (-33%) | |
|  | Anemia | 1975 | 36 (3.7) | 35 (3.8) (-3%) | | 27 (2.7) | 14 (1.5) (44%) | | 14 (1.4) | 14 (1.5) (-7%) | |
|  | Liver Disease | 1905 | 22 (2.3) | 17 (1.9) (17%) | | 35 (3.7) | 19 (2.1) (43%) | | 4 (0.4) | 10 (1.1) (-175%) | |
|  | MI or Coronary Artery Disease | 1628 | 45 (5.5) | 30 (4) (27%) | | 9 (1.1) | 6 (0.8) (27%) | | 4 (0.5) | 5 (0.7) (-40%) | |
|  | Peripheral Vascular Disease | 1113 | 26 (4.7) | 20 (3.9) (17%) | | 11 (2) | 3 (0.6) (70%) | | 8 (1.4) | 10 (2) (-43%) | |
|  | Renal Disease | 985 | 22 (4.5) | 21 (4.6) (-2%) | | 9 (1.8) | 10 (2.2) (-22%) | | 6 (1.2) | 5 (1.1) (8%) | |
|  | Heart Failure | 706 | 38 (10.8) | 11 (3.4) (69%) | | 9 (2.6) | 8 (2.5) (4%) | | 5 (1.4) | 2 (0.6) (57%) | |
|  | Alcohol | 238 | 6 (5.1) | 1 (0.9) (82%) | | 7 (5.9) | 4 (3.6) (39%) | | 0 (0) | 0 (0) (NaN%) | |
|  | Rheumatic | 856 | 11 (2.6) | 8 (2) (23%) | | 2 (0.5) | 9 (2.3) (-360%) | | 1 (0.2) | 5 (1.3) (-550%) | |
|  | Blood Loss | 275 | 1 (0.7) | 4 (3.2) (-357%) | | 5 (3.6) | 3 (2.4) (33%) | | 2 (1.5) | 3 (2.4) (-60%) | |
|  | Coagulopathy | 341 | 13 (7.7) | 3 (1.9) (75%) | | 11 (6.5) | 8 (5) (23%) | | 5 (2.9) | 3 (1.9) (34%) | |
|  | Lymphoma | 92 | 4 (8.7) | 1 (2.3) (74%) | | 0 (0) | 0 (0) (NaN%) | | 0 (0) | 0 (0) (NaN%) | |
|  | Fluids Lytes | 1885 | 59 (6.3) | 34 (3.9) (38%) | | 31 (3.3) | 14 (1.6) (52%) | | 17 (1.8) | 9 (1) (44%) | |
|  | Mets | 133 | 4 (6) | 2 (3.3) (45%) | | 4 (6) | 3 (5) (7%) | | 1 (1.5) | 5 (8.4) (-460%) | |
|  | Neuro Other | 971 | 63 (13) | 28 (6.2) (52%) | | 8 (1.7) | 9 (2) (-18%) | | 4 (0.8) | 5 (1.1) (-38%) | |
|  | Paralysis | 167 | 49 (58.9) | 5 (6.5) (89%) | | 2 (2.4) | 0 (0) (100%) | | 3 (3.6) | 2 (2.6) (28%) | |
|  | Psychoses | 552 | 12 (4.4) | 4 (1.6) (64%) | | 2 (0.7) | 3 (1.2) (-71%) | | 2 (0.7) | 3 (1.2) (-71%) | |
|  | PulmCircD | 213 | 8 (7.5) | 3 (3) (60%) | | 1 (0.9) | 1 (1) (-11%) | | 0 (0) | 1 (1) (-Inf%) | |
|  | Tumor | 704 | 12 (3.4) | 8 (2.5) (26%) | | 7 (2) | 9 (2.8) (-40%) | | 3 (0.9) | 8 (2.5) (-178%) | |
|  | PepticUlcer | 202 | 5 (5) | 4 (4.5) (10%) | | 10 (9.9) | 0 (0) (100%) | | 0 (0) | 0 (0) (NaN%) | |
|  | Valvular | 1061 | 47 (8.9) | 14 (2.9) (67%) | | 9 (1.7) | 7 (1.4) (18%) | | 4 (0.8) | 5 (1) (-25%) | |
|  | WeightLoss | 501 | 13 (5.2) | 9 (3.9) (25%) | | 9 (3.6) | 8 (3.5) (3%) | | 5 (2) | 3 (1.3) (35%) | |
| Insulin Usage Status | Insulin (short -or rapid-acting) | 3984 | 55 (2.8) | 36 (1.9) (32%) | | 28 (1.4) | 15 (0.8) (43%) | | 6 (0.3) | 13 (0.7) (-133%) | |
| Non-Insulin Diabetes Medications | Non-insulin therapy | 6298 | 44 (1.4) | 31 (1.1) (21%) | | 20 (0.6) | 17 (0.6) (0%) | | 15 (0.5) | 14 (0.5) (0%) | |
|  | Biguanide | 7321 | 52 (1.4) | 37 (1.1) (21%) | | 28 (0.8) | 20 (0.6) (25%) | | 15 (0.4) | 15 (0.4) (0%) | |
|  | Sulfonylurea | 3127 | 35 (2.2) | 11 (0.8) (64%) | | 17 (1.1) | 8 (0.5) (55%) | | 8 (0.5) | 5 (0.3) (40%) | |
|  | GLP1a | 3116 | 15 (1) | 12 (0.8) (20%) | | 5 (0.3) | 5 (0.3) (0%) | | 5 (0.3) | 5 (0.3) (0%) | |
|  | SGLT2i | 2691 | 13 (1) | 8 (0.6) (40%) | | 7 (0.5) | 6 (0.5) (0%) | | 5 (0.4) | 6 (0.5) (-25%) | |
|  | DPP4i | 2121 | 20 (1.9) | 11 (1.1) (42%) | | 8 (0.8) | 10 (1) (-25%) | | 3 (0.3) | 4 (0.4) (-33%) | |
|  | TZD | 761 | 4 (1.1) | 1 (0.3) (73%) | | 2 (0.5) | 3 (0.8) (-60%) | | 0 (0) | 3 (0.8) (-Inf%) | |
|  | Meglitinides | 161 | 2 (2.5) | 1 (1.4) (44%) | | 1 (1.2) | 0 (0) (100%) | | 1 (1.2) | 1 (1.4) (-17%) | |
|  | Alpha-Glucosidase Inhibitor | 41 | 0 (0) | 1 (5.2) (-Inf%) | | 0 (0) | 0 (0) (NaN%) | | 0 (0) | 0 (0) (NaN%) | |

FIG. 24F

|  |  | Sample size, N | Diseases & Disorders of the Eye | | | Diseases & Disorders of the Ear, Nose, Mouth & Throat | |
|---|---|---|---|---|---|---|---|
|  |  |  | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) |
|  | Full Cohort | 10282 | 3 (0.1) | 0 (0) (100%) | | 4 (0.1) | 6 (0.1) (0%) |
| Age | Age 18 – 49 | 3321 | 1 (0.1) | 0 (0) (100%) | | 1 (0.1) | 3 (0.2) (-100%) |
|  | Age 50 – 64 | 6425 | 2 (0.1) | 0 (0) (100%) | | 3 (0.1) | 3 (0.1) (0%) |
|  | Age 65+ | 536 | 0 (0) | 0 (0) (NaN%) | | 0 (0) | 0 (0) (NaN%) |
| Gender | Male | 5341 | 0 (0) | 0 (0) (100%) | | 2 (0.1) | 3 (0.1) (0%) |
|  | Female | 4941 | 3 (0.1) | 0 (0) (100%) | | 2 (0.1) | 3 (0.1) (0%) |
| Comorbidities | Hypertension | 8286 | 3 (0.1) | 0 (0) (100%) | | 4 (0.1) | 5 (0.1) (0%) |
|  | Obesity | 5713 | 2 (0.1) | 0 (0) (100%) | | 2 (0.1) | 3 (0.1) (0%) |
|  | Pulmonary Disease | 2520 | 1 (0.1) | 0 (0) (100%) | | 2 (0.2) | 2 (0.2) (0%) |
|  | Depression | 2488 | 2 (0.2) | 0 (0) (100%) | | 0 (0) | 1 (0.1) (-Inf%) |
|  | Hypothyroid Disease | 2210 | 0 (0) | 0 (0) (NaN%) | | 0 (0) | 3 (0.3) (-Inf%) |
|  | Anemia | 1975 | 1 (0.1) | 0 (0) (100%) | | 0 (0) | 3 (0.3) (-Inf%) |
|  | Liver Disease | 1905 | 0 (0) | 0 (0) (NaN%) | | 1 (0.1) | 2 (0.2) (-100%) |
|  | MI or Coronary Artery Disease | 1628 | 0 (0) | 0 (0) (NaN%) | | 1 (0.1) | 2 (0.3) (-200%) |
|  | Peripheral Vascular Disease | 1113 | 0 (0) | 0 (0) (NaN%) | | 0 (0) | 1 (0.2) (-Inf%) |
|  | Renal Disease | 985 | 0 (0) | 0 (0) (NaN%) | | 0 (0) | 1 (0.2) (-Inf%) |
|  | Heart Failure | 706 | 0 (0) | 0 (0) (NaN%) | | 0 (0) | 0 (0) (NaN%) |
|  | Alcohol | 238 | 0 (0) | 0 (0) (NaN%) | | 0 (0) | 1 (0.9) (-Inf%) |
|  | Rheumatic | 856 | 1 (0.2) | 0 (0) (100%) | | 0 (0.2) | 0 (0) (100%) |
|  | Blood Loss | 275 | 0 (0) | 0 (0) (NaN%) | | 0 (0) | 0 (0) (NaN%) |
|  | Coagulopathy | 341 | 0 (0) | 0 (0) (NaN%) | | 0 (0) | 1 (0.6) (-Inf%) |
|  | Lymphoma | 92 | 0 (0) | 0 (0) (NaN%) | | 0 (0) | 2 (0.6) (-Inf%) |
|  | Fluids Lytes | 1885 | 1 (0.1) | 0 (0) (100%) | | 0 (0) | 0 (0) (NaN%) |
|  | Mets | 133 | 0 (0) | 0 (0) (NaN%) | | 0 (0) | 3 (0.3) (-Inf%) |
|  | Neuro Other | 971 | 0 (0) | 0 (0) (NaN%) | | 1 (0.2) | 1 (0.2) (-Inf%) |
|  | Paralysis | 167 | 0 (0) | 0 (0) (NaN%) | | 0 (0) | 3 (0.7) (-250%) |
|  | Psychoses | 552 | 0 (0) | 0 (0) (NaN%) | | 0 (0) | 1 (1.3) (-Inf%) |
|  | PulmCircD | 213 | 0 (0) | 0 (0) (NaN%) | | 2 (0.7) | 0 (0) (100%) |
|  | Tumor | 341 | 0 (0) | 0 (0) (NaN%) | | 0 (0) | 0 (0) (NaN%) |
|  | PepticUlcer | 202 | 1 (1) | 0 (0) (100%) | | 0 (0) | 0 (0) (NaN%) |
|  | Valvular | 1061 | 0 (0) | 0 (0) (NaN%) | | 0 (0) | 3 (0.3) (-Inf%) |
|  | WeightLoss | 501 | 0 (0) | 0 (0) (NaN%) | | 0 (0) | 1 (0.2) (-Inf%) |
| Insulin Usage Status | Insulin (short- or rapid-acting) | 3984 | 1 (0.1) | 0 (0) (100%) | | 2 (0.1) | 2 (0.1) (0%) |
| Non-Insulin Diabetes Medications | Non-insulin therapy | 6298 | 2 (0.1) | 0 (0) (100%) | | 2 (0.1) | 4 (0.1) (0%) |
|  | Biguanide | 7321 | 3 (0.1) | 0 (0) (100%) | | 3 (0.1) | 3 (0.1) (0%) |
|  | Sulfonylurea | 3127 | 1 (0.1) | 0 (0) (100%) | | 1 (0.1) | 2 (0.1) (0%) |
|  | GLP1a | 3116 | 1 (0.1) | 0 (0) (100%) | | 3 (0.2) | 3 (0.2) (0%) |
|  | SGLT2i | 2691 | 1 (0.1) | 0 (0) (100%) | | 0 (0) | 3 (0.2) (-Inf%) |
|  | DPP4i | 2121 | 1 (0.1) | 0 (0) (100%) | | 0 (0) | 3 (0.3) (-Inf%) |
|  | TZD | 761 | 0 (0) | 0 (0) (NaN%) | | 0 (0) | 0 (0) (NaN%) |
|  | Meglitinides | 161 | 0 (0) | 0 (0) (NaN%) | | 0 (0) | 0 (0) (NaN%) |
|  | Alpha-Glucosidase Inhibitor | 41 | 0 (0) | 0 (0) (NaN%) | | 0 (0) | 0 (0) (NaN%) |

FIG. 24G

| | | Sample size, N | Diseases & Disorders of the Male Reproductive System | | Diseases & Disorders of the Female Reproductive System | |
|---|---|---|---|---|---|---|
| | | | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
| | Full Cohort | 10282 | 1 (0) | 2 (0) (NaN%) | 10 (0.2) | 8 (0.2) (0%) |
| Age | Age 18 – 49 | 3321 | 1 (0.1) | 0 (0) (100%) | 7 (0.4) | 4 (0.3) (25%) |
| | Age 50 – 64 | 6425 | 0 (0) | 1 (0) (NaN%) | 3 (0.1) | 4 (0.1) (0%) |
| | Age 65+ | 536 | 0 (0) | 1 (0.4) (-Inf%) | 0 (0) | 0 (0) (NaN%) |
| Gender | Male | 5341 | 1 (0) | 2 (0.1) (-Inf%) | 0 (0) | 0 (0) (NaN%) |
| | Female | 4941 | 0 (0) | 0 (0) (NaN%) | 10 (0.4) | 8 (0.3) (25%) |
| Comorbidities | Hypertension | 8286 | 1 (0) | 2 (0.1) (-Inf%) | 8 (0.2) | 3 (0.2) (0%) |
| | Obesity | 5713 | 1 (0) | 1 (0) (NaN%) | 10 (0.4) | 7 (0.3) (25%) |
| | Pulmonary Disease | 2520 | 0 (0) | 0 (0) (NaN%) | 4 (0.3) | 2 (0.2) (33%) |
| | Depression | 2488 | 1 (0.1) | 0 (0) (100%) | 4 (0.3) | 1 (0.1) (67%) |
| | Hypothyroid Disease | 2210 | 0 (0) | 1 (0.1) (-Inf%) | 4 (0.4) | 2 (0.2) (50%) |
| | Anemia | 1975 | 0 (0) | 1 (0.1) (-Inf%) | 7 (0.7) | 3 (0.3) (57%) |
| | Liver Disease | 1905 | 0 (0) | 0 (0) (NaN%) | 6 (0.6) | 2 (0.2) (67%) |
| | MI or Coronary Artery Disease | 1628 | 0 (0) | 1 (0.1) (-Inf%) | 0 (0) | 1 (0.1) (-Inf%) |
| | Peripheral Vascular Disease | 1113 | 1 (0.2) | 1 (0.2) (0%) | 2 (0.4) | 1 (0.2) (50%) |
| | Renal Disease | 985 | 0 (0) | 0 (0) (NaN%) | 1 (0.2) | 1 (0.2) (0%) |
| | Heart Failure | 706 | 0 (0) | 2 (0.4) (-Inf%) | 0 (0) | 1 (0.3) (-Inf%) |
| | Alcohol | 238 | 0 (0) | 1 (0.3) (-Inf%) | 0 (0) | 0 (0) (NaN%) |
| | Rheumatic | 856 | 0 (0) | 0 (0) (NaN%) | 4 (0.9) | 2 (0.5) (44%) |
| | Blood Loss | 275 | 0 (0) | 0 (0) (NaN%) | 1 (0.7) | 1 (0.8) (-14%) |
| | Coagulopathy | 341 | 0 (0) | 0 (0) (NaN%) | 2 (1.2) | 2 (1.3) (-8%) |
| | Lymphoma | 92 | 0 (0) | 1 (0.2) (-Inf%) | 0 (0) | 2 (4.7) (-Inf%) |
| | Fluids Lytes | 1885 | 0 (0) | 2 (0.2) (-Inf%) | 4 (0.4) | 3 (0.3) (25%) |
| | Mets | 133 | 0 (0) | 0 (01) (NaN%) | 2 (.3) | 1 (1.7) (43%) |
| | Neuro Other | 971 | 0 (0) | 2 (0.4) (-Inf%) | 2 (0.4) | 1 (0.2) (50%) |
| | Paralysis | 167 | 0 (0) | 0 (0) (NaN%) | 0 (0) | 0 (0) (NaN%) |
| | Psychoses | 552 | 0 (0) | 0 (0) (NaN%) | 1 (0.4) | 0 (0) (100%) |
| | PulmCircD | 213 | 0 (0) | 0 (0) (NaN%) | 0 (0) | 0 (0) (NaN%) |
| | Tumor | 704 | 0 (0) | 0 (0) (NaN%) | 2 (0.6) | 3 (0.9) (-50%) |
| | PepticUlcer | 202 | 0 (0) | 0 (0) (NaN%) | 0 (0) | 1 (1.1) (-Inf%) |
| | Valvular | 1061 | 0 (0) | 0 (0) (NaN%) | 0 (0) | 1 (0.2) (-Inf%) |
| | WeightLoss | 501 | 0 (0) | 0 (0) (NaN%) | 1 (0.4) | 0 (0) (100%) |
| Insulin Usage Status | Insulin (short -or rapid-acting) | 3984 | 1 (0.1) | 2 (0.1) (0%) | 5 (0.3) | 2 (0.1) (67%) |
| Non-Insulin Diabetes Medications | Non-insulin therapy | 6298 | 0 (0) | 0 (0) (NaN%) | 5 (0.2) | 6 (0.2) (0%) |
| | Biguanide | 7321 | 1 (0) | 1 (0) (NaN%) | 5 (0.1) | 6 (0.2) (-100%) |
| | Sulfonylurea | 3127 | 0 (0) | 0 (0) (NaN%) | 3 (0.2) | 3 (0.2) (0%) |
| | GLP1a | 3116 | 0 (0) | 0 (0) (NaN%) | 4 (0.3) | 2 (0.1) (67%) |
| | SGLT2i | 2691 | 0 (0) | 0 (0) (NaN%) | 2 (0.1) | 1 (0.1) (0%) |
| | DPP4i | 2121 | 0 (0) | 0 (0) (NaN%) | 3 (0.3) | 1 (0.1) (67%) |
| | TZD | 761 | 0 (0) | 0 (0) (NaN%) | 1 (0.3) | 0 (0) (100%) |
| | Meglitinides | 161 | 0 (0) | 0 (0) (NaN%) | 0 (0) | 0 (0) (NaN%) |
| | Alpha-Glucosidase Inhibitor | 41 | 0 (0) | 0 (0) (NaN%) | 0 (0) | 0 (0) (NaN%) |

FIG. 24H

|  |  | Sample size, N | Mental Diseases & Disorders | | | Alcohol/Drug Use & Alcohol/Drug Induced Organic Mental Disorders | | | Injuries, Poisonings & Toxic Effects of Drugs | |
|---|---|---|---|---|---|---|---|---|---|---|
|  |  |  | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) |
|  | Full Cohort | 10282 | 15 (0.3) | 10 (0.2) (33%) | | 6 (0.1) | 8 (0.2) (-100%) | | 16 (0.3) | 10 (0.2) (33%) |
| Age | Age 18 – 49 | 3321 | 5 (0.3) | 3 (0.2) (33%) | | 2 (0.1) | 5 (0.3) (-200%) | | 6 (0.4) | 3 (0.2) (50%) |
|  | Age 50 – 64 | 6425 | 9 (0.3) | 6 (0.2) (33%) | | 4 (0.1) | 2 (0.1) (0%) | | 8 (0.2) | 7 (0.2) (0%) |
|  | Age 65+ | 536 | 1 (0.4) | 1 (0.4) (0%) | | 0 (0) | 1 (0.4) (-Inf%) | | 2 (0.7) | 0 (0) (100%) |
| Gender | Male | 5341 | 10 (0.4) | 3 (0.1) (75%) | | 6 (0.2) | 4 (0.2) (0%) | | 10 (0.4) | 6 (0.2) (50%) |
|  | Female | 4941 | 5 (0.2) | 7 (0.3) (-50%) | | 0 (0) | 4 (0.2) (-Inf%) | | 6 (0.2) | 4 (0.2) (0%) |
| Comorbidities | Hypertension | 8286 | 14 (0.3) | 7 (0.2) (33%) | | 6 (0.1) | 8 (0.2) (-100%) | | 14 (0.3) | 9 (0.2) (33%) |
|  | Obesity | 5713 | 12 (0.4) | 7 (0.3) (25%) | | 2 (0.1) | 4 (0.1) (0%) | | 7 (0.2) | 8 (0.3) (-50%) |
|  | Pulmonary Disease | 2520 | 5 (0.4) | 3 (0.3) (25%) | | 1 (0.1) | 3 (0.3) (-200%) | | 6 (0.5) | 6 (0.5) (0%) |
|  | Depression | 2488 | 14 (1.1) | 8 (0.7) (36%) | | 4 (0.3) | 7 (0.6) (-100%) | | 8 (0.6) | 4 (0.3) (50%) |
|  | Hypothyroid Disease | 2210 | 7 (0.6) | 2 (0.2) (67%) | | 1 (0.1) | 2 (0.2) (-100%) | | 3 (0.3) | 2 (0.2) (33%) |
|  | Anemia | 1975 | 2 (0.2) | 3 (0.3) (-50%) | | 2 (0.2) | 3 (0.3) (-50%) | | 7 (0.7) | 4 (0.4) (43%) |
|  | Liver Disease | 1905 | 3 (0.3) | 1 (0.1) (67%) | | 4 (0.4) | 4 (0.4) (0%) | | 3 (0.3) | 5 (0.6) (-100%) |
|  | MI or Coronary Artery Disease | 1628 | 0 (0) | 3 (0.4) (-Inf%) | | 0 (0) | 5 (0.7) (-Inf%) | | 9 (1.1) | 2 (0.3) (73%) |
|  | Peripheral Vascular Disease | 1113 | 2 (0.4) | 2 (0.4) (0%) | | 0 (0) | 1 (0.2) (-Inf%) | | 8 (1.4) | 1 (0.2) (86%) |
|  | Renal Disease | 985 | 1 (0.2) | 1 (0.2) (0%) | | 2 (0.4) | 1 (0.3) (50%) | | 7 (1.4) | 2 (0.4) (71%) |
|  | Heart Failure | 706 | 1 (0.3) | 1 (0.3) (0%) | | 1 (0.3) | 2 (0.6) (-100%) | | 7 (2) | 2 (0.6) (70%) |
|  | Alcohol | 238 | 4 (3.4) | 1 (0.9) (74%) | | 5 (4.2) | 6 (5.4) (-29%) | | 4 (3.4) | 4 (3.6) (-6%) |
|  | Rheumatic | 856 | 3 (0.7) | 1 (0.3) (57%) | | 0 (0) | 0 (0) (NaN%) | | 1 (0.2) | 4 (1) (-400%) |
|  | Blood Loss | 275 | 0 (0) | 1 (0.8) (-Inf%) | | 0 (0) | 0 (0) (NaN%) | | 2 (1.5) | 0 (0) (100%) |
|  | Coagulopathy | 341 | 0 (0) | 1 (0.6) (-Inf%) | | 1 (0.6) | 3 (1.9) (-217%) | | 2 (1.2) | 3 (1.9) (-58%) |
|  | Lymphoma | 92 | 0 (0) | 2 (2.3) (-Inf%) | | 2 (2.2) | 0 (0) (100%) | | 0 (0) | 0 (0) (NaN%) |
|  | Fluids Lytes | 1885 | 7 (0.7) | 1 (0.1) (86%) | | 4 (0.4) | 4 (0.5) (-25%) | | 10 (1.1) | 6 (0.7) (36%) |
|  | Mets | 133 | 0 (0) | 0 (0) (NaN%) | | 1 (1) | 0 (0) (100%) | | 0 (0) | 0 (0) (100%) |
|  | Neuro Other | 971 | 6 (1.2) | 3 (0.7) (42%) | | 4 (0.8) | 2 (0.4) (50%) | | 8 (1.7) | 6 (1.3) (24%) |
|  | Paralysis | 167 | 0 (0) | 0 (0) (NaN%) | | 0 (0) | 1 (1.3) (-Inf%) | | 3 (3.6) | 1 (1.3) (64%) |
|  | Psychoses | 552 | 8 (2.9) | 6 (2.3) (21%) | | 2 (0.7) | 1 (0.4) (43%) | | 2 (0.7) | 2 (0.8) (-14%) |
|  | PulmCircD | 213 | 0 (0) | 0 (0) (NaN%) | | 0 (0) | 0 (0) (NaN%) | | 1 (0.9) | 1 (1) (-11%) |
|  | Tumor | 704 | 0 (0) | 2 (0.6) (-Inf%) | | 0 (0) | 0 (0) (NaN%) | | 2 (0.6) | 3 (0.9) (-50%) |
|  | PepticUlcer | 292 | 0 (0) | 2 (2.2) (-Inf%) | | 1 (1) | 0 (0) (100%) | | 1 (1) | 0 (0) (100%) |
|  | Valvular | 1061 | 1 (0.2) | 2 (0.4) (-100%) | | 2 (0.4) | 1 (0.1) (-Inf%) | | 5 (0.9) | 1 (0.2) (78%) |
|  | WeightLoss | 501 | 2 (0.8) | 2 (0.9) (-12%) | | 0 (0) | 1 (0.4) (-Inf%) | | 3 (1.2) | 1 (0.4) (67%) |
| Insulin Usage Status | Insulin (short -or rapid-acting) | 3984 | 7 (0.4) | 3 (0.2) (50%) | | 3 (0.2) | 2 (0.1) (50%) | | 4 (0.2) | 4 (0.2) (0%) |
| Non-Insulin Diabetes Medications | Non-insulin therapy | 6298 | 8 (0.3) | 7 (0.2) (33%) | | 3 (0.1) | 6 (0.2) (-100%) | | 12 (0.4) | 6 (0.2) (50%) |
|  | Biguanide | 7321 | 9 (0.2) | 10 (0.3) (-50%) | | 3 (0.1) | 4 (0.1) (0%) | | 9 (0.2) | 6 (0.2) (0%) |
|  | Sulfonylurea | 3127 | 5 (0.3) | 2 (0.1) (67%) | | 1 (0.1) | 1 (0.1) (0%) | | 3 (0.2) | 3 (0.2) (0%) |
|  | GLP1a | 3116 | 6 (0.4) | 8 (0.5) (-25%) | | 1 (0.1) | 3 (0.2) (-100%) | | 2 (0.1) | 2 (0.1) (0%) |
|  | SGLT2i | 2691 | 5 (0.4) | 5 (0.4) (0%) | | 0 (0) | 1 (0.1) (-Inf%) | | 1 (0.1) | 2 (0.2) (-100%) |
|  | DPP4i | 2121 | 3 (0.3) | 2 (0.2) (33%) | | 3 (0.3) | 2 (0.2) (33%) | | 4 (0.4) | 1 (0.1) (75%) |
|  | TZD | 761 | 0 (0) | 1 (0.3) (-Inf%) | | 1 (0.3) | 0 (0) (100%) | | 0 (0) | 1 (0.3) (-Inf%) |
|  | Meglitinides | 161 | 0 (0) | 1 (1.4) (-Inf%) | | 0 (0) | 0 (0) (NaN%) | | 2 (2.5) | 0 (0) (100%) |
|  | Alpha-Glucosidase Inhibitor | 41 | 0 (0) | 0 (0) (NaN%) | | 0 (0) | 0 (0) (NaN%) | | 0 (0) | 0 (0) (NaN%) |

FIG. 24I

|  |  | Sample size, N | Multiple Significant Trauma | | Diseases & Disorders of Blood, Blood Forming Organs, Immunologic Disorders | | Burns | |
|---|---|---|---|---|---|---|---|---|
|  |  |  | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
|  | Full Cohort | 10282 | 0 (0) | 0 (0) (NaN%) | 6 (0.1) | 5 (0.1) (0%) | 0 (0) | 0 (0) (NaN%) |
| Age | Age 18 – 49 | 3321 | 0 (0) | 0 (0) (NaN%) | 1 (0.1) | 1 (0.1) (0%) | 0 (0) | 0 (0) (NaN%) |
|  | Age 50 – 64 | 6425 | 0 (0) | 0 (0) (NaN%) | 5 (0.2) | 4 (0.1) (50%) | 0 (0) | 0 (0) (NaN%) |
|  | Age 65+ | 536 | 0 (0) | 0 (0) (NaN%) | 1 (0.4) | 0 (0) (100%) | 0 (0) | 0 (0) (NaN%) |
| Gender | Male | 5341 | 0 (0) | 0 (0) (NaN%) | 6 (0.2) | 1 (0) (100%) | 0 (0) | 0 (0) (NaN%) |
|  | Female | 4941 | 0 (0) | 0 (0) (NaN%) | 1 (0) | 4 (0.2) (-Inf%) | 0 (0) | 0 (0) (NaN%) |
| Comorbidities | Hypertension | 8286 | 0 (0) | 0 (0) (NaN%) | 7 (0.2) | 5 (0.1) (50%) | 0 (0) | 0 (0) (NaN%) |
|  | Obesity | 5713 | 0 (0) | 0 (0) (NaN%) | 2 (0.1) | 2 (0.1) (0%) | 0 (0) | 0 (0) (NaN%) |
|  | Pulmonary Disease | 2520 | 0 (0) | 0 (0) (NaN%) | 2 (0.2) | 3 (0.3) (-50%) | 0 (0) | 0 (0) (NaN%) |
|  | Depression | 2488 | 0 (0) | 0 (0) (NaN%) | 5 (0.4) | 4 (0.3) (25%) | 0 (0) | 0 (0) (NaN%) |
|  | Hypothyroid Disease | 2210 | 0 (0) | 0 (0) (NaN%) | 2 (0.2) | 3 (0.3) (-50%) | 0 (0) | 0 (0) (NaN%) |
|  | Anemia | 1975 | 0 (0) | 0 (0) (NaN%) | 6 (0.6) | 4 (0.4) (33%) | 0 (0) | 0 (0) (NaN%) |
|  | Liver Disease | 1905 | 0 (0) | 0 (0) (NaN%) | 5 (0.5) | 0 (0) (100%) | 0 (0) | 0 (0) (NaN%) |
|  | MI or Coronary Artery Disease | 1628 | 0 (0) | 0 (0) (NaN%) | 4 (0.5) | 3 (0.4) (20%) | 0 (0) | 0 (0) (NaN%) |
|  | Peripheral Vascular Disease | 1113 | 0 (0) | 0 (0) (NaN%) | 1 (0.2) | 1 (0.2) (0%) | 0 (0) | 0 (0) (NaN%) |
|  | Renal Disease | 985 | 0 (0) | 0 (0) (NaN%) | 2 (0.4) | 1 (0.2) (50%) | 0 (0) | 0 (0) (NaN%) |
|  | Heart Failure | 706 | 0 (0) | 0 (0) (NaN%) | 3 (0.9) | 2 (0.6) (33%) | 0 (0) | 0 (0) (NaN%) |
|  | Alcohol | 238 | 0 (0) | 0 (0) (NaN%) | 0 (0) | 0 (0) (NaN%) | 0 (0) | 0 (0) (NaN%) |
|  | Rheumatic | 856 | 0 (0) | 0 (0) (NaN%) | 2 (0.5) | 1 (0.3) (40%) | 0 (0) | 0 (0) (NaN%) |
|  | Blood Loss | 275 | 0 (0) | 0 (0) (NaN%) | 2 (1.5) | 0 (0) (100%) | 0 (0) | 0 (0) (NaN%) |
|  | Coagulopathy | 341 | 0 (0) | 0 (0) (NaN%) | 4 (2.4) | 0 (0) (100%) | 0 (0) | 0 (0) (NaN%) |
|  | Lymphoma | 92 | 0 (0) | 0 (0) (NaN%) | 1 (2.2) | 0 (0) (100%) | 0 (0) | 0 (0) (NaN%) |
|  | Fluids Lytes | 1885 | 0 (0) | 0 (0) (NaN%) | 6 (0.6) | 3 (0.3) (50%) | 0 (0) | 0 (0) (NaN%) |
|  | Mets | 133 | 0 (0) | 0 (0) (NaN%) | 4 (6) | 0 (0) (100%) | 0 (0) | 0 (0) (NaN%) |
|  | Neuro Other | 971 | 0 (0) | 0 (0) (NaN%) | 1 (0.2) | 2 (0.4) (-100%) | 0 (0) | 0 (0) (NaN%) |
|  | Paralysis | 167 | 0 (0) | 0 (0) (NaN%) | 0 (0) | 1 (1.3) (-Inf%) | 0 (0) | 0 (0) (NaN%) |
|  | Psychoses | 552 | 0 (0) | 0 (0) (NaN%) | 1 (0.4) | 0 (0) (100%) | 0 (0) | 0 (0) (NaN%) |
|  | PulmCircD | 213 | 0 (0) | 0 (0) (NaN%) | 1 (0.9) | 1 (1) (-11%) | 0 (0) | 0 (0) (NaN%) |
|  | Tumor | 704 | 0 (0) | 0 (0) (NaN%) | 2 (0.6) | 0 (0) (100%) | 0 (0) | 0 (0) (NaN%) |
|  | PepticUlcer | 202 | 0 (0) | 0 (0) (NaN%) | 0 (0) | 0 (0) (NaN%) | 0 (0) | 0 (0) (NaN%) |
|  | Valvular | 1061 | 0 (0) | 0 (0) (NaN%) | 1 (0.1) | 1 (0.1) (-Inf%) | 0 (0) | 0 (0) (NaN%) |
|  | WeightLoss | 593 | 0 (0) | 0 (0) (NaN%) | 7 (1.3) | 3 (0.6) (54%) | 0 (0) | 0 (0) (NaN%) |
| Insulin Usage Status | Insulin (short -or rapid-acting) | 3984 | 0 (0) | 0 (0) (NaN%) | 1 (0.4) | 2 (0.9) (-125%) | 0 (0) | 0 (0) (NaN%) |
| Non-Insulin Diabetes Medications | Non-insulin therapy | 6298 | 0 (0) | 0 (0) (NaN%) | 5 (0.3) | 2 (0.1) (67%) | 0 (0) | 0 (0) (NaN%) |
|  | Biguanide | 7321 | 0 (0) | 0 (0) (NaN%) | 2 (0.1) | 3 (0.1) (0%) | 0 (0) | 0 (0) (NaN%) |
|  | Sulfonylurea | 3127 | 0 (0) | 0 (0) (NaN%) | 0 (0) | 3 (0.1) (-Inf%) | 0 (0) | 0 (0) (NaN%) |
|  | GLP1a | 3116 | 0 (0) | 0 (0) (NaN%) | 1 (0.1) | 1 (0.1) (0%) | 0 (0) | 0 (0) (NaN%) |
|  | SGLT2i | 2691 | 0 (0) | 0 (0) (NaN%) | 0 (0) | 0 (0) (NaN%) | 0 (0) | 0 (0) (NaN%) |
|  | DPP4i | 2121 | 0 (0) | 0 (0) (NaN%) | 1 (0.1) | 1 (0.1) (50%) | 0 (0) | 0 (0) (NaN%) |
|  | TZD | 761 | 0 (0) | 0 (0) (NaN%) | 2 (0.2) | 1 (0.3) (-Inf%) | 0 (0) | 0 (0) (NaN%) |
|  | Meglitinides | 161 | 0 (0) | 0 (0) (NaN%) | 0 (0) | 0 (0) (NaN%) | 0 (0) | 0 (0) (NaN%) |
|  | Alpha-Glucosidase Inhibitor | 41 | 0 (0) | 0 (0) (NaN%) | 0 (0) | 0 (0) (NaN%) | 0 (0) | 0 (0) (NaN%) |

FIG. 24J

|  |  | Sample size, N | Total ADE | | Hypoglycemic ADE | | Hyperglycemic ADE | |
|---|---|---|---|---|---|---|---|---|
|  |  |  | Before flash CGM # events (# affected) | After flash CGM # events (# affected) | Before flash CGM # events (# affected) | After flash CGM # events (# affected) | Before flash CGM # events (# affected) | After flash CGM # events (# affected) |
| Medication Therapy Group | Antihistamines & Comb. (Class 1) | 532 | 36 (29) | 19 (18) | 2 (2) | 4 (4) | 34 (28) | 16 (15) |
|  | Gastrointestinal Drugs (Classes 147-162, 273) | 2864 | 155 (129) | 96 (84) | 14 (12) | 18 (16) | 142 (120) | 79 (71) |
|  | Anti-infective Agents (Classes 2-20) | 4784 | 246 (204) | 147 (119) | 24 (23) | 27 (23) | 224 (186) | 122 (101) |
|  | Antineoplastic Agents (Classes 21-22, 260-265) | 205 | 10 (6) | 9 (8) | 3 (2) | 3 (3) | 7 (4) | 6 (5) |
|  | Autonomic Drugs (Classes 23-33) | 2327 | 135 (114) | 83 (73) | 19 (17) | 13 (13) | 117 (100) | 72 (63) |
|  | Hormones & Synthetic Substitutes (Classes 165-180 246 252-253 256 266-268) | 9767 | 373 (309) | 222 (190) | 32 (30) | 38 (34) | 344 (284) | 188 (162) |
|  | Immunosuppressants (Class 181) | 223 | 9 (8) | 10 (9) | 1 (1) | 2 (2) | 8 (7) | 8 (7) |
|  | Blood Form/Coagul Agents (Classes 35-45, 259) | 802 | 43 (31) | 33 (27) | 4 (4) | 4 (3) | 39 (27) | 30 (25) |
|  | Cardiovascular Agents (Classes 46-56, 245, 250, 271) | 8696 | 309 (262) | 192 (171) | 32 (30) | 29 (28) | 280 (239) | 165 (147) |
|  | Central Nervous System (Classes 57-77, 272) | 5912 | 276 (227) | 175 (149) | 26 (24) | 31 (30) | 251 (207) | 147 (124) |
|  | Serums, Toxoids, Vaccines (Classes 185-189) | 1045 | 25 (20) | 19 (16) | 5 (5) | 6 (5) | 20 (16) | 14 (13) |
|  | Dental Agents (Classes 79-83) | 52 | 1 (1) | 0 (0) | 0 (0) | 0 (0) | 1 (1) | 0 (0) |
|  | Skin & Mucous Membrane (Classes 190-213, 242) | 2337 | 104 (87) | 87 (70) | 7 (7) | 13 (12) | 97 (82) | 75 (62) |
|  | Diagnostic Agents (Classes 84-98, 239, 243-244, 247) | 10282 | 391 (324) | 252 (211) | 35 (33) | 44 (39) | 359 (298) | 212 (181) |
|  | Smooth Muscles Relaxants (Classes 214-216) | 208 | 10 (9) | 5 (5) | 0 (0) | 1 (1) | 10 (9) | 5 (5) |
|  | Vitamins & Comb (Classes 217-233) | 1181 | 60 (48) | 37 (32) | 7 (6) | 3 (3) | 53 (43) | 34 (30) |
|  | Electrolytic, Caloric, Water (Classes 100-126, 241, 292) | 2056 | 111 (86) | 73 (58) | 14 (13) | 17 (13) | 98 (78) | 58 (48) |
|  | Unclassified Agents (Classes 234 236, 251, 254, 257-258, 270) | 952 | 41 (37) | 34 (28) | 6 (5) | 7 (7) | 35 (32) | 27 (21) |
|  | Devices and Non-drug Items (Class 237) | 455 | 28 (25) | 15 (12) | 4 (4) | 5 (5) | 25 (22) | 10 (8) |
|  | Antituss/Expector/Mucolytic (Classes 128-131, 248, 255) | 1375 | 48 (42) | 39 (34) | 4 (3) | 8 (8) | 45 (40) | 32 (27) |
|  | Pharmaceutical Aids/Adjuvants (Class 238) | 137 | 9 (7) | 4 (4) | 1 (1) | 0 (0) | 8 (6) | 4 (4) |
|  | Eye, Ear, Nose Throat (Classes 132-146, 240, 290) | 1791 | 74 (61) | 46 (44) | 9 (9) | 9 (9) | 66 (56) | 37 (36) |
| Other Diabetic Therapy | Insulin Pump | 23 | 2 (2) | 1 (1) | 0 (0) | 0 (0) | 2 (2) | 1 (1) |
|  | >= 4 Strips per day | 215 | 5 (4) | 4 (4) | 1 (1) | 0 (0) | 4 (3) | 4 (4) |
|  | < 4 Strips per day | 10067 | 386 (320) | 248 (207) | 34 (32) | 44 (39) | 355 (295) | 208 (177) |

FIG. 24K

| | | Sample size, N | Total ACH | | | | Circulatory System | |
|---|---|---|---|---|---|---|---|---|
| | | | Before flash CGM # events (# affected) | After flash CGM # events (# affected) | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
| Medication Therapy Group | Antihistamines & Comb. (Class 1) | 532 | 86 (58) | 69 (53) | 86 (32.4) | 69 (27.7) (15%) | 16 (6) | 9 (3.6) (40%) |
| | Gastrointestinal Drugs (Classes 147-162, 273) | 2864 | 467 (331) | 324 (235) | 467 (32.7) | 324 (24.2) (26%) | 77 (5.4) | 57 (4.3) (20%) |
| | Anti-infective Agents (Classes 2-20) | 4784 | 639 (470) | 463 (344) | 639 (26.8) | 463 (20.6) (23%) | 101 (4.2) | 80 (3.6) (14%) |
| | Antineoplastic Agents (Classes 21-22, 260-265) | 205 | 36 (22) | 29 (22) | 36 (35.2) | 29 (30.2) (14%) | 2 (2) | 5 (5.2) (-160%) |
| | Autonomic Drugs (Classes 23-33) | 2327 | 349 (249) | 255 (191) | 349 (30.1) | 255 (23.4) (22%) | 63 (5.4) | 41 (3.8) (30%) |
| | Hormones & Synthetic Substitutes (Classes 165-180 246 252-253 256 266-268) | 9767 | 853 (645) | 675 (520) | 853 (17.5) | 675 (14.7) (16%) | 167 (3.4) | 131 (2.9) (15%) |
| | Immunosuppressants (Class 183) | 223 | 53 (37) | 48 (32) | 53 (47.7) | 48 (45.5) (5%) | 7 (6.3) | 8 (7.6) (-21%) |
| | Blood Form/Coagul Agents (Classes 35-45, 259) | 802 | 264 (187) | 116 (90) | 264 (66.1) | 116 (31.5) (52%) | 95 (23.8) | 34 (9.2) (61%) |
| | Cardiovascular Agents (Classes 46-56, 245, 250, 271) | 8696 | 809 (615) | 630 (483) | 809 (18.7) | 630 (15.5) (17%) | 164 (3.8) | 131 (3.2) (16%) |
| | Central Nervous System (Classes 57-77, 272) | 5912 | 751 (556) | 547 (409) | 751 (25.5) | 547 (19.9) (22%) | 140 (4.8) | 98 (3.6) (25%) |
| | Serums, Toxoids, Vaccines (Classes 185-189) | 1045 | 58 (51) | 53 (48) | 58 (11.1) | 53 (10.9) (2%) | 4 (0.8) | 8 (1.6) (-100%) |
| | Dental Agents (Classes 79-83) | 52 | 10 (8) | 5 (4) | 10 (38.6) | 5 (20.7) (46%) | 3 (11.6) | 2 (8.3) (28%) |
| | Skin & Mucous Membrane (Classes 100-126, 241, 292) | 2337 | 336 (244) | 225 (179) | 336 (28.9) | 225 (20.7) (28%) | 52 (4.5) | 43 (4) (11%) |
| | Diagnostic Agents (Classes 84-98, 239, 243-244, 247) | 10282 | 905 (688) | 726 (558) | 905 (17.7) | 726 (15.1) (15%) | 175 (3.4) | 143 (3) (12%) |
| | Smooth Muscles Relaxants (Classes 214-216) | 208 | 23 (19) | 30 (24) | 23 (22.2) | 30 (31.4) (-41%) | 3 (2.9) | 1 (1) (66%) |
| | Vitamins & Comb (Classes 217-233) | 1181 | 185 (118) | 125 (93) | 185 (31.4) | 125 (22.5) (28%) | 34 (5.8) | 23 (4.1) (29%) |
| | Electrolytic, Caloric, Water (Classes 100-126, 241, 292) | 2056 | 416 (291) | 289 (197) | 416 (40.6) | 289 (30.3) (25%) | 102 (10) | 80 (8.4) (16%) |
| | Unclassified Agents (Classes 234 236, 251, 254, 257-258, 270) | 952 | 142 (101) | 116 (81) | 142 (29.9) | 116 (26.5) (11%) | 27 (5.7) | 21 (4.8) (16%) |
| | Devices and Non-drug Items (Class 237) | 455 | 48 (39) | 51 (36) | 48 (21.2) | 51 (23.8) (-12%) | 10 (4.4) | 9 (4.2) (5%) |
| | Antituss/Expector/Mucolytic (Classes 128-131, 248, 255) | 1375 | 113 (87) | 107 (82) | 113 (16.5) | 107 (16.5) (0%) | 25 (3.6) | 26 (4) (-11%) |
| | Pharmaceutical Aids/Adjuvants (Class 238) | 137 | 41 (23) | 21 (13) | 41 (60.1) | 21 (33.4) (44%) | 4 (5.9) | 3 (4.8) (19%) |
| | Eye, Ear, Nose Throat (Classes 132-146, 240, 290) | 1791 | 183 (145) | 163 (119) | 183 (20.5) | 163 (19.5) (5%) | 32 (3.6) | 33 (3.9) (-8%) |
| Other Diabetic Therapy | Insulin Pump | 23 | 4 (3) | 1 (1) | 4 (34.9) | 1 (9.9) (72%) | 0 (0) | 0 (0) (NaN%) |
| | >=4 Strips per day | 215 | 20 (16) | 27 (21) | 20 (18.7) | 27 (27.1) (-45%) | 3 (2.8) | 3 (3) (-7%) |
| | <4 Strips per day | 10067 | 885 (672) | 699 (537) | 885 (17.6) | 699 (14.8) (16%) | 172 (3.4) | 140 (3) (12%) |

FIG. 24L

| | | Sample size, N | Endocrine, Nutritional and Metabolic System | | | Infectious and Parasitic DDs (Systemic or unspecified sites) | | | Respiratory System | | |
|---|---|---|---|---|---|---|---|---|---|---|---|
| | | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | |
| Medication Therapy Group | Antihistamines & Comb (Class 1) | 532 | 8 (3) | 4 (1.6) (47%) | | 12 (4.5) | 3 (1.2) (73%) | | 6 (2.3) | 5 (2) (13%) | |
| | Gastrointestinal Drugs (Classes 147-162, 273) | 2864 | 60 (4.2) | 37 (2.8) (33%) | | 47 (3.3) | 22 (1.6) (52%) | | 31 (2.2) | 24 (1.8) (18%) | |
| | Anti-infective Agents (Classes 2-20) | 4784 | 84 (3.5) | 52 (2.3) (34%) | | 80 (3.4) | 41 (1.8) (47%) | | 48 (2) | 31 (1.4) (30%) | |
| | Antineoplastic Agents (Classes 21-22, 260-265) | 205 | 3 (2.9) | 1 (1) (66%) | | 5 (4.9) | 4 (4.2) (14%) | | 3 (2.9) | 3 (3.1) (-7%) | |
| | Autonomic Drugs (Classes 23-33) | 2327 | 36 (3.1) | 20 (1.8) (42%) | | 44 (3.8) | 25 (2.3) (39%) | | 42 (3.6) | 17 (1.6) (56%) | |
| | Hormones & Synthetic Substitutes (Classes 165-180, 246, 252-253, 256, 266-268) | 9767 | 110 (2.3) | 74 (1.6) (30%) | | 86 (1.8) | 53 (1.2) (33%) | | 57 (1.2) | 35 (0.8) (33%) | |
| | Immunosuppressants (Class 181) | 223 | 5 (4.5) | 6 (5.7) (-27%) | | 10 (9) | 5 (4.7) (48%) | | 5 (4.5) | 5 (4.7) (-4%) | |
| | Blood Form/Coagul Agents (Classes 35-45, 259) | 802 | 16 (4) | 6 (1.6) (60%) | | 15 (3.8) | 9 (2.4) (37%) | | 17 (4.3) | 9 (2.4) (44%) | |
| | Cardiovascular Agents (Classes 46-56, 245, 250, 271) | 8696 | 104 (2.4) | 66 (1.6) (33%) | | 83 (1.9) | 48 (1.2) (37%) | | 54 (1.2) | 32 (0.8) (33%) | |
| | Central Nervous System (Classes 57-77, 272) | 5912 | 91 (3.1) | 50 (1.8) (42%) | | 83 (2.8) | 48 (1.7) (39%) | | 51 (1.7) | 32 (1.2) (29%) | |
| | Serums, Toxoids, Vaccines (Classes 185-189) | 1045 | 8 (1.5) | 7 (1.4) (7%) | | 5 (1) | 4 (0.8) (20%) | | 1 (0.2) | 4 (0.8) (-300%) | |
| | Dental Agents (Classes 79-83) | 52 | 1 (3.9) | 1 (4.1) (-5%) | | 1 (3.9) | 0 (0) (100%) | | 0 (0) | 0 (0) (NaN%) | |
| | Skin & Mucous Membrane (Classes 190-213, 242) | 2337 | 43 (3.7) | 33 (3) (19%) | | 45 (3.9) | 20 (1.8) (54%) | | 22 (1.9) | 12 (1.1) (42%) | |
| | Diagnostic Agents (Classes 84-98, 239, 243-244, 247) | 10282 | 118 (2.3) | 81 (1.7) (26%) | | 94 (1.8) | 60 (1.2) (33%) | | 59 (1.2) | 38 (0.8) (33%) | |
| | Smooth Muscles Relaxants (Classes 214-216) | 208 | 1 (1) | 6 (6.3) (-530%) | | 6 (5.8) | 2 (2.1) (64%) | | 1 (1) | 5 (5.2) (-420%) | |
| | Vitamins & Comb (Classes 217-233) | 1181 | 25 (4.2) | 22 (4) (5%) | | 17 (2.9) | 5 (0.9) (69%) | | 12 (2) | 4 (0.7) (65%) | |
| | Electrolytic, Caloric, Water (Classes 100-126, 241, 292) | 2056 | 53 (5.2) | 31 (3.2) (38%) | | 45 (4.4) | 22 (2.3) (48%) | | 34 (3.3) | 16 (1.7) (48%) | |
| | Unclassified Agents (Classes 234-236, 251, 254, 257-258, 270) | 952 | 11 (2.3) | 10 (2.3) (8%) | | 16 (3.4) | 14 (3.2) (6%) | | 9 (1.9) | 9 (2.1) (-11%) | |
| | Devices and Non-drug Items (Class 237) | 455 | 15 (6.6) | 7 (3.3) (50%) | | 4 (1.8) | 4 (1.9) (-6%) | | 1 (0.4) | 0 (0) (100%) | |
| | Antituss/Expector/Mucolytic (Classes 128-131, 248, 255) | 1375 | 7 (1) | 9 (1.4) (-40%) | | 15 (2.2) | 6 (0.9) (59%) | | 20 (2.9) | 8 (1.2) (59%) | |
| | Pharmaceutical Aids/Adjuvants (Class 238) | 137 | 5 (7.3) | 1 (1.6) (78%) | | 4 (5.9) | 0 (0) (100%) | | 1 (1.5) | 2 (3.2) (-113%) | |
| | Eye, Ear, Nose Throat (Classes 132-146, 240, 290) | 1791 | 21 (2.4) | 13 (1.6) (33%) | | 16 (1.8) | 8 (1) (44%) | | 12 (1.3) | 10 (1.2) (8%) | |
| Other Diabetic Therapy | Insulin Pump | 23 | 1 (8.7) | 0 (0) (100%) | | 0 (0) | 0 (0) (NaN%) | | 2 (17.5) | 0 (0) (100%) | |
| | >= 4 Strips per day | 215 | 2 (1.9) | 1 (1) (47%) | | 0 (0) | 1 (-Inf%) | | 3 (2.8) | 1 (1) (64%) | |
| | < 4 Strips per day | 10067 | 116 (2.3) | 80 (1.7) (26%) | | 94 (1.9) | 59 (1.3) (32%) | | 56 (1.1) | 37 (0.8) (27%) | |

FIG. 24M

|  |  | Sample size, N | Kidney and Urinary Tract | | Musculoskeletal System and Connective Tissue | | Digestive System | |
|---|---|---|---|---|---|---|---|---|
|  |  |  | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
| Medication Therapy Group | Antihistamines & Comb. (Class 1) | 532 | 5 (1.9) | 3 (1.2) (37%) | 8 (3) | 9 (3.6) (-20%) | 7 (2.6) | 15 (6) (-131%) |
|  | Gastrointestinal Drugs (Classes 147-162, 273) | 2864 | 34 (2.4) | 20 (1.5) (38%) | 44 (3.1) | 32 (2.4) (23%) | 48 (3.4) | 48 (3.6) (-6%) |
|  | Anti-infective Agents (Classes 2-20) | 4784 | 48 (2) | 29 (1.3) (35%) | 56 (2.3) | 52 (2.3) (10%) | 56 (2.3) | 47 (2.1) (9%) |
|  | Antineoplastic Agents (Classes 21-22, 260-265) | 205 | 1 (1) | 2 (2.1) (-110%) | 6 (5.9) | 2 (2.1) (64%) | 4 (3.9) | 3 (3.1) (21%) |
|  | Autonomic Drugs (Classes 23-33) | 2327 | 17 (1.5) | 15 (1.4) (7%) | 43 (3.7) | 28 (2.6) (30%) | 25 (2.2) | 26 (2.4) (-9%) |
|  | Hormones & Synthetic Substitutes (Classes 165-180 246 252-253 256 266-268) | 9767 | 61 (1.3) | 40 (0.9) (31%) | 74 (1.5) | 88 (1.7) (-13%) | 63 (1.3) | 67 (1.5) (-15%) |
|  | Immunosuppressants (Class 181) | 223 | 8 (7.2) | 7 (6.6) (8%) | 3 (2.7) | 2 (1.9) (30%) | 2 (1.8) | 6 (5.7) (-217%) |
|  | Blood Form/Coagul Agents (Classes 35-45, 259) | 802 | 9 (2.3) | 10 (2.7) (-17%) | 18 (4.5) | 15 (4.1) (9%) | 16 (4) | 8 (2.2) (45%) |
|  | Cardiovascular Agents (Classes 46-56, 245, 250, 271) | 8696 | 61 (1.4) | 40 (1) (29%) | 65 (1.5) | 76 (1.9) (-27%) | 57 (1.3) | 67 (1.6) (-23%) |
|  | Central Nervous System (Classes 57-77, 272) | 5912 | 55 (1.9) | 31 (1.1) (42%) | 73 (2.5) | 74 (2.7) (-8%) | 56 (1.9) | 58 (2.1) (-11%) |
|  | Serums, Toxoids, Vaccines (Classes 185-189) | 1045 | 5 (1) | 2 (0.4) (60%) | 8 (1.5) | 10 (2.1) (-40%) | 9 (1.7) | 5 (1) (41%) |
|  | Dental Agents (Classes 79-83) | 52 | 0 (0) | 2 (8.3) (-Inf%) | 1 (3.9) | 0 (0) (100%) | 0 (0) | 0 (0) (NaN%) |
|  | Skin & Mucous Membrane (Classes 190-213, 242) | 2337 | 19 (1.6) | 14 (1.3) (19%) | 42 (3.6) | 26 (2.4) (33%) | 28 (2.4) | 21 (1.9) (21%) |
|  | Diagnostic Agents (Classes 84-98, 239, 243-244, 247) | 10282 | 68 (1.3) | 44 (0.9) (31%) | 75 (1.5) | 81 (1.7) (-13%) | 67 (1.3) | 71 (1.5) (-15%) |
|  | Smooth Muscles Relaxants (Classes 214-216) | 208 | 6 (5.8) | 3 (3.1) (47%) | 2 (1.9) | 2 (2.1) (-11%) | 0 (0) | 4 (4.2) (-Inf%) |
|  | Vitamins & Comb (Classes 217-233) | 1181 | 16 (2.7) | 9 (1.6) (41%) | 14 (2.4) | 15 (2.7) (-13%) | 12 (2) | 16 (2.9) (-45%) |
|  | Electrolyte, Caloric, Water (Classes 100-126, 241, 292) | 2056 | 33 (3.2) | 21 (2.2) (31%) | 26 (2.5) | 27 (2.8) (-12%) | 23 (2.2) | 28 (2.9) (-32%) |
|  | Unclassified Agents (Classes 234 236, 251, 254, 257-258, 270) | 952 | 20 (4.2) | 11 (2.5) (40%) | 12 (2.5) | 7 (1.6) (36%) | 14 (3) | 10 (2.3) (23%) |
|  | Devices and Non-drug Items (Class 237) | 455 | 2 (0.9) | 4 (1.9) (-111%) | 3 (1.3) | 4 (1.9) (-46%) | 3 (1.3) | 5 (2.3) (-77%) |
|  | Antituss/Expector/Mucolytic (Classes 128-131, 248, 255) | 1375 | 8 (1.2) | 5 (0.8) (33%) | 11 (1.6) | 20 (3.1) (-94%) | 6 (0.9) | 6 (0.9) (0%) |
|  | Pharmaceutical Aids/Adjuvants (Class 238) | 137 | 1 (1.5) | 1 (1.6) (-7%) | 5 (7.3) | 2 (3.3) (56%) | 7 (10.3) | 7 (11.1) (-8%) |
|  | Eye, Ear, Nose Throat (Classes 132-146, 240, 290) | 1791 | 15 (1.7) | 10 (1.2) (29%) | 27 (3) | 19 (2.3) (23%) | 17 (1.9) | 20 (2.4) (-26%) |
| Other Diabetic Therapy | Insulin Pump | 23 | 0 (0) | 0 (0) (NaN%) | 0 (0) | 0 (0) (NaN%) | 1 (8.7) | 1 (9.9) (-14%) |
|  | >= 4 Strips per day | 215 | 2 (1.9) | 2 (2) (-5%) | 1 (0.9) | 6 (6) (-567%) | 1 (0.9) | 5 (5) (-456%) |
|  | < 4 Strips per day | 10067 | 65 (1.3) | 42 (0.9) (31%) | 74 (1.5) | 75 (1.6) (-7%) | 66 (1.3) | 66 (1.4) (-8%) |

FIG. 24N

| | | Sample size, N | Nervous System | | | Hepatobiliary System and Pancreas | | | Skin, Subcutaneous Tissue and Breast | | |
|---|---|---|---|---|---|---|---|---|---|---|---|
| | | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | |
| Medication Therapy Group | Antihistamines & Comb. (Class 1) | 532 | 9 (3.4) | 6 (2.4) (29%) | | 4 (1.5) | 2 (0.8) (47%) | | 1 (0.4) | 2 (0.8) (-100%) | |
| | Gastrointestinal Drugs (Classes 147-162, 273) | 2864 | 45 (3.2) | 25 (1.9) (41%) | | 27 (1.9) | 14 (1) (47%) | | 11 (0.8) | 9 (0.7) (13%) | |
| | Anti-infective Agents (Classes 2-20) | 4784 | 49 (2.1) | 38 (1.7) (19%) | | 39 (1.6) | 20 (0.9) (44%) | | 20 (0.8) | 18 (0.8) (0%) | |
| | Antineoplastic Agents (Classes 21-22, 260-265) | 205 | 4 (3.9) | 0 (0) (100%) | | 2 (2) | 2 (2.1) (-5%) | | 1 (1) | 2 (2.1) (-110%) | |
| | Autonomic Drugs (Classes 23-33) | 2327 | 31 (2.7) | 30 (2.7) (0%) | | 14 (1.2) | 8 (0.7) (42%) | | 5 (0.4) | 9 (0.8) (-100%) | |
| | Hormones & Synthetic Substitutes (Classes 165-180 246 252-253 256 266-268) | 9767 | 95 (2) | 61 (1.3) (35%) | | 46 (0.9) | 32 (0.7) (22%) | | 20 (0.4) | 25 (0.5) (-25%) | |
| | Immunosuppressants (Class 181) | 223 | 4 (3.6) | 0 (0) (100%) | | 3 (2.7) | 6 (5.7) (-111%) | | 2 (1.8) | 3 (2.8) (-56%) | |
| | Blood Form/Coagul Agents (Classes 35-45, 259) | 802 | 48 (12) | 15 (4.1) (66%) | | 9 (2.3) | 2 (0.5) (76%) | | 5 (1.3) | 1 (0.3) (77%) | |
| | Cardiovascular Agents (Classes 46-56, 245, 250, 271) | 8696 | 97 (2.2) | 56 (1.4) (36%) | | 43 (1) | 30 (0.7) (30%) | | 14 (0.3) | 23 (0.6) (-100%) | |
| | Central Nervous System (Classes 57-77, 272) | 5912 | 73 (2.5) | 52 (1.9) (24%) | | 38 (1.3) | 24 (0.9) (31%) | | 15 (0.5) | 18 (0.7) (-40%) | |
| | Serums, Toxoids, Vaccines (Classes 185-189) | 1045 | 5 (1) | 3 (0.6) (40%) | | 6 (1.2) | 3 (0.6) (50%) | | 0 (0) | 2 (0.4) (-Inf%) | |
| | Dental Agents (Classes 79-83) | 52 | 2 (7.7) | 0 (0) (100%) | | 1 (3.9) | 0 (0) (100%) | | 0 (0) | 0 (0) (NaN%) | |
| | Skin & Mucous Membrane (Classes 190-213, 242) | 2337 | 35 (3) | 17 (1.6) (47%) | | 8 (0.7) | 6 (0.6) (14%) | | 13 (1.1) | 14 (1.3) (-18%) | |
| | Diagnostic Agents (Classes 84-98, 239, 243-244, 247) | 10282 | 99 (1.9) | 67 (1.4) (26%) | | 48 (0.9) | 32 (0.7) (22%) | | 21 (0.4) | 27 (0.6) (-50%) | |
| | Smooth Muscles Relaxants (Classes 214-216) | 208 | 0 (0) | 3 (3.1) (-Inf%) | | 0 (0) | 1 (1) (-Inf%) | | 0 (0) | 1 (1) (-Inf%) | |
| | Vitamins & Comb (Classes 217-233) | 1181 | 18 (3.1) | 8 (1.4) (55%) | | 10 (1.7) | 8 (1.4) (18%) | | 3 (0.5) | 4 (0.7) (-40%) | |
| | Electrolytic, Caloric, Water (Classes 100-126, 241, 292) | 2056 | 32 (3.1) | 25 (2.6) (16%) | | 25 (2.4) | 9 (0.9) (62%) | | 8 (0.8) | 10 (1) (-25%) | |
| | Unclassified Agents (Classes 234-236, 251, 254, 257-258, 270) | 952 | 10 (2.1) | 10 (2.3) (-10%) | | 3 (0.6) | 3 (0.7) (-17%) | | 4 (0.8) | 6 (1.4) (-75%) | |
| | Devices and Non-drug Items (Class 237) | 455 | 7 (3.1) | 7 (3.3) (-6%) | | 1 (0.4) | 2 (0.9) (-125%) | | 4 (0.8) | 4 (1.9) (-Inf%) | |
| | Antituss/Expector/Mucolytic (Classes 128-131, 248, 255) | 1375 | 9 (1.3) | 10 (1.5) (-15%) | | 3 (0.4) | 2 (0.3) (25%) | | 1 (0.1) | 5 (0.8) (-700%) | |
| | Pharmaceutical Aids/Adjuvants (Class 238) | 137 | 3 (4.4) | 3 (4.8) (-9%) | | 2 (2.9) | 1 (1.6) (45%) | | 2 (2.9) | 1 (1.6) (45%) | |
| | Eye, Ear, Nose Throat (Classes 132-146, 240, 290) | 1791 | 17 (1.9) | 14 (1.7) (11%) | | 8 (0.9) | 3 (0.4) (56%) | | 1 (0.1) | 5 (0.6) (-500%) | |
| Other Diabetic Therapy | Insulin Pump | 23 | 0 (0) | 0 (0) (NaN%) | | 0 (0) | 0 (0) (NaN%) | | 0 (0) | 0 (0) (NaN%) | |
| | >= 4 Strips per day | 215 | 2 (1.9) | 5 (5) (-163%) | | 1 (0.9) | 2 (2) (-132%) | | 0 (0) | 1 (1) (-Inf%) | |
| | < 4 Strips per day | 10067 | 97 (1.9) | 62 (1.3) (32%) | | 47 (0.9) | 30 (0.6) (33%) | | 21 (0.4) | 26 (0.6) (-50%) | |

FIG. 240

| | | Sample size, N | Diseases & Disorders of the Eye | | | Diseases & Disorders of the Ear, Nose, Mouth & Throat | | | Diseases & Disorders of the Male Reproductive System | | |
|---|---|---|---|---|---|---|---|---|---|---|---|
| | | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | |
| Medication Therapy Group | Antihistamines & Comb. (Class 1) | 532 | 0 (0) | 0 (0) (NaN%) | | 0 (0) | 1 (0.4) (-Inf%) | | 0 (0) | 0 (0) (NaN%) | |
| | Gastrointestinal Drugs (Classes 147-162, 273) | 2864 | 1 (0.1) | 0 (0) (100%) | | 1 (0.1) | 2 (0.1) (0%) | | 0 (0) | 1 (0.1) (-Inf%) | |
| | Anti-infective Agents (Classes 2-20) | 4784 | 3 (0.1) | 0 (0) (100%) | | 3 (0.1) | 2 (0.1) (0%) | | 1 (0) | 1 (0) (NaN%) | |
| | Antineoplastic Agents (Classes 21-22, 260-265) | 205 | 0 (0) | 0 (0) (NaN%) | | 0 (0) | 0 (0) (NaN%) | | 0 (0) | 0 (0) (NaN%) | |
| | Autonomic Drugs (Classes 23-33) | 2327 | 1 (0.1) | 0 (0) (100%) | | 1 (0.1) | 1 (0.1) (0%) | | 0 (0) | 0 (0) (NaN%) | |
| | Hormones & Synthetic Substitutes (Classes 165-180 246 252-253 256 266-268) | 9767 | 3 (0.1) | 0 (0) (100%) | | 4 (0.1) | 5 (0.1) (0%) | | 1 (0) | 2 (0) (NaN%) | |
| | Immunosuppressants (Class 181) | 223 | 1 (0.9) | 0 (0) (100%) | | 1 (0.9) | 0 (0) (100%) | | 0 (0) | 0 (0) (NaN%) | |
| | Blood Form/Coagul Agents (Classes 35-45, 259) | 302 | 1 (0.3) | 0 (0) (100%) | | 1 (0.3) | 1 (0.3) (0%) | | 0 (0) | 0 (0) (NaN%) | |
| | Cardiovascular Agents (Classes 46-56, 245, 250, 271) | 8696 | 3 (0.1) | 0 (0) (100%) | | 4 (0.1) | 3 (0.1) (0%) | | 0 (0) | 2 (0) (NaN%) | |
| | Central Nervous System (Classes 57-77, 272) | 5912 | 3 (0.1) | 0 (0) (100%) | | 4 (0.1) | 4 (0.1) (0%) | | 0 (0) | 1 (0) (NaN%) | |
| | Serums, Toxoids, Vaccines (Classes 185-189) | 1045 | 1 (0.2) | 0 (0) (100%) | | 1 (0.2) | 0 (0) (100%) | | 0 (0) | 0 (0) (NaN%) | |
| | Dental Agents (Classes 79-83) | 52 | 0 (0) | 0 (0) (NaN%) | | 0 (0) | 0 (0) (NaN%) | | 0 (0) | 0 (0) (NaN%) | |
| | Skin & Mucous Membrane (Classes 190-213, 242) | 2337 | 1 (0.1) | 0 (0) (100%) | | 1 (0.1) | 3 (0.3) (-200%) | | 1 (0.1) | 0 (0) (100%) | |
| | Diagnostic Agents (Classes 84-98, 239, 243-244, 247) | 10282 | 3 (0.1) | 0 (0) (100%) | | 4 (0.1) | 6 (0.1) (0%) | | 1 (0) | 2 (0) (NaN%) | |
| | Smooth Muscles Relaxants (Classes 214-216) | 298 | 1 (1) | 0 (0) (100%) | | 0 (0) | 0 (0) (NaN%) | | 0 (0) | 0 (0) (NaN%) | |
| | Vitamins & Comb (Classes 217-233) | 1181 | 1 (0.2) | 0 (0) (100%) | | 1 (0.2) | 1 (0.2) (0%) | | 0 (0) | 0 (0) (NaN%) | |
| | Electrolytic, Caloric, Water (Classes 100-126, 241, 292) | 2056 | 0 (0) | 0 (0) (100%) | | 1 (0.1) | 3 (0.3) (-200%) | | 1 (0.1) | 1 (0.1) (-Inf%) | |
| | Unclassified Agents (Classes 234-236, 251, 254, 257-258, 270) | 952 | 0 (0) | 0 (0) (100%) | | 1 (0.2) | 3 (0.7) (-250%) | | 0 (0) | 0 (0) (100%) | |
| | Devices and Non-drug Items (Class 237) | 455 | 0 (0) | 0 (0) (100%) | | 1 (0.1) | 1 (0.5) (-Inf%) | | 0 (0) | 2 (0) (NaN%) | |
| | Antituss/Expector/Mucolytic (Classes 128-131, 248, 255) | 1375 | 0 (0) | 0 (0) (NaN%) | | 0 (0) | 2 (0.3) (-Inf%) | | 0 (0) | 0 (0) (NaN%) | |
| | Pharmaceutical Aids/Adjuvants (Class 238) | 137 | 0 (0) | 0 (0) (NaN%) | | 0 (0) | 0 (0) (NaN%) | | 0 (0) | 0 (0) (NaN%) | |
| | Eye, Ear, Nose Throat (Classes 132-146, 240, 290) | 1791 | 2 (0.2) | 0 (0) (100%) | | 1 (0.1) | 3 (0.4) (-300%) | | 0 (0) | 1 (0) (-Inf%) | |
| Other Diabetic Therapy | Insulin Pump | 23 | 0 (0) | 0 (0) (NaN%) | | 0 (0) | 0 (0) (NaN%) | | 0 (0) | 0 (0) (NaN%) | |
| | >= 4 Strips per day | 215 | 0 (0) | 0 (0) (NaN%) | | 0 (0) | 0 (0) (NaN%) | | 0 (0) | 0 (0) (NaN%) | |
| | < 4 Strips per day | 10067 | 3 (0.1) | 0 (0) (100%) | | 4 (0.1) | 6 (0.1) (0%) | | 1 (0) | 2 (0) (NaN%) | |

FIG. 24P

| | | Sample size, N | Diseases & Disorders of the Female Reproductive System | | | Mental Diseases & Disorders | | | Alcohol/Drug Use & Alcohol/Drug Induced Organic Mental Disorders | | |
|---|---|---|---|---|---|---|---|---|---|---|---|
| | | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | |
| Medication Therapy Group | Antihistamines & Comb. (Class 1) | 532 | 2 (0.8) | 2 (0.8) (0%) | | 3 (1.1) | 2 (0.8) (-27%) | | 0 (0) | 0 (0) (NaN%) | |
| | Gastrointestinal Drugs (Classes 147-162, 273) | 2864 | 5 (0.4) | 3 (0.2) (50%) | | 2 (0.1) | 7 (0.5) (-400%) | | 5 (0.4) | 3 (0.2) (50%) | |
| | Anti-infective Agents (Classes 2-20) | 4784 | 7 (0.3) | 6 (0.3) (0%) | | 6 (0.3) | 5 (0.2) (33%) | | 4 (0.2) | 4 (0.2) (0%) | |
| | Antineoplastic Agents (Classes 21-22, 260-265) | 205 | 0 (0) | 1 (1) (-Inf%) | | 0 (0) | 0 (0) (NaN%) | | 0 (0) | 0 (0) (NaN%) | |
| | Autonomic Drugs (Classes 23-33) | 2327 | 6 (0.5) | 4 (0.4) (20%) | | 2 (0.2) | 6 (0.5) (-150%) | | 2 (0.2) | 3 (0.3) (-50%) | |
| | Hormones & Synthetic Substitutes (Classes 165-180 246 252-253 256 266-268) | 9767 | 9 (0.2) | 8 (0.2) (0%) | | 14 (0.3) | 10 (0.2) (33%) | | 6 (0.1) | 8 (0.2) (-100%) | |
| | Immunosuppressants (Class 181) | 223 | 0 (0) | 0 (0) (NaN%) | | 0 (0) | 0 (0) (NaN%) | | 0 (0) | 0 (0) (NaN%) | |
| | Blood Form/Coagul Agents (Classes 35-45, 259) | 802 | 1 (0.3) | 1 (0.3) (0%) | | 1 (0.3) | 3 (0.8) (-167%) | | 0 (0) | 0 (0) (NaN%) | |
| | Cardiovascular Agents (Classes 46-56, 245, 250, 271) | 8696 | 7 (0.2) | 8 (0.2) (33%) | | 12 (0.3) | 8 (0.2) (33%) | | 6 (0.1) | 7 (0.2) (-100%) | |
| | Central Nervous System (Classes 57-77, 272) | 5912 | 10 (0.3) | 6 (0.2) (33%) | | 14 (0.5) | 8 (0.3) (40%) | | 6 (0.2) | 8 (0.3) (-50%) | |
| | Serums, Toxoids, Vaccines (Classes 185-189) | 1045 | 0 (0) | 0 (0) (NaN%) | | 0 (0) | 2 (0.4) (-Inf%) | | 0 (0) | 0 (0) (NaN%) | |
| | Dental Agents (Classes 79-83) | 52 | 0 (0) | 0 (0) (NaN%) | | 0 (0) | 0 (0) (NaN%) | | 0 (0) | 0 (0) (NaN%) | |
| | Skin & Mucous Membrane (Classes 190-213, 242) | 2337 | 4 (0.3) | 2 (0.2) (33%) | | 4 (0.3) | 3 (0.3) (0%) | | 2 (0.2) | 2 (0.2) (0%) | |
| | Diagnostic Agents (Classes 84-98, 239, 243-244, 247) | 10282 | 10 (0.2) | 8 (0.2) (0%) | | 15 (0.3) | 10 (0.2) (33%) | | 6 (0.1) | 8 (0.2) (-100%) | |
| | Smooth Muscles Relaxants (Classes 214-216) | 208 | 1 (1) | 0 (0) (100%) | | 0 (0) | 0 (0) (NaN%) | | 0 (0) | 0 (0) (NaN%) | |
| | Vitamins & Comb (Classes 217-233) | 1181 | 2 (0.3) | 1 (0.2) (33%) | | 2 (0.3) | 1 (0.2) (33%) | | 4 (0.7) | 2 (0.4) (43%) | |
| | Electrolytic, Caloric, Water (Classes 100-126, 241, 292) | 2956 | 4 (0.4) | 3 (0.3) (25%) | | 2 (0.2) | 3 (0.3) (-50%) | | 4 (0.4) | 3 (0.3) (25%) | |
| | Unclassified Agents (Classes 234-236, 251, 254, 257-258, 270) | 952 | 1 (0.2) | 0 (0) (100%) | | 3 (0.6) | 0 (0) (100%) | | 2 (0.4) | 0 (0) (100%) | |
| | Pharmaceutical Aids/Adjuvants (Class 238) | 137 | 1 (1.5) | 0 (0) (100%) | | 1 (1.5) | 0 (0) (100%) | | 0 (0) | 0 (0) (NaN%) | |
| | Eye, Ear, Nose Throat (Classes 132-146, 240, 290) | 1791 | 2 (0.2) | 3 (0.4) (-100%) | | 2 (0.2) | 2 (0.2) (0%) | | 2 (0.2) | 0 (0) (100%) | |
| Other Diabetic Therapy | Insulin Pump | 23 | 0 (0) | 0 (0) (NaN%) | | 0 (0) | 0 (0) (NaN%) | | 0 (0) | 0 (0) (NaN%) | |
| | >= 4 Strips per day | 215 | 0 (0) | 0 (0) (NaN%) | | 1 (0.9) | 0 (0) (100%) | | 1 (0.9) | 0 (0) (100%) | |
| | < 4 Strips per day | 10067 | 10 (0.2) | 8 (0.2) (0%) | | 14 (0.3) | 10 (0.2) (33%) | | 5 (0.1) | 8 (0.2) (-100%) | |

FIG. 24Q

| | | Sample size, N | Injuries, Poisonings & Toxic Effects of Drugs | |
|---|---|---|---|---|
| | | | Before flash CGM Hospitalizations (Events/100 pt-yr) | After flash CGM Hospitalizations (Events/100 pt-yr) (% reduction) |
| Medication Therapy Group | Antihistamines & Comb. (Class 1) | 532 | 2 (0.8) | 0 (0) (100%) |
| | Gastrointestinal Drugs (Classes 147-162, 273) | 2864 | 8 (0.6) | 7 (0.5) (17%) |
| | Anti-infective Agents (Classes 2-20) | 4784 | 12 (0.5) | 5 (0.2) (60%) |
| | Antineoplastic Agents (Classes 21-22, 260-265) | 205 | 0 (0) | 1 (1) (-Inf%) |
| | Autonomic Drugs (Classes 23-33) | 2327 | 6 (0.5) | 5 (0.5) (0%) |
| | Hormones & Synthetic Substitutes (Classes 165-180 246 252-253 256 266-268) | 9767 | 13 (0.3) | 10 (0.2) (33%) |
| | Immunosuppressants (Class 181) | 223 | 0 (0) | 0 (0) (NaN%) |
| | Blood Form/Coagul Agents (Classes 35-45, 259) | 802 | 6 (1.5) | 1 (0.3) (80%) |
| | Cardiovascular Agents (Classes 46-56, 245, 250, 271) | 8696 | 13 (0.3) | 9 (0.2) (33%) |
| | Central Nervous System (Classes 57-77, 272) | 5913 | 14 (0.5) | 8 (0.3) (40%) |
| | Serums, Toxoids, Vaccines (Classes 185-189) | 1045 | 3 (0.6) | 1 (0.2) (67%) |
| | Dental Agents (Classes 79-83) | 52 | 0 (0) | 0 (0) (NaN%) |
| | Skin & Mucous Membrane (Classes 190-213, 242) | 2337 | 5 (0.4) | 3 (0.3) (25%) |
| | Diagnostic Agents (Classes 84-98, 239, 243-244, 247) | 10282 | 16 (0.3) | 10 (0.2) (33%) |
| | Smooth Muscles Relaxants (Classes 214-216) | 208 | 0 (0) | 0 (0) (NaN%) |
| | Vitamins & Comb (Classes 217-233) | 1181 | 3 (0.5) | 1 (0.2) (60%) |
| | Electrolytic, Caloric, Water (Classes 100-126, 241, 292) | 2056 | 10 (1) | 2 (0.2) (80%) |
| | Unclassified Agents (Classes 234-236, 251, 254, 257-258, 270) | 952 | 3 (0.6) | 2 (0.5) (17%) |
| | Devices and Non-drug Items (Class 237) | 455 | 1 (0.4) | 1 (0.5) (-25%) |
| | Antituss/Expector/Mucolytic (Classes 128-131, 248, 255) | 1375 | 4 (0.6) | 2 (0.3) (50%) |
| | Pharmaceutical Aids/Adjuvants (Class 238) | 137 | 1 (1.5) | 0 (0) (100%) |
| | Eye, Ear, Nose Throat (Classes 132-146, 240, 290) | 1791 | 2 (0.2) | 4 (0.5) (-150%) |
| Other Diabetic Therapy | Insulin Pump | 23 | 0 (0) | 0 (0) (NaN%) |
| | >=4 Strips per day | 215 | 0 (0) | 0 (0) (NaN%) |
| | <4 Strips per day | 10067 | 16 (0.3) | 10 (0.2) (33%) |

FIG. 24R

|  |  | Sample size, N | Multiple Significant Trauma | | | Diseases & Disorders of Blood, Blood Forming Organs, Immunologic Disorders | | | Burns | |
|---|---|---|---|---|---|---|---|---|---|---|
|  |  |  | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) |
| Medication Therapy Group | Antihistamines & Comb (Class 1) | 532 | 0 (0) | 0 (0) (NaN%) | | 2 (0.8) | 2 (0.8) (0%) | | 0 (0) | 0 (0) (NaN%) |
|  | Gastrointestinal Drugs (Classes 147-162, 273) | 2864 | 0 (0) | 0 (0) (NaN%) | | 6 (0.4) | 3 (0.2) (50%) | | 0 (0) | 0 (0) (NaN%) |
|  | Anti-infective Agents (Classes 2-20) | 4784 | 0 (0) | 0 (0) (NaN%) | | 6 (0.3) | 4 (0.2) (33%) | | 0 (0) | 0 (0) (NaN%) |
|  | Antineoplastic Agents (Classes 21-22, 260-265) | 205 | 0 (0) | 0 (0) (NaN%) | | 2 (2) | 0 (0) (100%) | | 0 (0) | 0 (0) (NaN%) |
|  | Autonomic Drugs (Classes 23-33) | 2327 | 0 (0) | 0 (0) (NaN%) | | 4 (0.3) | 2 (0.2) (33%) | | 0 (0) | 0 (0) (NaN%) |
|  | Hormones & Synthetic Substitutes (Classes 165-180 246 252-253 256 266-268) | 9767 | 0 (0) | 0 (0) (NaN%) | | 4 (0.1) | 4 (0.1) (0%) | | 0 (0) | 0 (0) (NaN%) |
|  | Immunosuppressants (Class 181) | 223 | 0 (0) | 0 (0) (NaN%) | | 2 (1.8) | 0 (0) (100%) | | 0 (0) | 0 (0) (NaN%) |
|  | Blood Form/Coagul Agents (Classes 35-45, 259) | 802 | 0 (0) | 0 (0) (NaN%) | | 3 (0.8) | 1 (0.3) (62%) | | 0 (0) | 0 (0) (NaN%) |
|  | Cardiovascular Agents (Classes 46-56, 245, 250, 271) | 8696 | 0 (0) | 0 (0) (NaN%) | | 5 (0.1) | 5 (0.1) (0%) | | 0 (0) | 0 (0) (NaN%) |
|  | Central Nervous System (Classes 57-77, 272) | 5912 | 0 (0) | 0 (0) (NaN%) | | 6 (0.2) | 5 (0.2) (0%) | | 0 (0) | 0 (0) (NaN%) |
|  | Serums, Toxoids, Vaccines (Classes 185-189) | 1045 | 0 (0) | 0 (0) (NaN%) | | 1 (0.2) | 1 (0.2) (0%) | | 0 (0) | 0 (0) (NaN%) |
|  | Dental Agents (Classes 79-83) | 52 | 0 (0) | 0 (0) (NaN%) | | 0 (0) | 0 (0) (NaN%) | | 0 (0) | 0 (0) (NaN%) |
|  | Skin & Mucous Membrane (Classes 190-213, 242) | 2337 | 0 (0) | 0 (0) (NaN%) | | 5 (0.4) | 1 (0.1) (75%) | | 0 (0) | 0 (0) (NaN%) |
|  | Diagnostic Agents (Classes 84-98, 239, 243-244, 247) | 10282 | 0 (0) | 0 (0) (NaN%) | | 6 (0.1) | 5 (0.1) (0%) | | 0 (0) | 0 (0) (NaN%) |
|  | Smooth Muscles Relaxants (Classes 214-216) | 208 | 0 (0) | 0 (0) (NaN%) | | 2 (1.9) | 1 (1) (47%) | | 0 (0) | 0 (0) (NaN%) |
|  | Vitamins & Comb (Classes 217-233) | 1181 | 0 (0) | 0 (0) (NaN%) | | 5 (0.8) | 0 (0) (100%) | | 0 (0) | 0 (0) (NaN%) |
|  | Electrolytic, Caloric, Water (Classes 100-126, 241, 292) | 2056 | 0 (0) | 0 (0) (NaN%) | | 5 (0.5) | 2 (0.2) (60%) | | 0 (0) | 0 (0) (NaN%) |
|  | Unclassified Agents (Classes 234-236, 251, 254, 257-258, 270) | 952 | 0 (0) | 0 (0) (NaN%) | | 2 (0.4) | 0 (0) (100%) | | 0 (0) | 0 (0) (NaN%) |
|  | Devices and Non-drug Items (Class 237) | 455 | 0 (0) | 0 (0) (NaN%) | | 0 (0) | 0 (0) (NaN%) | | 0 (0) | 0 (0) (NaN%) |
|  | Antituss/Expector/Mucolytic (Classes 128-131, 248, 255) | 1375 | 0 (0) | 0 (0) (NaN%) | | 1 (0.1) | 1 (0.2) (-100%) | | 0 (0) | 0 (0) (NaN%) |
|  | Pharmaceutical Aids/Adjuvants (Class 238) | 137 | 0 (0) | 0 (0) (NaN%) | | 1 (1.5) | 0 (0) (100%) | | 0 (0) | 0 (0) (NaN%) |
|  | Eye, Ear, Nose Throat (Classes 132-146, 240, 290) | 1791 | 0 (0) | 0 (0) (NaN%) | | 1 (0.1) | 2 (0.2) (-100%) | | 0 (0) | 0 (0) (NaN%) |
| Other Diabetic Therapy | Insulin Pump | 23 | 0 (0) | 0 (0) (NaN%) | | 0 (0) | 0 (0) (NaN%) | | 0 (0) | 0 (0) (NaN%) |
|  | >= 4 Strips per day | 215 | 0 (0) | 0 (0) (NaN%) | | 0 (0) | 0 (0) (NaN%) | | 0 (0) | 0 (0) (NaN%) |
|  | < 4 Strips per day | 10667 | 0 (0) | 0 (0) (NaN%) | | 7 (0.1) | 5 (0.1) (0%) | | 0 (0) | 0 (0) (NaN%) |

FIG. 24S

|  |  | | Total ADE | | | Hypoglycemic ADE | |
|---|---|---|---|---|---|---|---|
|  |  | Sample size, N | Before flash CGM<br># events<br>(# affected) | After flash CGM<br># events<br>(# affected) | | Before flash CGM<br># events<br>(# affected) | After flash CGM<br># events<br>(# affected) |
|  | Full Cohort | 2463 | 221 (181) | 83 (73) | | 24 (21) | 17 (16) |
| Age | Age 18 – 49 | 670 | 70 (59) | 33 (31) | | 4 (4) | 4 (4) |
|  | Age 50 – 64 | 1627 | 129 (104) | 48 (40) | | 12 (11) | 12 (11) |
|  | Age 65+ | 166 | 22 (18) | 2 (2) | | 8 (6) | 1 (1) |
| Gender | Male | 1304 | 106 (87) | 50 (43) | | 16 (14) | 11 (10) |
|  | Female | 1159 | 115 (94) | 33 (30) | | 8 (7) | 6 (6) |
| Comorbidities | Hypertension | 2155 | 201 (166) | 74 (64) | | 24 (21) | 15 (14) |
|  | Obesity | 1479 | 128 (107) | 46 (41) | | 15 (14) | 10 (10) |
|  | Pulmonary Disease | 709 | 76 (60) | 34 (32) | | 11 (8) | 9 (8) |
|  | Depression | 724 | 89 (68) | 35 (31) | | 5 (5) | 8 (8) |
|  | Hypothyroid Disease | 646 | 46 (41) | 17 (16) | | 13 (11) | 3 (3) |
|  | Anemia | 635 | 72 (56) | 30 (26) | | 15 (12) | 8 (7) |
|  | Liver Disease | 513 | 54 (48) | 20 (17) | | 6 (6) | 2 (2) |
|  | MI or Coronary Artery Disease | 606 | 66 (50) | 27 (24) | | 11 (8) | 8 (7) |
|  | Peripheral Vascular Disease | 429 | 50 (38) | 14 (13) | | 14 (11) | 3 (3) |
|  | Renal Disease | 480 | 63 (49) | 18 (15) | | 16 (13) | 7 (6) |
|  | Heart Failure | 323 | 48 (35) | 15 (13) | | 12 (9) | 4 (4) |
|  | Alcohol | 52 | 18 (12) | 4 (4) | | 0 (0) | 0 (0) |
|  | Rheumatic | 260 | 27 (21) | 16 (13) | | 3 (3) | 3 (3) |
|  | Blood Loss | 78 | 17 (9) | 7 (5) | | 3 (2) | 3 (2) |
|  | Coagulopathy | 172 | 21 (16) | 9 (6) | | 5 (4) | 3 (3) |
|  | Lymphoma | 24 | 2 (2) | 0 (0) | | 0 (0) | 0 (0) |
|  | Fluids Lytes | 732 | 141 (110) | 38 (34) | | 18 (15) | 10 (9) |
|  | Mets | 53 | 5 (5) | 3 (3) | | 0 (0) | 1 (1) |
|  | Neuro Other | 333 | 65 (47) | 21 (19) | | 12 (10) | 3 (3) |
|  | Paralysis | 54 | 9 (9) | 5 (4) | | 1 (1) | 0 (0) |
|  | Psychoses | 169 | 16 (14) | 6 (5) | | 3 (3) | 3 (3) |
|  | PulmCircD | 85 | 16 (10) | 4 (3) | | 5 (3) | 1 (1) |
|  | Tumor | 228 | 16 (13) | 6 (5) | | 2 (2) | 0 (0) |
|  | Peptic Ulcer | 64 | 5 (3) | 2 (2) | | 2 (1) | 0 (0) |
|  | Valvular | 356 | 45 (37) | 13 (12) | | 11 (9) | 4 (4) |
|  | Weight Loss | 160 | 24 (20) | 4 (3) | | 2 (2) | 1 (1) |
| Insulin Usage Status | Insulin (short - or rapid-acting) | 2463 | 221 (181) | 83 (73) | | 24 (21) | 17 (16) |
|  | Non-insulin therapy | NA | | | | | |
| Non-Insulin Diabetes Medications | Biguanide | 1250 | 87 (74) | 31 (28) | | 3 (3) | 4 (4) |
|  | Sulfonylurea | 284 | 33 (30) | 7 (7) | | 1 (1) | 3 (3) |
|  | GLP1a | 702 | 39 (34) | 22 (19) | | 3 (3) | 6 (6) |
|  | SGLT2i | 498 | 31 (28) | 14 (12) | | 1 (1) | 4 (4) |
|  | DPP4i | 241 | 27 (25) | 8 (8) | | 1 (1) | 1 (1) |
|  | TZD | 111 | 2 (2) | 2 (2) | | 0 (0) | 0 (0) |
|  | Meglitinides | 14 | 2 (2) | 0 (0) | | 0 (0) | 0 (0) |
|  | Alpha-Glucosidase Inhibitor | 8 | 1 (1) | 3 (2) | | 0 (0) | 0 (0) |

FIG. 25A

|  |  |  | Hyperglycemic ADE | | Total ACH | |
|---|---|---|---|---|---|---|
|  |  | Sample size, N | Before flash CGM # events (# affected) | After flash CGM # events (# affected) | Before flash CGM # events (# affected) | After flash CGM # events (# affected) |
|  | Full Cohort | 2463 | 199 (166) | 68 (62) | 516 (357) | 327 (237) |
| Age | Age 18 - 49 | 670 | 66 (56) | 29 (27) | 149 (100) | 83 (57) |
|  | Age 50 - 64 | 1627 | 118 (96) | 38 (34) | 316 (221) | 221 (160) |
|  | Age 65+ | 166 | 15 (14) | 1 (1) | 51 (36) | 23 (20) |
| Gender | Male | 1304 | 91 (77) | 40 (36) | 314 (212) | 179 (134) |
|  | Female | 1159 | 108 (89) | 28 (26) | 202 (145) | 148 (103) |
| Comorbidities | Hypertension | 2155 | 179 (151) | 61 (55) | 480 (329) | 296 (214) |
|  | Obesity | 1479 | 115 (98) | 37 (34) | 340 (232) | 218 (153) |
|  | Pulmonary Disease | 709 | 65 (54) | 26 (25) | 195 (129) | 143 (104) |
|  | Depression | 724 | 84 (65) | 28 (25) | 197 (128) | 126 (89) |
|  | Hypothyroid Disease | 646 | 34 (33) | 14 (14) | 144 (96) | 105 (75) |
|  | Anemia | 635 | 57 (47) | 23 (21) | 280 (165) | 163 (116) |
|  | Liver Disease | 513 | 49 (45) | 18 (16) | 197 (127) | 88 (70) |
|  | MI or Coronary Artery Disease | 606 | 55 (45) | 19 (19) | 236 (155) | 140 (103) |
|  | Peripheral Vascular Disease | 429 | 36 (30) | 11 (11) | 178 (112) | 116 (78) |
|  | Renal Disease | 480 | 48 (40) | 12 (10) | 229 (140) | 138 (93) |
|  | Heart Failure | 323 | 37 (29) | 12 (11) | 189 (117) | 108 (78) |
|  | Alcohol | 52 | 18 (12) | 4 (4) | 30 (17) | 22 (15) |
|  | Rheumatic | 260 | 24 (20) | 14 (12) | 96 (63) | 44 (35) |
|  | Blood Loss | 78 | 14 (9) | 4 (4) | 56 (28) | 22 (16) |
|  | Coagulopathy | 172 | 16 (14) | 6 (4) | 104 (53) | 47 (30) |
|  | Lymphoma | 24 | 2 (2) | 0 (0) | 10 (6) | 2 (2) |
|  | Fluids Lytes | 732 | 124 (100) | 29 (27) | 371 (235) | 172 (115) |
|  | Mets | 53 | 5 (5) | 2 (2) | 30 (22) | 24 (11) |
|  | Neuro Other | 333 | 53 (40) | 19 (18) | 179 (103) | 99 (71) |
|  | Paralysis | 54 | 8 (8) | 5 (4) | 27 (18) | 18 (11) |
|  | Psychoses | 169 | 13 (12) | 3 (3) | 51 (30) | 39 (27) |
|  | PulmCircD | 85 | 11 (9) | 3 (3) | 42 (25) | 24 (18) |
|  | Tumor | 228 | 14 (11) | 5 (4) | 93 (59) | 69 (45) |
|  | Peptic Ulcer | 64 | 3 (3) | 2 (2) | 43 (20) | 19 (15) |
|  | Valvular | 356 | 35 (31) | 9 (9) | 174 (105) | 86 (67) |
|  | Weight Loss | 160 | 22 (19) | 3 (3) | 86 (52) | 41 (28) |
| Insulin Usage Status | Insulin (short -or rapid-acting) | 2463 | 199 (166) | 68 (62) | 516 (357) | 327 (237) |
|  | Non-insulin therapy | NA |  |  |  |  |
| Non-Insulin Diabetes Medications | Biguanide | 1250 | 85 (72) | 28 (26) | 173 (130) | 104 (82) |
|  | Sulfonylurea | 284 | 32 (29) | 4 (4) | 57 (44) | 36 (27) |
|  | GLP1a | 702 | 36 (31) | 16 (14) | 106 (75) | 68 (50) |
|  | SGLT2i | 498 | 30 (28) | 10 (9) | 49 (38) | 31 (24) |
|  | DPP4i | 241 | 26 (24) | 7 (7) | 40 (30) | 31 (21) |
|  | TZD | 111 | 2 (2) | 2 (2) | 16 (10) | 10 (6) |
|  | Meglitinides | 14 | 2 (2) | 0 (0) | 8 (5) | 4 (3) |
|  | Alpha-Glucosidase Inhibitor | 8 | 1 (1) | 3 (2) | 2 (2) | 3 (2) |

FIG. 25B

| | | Sample size, N | Total ACH | | | Circulatory System | |
|---|---|---|---|---|---|---|---|
| | | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) |
| | Full Cohort | 2463 | 516 (42) | 327 (28.1) (33%) | | 96 (7.8) | 80 (6.9) (12%) |
| Age | Age 18 – 49 | 670 | 149 (44.6) | 83 (26.2) (41%) | | 14 (4.2) | 9 (2.8) (33%) |
| | Age 50 – 64 | 1627 | 316 (39) | 221 (28.6) (27%) | | 69 (8.5) | 61 (7.9) (7%) |
| | Age 65+ | 166 | 51 (61.7) | 23 (30.4) (51%) | | 13 (15.7) | 10 (13.2) (16%) |
| Gender | Male | 1304 | 314 (48.3) | 179 (29) (40%) | | 57 (8.8) | 48 (7.8) (11%) |
| | Female | 1159 | 202 (35) | 148 (27) (23%) | | 39 (6.8) | 32 (5.8) (15%) |
| Comorbidities | Hypertension | 2155 | 480 (44.7) | 296 (29) (35%) | | 94 (8.8) | 78 (7.6) (14%) |
| | Obesity | 1479 | 340 (46.1) | 218 (31.2) (32%) | | 60 (8.1) | 56 (8) (1%) |
| | Pulmonary Disease | 709 | 195 (55.2) | 143 (42.7) (23%) | | 35 (9.9) | 37 (11.1) (-12%) |
| | Depression | 724 | 197 (54.6) | 126 (37) (32%) | | 23 (6.4) | 34 (10) (-56%) |
| | Hypothyroid Disease | 646 | 144 (44.7) | 105 (34.2) (23%) | | 34 (10.6) | 22 (7.2) (32%) |
| | Anemia | 635 | 280 (88.5) | 163 (54.5) (38%) | | 55 (17.4) | 47 (15.7) (10%) |
| | Liver Disease | 513 | 197 (77.1) | 88 (36.5) (53%) | | 21 (8.2) | 18 (7.5) (9%) |
| | MI or Coronary Artery Disease | 606 | 236 (78.2) | 140 (49.7) (36%) | | 78 (25.8) | 49 (17.4) (33%) |
| | Peripheral Vascular Disease | 429 | 178 (83.3) | 116 (58.7) (30%) | | 41 (19.2) | 42 (21.2) (-10%) |
| | Renal Disease | 480 | 229 (95.7) | 138 (61.4) (36%) | | 56 (23.4) | 54 (24) (-3%) |
| | Heart Failure | 323 | 189 (117.4) | 108 (72.5) (38%) | | 60 (37.3) | 42 (28.2) (24%) |
| | Alcohol | 52 | 30 (115.8) | 22 (88.1) (24%) | | 1 (3.9) | 3 (12) (-208%) |
| | Rheumatic | 260 | 96 (74.1) | 44 (35.9) (52%) | | 19 (14.7) | 9 (7.3) (50%) |
| | Blood Loss | 78 | 56 (144.1) | 22 (62.1) (57%) | | 11 (28.3) | 5 (14.1) (50%) |
| | Coagulopathy | 172 | 104 (121.3) | 47 (59.1) (51%) | | 16 (18.3) | 17 (21.4) (-14%) |
| | Lymphoma | 24 | 10 (83.6) | 2 (18.2) (78%) | | 1 (8.4) | 0 (0) (100%) |
| | Fluids Lytes | 732 | 371 (101.7) | 172 (50.4) (50%) | | 73 (20) | 52 (15.2) (24%) |
| | Mets | 53 | 30 (113.6) | 24 (97) (15%) | | 3 (11.4) | 1 (4) (65%) |
| | Neuro Other | 333 | 179 (107.9) | 99 (63) (42%) | | 21 (12.7) | 22 (14) (-10%) |
| | Paralysis | 54 | 27 (100.3) | 18 (74.2) (26%) | | 2 (7.4) | 1 (4.1) (45%) |
| | Psychoses | 169 | 51 (60.6) | 39 (49.4) (18%) | | 2 (2.4) | 8 (10.1) (-321%) |
| | PulmCircD | 85 | 42 (99.2) | 24 (62.6) (37%) | | 5 (11.8) | 5 (13) (-10%) |
| | Tumor | 228 | 93 (81.9) | 69 (64.7) (21%) | | 12 (10.6) | 9 (8.4) (21%) |
| | Peptic Ulcer | 64 | 43 (134.8) | 19 (63.4) (53%) | | 4 (12.5) | 2 (6.7) (46%) |
| | Valvular | 356 | 174 (98.1) | 86 (51.9) (47%) | | 51 (28.8) | 34 (20.5) (29%) |
| | Weight Loss | 160 | 86 (107.9) | 41 (55.9) (48%) | | 4 (5) | 3 (10.9) (-118%) |
| Insulin Usage Status | Insulin (short- or rapid-acting) | 2463 | 516 (42) | 327 (28.1) (33%) | | 96 (7.8) | 80 (6.9) (12%) |
| | Non-insulin therapy | NA | | | | | |
| Non-Insulin Diabetes Medications | Biguanide | 1250 | 173 (27.8) | 104 (17.5) (37%) | | 23 (3.7) | 20 (3.4) (8%) |
| | Sulfonylurea | 284 | 57 (40.3) | 36 (26.3) (35%) | | 8 (5.7) | 6 (4.4) (23%) |
| | GLP1a | 702 | 106 (30.3) | 68 (20.4) (33%) | | 21 (6) | 19 (5.7) (5%) |
| | SGLT2i | 498 | 49 (19.7) | 31 (13.1) (34%) | | 6 (2.4) | 3 (1.3) (46%) |
| | DPP4i | 241 | 40 (33.3) | 31 (27.1) (19%) | | 7 (5.8) | 7 (6.1) (-5%) |
| | TZD | 111 | 16 (28.9) | 10 (18.9) (35%) | | 4 (7.2) | 1 (1.9) (74%) |
| | Meglitinides | 14 | 8 (114.7) | 4 (57.3) (50%) | | 4 (57.3) | 0 (0) (100%) |
| | Alpha-Glucosidase Inhibitor | 8 | 2 (50.2) | 3 (79.5) (-58%) | | 0 (0) | 1 (26.5) (-Inf%) |

FIG. 25C

| | | Sample size, N | Endocrine, Nutritional and Metabolic System | | Infectious and Parasitic DDs (Systemic or unspecified sites) | |
|---|---|---|---|---|---|---|
| | | | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
| | Full Cohort | 2463 | 78 (6.4) | 30 (2.6) (59%) | 59 (4.8) | 33 (2.8) (42%) |
| Age | Age 18 – 49 | 670 | 29 (8.7) | 15 (4.7) (46%) | 16 (4.8) | 9 (2.8) (42%) |
| | Age 50 – 64 | 1627 | 48 (5.9) | 15 (1.9) (68%) | 39 (4.8) | 22 (2.8) (42%) |
| | Age 65+ | 166 | 1 (1.2) | 0 (0) (100%) | 4 (4.8) | 2 (2.6) (46%) |
| Gender | Male | 1304 | 45 (6.9) | 18 (2.9) (58%) | 37 (5.7) | 17 (2.8) (51%) |
| | Female | 1159 | 33 (5.7) | 12 (2.2) (61%) | 22 (3.8) | 16 (2.9) (24%) |
| Comorbidities | Hypertension | 2155 | 70 (6.5) | 25 (2.4) (63%) | 54 (5) | 29 (2.8) (44%) |
| | Obesity | 1479 | 44 (6) | 24 (3.4) (43%) | 41 (5.6) | 24 (3.4) (39%) |
| | Pulmonary Disease | 709 | 21 (5.9) | 11 (3.3) (44%) | 19 (5.4) | 8 (2.4) (56%) |
| | Depression | 724 | 28 (7.8) | 16 (4.7) (40%) | 21 (5.8) | 11 (3.2) (45%) |
| | Hypothyroid Disease | 646 | 15 (4.7) | 13 (4.2) (11%) | 9 (2.8) | 8 (2.6) (7%) |
| | Anemia | 635 | 34 (10.7) | 12 (4) (63%) | 30 (9.5) | 14 (4.7) (51%) |
| | Liver Disease | 513 | 32 (12.5) | 7 (2.9) (77%) | 19 (7.4) | 9 (3.7) (50%) |
| | MI or Coronary Artery Disease | 606 | 24 (7.9) | 13 (4.6) (42%) | 21 (7) | 13 (4.6) (34%) |
| | Peripheral Vascular Disease | 429 | 22 (10.3) | 10 (5.1) (50%) | 18 (8.4) | 13 (6.6) (21%) |
| | Renal Disease | 480 | 22 (9.2) | 6 (2.7) (71%) | 22 (9.2) | 11 (4.9) (47%) |
| | Heart Failure | 323 | 15 (9.3) | 6 (4) (57%) | 21 (13) | 11 (7.4) (43%) |
| | Alcohol | 52 | 8 (30.9) | 1 (4) (87%) | 1 (3.9) | 4 (16) (-310%) |
| | Rheumatic | 260 | 7 (5.4) | 3 (2.4) (56%) | 15 (11.6) | 4 (3.3) (72%) |
| | Blood Loss | 78 | 2 (5.1) | 2 (5.6) (-10%) | 4 (10.3) | 0 (0) (100%) |
| | Coagulopathy | 172 | 11 (12.8) | 2 (2.5) (80%) | 8 (9.3) | 2 (2.5) (73%) |
| | Lymphoma | 24 | 1 (8.4) | 1 (9.1) (-8%) | 2 (16.7) | 0 (0) (100%) |
| | Fluids Lytes | 732 | 59 (16.2) | 12 (3.5) (78%) | 45 (12.3) | 17 (5) (59%) |
| | Mets | 53 | 2 (7.6) | 4 (16.2) (-113%) | 4 (15.1) | 2 (8.1) (46%) |
| | Neuro Other | 333 | 17 (10.2) | 11 (7) (31%) | 26 (15.7) | 9 (5.7) (64%) |
| | Paralysis | 54 | 2 (7.4) | 3 (12.4) (-68%) | 4 (14.9) | 5 (20.6) (-38%) |
| | Psychoses | 169 | 2 (2.4) | 8 (10.1) (-321%) | 5 (5.9) | 4 (5.1) (14%) |
| | PulmCircD | 85 | 2 (4.7) | 3 (7.8) (-66%) | 5 (11.8) | 3 (7.8) (34%) |
| | Tumor | 228 | 10 (8.8) | 6 (5.6) (36%) | 9 (7.9) | 6 (5.6) (29%) |
| | Peptic Ulcer | 64 | 1 (3.1) | 2 (6.7) (-116%) | 5 (15.7) | 0 (0) (100%) |
| | Valvular | 356 | 12 (6.8) | 5 (3) (56%) | 20 (11.3) | 8 (4.8) (58%) |
| | Weight Loss | 160 | 9 (11.3) | 3 (4.1) (64%) | 14 (17.6) | 8 (10.9) (38%) |
| Insulin Usage Status | Insulin (short -or rapid-acting) | 2463 | 78 (6.4) | 30 (2.6) (59%) | 59 (4.8) | 33 (2.8) (42%) |
| | Non-insulin therapy | NA | | | | |
| Non-Insulin Diabetes Medications | Biguanide | 1250 | 29 (4.7) | 12 (2) (57%) | 26 (4.2) | 10 (1.7) (60%) |
| | Sulfonylurea | 384 | 9 (6.4) | 5 (3.7) (42%) | 7 (4.9) | 3 (2.2) (55%) |
| | GLP1a | 702 | 11 (3.1) | 11 (3.3) (-6%) | 9 (2.6) | 7 (2.1) (19%) |
| | SGLT2i | 498 | 10 (4) | 8 (3.4) (15%) | 5 (2) | 3 (1.3) (35%) |
| | DPP4i | 241 | 7 (5.8) | 5 (4.4) (24%) | 7 (5.8) | 3 (2.6) (55%) |
| | TZD | 111 | 3 (5.4) | 2 (3.8) (30%) | 2 (3.6) | 0 (0) (100%) |
| | Meglitinides | 14 | 1 (14.3) | 0 (0) (100%) | 0 (0) | 1 (14.3) (-Inf%) |
| | Alpha-Glucosidase Inhibitor | 8 | 0 (0) | 0 (0) (NaN%) | 1 (25.1) | 0 (0) (100%) |

FIG. 25D

|  |  | Sample size, N | Respiratory System ||| Kidney and Urinary Tract |||
|---|---|---|---|---|---|---|---|---|
|  |  |  | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | |
|  | Full Cohort | 2463 | 43 (3.5) | 25 (2.1) (40%) | | 41 (3.3) | 20 (1.7) (48%) | |
| Age | Age 18 - 49 | 670 | 20 (6) | 8 (2.5) (58%) | | 14 (4.2) | 3 (0.9) (79%) | |
|  | Age 50 - 64 | 1627 | 22 (2.7) | 16 (2.1) (22%) | | 17 (2.1) | 15 (1.9) (10%) | |
|  | Age 65+ | 166 | 1 (1.2) | 1 (1.3) (-8%) | | 10 (12.1) | 2 (2.6) (79%) | |
| Gender | Male | 1304 | 24 (3.7) | 14 (2.3) (38%) | | 27 (4.2) | 7 (1.1) (74%) | |
|  | Female | 1159 | 19 (3.3) | 11 (2) (39%) | | 14 (2.4) | 13 (2.4) (0%) | |
| Comorbidities | Hypertension | 2155 | 33 (3.1) | 21 (2.1) (32%) | | 40 (3.7) | 20 (2) (46%) | |
|  | Obesity | 1479 | 25 (3.4) | 16 (2.3) (32%) | | 28 (3.8) | 10 (1.4) (63%) | |
|  | Pulmonary Disease | 709 | 28 (7.9) | 18 (5.4) (32%) | | 18 (5.1) | 13 (3.9) (24%) | |
|  | Depression | 724 | 16 (4.4) | 6 (1.8) (59%) | | 17 (4.7) | 8 (2.3) (51%) | |
|  | Hypothyroid Disease | 646 | 16 (5) | 8 (2.6) (48%) | | 8 (2.5) | 5 (1.6) (36%) | |
|  | Anemia | 635 | 19 (6) | 11 (3.7) (38%) | | 32 (10.1) | 13 (4.3) (57%) | |
|  | Liver Disease | 513 | 16 (6.3) | 6 (2.5) (60%) | | 16 (6.3) | 4 (1.7) (73%) | |
|  | MI or Coronary Artery Disease | 606 | 12 (4) | 10 (3.6) (10%) | | 23 (7.6) | 7 (2.5) (67%) | |
|  | Peripheral Vascular Disease | 429 | 8 (3.7) | 7 (3.5) (5%) | | 19 (8.9) | 9 (4.6) (48%) | |
|  | Renal Disease | 480 | 12 (5) | 8 (3.6) (28%) | | 32 (13.4) | 13 (5.8) (57%) | |
|  | Heart Failure | 323 | 9 (5.6) | 10 (6.7) (-20%) | | 14 (8.7) | 5 (3.4) (61%) | |
|  | Alcohol | 52 | 3 (11.6) | 0 (0) (100%) | | 1 (3.9) | 0 (0) (100%) | |
|  | Rheumatic | 260 | 10 (7.7) | 2 (1.6) (79%) | | 4 (3.1) | 2 (1.6) (48%) | |
|  | Blood Loss | 78 | 2 (5.1) | 3 (8.5) (-67%) | | 7 (18) | 1 (2.8) (84%) | |
|  | Coagulopathy | 172 | 9 (10.5) | 5 (6.3) (40%) | | 10 (11.7) | 5 (6.3) (46%) | |
|  | Lymphoma | 24 | 3 (25.1) | 0 (0) (100%) | | 0 (0) | 0 (0) (NaN%) | |
|  | Fluids Lytes | 732 | 27 (7.4) | 11 (3.2) (57%) | | 37 (10.1) | 13 (3.8) (62%) | |
|  | Mets | 53 | 3 (11.4) | 1 (4) (65%) | | 2 (7.6) | 2 (8.1) (-7%) | |
|  | Neuro Other | 333 | 11 (6.6) | 6 (3.8) (42%) | | 18 (10.8) | 5 (3.2) (70%) | |
|  | Paralysis | 54 | 3 (11.1) | 2 (8.2) (26%) | | 1 (3.7) | 0 (0) (100%) | |
|  | Psychoses | 169 | 8 (9.5) | 0 (0) (100%) | | 6 (7.1) | 0 (0) (100%) | |
|  | PulmCircD | 85 | 4 (9.4) | 2 (5.2) (45%) | | 3 (7.1) | 3 (7.8) (-10%) | |
|  | Tumor | 228 | 13 (11.4) | 7 (6.6) (42%) | | 7 (6.2) | 5 (4.7) (24%) | |
|  | Peptic Ulcer | 64 | 4 (12.5) | 1 (3.3) (74%) | | 1 (3.1) | 1 (3.3) (-6%) | |
|  | Valvular | 356 | 13 (7.3) | 9 (5.4) (26%) | | 16 (9) | 5 (3) (67%) | |
|  | Weight Loss | 160 | 8 (10) | 2 (2.7) (73%) | | 11 (13.8) | 2 (2.7) (80%) | |
| Insulin Usage Status | Insulin (short -or rapid-acting) | 2463 | 43 (3.5) | 25 (2.1) (40%) | | 41 (3.3) | 20 (1.7) (48%) | |
|  | Non-insulin therapy | NA | | 1 (26.5) (-Inf%) | | | | |
| Non-Insulin Diabetes Medications | Biguanide | 1250 | 16 (2.6) | 5 (0.8) (69%) | | 6 (1) | 4 (0.7) (30%) | |
|  | Sulfonylurea | 284 | 4 (2.8) | 2 (1.5) (46%) | | 2 (1.4) | 2 (1.5) (-7%) | |
|  | GLP1a | 702 | 9 (2.6) | 2 (0.6) (77%) | | 10 (2.9) | 1 (0.3) (90%) | |
|  | SGLT2i | 498 | 6 (2.4) | 1 (0.4) (83%) | | 3 (1.2) | 1 (0.4) (67%) | |
|  | DPP4i | 241 | 2 (1.7) | 2 (1.8) (-6%) | | 4 (3.3) | 2 (1.8) (45%) | |
|  | TZD | 111 | 2 (3.6) | 0 (0) (100%) | | 0 (0) | 1 (1.9) (-Inf%) | |
|  | Meglitinides | 14 | 0 (0) | 0 (0) (NaN%) | | 0 (0) | 0 (0) (NaN%) | |
|  | Alpha-Glucosidase Inhibitor | 8 | 0 (0) | 1 (26.5) (-Inf%) | | 0 (0) | 0 (0) (NaN%) | |

FIG. 25E

| | | Sample size, N | Musculoskeletal System and Connective Tissue | | Digestive System | |
|---|---|---|---|---|---|---|
| | | | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
| | Full Cohort | 2463 | 39 (3.2) | 32 (2.7) (16%) | 38 (3.1) | 32 (2.7) (13%) |
| Age | Age 18 – 49 | 670 | 7 (2.1) | 7 (2.2) (-5%) | 8 (2.4) | 8 (2.5) (-4%) |
| | Age 50 – 64 | 1627 | 24 (3) | 25 (3.2) (-7%) | 25 (3.1) | 21 (2.7) (13%) |
| | Age 65+ | 166 | 8 (9.7) | 0 (0) (100%) | 5 (6) | 3 (4) (33%) |
| Gender | Male | 1304 | 25 (3.8) | 14 (2.3) (39%) | 21 (3.2) | 22 (3.6) (-12%) |
| | Female | 1159 | 14 (2.4) | 18 (3.3) (-38%) | 17 (2.9) | 10 (1.8) (38%) |
| Comorbidities | Hypertension | 2155 | 37 (3.4) | 30 (2.9) (15%) | 37 (3.4) | 29 (2.8) (18%) |
| | Obesity | 1479 | 28 (3.8) | 23 (3.3) (13%) | 30 (4.1) | 18 (2.6) (37%) |
| | Pulmonary Disease | 709 | 15 (4.2) | 16 (4.8) (-14%) | 12 (3.4) | 10 (3) (12%) |
| | Depression | 724 | 17 (4.7) | 12 (3.5) (26%) | 13 (3.6) | 9 (2.6) (28%) |
| | Hypothyroid Disease | 646 | 12 (3.7) | 12 (3.9) (-5%) | 11 (3.4) | 7 (2.3) (32%) |
| | Anemia | 635 | 21 (6.6) | 13 (4.3) (35%) | 21 (6.6) | 18 (6) (9%) |
| | Liver Disease | 513 | 12 (4.7) | 7 (2.9) (38%) | 19 (7.4) | 13 (5.4) (27%) |
| | MI or Coronary Artery Disease | 606 | 16 (5.3) | 15 (5.3) (0%) | 14 (4.6) | 9 (3.2) (30%) |
| | Peripheral Vascular Disease | 429 | 20 (9.4) | 12 (6.1) (35%) | 10 (4.7) | 5 (2.5) (47%) |
| | Renal Disease | 480 | 22 (9.2) | 8 (3.6) (61%) | 15 (6.3) | 16 (7.1) (-13%) |
| | Heart Failure | 323 | 15 (9.3) | 11 (7.4) (20%) | 11 (6.8) | 7 (4.7) (31%) |
| | Alcohol | 52 | 0 (0) | 0 (0) (NaN%) | 1 (3.9) | 2 (8) (-105%) |
| | Rheumatic | 260 | 13 (10) | 7 (5.7) (43%) | 3 (2.3) | 4 (3.3) (-43%) |
| | Blood Loss | 78 | 6 (15.4) | 1 (2.8) (82%) | 6 (15.4) | 5 (14.1) (8%) |
| | Coagulopathy | 172 | 7 (8.2) | 1 (1.3) (84%) | 7 (8.2) | 3 (3.8) (54%) |
| | Lymphoma | 24 | 1 (8.4) | 0 (0) (100%) | 1 (8.4) | 0 (0) (100%) |
| | Fluids Lytes | 732 | 27 (7.4) | 15 (4.4) (41%) | 18 (4.9) | 17 (5) (-2%) |
| | Mets | 53 | 2 (7.6) | 0 (0) (100%) | 4 (15.1) | 3 (12.1) (20%) |
| | Neuro Other | 333 | 10 (6) | 7 (4.5) (25%) | 8 (4.8) | 8 (5.1) (-6%) |
| | Paralysis | 54 | 0 (0) | 3 (12.4) (-Inf%) | 0 (0) | 1 (4.1) (-Inf%) |
| | Psychoses | 169 | 3 (3.6) | 3 (3.8) (-6%) | 2 (2.4) | 2 (2.5) (-4%) |
| | PulmCircD | 85 | 5 (11.8) | 2 (5.2) (56%) | 3 (7.1) | 3 (7.8) (-10%) |
| | Tumor | 228 | 7 (6.2) | 4 (3.8) (39%) | 9 (7.9) | 7 (6.6) (16%) |
| | Peptic Ulcer | 64 | 2 (6.3) | 7 (3) (-150%) | 9 (28.2) | 4 (13.4) (52%) |
| | Valvular | 356 | 15 (8.5) | 8 (4.8) (44%) | 8 (4.5) | 5 (3) (33%) |
| | Weight Loss | 160 | 7 (8.8) | 4 (5.5) (38%) | 6 (7.5) | 3 (4.1) (45%) |
| Insulin Usage Status | Insulin (short- or rapid-acting) | 2463 | 39 (3.2) | 32 (2.7) (16%) | 38 (3.1) | 32 (2.7) (13%) |
| | Non-insulin therapy | NA | | | | |
| Non-Insulin Diabetes Medications | Biguanide | 1250 | 13 (2.1) | 10 (1.7) (19%) | 18 (2.9) | 12 (2) (31%) |
| | Sulfonylurea | 284 | 7 (4.9) | 4 (2.9) (41%) | 4 (2.8) | 4 (2.9) (-4%) |
| | GLP1a | 702 | 11 (3.1) | 7 (2.1) (32%) | 12 (3.4) | 2 (0.6) (82%) |
| | SGLT2i | 498 | 3 (1.2) | 7 (3) (-150%) | 5 (2) | 3 (1.3) (35%) |
| | DPP4i | 241 | 5 (4.2) | 4 (3.5) (17%) | 0 (0) | 4 (3.5) (-Inf%) |
| | TZD | 111 | 2 (3.6) | 0 (0) (100%) | 0 (0) | 2 (3.8) (-Inf%) |
| | Meglitinides | 14 | 0 (0) | 1 (14.3) (-Inf%) | 1 (14.3) | 2 (28.7) (-101%) |
| | Alpha-Glucosidase Inhibitor | 8 | 0 (0) | 0 (0) (NaN%) | 0 (0) | 0 (0) (NaN%) |

FIG. 25F

|  |  | Sample size, N | Nervous System | | Hepatobiliary System and Pancreas | |
|---|---|---|---|---|---|---|
|  |  |  | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
|  | Full Cohort | 2463 | 36 (2.9) | 19 (1.6) (45%) | 30 (2.4) | 16 (1.4) (42%) |
| Age | Age 18 – 49 | 670 | 11 (3.3) | 4 (1.3) (61%) | 15 (4.5) | 7 (2.2) (51%) |
|  | Age 50 – 64 | 1627 | 21 (2.6) | 12 (1.6) (38%) | 15 (1.9) | 9 (1.2) (37%) |
|  | Age 65+ | 166 | 4 (4.8) | 3 (4) (17%) | 0 (0) | 0 (0) (NaN%) |
| Gender | Male | 1304 | 24 (3.7) | 7 (1.1) (70%) | 17 (2.6) | 13 (2.1) (19%) |
|  | Female | 1159 | 12 (2.1) | 12 (2.2) (-5%) | 13 (2.3) | 3 (0.5) (78%) |
| Comorbidities | Hypertension | 2155 | 34 (3.2) | 17 (1.7) (47%) | 28 (2.6) | 16 (1.6) (38%) |
|  | Obesity | 1479 | 23 (3.1) | 15 (2.1) (32%) | 18 (2.4) | 12 (1.7) (29%) |
|  | Pulmonary Disease | 709 | 18 (5.1) | 10 (3) (41%) | 10 (2.8) | 3 (0.9) (68%) |
|  | Depression | 724 | 17 (4.7) | 7 (2.1) (55%) | 16 (4.4) | 8 (2.3) (48%) |
|  | Hypothyroid Disease | 646 | 8 (2.5) | 6 (2) (20%) | 15 (4.7) | 8 (2.6) (45%) |
|  | Anemia | 635 | 19 (6) | 7 (2.3) (62%) | 21 (6.6) | 9 (3) (55%) |
|  | Liver Disease | 513 | 10 (3.9) | 4 (1.7) (56%) | 26 (10.2) | 11 (4.6) (55%) |
|  | MI or Coronary Artery Disease | 606 | 17 (5.6) | 6 (2.1) (62%) | 12 (4) | 2 (1.1) (48%) |
|  | Peripheral Vascular Disease | 429 | 16 (7.5) | 3 (1.5) (80%) | 8 (3.7) | 4 (2) (46%) |
|  | Renal Disease | 480 | 17 (7.1) | 6 (2.7) (62%) | 12 (5) | 8 (3.6) (28%) |
|  | Heart Failure | 323 | 16 (9.9) | 3 (2) (80%) | 9 (5.6) | 5 (3.4) (39%) |
|  | Alcohol | 52 | 1 (3.9) | 1 (4) (-3%) | 6 (23.2) | 6 (24) (-3%) |
|  | Rheumatic | 260 | 9 (6.9) | 4 (3.3) (52%) | 4 (3.1) | 4 (3.1) (-6%) |
|  | Blood Loss | 78 | 6 (15.4) | 2 (2.8) (82%) | 4 (18) | 2 (5.6) (69%) |
|  | Coagulopathy | 172 | 8 (9.3) | 1 (1.3) (86%) | 18 (21) | 7 (8.8) (58%) |
|  | Lymphoma | 24 | 1 (8.4) | 0 (0) (100%) | 0 (0) | 0 (0) (NaN%) |
|  | Fluids Lytes | 732 | 23 (6.3) | 9 (2.6) (59%) | 24 (6.6) | 12 (3.5) (47%) |
|  | Mets | 55 | 1 (3.8) | 4 (16.2) (-326%) | 6 (22.7) | 3 (12.1) (47%) |
|  | Neuro Other | 333 | 27 (16.3) | 8 (5.1) (69%) | 15 (9) | 7 (4.5) (50%) |
|  | Paralysis | 54 | 12 (44.6) | 4 (4.1) (91%) | 0 (0) | 2 (8.2) (-Inf%) |
|  | Psychoses | 169 | 4 (4.7) | 2 (2.5) (47%) | 9 (10.7) | 6 (7.6) (29%) |
|  | PulmCircD | 85 | 7 (16.5) | 0 (0) (100%) | 1 (2.4) | 2 (5.2) (-117%) |
|  | Tumor | 228 | 6 (5.3) | 6 (5.6) (-6%) | 11 (9.7) | 9 (8.4) (13%) |
|  | Peptic Ulcer | 64 | 6 (18.8) | 1 (3.3) (82%) | 6 (18.8) | 2 (6.7) (64%) |
|  | Valvular | 356 | 17 (9.6) | 3 (1.8) (81%) | 9 (5.1) | 3 (1.8) (65%) |
|  | Weight Loss | 160 | 7 (8.8) | 1 (1.4) (84%) | 11 (13.8) | 3 (4.1) (70%) |
| Insulin Usage Status | Insulin (short- or rapid-acting) | 2463 | 36 (2.9) | 19 (1.6) (45%) | 30 (2.4) | 16 (1.4) (42%) |
|  | Non-insulin therapy | NA |  |  |  |  |
| Non-Insulin Diabetes Medications | Biguanide | 1250 | 11 (1.8) | 10 (1.7) (6%) | 7 (1.1) | 3 (0.5) (55%) |
|  | Sulfonylurea | 284 | 3 (2.1) | 2 (1.5) (29%) | 3 (2.1) | 2 (1.5) (29%) |
|  | GLP1a | 702 | 9 (2.6) | 6 (1.8) (31%) | 4 (1.1) | 3 (0.9) (18%) |
|  | SGLT2i | 498 | 2 (0.8) | 1 (0.4) (50%) | 6 (2.4) | 3 (1.3) (46%) |
|  | DPP4i | 241 | 2 (1.7) | 2 (1.8) (-6%) | 1 (0.8) | 1 (0.9) (-12%) |
|  | TZD | 111 | 1 (1.8) | 3 (5.7) (-217%) | 0 (0) | 1 (1.9) (-Inf%) |
|  | Meglitinides | 14 | 1 (14.3) | 0 (0) (NaN%) | 0 (0) | 0 (0) (NaN%) |
|  | Alpha-Glucosidase Inhibitor | 8 | 0 (0) | 0 (0) (NaN%) | 0 (0) | 0 (0) (NaN%) |

FIG. 25G

|  |  |  | Skin, Subcutaneous Tissue and Breast | | Diseases & Disorders of the Eye | |
|---|---|---|---|---|---|---|
|  |  | Sample size, N | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
|  | Full Cohort | 2463 | 13 (1.1) | 8 (0.7) (36%) | 0 (0) | 0 (0) (NaN%) |
| Age | Age 18 - 49 | 670 | 3 (0.9) | 2 (0.6) (33%) | 0 (0) | 0 (0) (NaN%) |
|  | Age 50 - 64 | 1627 | 8 (1) | 6 (0.8) (20%) | 0 (0) | 0 (0) (NaN%) |
|  | Age 65+ | 166 | 2 (2.4) | 0 (0) (100%) | 0 (0) | 0 (0) (NaN%) |
| Gender | Male | 1304 | 7 (1.1) | 4 (0.6) (45%) | 0 (0) | 0 (0) (NaN%) |
|  | Female | 1159 | 6 (1) | 4 (0.7) (30%) | 0 (0) | 0 (0) (NaN%) |
| Comorbidities | Hypertension | 2155 | 12 (1.1) | 6 (0.6) (45%) | 0 (0) | 0 (0) (NaN%) |
|  | Obesity | 1479 | 10 (1.4) | 2 (0.3) (79%) | 0 (0) | 0 (0) (NaN%) |
|  | Pulmonary Disease | 709 | 2 (0.6) | 2 (0.6) (0%) | 0 (0) | 0 (0) (NaN%) |
|  | Depression | 724 | 4 (1.1) | 2 (0.6) (45%) | 0 (0) | 0 (0) (NaN%) |
|  | Hypothyroid Disease | 646 | 5 (1.6) | 3 (1) (38%) | 0 (0) | 0 (0) (NaN%) |
|  | Anemia | 635 | 7 (2.2) | 5 (1.7) (23%) | 0 (0) | 0 (0) (NaN%) |
|  | Liver Disease | 513 | 4 (1.6) | 3 (1.2) (25%) | 0 (0) | 0 (0) (NaN%) |
|  | MI or Coronary Artery Disease | 606 | 5 (1.7) | 3 (1.1) (35%) | 0 (0) | 0 (0) (NaN%) |
|  | Peripheral Vascular Disease | 429 | 4 (1.9) | 4 (2) (-5%) | 0 (0) | 0 (0) (NaN%) |
|  | Renal Disease | 480 | 4 (1.7) | 4 (1.8) (-6%) | 0 (0) | 0 (0) (NaN%) |
|  | Heart Failure | 323 | 4 (2.5) | 2 (1.3) (48%) | 0 (0) | 0 (0) (NaN%) |
|  | Alcohol | 52 | 0 (0) | 0 (0) (NaN%) | 0 (0) | 0 (0) (NaN%) |
|  | Rheumatic | 260 | 3 (2.3) | 3 (1.9) (47%) | 0 (0) | 0 (0) (NaN%) |
|  | Blood Loss | 78 | 1 (2.6) | 0 (0) (100%) | 0 (0) | 0 (0) (NaN%) |
|  | Coagulopathy | 172 | 1 (1.2) | 1 (1.3) (-8%) | 0 (0) | 0 (0) (NaN%) |
|  | Lymphoma | 24 | 0 (0) | 0 (0) (NaN%) | 0 (0) | 0 (0) (NaN%) |
|  | Fluids Lytes | 732 | 7 (1.9) | 4 (1.2) (37%) | 0 (0) | 0 (0) (NaN%) |
|  | Mets | 53 | 0 (0) | 1 (4) (-Inf%) | 0 (0) | 0 (0) (NaN%) |
|  | Neuro Other | 333 | 6 (3.6) | 3 (1.9) (47%) | 0 (0) | 0 (0) (NaN%) |
|  | Paralysis | 54 | 1 (3.7) | 0 (0) (100%) | 0 (0) | 0 (0) (NaN%) |
|  | Psychoses | 169 | 1 (1.2) | 1 (1.3) (-8%) | 0 (0) | 0 (0) (NaN%) |
|  | PulmCircD | 85 | 3 (7.1) | 0 (0) (100%) | 0 (0) | 0 (0) (NaN%) |
|  | Tumor | 228 | 0 (0) | 4 (3.8) (-Inf%) | 0 (0) | 0 (0) (NaN%) |
|  | Peptic Ulcer | 64 | 2 (6.3) | 1 (3.3) (48%) | 0 (0) | 0 (0) (NaN%) |
|  | Valvular | 356 | 3 (1.7) | 1 (0.6) (65%) | 0 (0) | 0 (0) (NaN%) |
|  | Weight Loss | 160 | 3 (3.8) | 0 (0) (100%) | 0 (0) | 0 (0) (NaN%) |
| Insulin Usage Status | Insulin (short -or rapid-acting) | 2463 | 13 (1.1) | 8 (0.7) (36%) | 0 (0) | 0 (0) (NaN%) |
|  | Non-insulin therapy | NA |  |  |  |  |
| Non-Insulin Diabetes Medications | Biguanide | 1250 | 6 (1) | 4 (0.7) (30%) | 0 (0) | 0 (0) (NaN%) |
|  | Sulfonylurea | 284 | 2 (1.4) | 1 (0.7) (50%) | 0 (0) | 0 (0) (NaN%) |
|  | GLP1a | 702 | 0 (0) | 2 (0.6) (-Inf%) | 0 (0) | 0 (0) (NaN%) |
|  | SGLT2i | 498 | 2 (0.8) | 0 (0) (100%) | 0 (0) | 0 (0) (NaN%) |
|  | DPP4i | 241 | 3 (2.5) | 0 (0) (100%) | 0 (0) | 0 (0) (NaN%) |
|  | TZD | 111 | 0 (0) | 0 (0) (NaN%) | 0 (0) | 0 (0) (NaN%) |
|  | Meglitinides | 14 | 0 (0) | 0 (0) (NaN%) | 0 (0) | 0 (0) (NaN%) |
|  | Alpha-Glucosidase Inhibitor | 8 | 0 (0) | 0 (0) (NaN%) | 0 (0) | 0 (0) (NaN%) |

FIG. 25H

|  |  | Sample size, N | Diseases & Disorders of the Ear, Nose, Mouth & Throat | | | Diseases & Disorders of the Male Reproductive System | |
|---|---|---|---|---|---|---|---|
|  |  |  | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) |
|  | Full Cohort | 2463 | 2 (0.2) | 1 (0.1) (50%) | | 2 (0.2) | 3 (0.3) (-50%) |
| Age | Age 18 - 49 | 670 | 1 (0.3) | 0 (0) (100%) | | 1 (0.3) | 0 (0) (100%) |
|  | Age 50 - 64 | 1627 | 1 (0.1) | 1 (0.1) (0%) | | 1 (0.1) | 3 (0.4) (-300%) |
|  | Age 65+ | 166 | 0 (0) | 0 (0) (NaN%) | | 0 (0) | 0 (0) (NaN%) |
| Gender | Male | 1304 | 1 (0.2) | 1 (0.2) (0%) | | 2 (0.3) | 3 (0.5) (-67%) |
|  | Female | 1159 | 1 (0.2) | 0 (0) (100%) | | 0 (0) | 0 (0) (NaN%) |
| Comorbidities | Hypertension | 2155 | 2 (0.2) | 1 (0.1) (50%) | | 2 (0.2) | 3 (0.3) (-50%) |
|  | Obesity | 1479 | 1 (0.1) | 0 (0) (100%) | | 0 (0.1) | 3 (0.4) (-300%) |
|  | Pulmonary Disease | 709 | 0 (0) | 1 (0.3) (-Inf%) | | 0 (0) | 2 (0.6) (-Inf%) |
|  | Depression | 724 | 1 (0.3) | 0 (0) (100%) | | 1 (0.3) | 1 (0.3) (0%) |
|  | Hypothyroid Disease | 646 | 0 (0) | 0 (0) (NaN%) | | 0 (0) | 2 (0.7) (-Inf%) |
|  | Anemia | 635 | 0 (0) | 1 (0.3) (-Inf%) | | 1 (0.3) | 1 (0.3) (0%) |
|  | Liver Disease | 513 | 0 (0) | 0 (0) (NaN%) | | 0 (0) | 0 (0) (NaN%) |
|  | MI or Coronary Artery Disease | 606 | 0 (0) | 1 (0.4) (-Inf%) | | 0 (0) | 1 (0.4) (-33%) |
|  | Peripheral Vascular Disease | 429 | 1 (0.5) | 0 (0) (100%) | | 1 (0.5) | 0 (0) (100%) |
|  | Renal Disease | 480 | 0 (0) | 1 (0.4) (-Inf%) | | 1 (0.4) | 0 (0) (0%) |
|  | Heart Failure | 323 | 1 (0.6) | 1 (0.7) (-17%) | | 0 (0) | 0 (0) (NaN%) |
|  | Alcohol | 52 | 0 (0) | 0 (0) (NaN%) | | 0 (0) | 0 (0) (NaN%) |
|  | Rheumatic | 260 | 0 (0) | 0 (0) (NaN%) | | 0 (0) | 0 (0) (NaN%) |
|  | Blood Loss | 78 | 0 (0) | 0 (0) (NaN%) | | 0 (0) | 0 (0) (NaN%) |
|  | Coagulopathy | 172 | 0 (0) | 0 (0) (NaN%) | | 0 (0) | 0 (0) (NaN%) |
|  | Lymphoma | 24 | 0 (0) | 0 (0) (NaN%) | | 0 (0) | 0 (0) (NaN%) |
|  | Fluids Lytes | 732 | 0 (0) | 1 (0.3) (-Inf%) | | 0 (0) | 2 (0.6) (-Inf%) |
|  | Mets | 53 | 0 (0) | 0 (0) (NaN%) | | 0 (0) | 0 (0) (NaN%) |
|  | Neuro Other | 333 | 1 (0.6) | 0 (0) (100%) | | 0 (0) | 0 (0) (NaN%) |
|  | Paralysis | 54 | 0 (0) | 0 (0) (NaN%) | | 0 (0) | 0 (0) (NaN%) |
|  | Psychoses | 169 | 0 (0) | 0 (0) (NaN%) | | 0 (0) | 0 (0) (NaN%) |
|  | PulmCircD | 85 | 0 (0) | 1 (2.6) (-Inf%) | | 1 (2.4) | 0 (0) (100%) |
|  | Tumor | 228 | 0 (0) | 0 (0) (NaN%) | | 1 (0.9) | 2 (1.9) (-111%) |
|  | Peptic Ulcer | 64 | 0 (0) | 1 (0.6) (-Inf%) | | 0 (0) | 1 (3.3) (-Inf%) |
|  | Valvular | 356 | 0 (0) | 0 (0) (NaN%) | | 0 (0) | 0 (0) (NaN%) |
|  | Weight Loss | 160 | 0 (0) | 1 (1.4) (-Inf%) | | 1 (1.8) | 1 (1.4) (-Inf%) |
| Insulin Usage Status | Insulin (short -or rapid-acting) | 2463 | 2 (0.2) | 1 (0.1) (50%) | | 2 (0.2) | 3 (0.3) (-50%) |
|  | Non-insulin therapy | NA |  |  | |  |  |
| Non-Insulin Diabetes Medications | Biguanide | 1250 | 1 (0.2) | 0 (0) (100%) | | 1 (0.2) | 1 (0.2) (0%) |
|  | Sulfonylurea | 284 | 0 (0) | 0 (0) (NaN%) | | 0 (0) | 0 (0) (NaN%) |
|  | GLP1a | 702 | 0 (0) | 0 (0) (NaN%) | | 1 (0.3) | 1 (0.3) (0%) |
|  | SGLT2i | 498 | 0 (0) | 0 (0) (NaN%) | | 0 (0) | 0 (0) (NaN%) |
|  | DPP4i | 241 | 0 (0) | 1 (0.9) (-Inf%) | | 0 (0) | 0 (0) (NaN%) |
|  | TZD | 111 | 0 (0) | 0 (0) (NaN%) | | 1 (1.8) | 0 (0) (100%) |
|  | Meglitinides | 14 | 0 (0) | 0 (0) (NaN%) | | 0 (0) | 0 (0) (NaN%) |
|  | Alpha-Glucosidase Inhibitor | 8 | 0 (0) | 0 (0) (NaN%) | | 0 (0) | 0 (0) (NaN%) |

FIG. 25I

| | | | Diseases & Disorders of the Female Reproductive System | | Mental Diseases & Disorders | |
|---|---|---|---|---|---|---|
| | | Sample size, N | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
| | Full Cohort | 2463 | 3 (0.2) | 3 (0.3) (-50%) | 5 (0.4) | 6 (0.5) (-25%) |
| Age | Age 18 – 49 | 670 | 3 (0.9) | 0 (0) (100%) | 1 (0.3) | 3 (0.9) (-200%) |
| | Age 50 – 64 | 1627 | 0 (0) | 3 (0.4) (-Inf%) | 3 (0.4) | 3 (0.4) (0%) |
| | Age 65+ | 166 | 0 (0) | 0 (0) (NaN%) | 1 (1.2) | 0 (0) (100%) |
| Gender | Male | 1304 | 0 (0) | 0 (0) (NaN%) | 3 (0.5) | 1 (0.2) (60%) |
| | Female | 1159 | 3 (0.5) | 3 (0.5) (0%) | 2 (0.3) | 5 (0.9) (-200%) |
| Comorbidities | Hypertension | 2155 | 3 (0.3) | 3 (0.3) (0%) | 5 (0.5) | 4 (0.4) (20%) |
| | Obesity | 1479 | 3 (0.4) | 3 (0.4) (0%) | 4 (0.5) | 1 (0.1) (80%) |
| | Pulmonary Disease | 709 | 1 (0.3) | 3 (0.9) (-200%) | 2 (0.6) | 1 (0.3) (50%) |
| | Depression | 724 | 1 (0.3) | 2 (0.6) (-100%) | 5 (1.4) | 4 (1.2) (14%) |
| | Hypothyroid Disease | 646 | 0 (0) | 2 (0.7) (-Inf%) | 3 (0.9) | 3 (1) (-11%) |
| | Anemia | 635 | 3 (0.9) | 2 (0.7) (22%) | 3 (0.9) | 2 (0.7) (22%) |
| | Liver Disease | 513 | 1 (0.4) | 1 (0.4) (0%) | 2 (0.8) | 1 (0.4) (50%) |
| | MI or Coronary Artery Disease | 606 | 1 (0.3) | 1 (0.4) (-33%) | 3 (1) | 1 (0.4) (60%) |
| | Peripheral Vascular Disease | 429 | 1 (0.5) | 2 (1) (-100%) | 2 (0.9) | 1 (0.5) (44%) |
| | Renal Disease | 480 | 0 (0) | 0 (0) (NaN%) | 3 (1.3) | 0 (0) (100%) |
| | Heart Failure | 323 | 0 (0) | 0 (0) (NaN%) | 4 (2.5) | 0 (0) (100%) |
| | Alcohol | 52 | 0 (0) | 0 (0) (NaN%) | 1 (3.9) | 3 (12) (-208%) |
| | Rheumatic | 260 | 0 (0) | 0 (0) (NaN%) | 0 (0) | 0 (0) (NaN%) |
| | Blood Loss | 78 | 2 (5.1) | 0 (0) (100%) | 0 (0) | 0 (0) (NaN%) |
| | Coagulopathy | 172 | 1 (1.2) | 1 (1.3) (-8%) | 0 (0) | 0 (0) (NaN%) |
| | Lymphoma | 24 | 0 (0) | 0 (0) (NaN%) | 0 (0) | 0 (0) (NaN%) |
| | Fluids Lytes | 732 | 2 (0.5) | 1 (0.3) (40%) | 4 (1.1) | 3 (0.9) (18%) |
| | Mets | 53 | 1 (3.8) | 2 (8.1) (-113%) | 0 (0) | 0 (0) (NaN%) |
| | Neuro Other | 333 | 1 (0.6) | 0 (0) (100%) | 3 (1.8) | 5 (3.2) (-78%) |
| | Paralysis | 54 | 0 (0) | 0 (0) (NaN%) | 0 (0) | 0 (0) (NaN%) |
| | Psychoses | 169 | 0 (0) | 0 (0) (NaN%) | 2 (2.4) | 3 (3.8) (-58%) |
| | PulmCircD | 85 | 0 (0) | 0 (0) (NaN%) | 1 (2.4) | 0 (0) (100%) |
| | Tumor | 228 | 1 (0.9) | 2 (1.9) (-111%) | 2 (1.8) | 1 (0.9) (50%) |
| | Peptic Ulcer | 64 | 1 (3.1) | 0 (0) (100%) | 0 (0) | 0 (0) (NaN%) |
| | Valvular | 356 | 1 (0.6) | 1 (0.6) (0%) | 2 (1.1) | 0 (0) (100%) |
| | Weight Loss | 160 | 0 (0) | 0 (0) (NaN%) | 2 (2.5) | 3 (4.1) (-64%) |
| Insulin Usage Status | Insulin (short- or rapid-acting) | 2463 | 3 (0.2) | 3 (0.3) (-50%) | 5 (0.4) | 6 (0.5) (-25%) |
| | Non-insulin therapy | NA | | | | |
| Non-Insulin Diabetes Medications | Biguanide | 1250 | 2 (0.3) | 1 (0.2) (33%) | 1 (0.2) | 2 (0.3) (-50%) |
| | Sulfonylurea | 284 | 0 (0) | 1 (0.7) (-Inf%) | 1 (0.7) | 0 (0) (100%) |
| | GLP1a | 702 | 0 (0) | 1 (0.3) (-Inf%) | 1 (0.3) | 0 (0) (100%) |
| | SGLT2i | 498 | 0 (0) | 0 (0) (NaN%) | 0 (0) | 0 (0) (NaN%) |
| | DPP4i | 241 | 1 (0.8) | 0 (0) (100%) | 0 (0) | 0 (0) (NaN%) |
| | TZD | 111 | 0 (0) | 0 (0) (NaN%) | 0 (0) | 0 (0) (NaN%) |
| | Meglitinides | 14 | 0 (0) | 0 (0) (NaN%) | 1 (14.3) | 0 (0) (100%) |
| | Alpha-Glucosidase Inhibitor | 8 | 0 (0) | 0 (0) (NaN%) | 0 (0) | 0 (0) (NaN%) |

FIG. 25J

| | | Sample size, N | Alcohol/Drug Use & Alcohol/Drug Induced Organic Mental Disorders | | Injuries, Poisonings & Toxic Effects of Drugs | |
|---|---|---|---|---|---|---|
| | | | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
| | Full Cohort | 2463 | 8 (0.7) | 2 (0.2) (71%) | 5 (0.4) | 4 (0.3) (25%) |
| Age | Age 18 – 49 | 670 | 1 (0.3) | 1 (0.3) (0%) | 0 (0) | 0 (0) (NaN%) |
| | Age 50 – 64 | 1627 | 7 (0.9) | 1 (0.1) (89%) | 4 (0.5) | 3 (0.4) (20%) |
| | Age 65+ | 166 | 0 (0) | 0 (0) (NaN%) | 1 (1.2) | 1 (1.3) (-8%) |
| Gender | Male | 1304 | 8 (1.2) | 2 (0.3) (75%) | 3 (0.5) | 3 (0.5) (0%) |
| | Female | 1159 | 0 (0) | 0 (0) (NaN%) | 2 (0.3) | 1 (0.2) (33%) |
| Comorbidities | Hypertension | 2155 | 8 (0.7) | 1 (0.1) (86%) | 5 (0.5) | 4 (0.4) (20%) |
| | Obesity | 1479 | 6 (0.8) | 1 (0.1) (88%) | 5 (0.7) | 3 (0.4) (43%) |
| | Pulmonary Disease | 709 | 4 (1.1) | 1 (0.3) (73%) | 1 (0.3) | 3 (0.9) (-200%) |
| | Depression | 724 | 8 (2.2) | 1 (0.3) (86%) | 3 (0.8) | 2 (0.6) (25%) |
| | Hypothyroid Disease | 646 | 3 (0.9) | 0 (0) (100%) | 1 (0.3) | 2 (0.7) (-133%) |
| | Anemia | 635 | 3 (0.9) | 0 (0) (100%) | 3 (0.9) | 2 (0.7) (22%) |
| | Liver Disease | 513 | 4 (1.6) | 0 (0) (100%) | 3 (1.2) | 1 (0.4) (67%) |
| | MI or Coronary Artery Disease | 606 | 1 (0.3) | 0 (0) (100%) | 3 (1) | 0 (0) (100%) |
| | Peripheral Vascular Disease | 429 | 2 (0.9) | 0 (0) (100%) | 0 (0) | 0 (0) (100%) |
| | Renal Disease | 480 | 8 (2.2) | 0 (0) (100%) | 1 (0.5) | 1 (0.4) (69%) |
| | Heart Failure | 323 | 1 (0.4) | 0 (0) (100%) | 3 (1.3) | 0 (0) (100%) |
| | Alcohol | 52 | 1 (0.6) | 0 (0) (100%) | 1 (0.6) | 0 (0) (100%) |
| | Rheumatic | 260 | 7 (27) | 1 (4) (85%) | 0 (0) | 1 (4) (-Inf%) |
| | Blood Loss | 78 | 4 (3.1) | 1 (0.8) (74%) | 2 (1.5) | 1 (0.8) (47%) |
| | Coagulopathy | 172 | 1 (2.6) | 0 (0) (100%) | 0 (0) | 0 (0) (NaN%) |
| | Lymphoma | 24 | 2 (2.3) | 0 (0) (100%) | 1 (1.2) | 1 (1.3) (-8%) |
| | Fluids Lytes | 732 | 1 (0.4) | 0 (0) (100%) | 0 (0) | 0 (0) (NaN%) |
| | Mets | 53 | 0 (0) | 0 (0) (100%) | 1 (2.4) | 0 (0) (100%) |
| | Neuro Other | 333 | 4 (1.1) | 0 (0) (NaN%) | 0 (0) | 1 (0.9) (-Inf%) |
| | Paralysis | 54 | 0 (0) | 1 (0.6) (83%) | 5 (1.4) | 2 (0.6) (57%) |
| | Psychoses | 169 | 6 (3.6) | 0 (0) (NaN%) | 2 (6.3) | 1 (3) (48%) |
| | PulmCircD | 85 | 0 (0) | 0 (0) (100%) | 2 (1.2) | 2 (1.3) (-8%) |
| | Tumor | 228 | 4 (4.7) | 0 (0) (100%) | 0 (0) | 0 (0) (NaN%) |
| | Peptic Ulcer | 64 | 0 (0) | 0 (0) (NaN%) | 0 (0) | 0 (0) (100%) |
| | Valvular | 356 | 1 (0.9) | 0 (0) (100%) | 0 (0) | 1 (0.9) (-Inf%) |
| | Weight Loss | 160 | 0 (0) | 0 (0) (100%) | 2 (6.3) | 1 (3) (48%) |
| | | | 1 (0.6) | 0 (0) (100%) | 1 (0.6) | 1 (0.6) (0%) |
| | | | 1 (1.3) | 0 (0) (100%) | 0 (0) | 1 (1.4) (-Inf%) |
| Insulin Usage Status | Insulin (short- or rapid-acting) | 2463 | 8 (0.7) | 2 (0.2) (71%) | 5 (0.4) | 4 (0.3) (25%) |
| | Non-insulin therapy | NA | | | | |
| Non-Insulin Diabetes Medications | Biguanide | 1250 | 3 (0.5) | 1 (0.2) (60%) | 1 (0.2) | 2 (0.3) (-50%) |
| | Sulfonylurea | 284 | 0 (0) | 0 (0) (NaN%) | 1 (0.7) | 1 (0.7) (0%) |
| | GLP1a | 702 | 1 (0.3) | 0 (0) (100%) | 1 (0.3) | 2 (0.6) (-100%) |
| | SGLT2i | 498 | 0 (0) | 0 (0) (NaN%) | 1 (0.4) | 0 (0) (100%) |
| | DPP4i | 241 | 0 (0) | 0 (0) (NaN%) | 0 (0) | 0 (0) (NaN%) |
| | TZD | 111 | 0 (0) | 0 (0) (NaN%) | 0 (0) | 0 (0) (NaN%) |
| | Meglitinides | 14 | 0 (0) | 0 (0) (NaN%) | 0 (0) | 0 (0) (NaN%) |
| | Alpha-Glucosidase Inhibitor | 8 | 0 (0) | 0 (0) (NaN%) | 0 (0) | 0 (0) (NaN%) |

FIG. 25K

| | | Sample size, N | Multiple Significant Trauma | | | Diseases & Disorders of Blood, Blood Forming Organs, Immunologic Disorders | |
|---|---|---|---|---|---|---|---|
| | | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) |
| | Full Cohort | 2463 | 0 (0) | 0 (0) (NaN%) | | 5 (0.4) | 5 (0.4) (0%) |
| Age | Age 18 – 49 | 670 | 0 (0) | 0 (0) (NaN%) | | 0 (0) | 0 (0) (NaN%) |
| | Age 50 – 64 | 1627 | 0 (0) | 0 (0) (NaN%) | | 5 (0.6) | 4 (0.5) (17%) |
| | Age 65+ | 166 | 0 (0) | 0 (0) (NaN%) | | 0 (0) | 1 (1.3) (-Inf%) |
| Gender | Male | 1304 | 0 (0) | 0 (0) (NaN%) | | 4 (0.6) | 3 (0.5) (17%) |
| | Female | 1159 | 0 (0) | 0 (0) (NaN%) | | 1 (0.2) | 2 (0.4) (-100%) |
| Comorbidities | Hypertension | 2155 | 0 (0) | 0 (0) (NaN%) | | 5 (0.5) | 5 (0.5) (0%) |
| | Obesity | 1479 | 0 (0) | 0 (0) (NaN%) | | 5 (0.7) | 3 (0.4) (43%) |
| | Pulmonary Disease | 709 | 0 (0) | 0 (0) (NaN%) | | 4 (1.1) | 3 (0.9) (18%) |
| | Depression | 724 | 0 (0) | 0 (0) (NaN%) | | 0 (0) | 2 (0.6) (-Inf%) |
| | Hypothyroid Disease | 646 | 0 (0) | 0 (0) (NaN%) | | 1 (0.3) | 2 (0.7) (-133%) |
| | Anemia | 635 | 0 (0) | 0 (0) (NaN%) | | 1 (0.3) | 4 (1.3) (-333%) |
| | Liver Disease | 513 | 0 (0) | 0 (0) (NaN%) | | 5 (2) | 2 (0.8) (60%) |
| | MI or Coronary Artery Disease | 606 | 0 (0) | 0 (0) (NaN%) | | 2 (0.7) | 3 (1.1) (-57%) |
| | Peripheral Vascular Disease | 429 | 0 (0) | 0 (0) (NaN%) | | 1 (0.5) | 2 (1) (-100%) |
| | Renal Disease | 480 | 0 (0) | 0 (0) (NaN%) | | 1 (0.4) | 0 (0) (100%) |
| | Heart Failure | 323 | 0 (0) | 0 (0) (NaN%) | | 5 (3.1) | 2 (1.3) (58%) |
| | Alcohol | 52 | 0 (0) | 0 (0) (NaN%) | | 0 (0) | 0 (0) (NaN%) |
| | Rheumatic | 260 | 0 (0) | 0 (0) (NaN%) | | 1 (0.8) | 2 (1.6) (-100%) |
| | Blood Loss | 78 | 0 (0) | 0 (0) (NaN%) | | 1 (2.6) | 2 (5.6) (-115%) |
| | Coagulopathy | 172 | 0 (0) | 0 (0) (NaN%) | | 3 (3.5) | 0 (0) (100%) |
| | Lymphoma | 24 | 0 (0) | 0 (0) (NaN%) | | 0 (0) | 1 (9.1) (-Inf%) |
| | Fluids Lytes | 732 | 0 (0) | 0 (0) (NaN%) | | 4 (1.1) | 1 (0.3) (73%) |
| | Mets | 53 | 0 (0) | 0 (0) (NaN%) | | 0 (0) | 0 (0) (NaN%) |
| | Neuro Other | 333 | 0 (0) | 0 (0) (NaN%) | | 4 (2.4) | 4 (2.5) (-4%) |
| | Paralysis | 54 | 0 (0) | 0 (0) (NaN%) | | 0 (0) | 0 (0) (NaN%) |
| | Psychoses | 169 | 0 (0) | 0 (0) (NaN%) | | 0 (0) | 1 (1.3) (-Inf%) |
| | PulmCircD | 85 | 0 (0) | 0 (0) (NaN%) | | 0 (0) | 0 (0) (NaN%) |
| | Tumor | 228 | 0 (0) | 0 (0) (NaN%) | | 4 (1.1) | 0 (0) (NaN%) |
| | Peptic Ulcer | 64 | 0 (0) | 0 (0) (NaN%) | | 0 (0) | 0 (0) (NaN%) |
| | Valvular | 356 | 0 (0) | 0 (0) (NaN%) | | 2 (1.1) | 2 (1.2) (-9%) |
| | Weight Loss | 160 | 0 (0) | 0 (0) (NaN%) | | 0 (0) | 1 (1.4) (-Inf%) |
| Insulin Usage Status | Insulin (short- or rapid-acting) | 2463 | 0 (0) | 0 (0) (NaN%) | | 5 (0.4) | 5 (0.4) (0%) |
| | Non-insulin therapy | NA | | | | | |
| Non-Insulin Diabetes Medications | Biguanide | 1250 | 0 (0) | 0 (0) (NaN%) | | 4 (0.6) | 4 (0.7) (-17%) |
| | Sulfonylurea | 284 | 0 (0) | 0 (0) (NaN%) | | 3 (2.1) | 0 (0) (100%) |
| | GLP1a | 702 | 0 (0) | 0 (0) (NaN%) | | 4 (1.1) | 3 (0.9) (18%) |
| | SGLT2i | 498 | 0 (0) | 0 (0) (NaN%) | | 0 (0) | 0 (0) (NaN%) |
| | DPP4i | 241 | 0 (0) | 0 (0) (NaN%) | | 0 (0) | 0 (0) (NaN%) |
| | TZD | 111 | 0 (0) | 0 (0) (NaN%) | | 0 (0) | 0 (0) (NaN%) |
| | Meglitinides | 14 | 0 (0) | 0 (0) (NaN%) | | 0 (0) | 0 (0) (NaN%) |
| | Alpha-Glucosidase Inhibitor | 8 | 0 (0) | 0 (0) (NaN%) | | 1 (25.1) | 1 (26.5) (-6%) |

FIG. 25L

|  |  |  | Burns | |
|---|---|---|---|---|
|  |  | Sample size, N | Before flash CGM Hospitalizations (Events/100 pt-yr) | After flash CGM Hospitalizations (Events/100 pt-yr) (% reduction) |
|  | Full Cohort | 2463 | 2 (0.2) | 0 (0) (100%) |
| Age | Age 18 – 49 | 670 | 1 (0.3) | 0 (0) (100%) |
|  | Age 50 – 64 | 1627 | 0 (0) | 0 (0) (NaN%) |
|  | Age 65+ | 166 | 1 (1.2) | 0 (0) (100%) |
| Gender | Male | 1304 | 2 (0.3) | 0 (0) (100%) |
|  | Female | 1159 | 0 (0) | 0 (0) (NaN%) |
| Comorbidities | Hypertension | 2155 | 2 (0.2) | 0 (0) (100%) |
|  | Obesity | 1479 | 2 (0.3) | 0 (0) (100%) |
|  | Pulmonary Disease | 709 | 1 (0.3) | 0 (0) (100%) |
|  | Depression | 724 | 0 (0) | 0 (0) (NaN%) |
|  | Hypothyroid Disease | 646 | 0 (0) | 0 (0) (NaN%) |
|  | Anemia | 635 | 1 (0.3) | 0 (0) (100%) |
|  | Liver Disease | 513 | 0 (0) | 0 (0) (NaN%) |
|  | MI or Coronary Artery Disease | 606 | 1 (0.3) | 0 (0) (100%) |
|  | Peripheral Vascular Disease | 429 | 2 (0.9) | 0 (0) (100%) |
|  | Renal Disease | 480 | 2 (0.8) | 0 (0) (100%) |
|  | Heart Failure | 323 | 1 (0.6) | 0 (0) (100%) |
|  | Alcohol | 52 | 0 (0) | 0 (0) (NaN%) |
|  | Rheumatic | 260 | 0 (0) | 0 (0) (NaN%) |
|  | Blood Loss | 78 | 0 (0) | 0 (0) (NaN%) |
|  | Coagulopathy | 172 | 0 (0) | 0 (0) (NaN%) |
|  | Lymphoma | 24 | 0 (0) | 0 (0) (NaN%) |
|  | Fluids Lytes | 732 | 2 (0.5) | 0 (0) (100%) |
|  | Mets | 55 | 0 (0) | 0 (0) (NaN%) |
|  | Neuro Other | 333 | 0 (0) | 0 (0) (NaN%) |
|  | Paralysis | 54 | 0 (0) | 0 (0) (NaN%) |
|  | Psychoses | 169 | 0 (0) | 0 (0) (NaN%) |
|  | PulmCircD | 85 | 1 (2.4) | 0 (0) (100%) |
|  | Tumor | 228 | 0 (0) | 0 (0) (NaN%) |
|  | Peptic Ulcer | 64 | 0 (0) | 0 (0) (NaN%) |
|  | Valvular | 356 | 1 (0.6) | 0 (0) (NaN%) |
|  | Weight Loss | 160 | 0 (0) | 0 (0) (NaN%) |
| Insulin Usage Status | Insulin (short- or rapid-acting) | 2463 | 2 (0.2) | 0 (0) (100%) |
|  | Non-insulin therapy | NA | | |
| Non-Insulin Diabetes Medications | Biguanide | 1250 | 1 (0.2) | 0 (0) (100%) |
|  | Sulfonylurea | 284 | 1 (0.7) | 0 (0) (100%) |
|  | GLP1a | 702 | 1 (0.3) | 0 (0) (100%) |
|  | SGLT2i | 498 | 0 (0) | 0 (0) (NaN%) |
|  | DPP4i | 241 | 0 (0) | 0 (0) (NaN%) |
|  | TZD | 111 | 0 (0) | 0 (0) (NaN%) |
|  | Meglitinides | 14 | 0 (0) | 0 (0) (NaN%) |
|  | Alpha-Glucosidase Inhibitor | 8 | 0 (0) | 0 (0) (NaN%) |

FIG. 25M

| | | | Total ADE | | | Hypoglycemic ADE | | | Hyperglycemic ADE | |
|---|---|---|---|---|---|---|---|---|---|---|
| | | Sample size, N | Before flash CGM # events (# affected) | After flash CGM # events (# affected) | Before flash CGM # events (# affected) | After flash CGM # events (# affected) | Before flash CGM # events (# affected) | After flash CGM # events (# affected) | | |
| Medication Therapy Group | Antihistamines & Comb (Class 1) | 150 | 29 (25) | 12 (9) | 4 (4) | 3 (3) | 25 (22) | 10 (8) | | |
| | Gastrointestinal Drugs (Classes 147-162, 273) | 858 | 116 (91) | 37 (34) | 13 (10) | 6 (6) | 104 (85) | 32 (30) | | |
| | Anti-infective Agents (Classes 2-29) | 1337 | 152 (120) | 59 (53) | 12 (11) | 12 (11) | 142 (113) | 48 (45) | | |
| | Antineoplastic Agents (Classes 21-22, 260-265) | 67 | 5 (4) | 3 (2) | 1 (1) | 1 (1) | 4 (4) | 2 (2) | | |
| | Autonomic Drugs (Classes 23-33) | 674 | 75 (63) | 35 (32) | 10 (8) | 7 (7) | 65 (58) | 28 (27) | | |
| | Hormones & Synthetic Substitutes (Classes 165-180 246 252-253 256 266-268) | 2463 | 221 (181) | 83 (73) | 24 (21) | 17 (16) | 199 (166) | 68 (62) | | |
| | Immunosuppressants (Class 181) | 114 | 11 (10) | 6 (4) | 1 (1) | 3 (2) | 10 (10) | 3 (3) | | |
| | Blood Form/Coagul Agents (Classes 35-45, 259) | 380 | 47 (40) | 13 (11) | 8 (7) | 3 (3) | 40 (37) | 10 (10) | | |
| | Cardiovascular Agents (Classes 46-56, 245, 250, 271) | 2193 | 197 (161) | 75 (66) | 24 (21) | 17 (16) | 175 (146) | 60 (55) | | |
| | Central Nervous System (Classes 57-77, 272) | 1596 | 174 (139) | 61 (52) | 17 (14) | 9 (9) | 158 (129) | 53 (47) | | |
| | Serums, Toxoids, Vaccines (Classes 185-189) | 169 | 6 (5) | 7 (3) | 2 (2) | 3 (3) | 4 (4) | 4 (2) | | |
| | Dental Agents (Classes 79-83) | 8 | 2 (2) | 1 (1) | 0 (0) | 1 (1) | 2 (2) | 0 (0) | | |
| | Skin & Mucous Membrane (Classes 190-213, 242) | 575 | 62 (46) | 23 (18) | 4 (3) | 5 (5) | 58 (45) | 19 (16) | | |
| | Diagnostic Agents (Classes 84-98, 239, 243-244, 247) | 2463 | 221 (181) | 83 (73) | 24 (21) | 17 (16) | 199 (166) | 68 (62) | | |
| | Smooth Muscles Relaxants (Classes 214-216) | 46 | 5 (4) | 1 (1) | 2 (2) | 0 (0) | 3 (3) | 1 (1) | | |
| | Vitamins & Comb (Classes 217-233) | 371 | 40 (30) | 15 (13) | 6 (4) | 1 (1) | 34 (27) | 14 (13) | | |
| | Electrolytic, Caloric, Water (Classes 100-126, 241, 292) | 759 | 70 (60) | 26 (24) | 14 (12) | 7 (7) | 58 (52) | 19 (18) | | |
| | Antitussive/Expector/Mucolytic (Classes 128-131, 248, 255) | 304 | 29 (23) | 18 (13) | 4 (4) | 6 (5) | 26 (20) | 13 (10) | | |
| | Unclassified Agents (Classes 234-236, 251, 254, 257-258, 270) | 344 | 48 (34) | 16 (14) | 4 (3) | 4 (4) | 44 (32) | 13 (12) | | |
| | Pharmaceutical Aids/Adjuvants (Class 238) | 374 | 27 (22) | 13 (13) | 1 (1) | 2 (2) | 26 (21) | 11 (11) | | |
| | Eye, Ear, Nose Throat (Classes 132, 146, 240, 290) | 49 | 10 (7) | 5 (3) | 1 (1) | 1 (1) | 9 (7) | 4 (3) | | |
| Other Diabetic Therapy | Insulin Pump | 452 | 55 (42) | 21 (18) | 12 (10) | 2 (2) | 44 (36) | 19 (17) | | |
| | >= 4 Strips per day | 155 | 3 (2) | 5 (4) | 0 (0) | 1 (1) | 3 (2) | 5 (4) | | |
| | < 4 Strips per day | 391 | 21 (16) | 9 (8) | 4 (3) | 2 (2) | 18 (15) | 7 (7) | | |
| | | 2162 | 200 (165) | 74 (65) | 20 (18) | 15 (14) | 181 (151) | 61 (55) | | |

FIG. 25N

|  |  | Sample size, N | Total ACB | | Total ACB | | Circulatory System | |
|---|---|---|---|---|---|---|---|---|
|  |  |  | Before flash CGM # events (# affected) | After flash CGM # events (# affected) | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
| Medication Therapy Group | Antihistamines & Comb. (Class 1) | 150 | 67 (41) | 38 (25) | 67 (89.6) | 38 (54) (40%) | 8 (10.7) | 5 (7.1) (34%) |
|  | Gastrointestinal Drugs (Classes 147, 162, 273) | 858 | 316 (203) | 170 (119) | 316 (73.9) | 170 (42) (43%) | 46 (10.8) | 33 (8.1) (25%) |
|  | Anti-infective Agents (Classes 2-20) | 1337 | 387 (264) | 240 (168) | 387 (58.1) | 240 (38.1) (34%) | 69 (10.4) | 55 (8.7) (16%) |
|  | Antineoplastic Agents (Classes 21-22, 260-265) | 67 | 26 (17) | 12 (10) | 26 (77.9) | 12 (39.8) (49%) | 3 (9) | 1 (3.3) (63%) |
|  | Autonomic Drugs (Classes 23-33) | 674 | 210 (143) | 133 (100) | 210 (62.5) | 133 (42.2) (32%) | 24 (7.1) | 23 (7.3) (-3%) |
|  | Hormones & Synthetic Substitutes (Classes 165-180 246 252-253 256 266-268) | 2463 | 516 (357) | 327 (237) | 516 (42) | 327 (28.1) (33%) | 96 (7.8) | 80 (6.9) (12%) |
|  | Immunosuppressants (Class 181) | 114 | 37 (25) | 28 (22) | 37 (65.1) | 28 (52.1) (20%) | 3 (5.3) | 7 (13) (-145%) |
|  | Blood Form/Coagul Agents (Classes 35-45, 259) | 380 | 177 (115) | 109 (75) | 177 (93.5) | 109 (61.9) (34%) | 59 (31.2) | 36 (20.5) (34%) |
|  | Cardiovascular Agents (Classes 46-56, 245, 250, 271) | 2193 | 471 (319) | 298 (215) | 471 (43.1) | 298 (28.7) (33%) | 96 (8.8) | 78 (7.5) (15%) |
|  | Central Nervous System (Classes 57-77, 272) | 1596 | 432 (290) | 265 (189) | 432 (54.3) | 265 (35.3) (35%) | 72 (9.1) | 61 (8.1) (11%) |
|  | Serums, Toxoids, Vaccines (Classes 185-189) | 169 | 24 (20) | 19 (13) | 24 (28.5) | 19 (24) (16%) | 4 (4.7) | 3 (3.8) (19%) |
|  | Dental Agents (Classes 79-83) | 8 | 1 (1) | 0 (0) | 1 (25.1) | 0 (0) (100%) | 0 (0) | 0 (0) (NaN%) |
|  | Skin & Mucous Membrane (Classes 190-213, 242) | 575 | 191 (124) | 125 (84) | 191 (66.7) | 125 (46.2) (31%) | 32 (11.2) | 22 (8.1) (28%) |
|  | Diagnostic Agents (Classes 84-98, 239, 243-244, 247) | 2463 | 516 (357) | 327 (237) | 516 (42) | 327 (28.1) (33%) | 96 (7.8) | 80 (6.9) (12%) |
|  | Smooth Muscles Relaxants (Classes 214-216) | 46 | 22 (13) | 14 (9) | 22 (96) | 14 (61.6) (36%) | 7 (30.5) | 3 (13.2) (57%) |
|  | Vitamins & Comb (Classes 217-213) | 371 | 121 (71) | 80 (53) | 121 (65.5) | 80 (45.4) (31%) | 18 (9.7) | 16 (9.1) (6%) |
|  | Electrolytic, Caloric, Water (Classes 100-126, 241, 292) | 759 | 269 (178) | 168 (115) | 269 (71.1) | 168 (47.3) (33%) | 72 (19) | 53 (14.9) (22%) |
|  | Antituss/Expector/Mucolytic (Classes 128-133, 248, 255) | 304 | 102 (71) | 63 (46) | 102 (67.3) | 63 (43.6) (35%) | 26 (17.2) | 20 (13.8) (20%) |
|  | Unclassified Agents (Classes 234-236, 251, 254, 257-258, 270) | 344 | 86 (59) | 64 (46) | 86 (50.2) | 64 (39.6) (21%) | 22 (12.8) | 12 (7.4) (42%) |
|  | Devices and Non-drug Items (Class 237) | 374 | 88 (56) | 59 (45) | 88 (47.2) | 59 (33.2) (30%) | 13 (7) | 13 (7.3) (-4%) |
|  | Pharmaceutical Aids/Adjuvants (Class 238) | 49 | 41 (21) | 20 (12) | 41 (167.9) | 20 (89.5) (47%) | 2 (8.2) | 4 (17.9) (-118%) |
|  | Eye, Ear, Nose Throat (Classes 132, 146, 240, 290) | 452 | 103 (70) | 78 (58) | 103 (45.7) | 78 (36.4) (20%) | 19 (8.4) | 22 (10.3) (-23%) |
| Other Diabetic Therapy | Insulin Pump | 155 | 10 (10) | 13 (11) | 10 (12.9) | 13 (17.9) (-39%) | 2 (2.6) | 2 (2.8) (-8%) |
|  | >= 4 Strips per day | 301 | 59 (39) | 40 (30) | 59 (39.3) | 40 (28.7) (27%) | 10 (6.7) | 9 (6.5) (3%) |
|  | < 4 Strips per day | 2162 | 457 (318) | 287 (207) | 457 (42.4) | 287 (28) (34%) | 86 (8) | 71 (6.9) (14%) |

FIG. 250

|  |  | Sample size, N | Endocrine, Nutritional and Metabolic System | | | Infectious and Parasitic DDs (Systemic or unspecified sites) | | | Respiratory System | | |
| --- | --- | --- | --- | --- | --- | --- | --- | --- | --- | --- | --- |
|  |  |  | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | |
| Medication Therapy Group | Antihistamines & Comb. (Class 1) | 150 | 8 (10.7) | 6 (8.5) (21%) | | 6 (8) | 2 (2.8) (65%) | | 5 (6.7) | 2 (2.8) (58%) | |
|  | Gastrointestinal Drugs (Classes 147-162, 273) | 858 | 43 (10.1) | 18 (4.4) (56%) | | 29 (6.8) | 13 (3.2) (53%) | | 25 (5.8) | 16 (3.9) (33%) | |
|  | Anti-infective Agents (Classes 2-20) | 1337 | 52 (7.8) | 22 (3.5) (55%) | | 51 (7.7) | 27 (4.3) (44%) | | 37 (5.6) | 19 (3) (46%) | |
|  | Antineoplastic Agents (Classes 21-22, 260-265) | 67 | 1 (3) | 1 (3.3) (-10%) | | 4 (12) | 1 (3.3) (72%) | | 4 (12) | 2 (6.6) (45%) | |
|  | Autonomic Drugs (Classes 23-33) | 674 | 18 (5.4) | 13 (4.1) (24%) | | 28 (8.3) | 14 (4.4) (47%) | | 27 (8) | 13 (4.1) (49%) | |
|  | Hormones & Synthetic Substitutes (Classes 165-180 246 252-253 256 266-268) | 2463 | 78 (6.4) | 30 (2.6) (59%) | | 59 (4.8) | 33 (2.8) (42%) | | 43 (3.5) | 25 (2.1) (40%) | |
|  | Immunosuppressants (Class 181) | 114 | 4 (7) | 2 (3.7) (47%) | | 4 (7) | 3 (5.6) (20%) | | 5 (8.8) | 0 (0) (100%) | |
|  | Blood Form/Coagul Agents (Classes 35-45, 259) | 380 | 16 (8.4) | 11 (6.2) (26%) | | 12 (6.3) | 14 (8) (-27%) | | 10 (5.3) | 7 (4) (25%) | |
|  | Cardiovascular Agents (Classes 46-56, 245, 250, 271) | 2193 | 66 (6) | 28 (2.7) (55%) | | 52 (4.8) | 30 (2.9) (46%) | | 35 (3.2) | 19 (1.8) (44%) | |
|  | Central Nervous System (Classes 57-77, 272) | 1596 | 63 (7.9) | 25 (3.3) (58%) | | 50 (6.3) | 27 (3.6) (43%) | | 31 (3.9) | 19 (2.5) (36%) | |
|  | Serums, Toxoids, Vaccines (Classes 185-189) | 169 | 2 (2.4) | 5 (6.3) (-162%) | | 2 (2.4) | 1 (1.3) (46%) | | 1 (1.2) | 1 (1.3) (-8%) | |
|  | Dental Agents (Classes 79-83) | 15 | 0 (0) | 0 (0) (NaN%) | | 0 (0) | 0 (0) (NaN%) | | 0 (0) | 0 (0) (NaN%) | |
|  | Skin & Mucous Membrane (Classes 190-213, 242) | 575 | 20 (7) | 10 (3.7) (47%) | | 22 (7.7) | 16 (5.9) (23%) | | 17 (5.9) | 13 (4.8) (19%) | |
|  | Diagnostic Agents (Classes 84-98, 239, 243-244, 247) | 2463 | 78 (6.4) | 30 (2.6) (59%) | | 59 (4.8) | 33 (2.8) (42%) | | 43 (3.5) | 25 (2.1) (40%) | |
|  | Smooth Muscles Relaxants (Classes 214-216) | 46 | 1 (4.4) | 0 (0) (100%) | | 4 (17.5) | 4 (17.6) (-1%) | | 3 (4.4) | 2 (8.8) (-100%) | |
|  | Vitamins & Comb (Classes 217-233) | 371 | 13 (7) | 7 (4) (43%) | | 19 (10.3) | 11 (6.2) (40%) | | 4 (2.2) | 3 (1.7) (23%) | |
|  | Electrolytic, Caloric, Water (Classes 100-126, 241, 292) | 759 | 19 (5) | 14 (3.9) (22%) | | 31 (8.2) | 16 (4.5) (45%) | | 21 (5.6) | 15 (4.2) (25%) | |
|  | Unclassified Agents (Classes 234-236, 251, 254, 257-258, 270) | 304 | 7 (4.6) | 5 (3.5) (24%) | | 13 (8.6) | 7 (4.8) (44%) | | 7 (4.6) | 1 (0.7) (85%) | |
|  | Devices and Non-drug Items (Class 237) | 344 | 8 (4.7) | 6 (3.7) (21%) | | 9 (5.3) | 7 (4.3) (19%) | | 14 (8.2) | 6 (3.7) (55%) | |
|  | Antituss/Expector/Mucolytic (Classes 128-131, 248, 255) | 374 | 10 (5.4) | 5 (2.8) (48%) | | 9 (4.8) | 5 (2.8) (42%) | | 19 (10.2) | 10 (5.6) (45%) | |
|  | Pharmaceutical Aids/Adjuvants (Class 228) | 49 | 2 (8.2) | 1 (4.5) (45%) | | 0 (0) | 1 (4.5) (-Inf%) | | 5 (20.5) | 3 (13.4) (35%) | |
|  | Eye, Ear, Nose Throat (Classes 132, 146, 240, 290) | 452 | 15 (6.7) | 5 (2.3) (66%) | | 4 (1.8) | 4 (1.9) (-6%) | | 5 (2.2) | 11 (5.1) (-132%) | |
| Other Diabetic Therapy | Insulin Pump | 155 | 0 (0) | 2 (2.8) (-Inf%) | | 2 (2.6) | 1 (1.4) (46%) | | 0 (0) | 0 (0) (NaN%) | |
|  | >= 4 Strips per day | 301 | 5 (3.3) | 5 (3.6) (-9%) | | 7 (4.7) | 2 (1.4) (70%) | | 9 (6) | 6 (4.3) (28%) | |
|  | < 4 Strips per day | 2162 | 73 (6.8) | 25 (2.4) (65%) | | 52 (4.8) | 31 (3) (38%) | | 34 (3.2) | 19 (1.9) (41%) | |

FIG. 25P

| | | Sample size, N | Kidney and Urinary Tract | | Musculoskeletal System and Connective Tissue | | Digestive System | |
|---|---|---|---|---|---|---|---|---|
| | | | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
| Medication Therapy Group | Antihistamines & Comb. (Class 1) | 150 | 3 (4) | 2 (2.8) (30%) | 4 (5.4) | 5 (7.1) (-31%) | 9 (12) | 5 (7.1) (41%) |
| | Gastrointestinal Drugs (Classes 147-162, 273) | 858 | 31 (7.3) | 10 (2.5) (66%) | 22 (5.1) | 18 (4.4) (14%) | 32 (7.5) | 18 (4.4) (41%) |
| | Anti-infective Agents (Classes 2-20) | 1337 | 33 (5) | 18 (2.9) (42%) | 28 (4.2) | 24 (3.8) (10%) | 27 (4.1) | 23 (3.6) (12%) |
| | Antineoplastic Agents (Classes 21-22, 260-265) | 67 | 1 (3) | 1 (3.3) (-10%) | 4 (12) | 1 (3.3) (72%) | 0 (0) | 1 (3.3) (-Inf%) |
| | Autonomic Drugs (Classes 23-33) | 674 | 10 (3) | 9 (2.9) (3%) | 20 (6) | 17 (5.4) (10%) | 22 (6.6) | 9 (2.9) (56%) |
| | Hormones & Synthetic Substitutes (Classes 165-180 246 252-253 256 266-268) | 2463 | 41 (3.3) | 20 (1.7) (48%) | 39 (3.2) | 32 (2.7) (16%) | 38 (3.1) | 32 (2.7) (13%) |
| | Immunosuppressants (Class 181) | 114 | 10 (17.6) | 5 (9.3) (47%) | 3 (5.3) | 1 (1.9) (64%) | 1 (1.8) | 7 (13) (-622%) |
| | Blood Form/Coagul Agents (Classes 35-45, 259) | 380 | 14 (7.4) | 8 (4.5) (39%) | 11 (5.8) | 7 (4) (31%) | 9 (4.8) | 10 (5.7) (-19%) |
| | Cardiovascular Agents (Classes 46-56, 245, 250, 271) | 2193 | 39 (3.6) | 20 (1.9) (47%) | 36 (3.3) | 30 (2.9) (12%) | 36 (3.3) | 31 (3) (9%) |
| | Central Nervous System (Classes 57-77, 272) | 1596 | 35 (4.4) | 19 (2.5) (43%) | 37 (4.7) | 26 (3.5) (26%) | 31 (3.9) | 25 (3.3) (15%) |
| | Serums, Toxoids, Vaccines (Classes 185-189) | 169 | 1 (1.2) | 0 (0) (100%) | 1 (1.2) | 2 (2.5) (-108%) | 3 (3.6) | 1 (1.3) (64%) |
| | Dental Agents (Classes 79-83) | 8 | 0 (0) | 0 (0) (NaN%) | 0 (0) | 0 (0) (NaN%) | 0 (0) | 0 (0) (NaN%) |
| | Skin & Mucous Membrane (Classes 190-213, 242) | 575 | 20 (7) | 9 (3.3) (53%) | 24 (8.4) | 16 (5.9) (30%) | 11 (3.8) | 9 (3.3) (13%) |
| | Diagnostic Agents (Classes 84-98, 239, 243-244, 247) | 2463 | 41 (3.3) | 20 (1.7) (48%) | 39 (3.2) | 32 (2.7) (16%) | 38 (3.1) | 32 (2.7) (13%) |
| | Smooth Muscles Relaxants (Classes 214-216) | 46 | 3 (13.1) | 2 (8.8) (33%) | 0 (0) | 2 (8.8) (-Inf%) | 1 (4.4) | 0 (0) (100%) |
| | Vitamins & Comb (Classes 217-233) | 371 | 15 (8.1) | 11 (6.2) (23%) | 12 (6.5) | 11 (6.2) (5%) | 14 (7.6) | 6 (3.4) (55%) |
| | Electrolytic, Caloric, Water (Classes 100-126, 241, 292) | 759 | 28 (7.4) | 13 (3.7) (50%) | 23 (6.1) | 17 (4.8) (21%) | 19 (5) | 11 (3.1) (38%) |
| | Unclassified Agents (Classes 234-236, 251, 254, 257-258, 270) | 304 | 14 (9.2) | 6 (4.2) (54%) | 8 (5.3) | 3 (2.1) (60%) | 11 (7.3) | 9 (6.2) (15%) |
| | Devices and Non-drug Items (Class 237) | 344 | 3 (1.8) | 1 (0.6) (67%) | 4 (2.3) | 12 (7.4) (-222%) | 4 (2.3) | 7 (4.3) (-87%) |
| | Antituss/Expector/Mucolytic (Classes 128-131, 248, 255) | 374 | 5 (2.7) | 3 (1.7) (37%) | 5 (2.7) | 5 (2.8) (-4%) | 6 (3.2) | 6 (3.4) (-6%) |
| | Pharmaceutical Aids/Adjuvants (Class 238) | 49 | 2 (8.2) | 1 (4.5) (45%) | 3 (12.3) | 0 (0) (100%) | 9 (36.9) | 4 (17.9) (51%) |
| | Eye, Ear, Nose Throat (Classes 132 146, 240, 290) | 452 | 10 (4.4) | 5 (2.3) (48%) | 8 (3.6) | 7 (3.3) (8%) | 9 (4) | 8 (3.7) (7%) |
| Other Diabetic Therapy | Insulin Pump | 155 | 0 (0) | 1 (1.4) (-Inf%) | 2 (2.6) | 4 (5.5) (-112%) | 1 (1.3) | 1 (1.4) (-8%) |
| | >= 4 Strips per day | 301 | 4 (2.7) | 3 (2.2) (19%) | 8 (5.3) | 6 (4.3) (19%) | 3 (2) | 3 (2.2) (-10%) |
| | < 4 Strips per day | 2162 | 37 (3.4) | 17 (1.7) (50%) | 31 (2.9) | 26 (2.5) (14%) | 35 (3.2) | 29 (2.8) (13%) |

FIG. 25Q

|  |  | Sample size, N | Nervous System | | | Hepatobiliary System and Pancreas | | | Skin, Subcutaneous Tissue and Breast | | |
|---|---|---|---|---|---|---|---|---|---|---|---|
|  |  |  | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | |
| Medication Therapy Group | Antihistamines & Comb (Class 1) | 150 | 7 (9.4) | 1 (1.4) (85%) | | 5 (6.7) | 3 (4.3) (36%) | | 4 (5.4) | 3 (4.3) (20%) | |
|  | Gastrointestinal Drugs (Classes 147-162, 273) | 858 | 22 (5.1) | 12 (3) (41%) | | 27 (6.3) | 13 (3.2) (49%) | | 8 (1.9) | 4 (1) (47%) | |
|  | Anti-infective Agents (Classes 2-20) | 1337 | 21 (3.2) | 12 (1.9) (41%) | | 23 (3.5) | 12 (1.9) (46%) | | 13 (2) | 7 (1.1) (45%) | |
|  | Antineoplastic Agents (Classes 21-22, 261-265) | 67 | 2 (6) | 0 (0) (100%) | | 5 (15) | 0 (0) (100%) | | 1 (3) | 1 (3.3) (-10%) | |
|  | Autonomic Drugs (Classes 23-33) | 674 | 22 (6.6) | 8 (2.5) (62%) | | 13 (3.9) | 5 (3.6) (59%) | | 5 (1.5) | 2 (0.6) (60%) | |
|  | Hormones & Synthetic Substitutes (Classes 165-180 246 252-253 256 266-268) | 2463 | 36 (2.9) | 19 (1.6) (45%) | | 30 (2.4) | 16 (1.4) (42%) | | 13 (1.1) | 8 (0.7) (36%) | |
|  | Immunosuppressants (Class 181) | 114 | 1 (1.8) | 1 (1.9) (-6%) | | 2 (3.5) | 0 (0) (100%) | | 1 (1.8) | 0 (0) (100%) | |
|  | Blood Form/Coagul Agents (Classes 35-45, 259) | 380 | 20 (10.6) | 2 (1.1) (90%) | | 9 (4.8) | 5 (2.8) (42%) | | 4 (2.1) | 3 (1.7) (19%) | |
|  | Cardiovascular Agents (Classes 46-56, 245, 250, 271) | 2193 | 33 (3) | 16 (1.5) (50%) | | 26 (2.4) | 15 (1.4) (42%) | | 13 (1.2) | 6 (0.6) (50%) | |
|  | Central Nervous System (Classes 57-77, 272) | 1596 | 33 (4.1) | 18 (2.4) (41%) | | 27 (3.4) | 14 (1.9) (44%) | | 11 (1.4) | 6 (0.8) (43%) | |
|  | Serums, Toxoids, Vaccines (Classes 185-189) | 169 | 1 (1.2) | 0 (0) (100%) | | 5 (5.9) | 2 (2.5) (58%) | | 2 (2.4) | 1 (1.3) (46%) | |
|  | Dental Agents (Classes 79-83) | 8 | 0 (0) | 0 (0) (NaN%) | | 0 (0) | 0 (0) (NaN%) | | 0 (0) | 0 (0) (NaN%) | |
|  | Skin & Mucous Membrane (Classes 190-213, 242) | 575 | 12 (4.2) | 9 (3.3) (21%) | | 10 (3.5) | 7 (2.6) (26%) | | 7 (2.4) | 6 (2.2) (8%) | |
|  | Diagnostic Agents (Classes 84-98, 239, 243-244, 247) | 2463 | 36 (2.9) | 19 (1.6) (45%) | | 30 (2.4) | 16 (1.4) (42%) | | 13 (1.1) | 8 (0.7) (36%) | |
|  | Smooth Muscles Relaxants (Classes 214-216) | 46 | 1 (4.4) | 0 (0) (100%) | | 0 (0) | 0 (0) (NaN%) | | 1 (4.4) | 0 (0) (100%) | |
|  | Vitamins & Comb (Classes 217-233) | 371 | 9 (4.9) | 2 (1.1) (78%) | | 7 (3.8) | 6 (3.4) (11%) | | 2 (1.1) | 0 (0) (100%) | |
|  | Electrolytic, Caloric, Water (Classes 100-126, 241, 292) | 759 | 11 (2.9) | 7 (2) (31%) | | 20 (5.3) | 8 (2.3) (57%) | | 4 (1.1) | 4 (1.1) (1%) | |
|  | Unclassified Agents (Classes 234-236, 251, 254, 257-258, 270) | 304 | 6 (4) | 3 (2.1) (48%) | | 2 (1.3) | 0 (0) (100%) | | 0 (0) | 3 (2.1) (-Inf%) | |
|  | Devices and Non-drug Items (Class 237) | 344 | 2 (1.2) | 5 (3.1) (-158%) | | 7 (4.1) | 4 (2.5) (39%) | | 3 (1.8) | 0 (0) (100%) | |
|  | Antituss/Expector/Mucolytic (Classes 128-131, 248, 255) | 374 | 3 (1.6) | 2 (1.1) (31%) | | 7 (3.8) | 1 (0.6) (84%) | | 0 (0) | 2 (1.1) (-Inf%) | |
|  | Pharmaceutical Aids/Adjuvants (Class 238) | 49 | 4 (16.4) | 0 (0) (100%) | | 7 (28.7) | 4 (17.9) (38%) | | 3 (12.3) | 1 (4.5) (63%) | |
|  | Eye, Ear, Nose Throat (Classes 132, 146, 240, 290) | 452 | 10 (4.4) | 3 (1.4) (68%) | | 2 (0.9) | 2 (0.9) (0%) | | 3 (1.3) | 2 (0.9) (31%) | |
| Other Diabetic Therapy | Insulin Pump | 155 | 1 (1.3) | 1 (1.4) (-8%) | | 0 (0) | 0 (0) (NaN%) | | 0 (0) | 0 (0) (NaN%) | |
|  | >=4 Strips per day | 301 | 5 (3.3) | 1 (0.7) (79%) | | 1 (0.7) | 1 (0.7) (0%) | | 2 (1.3) | 1 (0.7) (46%) | |
|  | <4 Strips per day | 2162 | 31 (2.9) | 18 (1.8) (38%) | | 29 (2.7) | 15 (1.5) (44%) | | 11 (1) | 7 (0.7) (30%) | |

FIG. 25R

| | | Sample size, N | Diseases & Disorders of the Eye | | Diseases & Disorders of the Ear, Nose, Mouth & Throat | | Diseases & Disorders of the Male Reproductive System | |
|---|---|---|---|---|---|---|---|---|
| | | | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) | Before flash CGM Hospitalizations (Events/100 pt-yr) | After flash CGM Hospitalizations (Events/100 pt-yr) (% reduction) |
| Medication Therapy Group | Antihistamines & Comb. (Class 1) | 159 | 0 (0) | 0 (0) (NaN%) | 1 (1.3) | 0 (0) (100%) | 0 (0) | 0 (0) (NaN%) |
| | Gastrointestinal Drugs (Classes 147-162, 273) | 858 | 0 (0) | 0 (0) (NaN%) | 1 (0.2) | 1 (0.2) (0%) | 1 (0.2) | 2 (0.5) (-150%) |
| | Anti-infective Agents (Classes 2-29) | 1337 | 0 (0) | 0 (0) (NaN%) | 1 (0.2) | 0 (0) (100%) | 2 (0.3) | 3 (0.5) (-67%) |
| | Antineoplastic Agents (Classes 21-22, 260-265) | 67 | 0 (0) | 0 (0) (NaN%) | 0 (0) | 0 (0) (NaN%) | 0 (0) | 0 (0) (NaN%) |
| | Autonomic Drugs (Classes 23-33) | 674 | 0 (0) | 0 (0) (NaN%) | 1 (0.3) | 1 (0.3) (50%) | 0 (0) | 2 (0.6) (-Inf%) |
| | Hormones & Synthetic Substitutes (Classes 165-180 246 252-253 256 266-268) | 2463 | 0 (0) | 0 (0) (NaN%) | 2 (0.2) | 0 (0) (-Inf%) | 2 (0.2) | 3 (0.3) (-50%) |
| | Immunosuppressants (Class 181) | 114 | 0 (0) | 0 (0) (NaN%) | 0 (0) | 1 (0.6) (-Inf%) | 0 (0) | 0 (0) (100%) |
| | Blood Form/Coagul Agents (Classes 35-45, 259) | 380 | 0 (0) | 0 (0) (NaN%) | 0 (0) | 1 (0.3) (50%) | 1 (0.5) | 0 (0) (100%) |
| | Cardiovascular Agents (Classes 46-56, 245, 250, 271) | 2,193 | 0 (0) | 0 (0) (NaN%) | 2 (0.2) | 0 (0) (NaN%) | 2 (0.2) | 3 (0.3) (-50%) |
| | Central Nervous System (Classes 57-77, 272) | 1,596 | 0 (0) | 0 (0) (NaN%) | 1 (0.1) | 1 (0.1) (0%) | 2 (0.3) | 2 (0.3) (0%) |
| | Serums, Toxoids, Vaccines (Classes 185-189) | 169 | 0 (0) | 0 (0) (NaN%) | 0 (0) | 0 (0) (NaN%) | 0 (0) | 1 (1.3) (-Inf%) |
| | Dental Agents (Classes 79-83) | 8 | 0 (0) | 0 (0) (NaN%) | 0 (0) | 0 (0) (NaN%) | 0 (0) | 0 (0) (NaN%) |
| | Skin & Mucous Membrane (Classes 190-213, 242) | 575 | 0 (0) | 0 (0) (NaN%) | 0 (0) | 0 (0) (NaN%) | 1 (0.3) | 2 (0.6) (-Inf%) |
| | Diagnostic Agents (Classes 84-98, 239, 243-244, 247) | 2463 | 0 (0) | 0 (0) (NaN%) | 2 (0.2) | 1 (0.1) (50%) | 2 (0.2) | 3 (0.3) (-50%) |
| | Smooth Muscles Relaxants (Classes 214-216) | 46 | 0 (0) | 0 (0) (NaN%) | 0 (0) | 0 (0) (NaN%) | 0 (0) | 0 (0) (NaN%) |
| | Devices and Non-drug Items (Class 237) | 371 | 0 (0) | 0 (0) (NaN%) | 0 (0) | 0 (0) (NaN%) | 0 (0) | 0 (0) (100%) |
| | Vitamins & Comb (Classes 217-233) | 759 | 0 (0) | 0 (0) (NaN%) | 1 (0.5) | 0 (0) (100%) | 1 (0.6) | 1 (0.6) (-Inf%) |
| | Electrolytic, Caloric, Water (Classes 100-126, 241, 292) | 304 | 0 (0) | 0 (0) (NaN%) | 1 (4.1) | 0 (0) (100%) | 0 (0) | 1 (4.5) (-Inf%) |
| | Unclassified Agents (Classes 234-236, 251, 254, 257-258, 270) | 344 | 0 (0) | 0 (0) (NaN%) | 0 (0) | 0 (0) (NaN%) | 0 (0) | 0 (0) (100%) |
| | Antituss/Expector/Mucolytic (Classes 128-131, 248, 255) | 374 | 0 (0) | 0 (0) (NaN%) | 0 (0) | 0 (0) (NaN%) | 0 (0) | 1 (0.6) (-Inf%) |
| | Pharmaceutical Aids/Adjuvants (Class 238) | 49 | 0 (0) | 0 (0) (NaN%) | 2 (0.9) | 0 (0) (100%) | 1 (0.4) | 2 (0.9) (-125%) |
| | Eye, Ear, Nose Throat (Classes 132, 146, 240, 290) | 452 | 0 (0) | 0 (0) (NaN%) | 0 (0) | 0 (0) (100%) | 0 (0) | 1 (1.4) (-Inf%) |
| Other Diabetic Therapy | Insulin Pump | 155 | 0 (0) | 0 (0) (NaN%) | 0 (0) | 0 (0) (NaN%) | 0 (0) | 0 (0) (NaN%) |
| | >= 4 Strips per day | 301 | 0 (0) | 0 (0) (NaN%) | 0 (0) | 0 (0) (NaN%) | 0 (0) | 0 (0) (NaN%) |
| | < 4 Strips per day | 2162 | 0 (0) | 0 (0) (NaN%) | 2 (0.2) | 1 (0.1) (50%) | 2 (0.2) | 3 (0.3) (-50%) |

FIG. 25S

| | | | Diseases & Disorders of the Female Reproductive System | | | Mental Diseases & Disorders | | | Alcohol/Drug Use & Alcohol/Drug Induced Organic Mental Disorders | | |
|---|---|---|---|---|---|---|---|---|---|---|---|
| | | Sample size, N | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | |
| Medication Therapy Group | Antihistamines & Comb. (Class 1) | 150 | 3 (4) | 0 (0) (100%) | | 0 (0) | 1 (1.4) (-Inf%) | | 0 (0) | 0 (0) (NaN%) | |
| | Gastrointestinal Drugs (Classes 147-162, 273) | 858 | 2 (0.5) | 1 (0.2) (60%) | | 5 (1.2) | 4 (1) (17%) | | 3 (0.7) | 0 (0) (100%) | |
| | Anti-infective Agents (Classes 2-20) | 1337 | 2 (0.3) | 1 (0.2) (33%) | | 4 (0.6) | 6 (1) (-67%) | | 5 (0.8) | 0 (0) (100%) | |
| | Antineoplastic Agents (Classes 21-22, 260-265) | 67 | 0 (0) | 0 (0) (NaN%) | | 0 (0) | 1 (3.3) (-Inf%) | | 0 (0) | 0 (0) (NaN%) | |
| | Autonomic Drugs (Classes 23-33) | 674 | 2 (0.6) | 2 (0.6) (0%) | | 2 (0.6) | 1 (0.3) (-117%) | | 1 (0.3) | 1 (0.3) (0%) | |
| | Hormones & Synthetic Substitutes (Classes 165-180 246 252-253 256 266-268) | 2463 | 3 (0.2) | 3 (0.3) (-50%) | | 5 (0.4) | 6 (0.5) (-25%) | | 8 (0.7) | 2 (0.2) (71%) | |
| | Immunosuppressants (Class 181) | 114 | 0 (0) | 0 (0) (NaN%) | | 1 (1.8) | 0 (0) (100%) | | 0 (0) | 0 (0) (NaN%) | |
| | Blood Form/Coagul Agents (Classes 35-45, 259) | 380 | 2 (1.1) | 1 (0.6) (45%) | | 2 (1.1) | 0 (0) (100%) | | 1 (0.5) | 0 (0) (100%) | |
| | Cardiovascular Agents (Classes 46-56, 245, 250, 271) | 2193 | 3 (0.3) | 3 (0.3) (0%) | | 5 (0.5) | 5 (0.5) (0%) | | 5 (0.5) | 2 (0.2) (71%) | |
| | Central Nervous System (Classes 57-77, 272) | 1596 | 3 (0.4) | 2 (0.3) (25%) | | 5 (0.6) | 6 (0.8) (-33%) | | 8 (1) | 2 (0.3) (70%) | |
| | Serums, Toxoids, Vaccines (Classes 185-189) | 169 | 0 (0) | 0 (0) (NaN%) | | 0 (0) | 1 (1.3) (-Inf%) | | 1 (1.2) | 0 (0) (100%) | |
| | Dental Agents (Classes 79-83) | 8 | 0 (0) | 0 (0) (NaN%) | | 0 (0) | 0 (0) (NaN%) | | 1 (25.1) | 0 (0) (NaN%) | |
| | Skin & Mucous Membrane (Classes 190-213, 242) | 575 | 0 (0) | 1 (0.4) (-Inf%) | | 3 (1) | 1 (0.4) (60%) | | 0 (0) | 0 (0) (NaN%) | |
| | Diagnostic Agents (Classes 84-98, 239, 243-244, 247) | 2463 | 3 (0.2) | 3 (0.3) (-50%) | | 5 (0.4) | 6 (0.5) (-25%) | | 8 (0.7) | 2 (0.2) (71%) | |
| | Smooth Muscles Relaxants (Classes 214-216) | 46 | 0 (0) | 0 (0) (NaN%) | | 1 (4.4) | 0 (0) (100%) | | 0 (0) | 0 (0) (NaN%) | |
| | Vitamins & Comb (Classes 217-233) | 371 | 1 (0.5) | 1 (0.6) (-20%) | | 3 (1.6) | 2 (1.1) (33%) | | 3 (1.6) | 0 (0) (100%) | |
| | Electrolytic, Caloric, Water (Classes 100-126, 241, 292) | 759 | 2 (0.5) | 0 (0) (100%) | | 3 (0.8) | 1 (0.3) (62%) | | 4 (1.1) | 1 (0.3) (73%) | |
| | Unclassified Agents (Classes 234-236, 251, 254, 257-258, 270) | 304 | 0 (0) | 0 (0) (NaN%) | | 3 (2) | 1 (0.7) (65%) | | 1 (0.7) | 0 (0) (100%) | |
| | Devices and Non-drug Items (Class 237) | 344 | 0 (0) | 0 (0) (NaN%) | | 0 (0) | 2 (1.2) (-Inf%) | | 5 (2.9) | 1 (0.6) (79%) | |
| | Antituss/Expector/Mucolytic (Classes 128-131, 248, 255) | 374 | 0 (0) | 2 (1.1) (-Inf%) | | 3 (1.6) | 0 (0) (100%) | | 0 (0) | 1 (0.6) (-Inf%) | |
| | Pharmaceutical Aids/Adjuvants (Class 238) | 49 | 0 (0) | 0 (0) (NaN%) | | 0 (0) | 0 (0) (NaN%) | | 0 (0) | 0 (0) (NaN%) | |
| | Eye, Ear, Nose Throat (Classes 132, 146, 240, 200) | 452 | 1 (0.4) | 1 (0.5) (-25%) | | 3 (1.3) | 3 (1.4) (-8%) | | 2 (0.9) | 0 (0) (100%) | |
| Other Diabetic Therapy | Insulin Pump | 155 | 0 (0) | 0 (0) (NaN%) | | 0 (0) | 0 (0) (NaN%) | | 1 (1.3) | 0 (0) (100%) | |
| | >= 4 Strips per day | 301 | 1 (0.7) | 0 (0) (100%) | | 0 (0) | 0 (0) (NaN%) | | 0 (0) | 0 (0) (NaN%) | |
| | < 4 Strips per day | 2162 | 2 (0.2) | 3 (0.3) (-50%) | | 5 (0.5) | 6 (0.6) (-20%) | | 8 (0.7) | 2 (0.2) (71%) | |

FIG. 25T

| | | | Injuries, Poisonings & Toxic Effects of Drugs | | | Multiple Significant Trauma | | | Diseases & Disorders of Blood, Blood Forming Organs, Immunologic Disorders | | |
|---|---|---|---|---|---|---|---|---|---|---|---|
| | | Sample size, N | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | | Before flash CGM Hospitalizations (Events/100 pt-yr) | After flash CGM Hospitalizations (Events/100 pt-yr) (% reduction) | |
| Medication Therapy Group | Antihistamines & Comb. (Class 1) | 150 | 1 (1.3) | 2 (2.8) (-115%) | | 0 (0) | 0 (0) (NaN%) | | 0 (0) | 1 (1.4) (-Inf%) | |
| | Gastrointestinal Drugs (Classes 147 162, 273) | 858 | 5 (1.2) | 2 (0.5) (58%) | | 0 (0) | 0 (0) (NaN%) | | 5 (1.2) | 2 (0.5) (58%) | |
| | Anti-infective Agents (Classes 2-20) | 1337 | 3 (0.5) | 4 (0.6) (-20%) | | 0 (0) | 0 (0) (NaN%) | | 5 (0.8) | 3 (0.5) (38%) | |
| | Antineoplastic Agents (Classes 21-22, 260-265) | 67 | 0 (0) | 0 (0) (NaN%) | | 0 (0) | 0 (0) (NaN%) | | 0 (0) | 1 (3.3) (-Inf%) | |
| | Autonomic Drugs (Classes 23-33) | 674 | 4 (1.2) | 3 (1) (17%) | | 0 (0) | 0 (0) (NaN%) | | 5 (1.5) | 4 (1.3) (13%) | |
| | Hormones & Synthetic Substitutes (Classes 165-180 246 252-253 256 266-268) | 2463 | 5 (0.4) | 4 (0.3) (25%) | | 0 (0) | 0 (0) (NaN%) | | 5 (0.4) | 5 (0.4) (0%) | |
| | Immunosuppressants (Class 181) | 114 | 0 (0) | 1 (1.9) (-Inf%) | | 0 (0) | 0 (0) (NaN%) | | 1 (1.8) | 1 (1.9) (-6%) | |
| | Blood Form/Coagul Agents (Classes 35-45, 259) | 380 | 0 (0) | 0 (0) (NaN%) | | 0 (0) | 0 (0) (NaN%) | | 5 (2.6) | 3 (1.7) (35%) | |
| | Cardiovascular Agents (Classes 40-56, 245, 250, 271) | 2193 | 5 (0.5) | 4 (0.4) (20%) | | 0 (0) | 0 (0) (NaN%) | | 5 (0.5) | 5 (0.5) (0%) | |
| | Central Nervous System (Classes 57-77, 272) | 1596 | 5 (0.6) | 3 (0.4) (33%) | | 0 (0) | 0 (0) (NaN%) | | 5 (0.6) | 5 (0.7) (-17%) | |
| | Serums, Toxoids, Vaccines (Classes 185-189) | 169 | 0 (0) | 0 (0) (NaN%) | | 0 (0) | 0 (0) (NaN%) | | 0 (0) | 1 (1.3) (-Inf%) | |
| | Dental Agents (Classes 79-83) | 8 | 0 (0) | 0 (0) (NaN%) | | 0 (0) | 0 (0) (NaN%) | | 0 (0) | 0 (0) (NaN%) | |
| | Skin & Mucous Membrane (Classes 190-213, 242) | 575 | 4 (1.4) | 2 (0.7) (50%) | | 0 (0) | 0 (0) (NaN%) | | 4 (1.4) | 1 (0.4) (71%) | |
| | Diagnostic Agents (Classes 84-98, 239, 243-244, 247) | 2463 | 5 (0.4) | 4 (0.3) (25%) | | 0 (0) | 0 (0) (NaN%) | | 5 (0.4) | 5 (0.4) (0%) | |
| | Smooth Muscles Relaxants (Classes 214-216) | 46 | 1 (4.4) | 0 (0) (100%) | | 0 (0) | 0 (0) (NaN%) | | 0 (0) | 1 (4.4) (-Inf%) | |
| | Vitamins & Comb (Classes 217-233) | 371 | 0 (0) | 1 (0.6) (-Inf%) | | 0 (0) | 0 (0) (NaN%) | | 0 (0) | 1 (0.6) (-Inf%) | |
| | Electrolytic, Caloric, Water (Classes 100-126, 241, 292) | 759 | 3 (0.8) | 2 (0.6) (25%) | | 0 (0) | 0 (0) (NaN%) | | 5 (1.3) | 2 (0.6) (54%) | |
| | Unclassified Agents (Classes 234-236, 251, 254, 257-258, 270) | 304 | 1 (0.7) | 1 (0.7) (0%) | | 0 (0) | 0 (0) (NaN%) | | 1 (0.7) | 2 (1.4) (-100%) | |
| | Devices and Non-drug Items (Class 237) | 344 | 2 (1.2) | 0 (0) (100%) | | 0 (0) | 0 (0) (NaN%) | | 0 (0) | 0 (0) (NaN%) | |
| | Antituss/Expector/Mucolytic (Classes 128-131, 248, 255) | 374 | 0 (0) | 1 (0.6) (-Inf%) | | 0 (0) | 0 (0) (NaN%) | | 5 (2.7) | 2 (1.1) (59%) | |
| | Pharmaceutical Aids/Adjuvants (Class 238) | 49 | 1 (4.1) | 0 (0) (100%) | | 0 (0) | 0 (0) (NaN%) | | 0 (0) | 0 (0) (NaN%) | |
| | Eye, Ear, Nose Throat (Classes 132 146, 240, 290) | 452 | 1 (0.4) | 1 (0.5) (-25%) | | 0 (0) | 0 (0) (NaN%) | | 4 (1.8) | 2 (0.9) (50%) | |
| Other Diabetic Therapy | Insulin Pump | 155 | 1 (1.3) | 0 (0) (100%) | | 0 (0) | 0 (0) (NaN%) | | 0 (0) | 0 (0) (NaN%) | |
| | >= 4 Strips per day | 301 | 0 (0) | 1 (0.7) (-Inf%) | | 0 (0) | 0 (0) (NaN%) | | 3 (2) | 0 (0) (100%) | |
| | < 4 Strips per day | 2162 | 5 (0.5) | 3 (0.3) (40%) | | 0 (0) | 0 (0) (NaN%) | | 2 (0.2) | 5 (0.5) (-150%) | |

FIG. 25U

| | | | Before flash CGM Hospitalizations (Events/100 pt-yr) | Burns | |
|---|---|---|---|---|---|
| | | Sample size, N | | After flash CGM Hospitalizations (Events/100 pt-yr) (% reduction) | |
| Medication Therapy Group | Antihistamines & Comb. (Class 1) | 156 | 0 (0) | 0 (0) (NaN%) | |
| | Gastrointestinal Drugs (Classes 142, 162, 273) | 858 | 0 (0) | 0 (0) (NaN%) | |
| | Anti-infective Agents (Classes 2-20) | 1337 | 2 (0.3) | 0 (0) (100%) | |
| | Antineoplastic Agents (Classes 21-22, 260-265) | 67 | 0 (0) | 0 (0) (NaN%) | |
| | Autonomic Drugs (Classes 23-33) | 674 | 2 (0.6) | 0 (0) (100%) | |
| | Hormones & Synthetic Substitutes (Classes 165-180 246 252-253 256 266-268) | 2463 | 2 (0.2) | 0 (0) (100%) | |
| | Immunosuppressants (Class 181) | 114 | 0 (0) | 0 (0) (NaN%) | |
| | Blood Form/Coagul Agents (Classes 35-45, 259) | 389 | 0 (0) | 0 (0) (NaN%) | |
| | Cardiovascular Agents (Classes 46-56, 245, 250, 271) | 2193 | 2 (0.2) | 0 (0) (100%) | |
| | Central Nervous System (Classes 57-77, 272) | 1596 | 2 (0.3) | 0 (0) (100%) | |
| | Serums, Toxoids, Vaccines (Classes 185-189) | 169 | 0 (0) | 0 (0) (NaN%) | |
| | Dental Agents (Classes 79-83) | 8 | 0 (0) | 0 (0) (100%) | |
| | Skin & Mucous Membrane (Classes 190-213, 242) | 575 | 3 (0.3) | 0 (0) (100%) | |
| | Diagnostic Agents (Classes 84-98, 239, 243-244, 247) | 2463 | 2 (0.2) | 0 (0) (100%) | |
| | Smooth Muscles Relaxants (Classes 214-216) | 46 | 1 (4.4) | 0 (0) (100%) | |
| | Vitamins & Comb (Classes 217-233) | 371 | 0 (0) | 0 (0) (NaN%) | |
| | Electrolytic, Caloric, Water (Classes 100-126, 241, 292) | 759 | 1 (0.3) | 0 (0) (100%) | |
| | Unclassified Agents (Classes 234-236, 251, 254, 257-258, 270) | 304 | 1 (0.7) | 0 (0) (100%) | |
| | Devices and Non-drug Items (Class 237) | 344 | 1 (0.6) | 0 (0) (100%) | |
| | Antituss/Expector/Mucolytic (Classes 128-131, 248, 255) | 374 | 0 (0) | 0 (0) (NaN%) | |
| | Pharmaceutical Aids/Adjuvants (Class 238) | 49 | 0 (0) | 0 (0) (NaN%) | |
| | Eye, Ear, Nose Throat (Classes 132 146, 240, 296) | 452 | 3 (0.4) | 0 (0) (100%) | |
| Other Diabetic Therapy | Insulin Pump | 155 | 0 (0) | 0 (0) (NaN%) | |
| | >= 4 Strips per day | 301 | 0 (0) | 0 (0) (NaN%) | |
| | < 4 Strips per day | 2162 | 2 (0.2) | 0 (0) (100%) | |

FIG. 25V

SYSTEMS, DEVICES, AND METHODS FOR ANALYTE MONITORING AND BENEFITS THEREOF

CROSS-REFERENCE TO RELATED APPLICATIONS

This application claims priority to and the benefit of U.S. Provisional Patent Application No. 63/029,339, filed May 22, 2020, and U.S. Provisional Patent Application No. 63/104,282, filed Oct. 22, 2020, which are incorporated by reference herein in their entirety for all purposes.

FIELD

The subject matter described herein relates generally to systems, devices, and methods for in vivo analyte monitoring and benefits thereof.

BACKGROUND

The detection and/or monitoring of analyte levels, such as glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, uric acid, etc., or the like, can be important to the health of an individual having diabetes. Patients suffering from diabetes mellitus can experience complications including loss of consciousness, cardiovascular disease, retinopathy, neuropathy, and nephropathy. Diabetics are generally required to monitor their glucose levels to ensure that they are being maintained within a clinically safe range, and may also use this information to determine if and/or when insulin is needed to reduce glucose levels in their bodies, or when additional glucose is needed to raise the level of glucose in their bodies.

Growing clinical data demonstrates a strong correlation between the frequency of glucose monitoring and glycemic control and a strong correlation between use glucose monitoring regimen and reduced hospitalizations. Despite such correlation, however, many individuals diagnosed with a diabetic condition do not monitor their glucose levels as frequently as they should due to a combination of factors including convenience, testing discretion, pain associated with glucose testing, and cost.

To increase patient adherence to a plan of frequent glucose monitoring, in vivo analyte monitoring systems can be utilized, in which a sensor control device may be worn on the body of an individual who requires analyte monitoring. To increase comfort and convenience for the individual, the sensor control device may have a small form-factor and can be applied by the individual with a sensor applicator. The application process includes inserting at least a portion of a sensor that senses a user's analyte level in a bodily fluid located in a layer of the human body, using an applicator or insertion mechanism, such that the sensor comes into contact with a bodily fluid. The sensor control device may also be configured to transmit analyte data to another device, from which the individual, her health care provider ("HCP"), or a caregiver can review the data and make therapy decisions.

Despite their advantages, however, some people are reluctant to use analyte monitoring systems for various reasons, including the complexity and volume of data presented, a learning curve associated with the software and user interfaces for analyte monitoring systems, and an overall paucity of actionable information presented.

Thus, needs exist for analyte monitoring systems, as well as methods and devices relating thereto, for improving clinical outcomes.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to systems, devices, and methods of analyte monitoring and benefits thereof. According to an embodiment, a method of treatment of type 2 diabetic patient can include selecting a type 2 diabetic patient having a predetermined comorbidity for treatment, initiating a continuous glucose monitor regimen for the selected type 2 diabetic patient, wherein after six months of initiation of the continuous glucose monitor regimen, a rate of hospitalization for a predetermined diagnostic category of the selected patient having the predetermined comorbidity can be reduced by at least 12% relative to an average rate of hospitalization for the predetermined diagnostic category of selected patients having the predetermined comorbidity without the continuous glucose monitor regimen.

According to embodiments, the predetermined comorbidity can be anemia.

As embodied herein, the selected patient can receive basal-bolus insulin therapy. As embodied herein, the predetermined diagnostic category is infectious and parasitic diseases, and the rate of hospitalization for infectious and parasitic diseases of the selected patient after six months can be reduced by 51% relative to an average rate of hospitalization for infectious and parasitic diseases of selected patients having anemia without the continuous glucose monitor regimen.

As embodied herein, the predetermined diagnostic category is respiratory diseases, and the rate of hospitalization for respiratory diseases of the selected patient after six months can be reduced by 38% relative to an average rate of hospitalization for respiratory diseases of selected patients having anemia without the continuous glucose monitor regimen. As embodied herein, the predetermined diagnostic category is kidney and urinary tract diseases, and the rate of hospitalization for kidney and urinary tract diseases of the selected patient after six months can be reduced by 57% relative to an average rate of hospitalization for kidney and urinary tract diseases of selected patients having anemia without the continuous glucose monitor regimen.

As embodied herein, the predetermined diagnostic category is hepatobiliary and pancreatic diseases, and the rate of hospitalization for hepatobiliary and pancreatic diseases of the selected patient after six months can be reduced by 55% relative to an average rate of hospitalization for hepatobiliary and pancreatic diseases of selected patients having anemia without the continuous glucose monitor regimen.

As embodied herein, the selected patient can be receiving non-multiple daily insulin injection therapy. As embodied herein, the predetermined diagnostic category is infectious and parasitic diseases, and the rate of hospitalization for infectious and parasitic diseases of the selected patient after six months can be reduced by 48% relative to an average rate of hospitalization for infectious and parasitic diseases of selected patients having anemia without the continuous glucose monitor regimen. As embodied herein, the predetermined diagnostic category is respiratory diseases, and the rate of hospitalization for respiratory diseases of the selected patient after six months can be reduced by 59% relative to an average rate of hospitalization for respiratory diseases of selected patients having anemia without the continuous glucose monitor regimen. As embodied herein, the predetermined diagnostic category is kidney and urinary tract diseases, and the rate of hospitalization for kidney and urinary tract diseases of the selected patient after six months can be reduced by 51% relative to an average rate of hospitalization for kidney and urinary tract diseases of selected patients having anemia without the continuous glucose monitor regimen. As embodied herein, the predetermined diagnostic category is hepatobiliary and pancreatic diseases, and the rate of hospitalization for hepatobiliary and pancreatic diseases of the selected patient after six months can be reduced by 44% relative to an average rate of hospitalization for hepatobiliary and pancreatic diseases of selected patients having anemia without the continuous glucose monitor regimen.

According to embodiments, the predetermined diagnostic category is infectious and parasitic diseases, and the rate of hospitalization for infectious and parasitic diseases of the selected patient after six months can be reduced by at least 33% relative to an average rate of hospitalization for infectious and parasitic diseases of selected patients having the predetermined comorbidity without the continuous glucose monitor regimen.

As embodied herein, the selected patient can be receiving basal-bolus insulin therapy. As embodied herein, the predetermined comorbidity is a fluid and electrolyte disorder, and the rate of hospitalization for infectious and parasitic diseases of the selected patient having fluid and electrolyte disorder after six months can be reduced by at least 59% relative to an average rate of hospitalization for infectious and parasitic diseases of selected patients having fluid and electrolyte disorder without the continuous glucose monitor regimen. As embodied herein, the predetermined comorbidity is a valvular disorder, and the rate of hospitalization for infectious and parasitic diseases of the selected patient having a valvular disorder after six months can be reduced at least by 58% relative to an average rate of hospitalization for infectious and parasitic diseases of selected patients having a valvular disorder without the continuous glucose monitor regimen. As embodied herein, the predetermined comorbidity is liver disease, and the rate of hospitalization for infectious and parasitic diseases of the selected patient having liver disease after six months can be reduced by at least 50% relative to an average rate of hospitalization for infectious and parasitic diseases of selected patients having liver disease without the continuous glucose monitor regimen.

As embodied herein, the selected patient can be receiving non-multiple daily insulin injection therapy. As embodied herein, the predetermined comorbidity is a fluid or electrolyte disorder, and the rate of hospitalization for infectious and parasitic diseases of the selected patient having a fluid or electrolyte disorder after six months can be reduced by at least 68% relative to an average rate of hospitalization for infectious and parasitic diseases of selected patients having fluid or electrolyte disorders without the continuous glucose monitor regimen. As embodied herein, the predetermined comorbidity is a valvular disorder, and the rate of hospitalization for infectious and parasitic diseases of the selected patient having a valvular disorder after six months can be reduced by at least 53% relative to an average rate of hospitalization for infectious and parasitic diseases of selected patients having valvular disorders without the continuous glucose monitor regimen. As embodied herein, the predetermined comorbidity is liver disease, and the rate of hospitalization for infectious and parasitic diseases of the selected patient having liver disease after six months can be reduced by at least 54% relative to an average rate of hospitalization for infectious and parasitic diseases of selected patients having liver disease without the continuous glucose monitor regimen.

In accordance with the disclosed subject matter, to some embodiments, a system to establish an analyte monitor regimen is also provided. The system includes a sensor control device comprising an analyte sensor coupled with sensor electronics, the sensor control device configured to transmit data indicative of an analyte level, and, a reader device comprising a display, wireless communication circuitry configured to receive the data indicative of the analyte level, and one or more processors coupled with a memory, the memory configured to store instructions that, when executed by the one or more processors, cause the one or more processors to output to the display an analyte level measurement, wherein after six months of initiating an analyte monitor regimen using the system for a type 2 diabetic patient having a predetermined comorbidity, a rate of hospitalization for a predetermined diagnostic category of the selected patient having the predetermined comorbidity can be reduced by at least 12% relative to an average rate of hospitalization for a predetermined diagnostic category of selected patients having the predetermined comorbidity without the continuous glucose monitor regimen. The system can include any of the features described hereinabove for the method of treatment.

In accordance with the disclosed subject matter, a method of treatment of a type 2 diabetic patient can include selecting a type 2 diabetic patient having a predetermined comorbidity for treatment, initiating a continuous glucose monitor regimen for the selected type 2 diabetic patient, wherein after six months of initiation of the continuous glucose monitor regimen, an average rate of hospitalization for a predetermined diagnostic category of the selected patient having the predetermined comorbidity can be reduced by at least 12% relative to an average rate of hospitalization for the predetermined diagnostic category of the selected patient having the predetermined comorbidity during a period of six months prior to initiating the continuous glucose monitor regimen.

As embodied herein, the selected patient can be receiving basal-bolus insulin therapy. As embodied herein, the predetermined diagnostic category is infectious and parasitic diseases, and the average rate of hospitalization for infectious and parasitic diseases of the selected patient after six months can be reduced by 51% relative to an average rate of hospitalization for infectious and parasitic diseases of the selected patient having anemia during a period of six months prior to initiating the continuous glucose monitor regimen. As embodied herein, the predetermined diagnostic category is respiratory diseases, and the average rate of hospitalization for respiratory diseases of the selected patient after six months can be reduced by 38% relative to an average rate of hospitalization for respiratory diseases of the selected patient having anemia during a period of six months prior to initiating the continuous glucose monitor regimen. As embodied herein, the predetermined diagnostic category is kidney and urinary tract diseases, and the average rate of hospitalization for kidney and urinary tract diseases of the selected patient after six months can be reduced by 57% relative to an average rate of hospitalization for kidney and urinary tract diseases of the selected patient having anemia during a period of six months prior to initiating the continuous glucose monitor regimen. As embodied herein, the predetermined diagnostic category is hepatobiliary and pancreatic diseases, and the average rate of hospitalization for hepatobiliary and pancreatic diseases of the selected patient after six months can be reduced by 55% relative to an average rate of hospitalization for hepatobiliary and pancreatic diseases of the selected patient having anemia during a period of six months prior to initiating the continuous glucose monitor regimen.

As embodied herein, the selected patient can be receiving non-multiple daily insulin injection therapy. As embodied herein, the predetermined diagnostic category is infectious and parasitic diseases, and the average rate of hospitalization for infectious and parasitic diseases of the selected patient after six months can be reduced by 48% relative to an average rate of hospitalization for infectious and parasitic diseases of the selected patient having anemia during a period of six months prior to initiating the continuous glucose monitor regimen. As embodied herein, the predetermined diagnostic category is respiratory diseases, and the average rate of hospitalization for respiratory diseases of the selected patient after six months can be reduced by 59% relative to an average rate of hospitalization for respiratory diseases of the selected patient having anemia during a period of six months prior to initiating the continuous glucose monitor regimen. As embodied herein, the predetermined diagnostic category is kidney and urinary tract diseases, and the average rate of hospitalization for kidney and urinary tract diseases of the selected patient after six months can be reduced by 51% relative to an average rate of hospitalization for kidney and urinary tract diseases of the selected patient having anemia during a period of six months prior to initiating the continuous glucose monitor regimen. As embodied herein, the predetermined diagnostic category is hepatobiliary and pancreatic diseases, and the average rate of hospitalization for hepatobiliary and pancreatic diseases of the selected patient after six months can be reduced by 44% relative to an average rate of hospitalization for hepatobiliary and pancreatic diseases of the selected patient having anemia during a period of six months prior to initiating the continuous glucose monitor regimen.

According to embodiments, the predetermined diagnostic category is infectious and parasitic diseases, and the average rate of hospitalization for infectious and parasitic diseases of the selected patient after six months can be reduced by at least 33% relative to an average rate of hospitalization for infectious and parasitic diseases of the selected patient having the predetermined comorbidity during a period of six months prior to initiating the continuous glucose monitor regimen.

As embodied herein, the selected patient can be receiving basal-bolus insulin therapy. As embodied herein, the predetermined comorbidity is a fluid and electrolyte disorder, and the average rate of hospitalization for infectious and parasitic diseases of the selected patient having fluid and electrolyte disorder after six months can be reduced by at least 59% relative to an average rate of hospitalization for infectious and parasitic diseases of the selected patient having fluid and electrolyte disorder during a period of six months prior to initiating the continuous glucose monitor regimen. As embodied herein, the predetermined comorbidity is a valvular disorder, and the average rate of hospitalization for infectious and parasitic diseases of the selected patient having a valvular disorder after six months can be reduced at least by 58% relative to an average rate of hospitalization for infectious and parasitic diseases of the selected patient having a valvular disorder during a period of six months prior to initiating the continuous glucose monitor regimen. As embodied herein, the predetermined comorbidity is liver disease, and the average rate of hospitalization for infectious and parasitic diseases of the selected patient having liver disease after six months can be reduced by at least 50% relative to an average rate of hospitalization for infectious and parasitic diseases of the selected patient having liver disease during a period of six months prior to initiating the continuous glucose monitor regimen.

As embodied herein, the selected patient can be receiving non-multiple daily insulin injection therapy. As embodied herein, the predetermined comorbidity is a fluid or electrolyte disorder, and the average rate of hospitalization for infectious and parasitic diseases of the selected patient having a fluid or electrolyte disorder after six months can be reduced by at least 68% relative to an average rate of hospitalization for infectious and parasitic diseases of the selected patient having fluid or electrolyte disorders during a period of six months prior to initiating the continuous glucose monitor regimen. As embodied herein, the predetermined comorbidity is a valvular disorder, and the average rate of hospitalization for infectious and parasitic diseases of the selected patient having a valvular disorder after six months can be reduced by at least 53% relative to an average rate of hospitalization for infectious and parasitic diseases of the selected patient having valvular disorders during a period of six months prior to initiating the continuous glucose monitor regimen. As embodied herein, the predetermined comorbidity is liver disease, and the average rate of hospitalization for infectious and parasitic diseases of the selected patient having liver disease after six months can be reduced by at least 54% relative to an average rate of hospitalization for infectious and parasitic diseases of the selected patient having liver disease during a period of six months prior to initiating the continuous glucose monitor regimen.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 2D to 2I are example embodiments of GUIs comprising sensor results interfaces.

FIGS. 8C to 8E are graphs depicting data at various stages of processing according to an example embodiment of a method for data merging in an analyte monitoring system.

FIGS. 11B to 11D are example embodiments of GUIs to be displayed according to an example embodiment of a method for generating a sensor termination system alarm.

FIGS. 13A-13E show the results of an exemplary retrospective study showing reduction in acute diabetes complications in patients associated with continuous glucose monitoring.

FIGS. 14A-14J the results of a real world study, using the Swedish National Diabetes register, comparing HbA1c levels in patients before and after use of a continuous glucose monitoring system.

FIGS. 15A-15K show the results of a cost impact analysis on adults using continuous flash glucose monitoring systems with optional alarms.

FIGS. 16A-16E show the results of a retrospective observational analysis which indicates reduction of HbA1c levels in adults using a flash glucose monitoring system.

FIGS. 17A-17E illustrate an exemplary kinetic model for predicting RBC lifespan and glucose uptake.

FIGS. 18A-18C show an analysis of several studies indicating HbA1c reduction in patients using a continuous glucose monitor system.

FIGS. 19A-19E show the results of a study analysis HbA1c reduction in patients after prescription of the FreeStyle Libre system.

FIGS. 21A-21J show a comparison of healthcare costs associated with use of various glycemic products, such as a continuous glucose monitor system.

FIGS. 22A-22C show the results of a meta-analysis of various studies which indicate improvement in several glycemic parameters in users with a continuous glucose monitor system.

FIGS. 23A-23K show an analysis of several studies which illustrate the clinical effects of diabetes management using flash glucose monitoring.

FIGS. 24A-24S show collected data from a plurality of patients with Type-2 diabetes who were treated with non-MDI therapy.

FIGS. 25A-25V show collected data from a plurality of patients with Type-2 diabetes who were treated with basal-bolus therapy.

DETAILED DESCRIPTION

Figure 1:
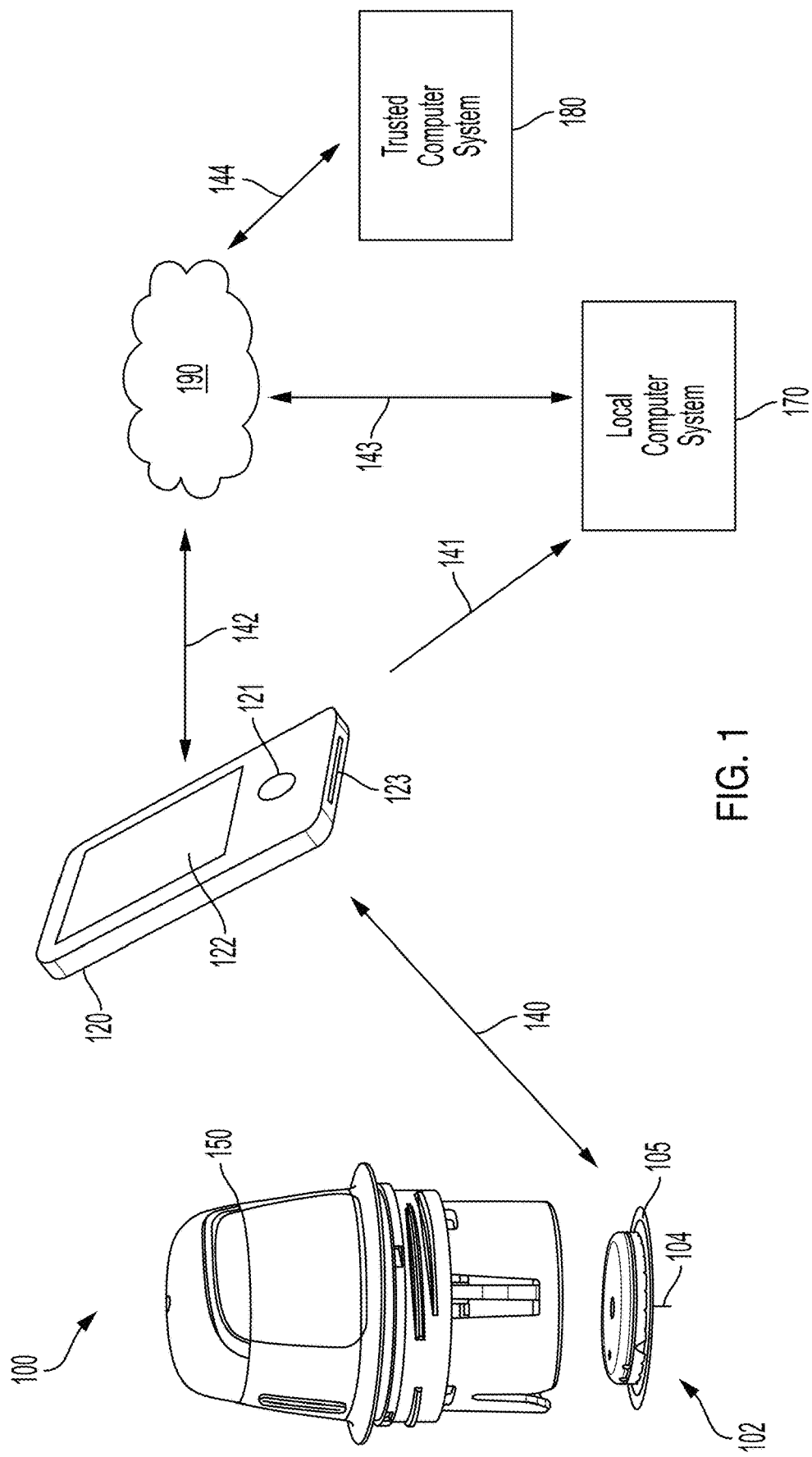
FIG. 1 is a system overview of an analyte monitoring system comprising a sensor applicator, a sensor control device, a reader device, a network, a trusted computer system, and a local computer system.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of this disclosure will be limited only by the appended claims.

As used herein and in the appended claims, the singular forms "a," "an," and "the" include plural referents unless the context clearly dictates otherwise.

The publications discussed herein are provided solely for their disclosure prior to the filing date of this application. Nothing herein is to be construed as an admission that this disclosure is not entitled to antedate such publication by virtue of prior disclosure. Further, the dates of publication provided may be different from the actual publication dates which may need to be independently confirmed.

Generally, embodiments of this disclosure include GUIs and digital interfaces for analyte monitoring systems, and methods and devices relating thereto. Accordingly, many embodiments include in vivo analyte sensors structurally configured so that at least a portion of the sensor is, or can be, positioned in the body of a user to obtain information about at least one analyte of the body. It should be noted, however, that the embodiments disclosed herein can be used with in vivo analyte monitoring systems that incorporate in vitro capability, as well as purely in vitro or ex vivo analyte monitoring systems, including systems that are entirely noninvasive.

Furthermore, for each and every embodiment of a method disclosed herein, systems and devices capable of performing each of those embodiments are covered within the scope of this disclosure. For example, embodiments of sensor control devices, reader devices, local computer systems, and trusted computer systems are disclosed, and these devices and systems can have one or more sensors, analyte monitoring circuits (e.g., an analog circuit), memories (e.g., for storing instructions), power sources, communication circuits, transmitters, receivers, processors and/or controllers (e.g., for executing instructions) that can perform any and all method steps or facilitate the execution of any and all method steps.

As previously described, a number of embodiments described herein provide for improved GUIs for analyte monitoring systems, wherein the GUIs are highly intuitive, user-friendly, and provide for rapid access to physiological information of a user. According to some embodiments, a Time-in-Ranges GUI of an analyte monitoring system is provided, wherein the Time-in-Ranges GUI comprises a plurality of bars or bar portions, wherein each bar or bar portion indicates an amount of time that a user's analyte level is within a predefined analyte range correlating with the bar or bar portion. According to another embodiment, an Analyte Level/Trend Alert GUI of an analyte monitoring system is provided, wherein the Analyte Level/Trend Alert GUI comprises a visual notification (e.g., alert, alarm, pop-up window, banner notification, etc.), and wherein the visual notification includes an alarm condition, an analyte level measurement associated with the alarm condition, and a trend indicator associated with the alarm condition. In sum, these embodiments provide for a robust, user-friendly interfaces that can increase user engagement with the analyte monitoring system and provide for timely and actionable responses by the user, to name a few advantages.

In addition, a number of embodiments described herein provide for improved digital interfaces for analyte monitoring systems. According to some embodiments, improved methods, as well as systems and device relating thereto, are provided for data backfilling, aggregation of disconnection and reconnection events for wireless communication links, expired or failed sensor transmissions, merging data from multiple devices, transitioning of previously activated sensors to new reader devices, generating sensor insertion failure system alarms, and generating sensor termination system alarms. Collectively and individually, these digital interfaces improve upon the accuracy and integrity of analyte data being collected by the analyte monitoring system, the flexibility of the analyte monitoring system by allowing users to transition between different reader devices, and the alarming capabilities of the analyte monitoring system by providing for more robust inter-device communications during certain adverse conditions, to name only a few. Other improvements and advantages are provided as well. The various configurations of these devices are described in detail by way of the embodiments which are only examples.

Before describing these aspects of the embodiments in detail, however, it is first desirable to describe examples of devices that can be present within, for example, an in vivo analyte monitoring system, as well as examples of their operation, all of which can be used with the embodiments described herein.

There are various types of in vivo analyte monitoring systems. "Continuous Analyte Monitoring" systems (or "Continuous Glucose Monitoring" systems), for example, can transmit data from a sensor control device to a reader device continuously without prompting, e.g., automatically according to a schedule. "Flash Analyte Monitoring" systems (or "Flash Glucose Monitoring" systems or simply "Flash" systems), as another example, can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo analyte monitoring systems can be differentiated from "in vitro" systems that contact a biological sample outside of the body (or "ex vivo") and that typically include a meter device that has a port for receiving an analyte test strip carrying bodily fluid of the user, which can be analyzed to determine the user's blood sugar level.

In vivo monitoring systems can include a sensor that, while positioned in vivo, makes contact with the bodily fluid of the user and senses the analyte levels contained therein. The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "handheld reader device," "reader device" (or simply a "reader"), "handheld electronics" (or simply a "handheld"), a "portable data processing" device or unit, a "data receiver," a "receiver" device or unit (or simply a "receiver"), or a "remote" device or unit, to name a few. Other devices such as personal computers have also been utilized with or incorporated into in vivo and in vitro monitoring systems.

Example Embodiment of In Vivo Analyte Monitoring System

FIG. 1 is a conceptual diagram depicting an example embodiment of an analyte monitoring system 100 that includes a sensor applicator 150, a sensor control device 102, and a reader device 120. Here, sensor applicator 150 can be used to deliver sensor control device 102 to a monitoring location on a user's skin where a sensor 104 is maintained in position for a period of time by an adhesive patch 105. Sensor control device 102 is further described in FIGS. 2B and 2C, and can communicate with reader device 120 via a communication path 140 using a wired or wireless technique. Example wireless protocols include Bluetooth, Bluetooth Low Energy (BLE, BTLE, Bluetooth SMART, etc.), Near Field Communication (NFC) and others. Users can view and use applications installed in memory on reader device 120 using screen 122 (which, in many embodiments, can comprise a touchscreen), and input 121. A device battery of reader device 120 can be recharged using power port 123. While only one reader device 120 is shown, sensor control device 102 can communicate with multiple reader devices 120. Each of the reader devices 120 can communicate and share data with one another. More details about reader device 120 is set forth with respect to FIG. 2A below. Reader device 120 can communicate with local computer system 170 via a communication path 141 using a wired or wireless communication protocol. Local computer system 170 can include one or more of a laptop, desktop, tablet, phablet, smartphone, set-top box, video game console, or other computing device and wireless communication can include any of a number of applicable wireless networking protocols including Bluetooth, Bluetooth Low Energy (BTLE), Wi-Fi or others. Local computer system 170 can communicate via communications path 143 with a network 190 similar to how reader device 120 can communicate via a communications path 142 with network 190, by a wired or wireless communication protocol as described previously. Network 190 can be any of a number of networks, such as private networks and public networks, local area or wide area networks, and so forth. A trusted computer system 180 can include a cloud-based platform or server, and can provide for authentication services, secured data storage, report generation, and can communicate via communications path 144 with network 190 by wired or wireless technique. In addition, although FIG. 1 depicts trusted computer system 180 and local computer system 170 communicating with a single sensor control device 102 and a single reader device 120, it will be appreciated by those of skill in the art that local computer system 170 and/or trusted computer system 180 are each capable of being in wired or wireless communication with a plurality of reader devices and sensor control devices.

Additional details of suitable analyte monitoring devices, systems, methods, components and the operation thereof along with related features are set forth in U.S. Pat. No. 9,913,600 to Taub et. al., International Publication No. WO2018/136898 to Rao et. al., International Publication No. WO2019/236850 to Thomas et. al., and U.S. Patent Publication No. 2020/01969191 to Rao et al., each of which is incorporated by reference in its entirety herein.

Example Embodiment of Reader Device

Figure 2A:
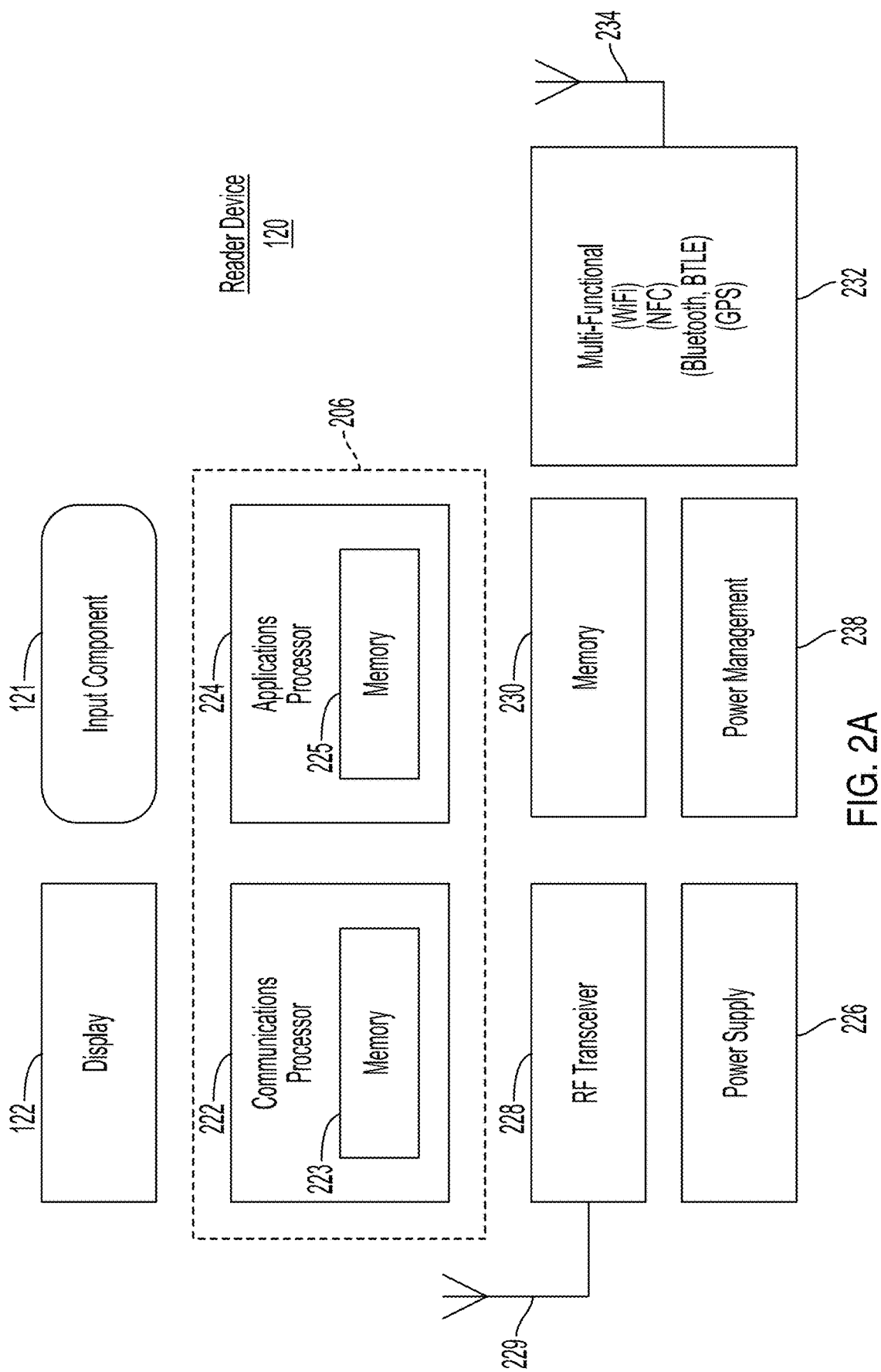
FIG. 2A is a block diagram depicting an example embodiment of a reader device.

FIG. 2A is a block diagram depicting an example embodiment of a reader device 120, which, As embodied herein, can comprise a smart phone. Here, reader device 120 can include a display 122, input component 121, and a processing core 206 including a communications processor 222 coupled with memory 223 and an applications processor 224 coupled with memory 225. Also included can be separate memory 230, RF transceiver 228 with antenna 229, and power supply 226 with power management module 238. Further, reader device 120 can also include a multi-functional transceiver 232, which can comprise wireless communication circuitry, and which can be configured to communicate over Wi-Fi, NFC, Bluetooth, BTLE, and GPS with an antenna 234. As understood by one of skill in the art, these components are electrically and communicatively coupled in a manner to make a functional device.

Example Embodiments of Sensor Control Devices

Figure 2B:
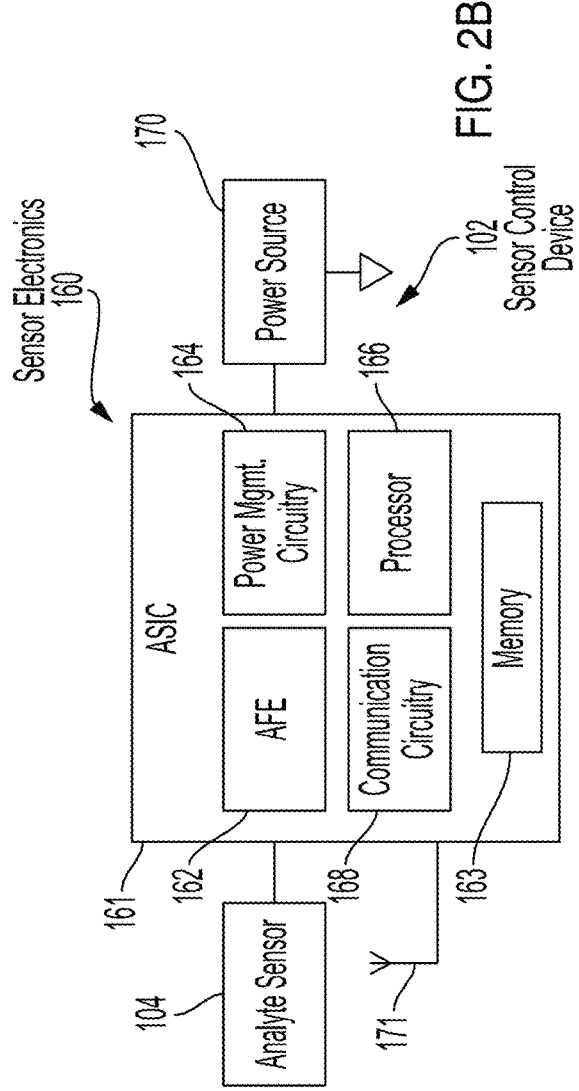
FIGS. 2B and 2C are block diagrams depicting example embodiments of sensor control devices.
Figure 2C:
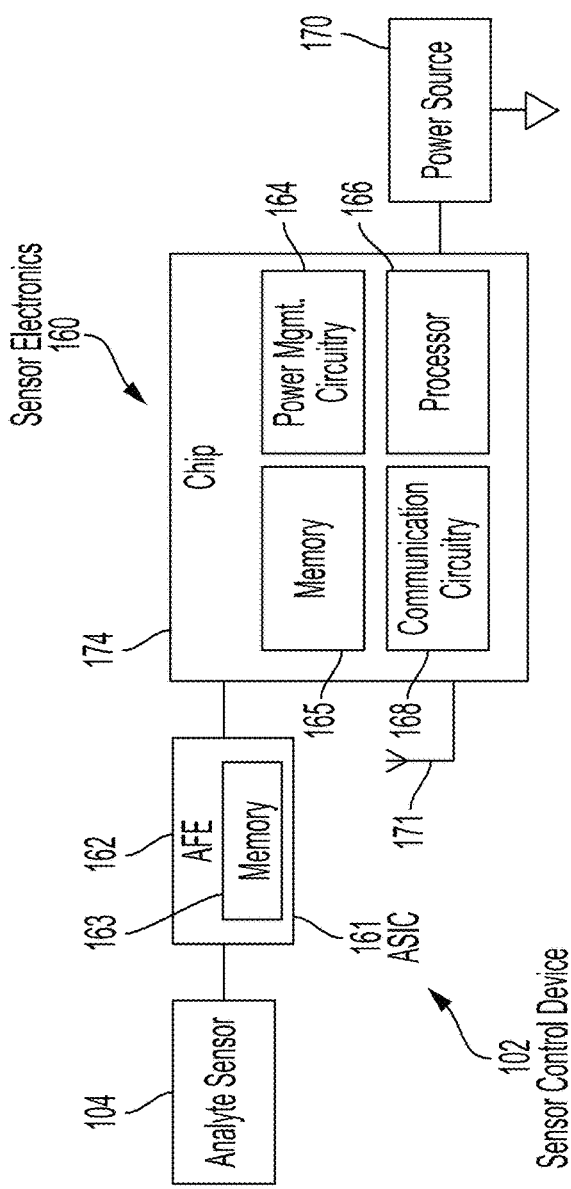

FIGS. 2B and 2C are block diagrams depicting example embodiments of sensor control devices 102 having analyte sensors 104 and sensor electronics 160 (including analyte monitoring circuitry) that can have the majority of the processing capability for rendering end-result data suitable for display to the user. In FIG. 2B, a single semiconductor chip 161 is depicted that can be a custom application specific integrated circuit (ASIC). Shown within ASIC 161 are certain high-level functional units, including an analog front end (AFE) 162, power management (or control) circuitry 164, processor 166, and communication circuitry 168 (which can be implemented as a transmitter, receiver, transceiver, passive circuit, or otherwise according to the communication protocol). In this embodiment, both AFE 162 and processor 166 are used as analyte monitoring circuitry, but in other embodiments either circuit can perform the analyte monitoring function. Processor 166 can include one or more processors, microprocessors, controllers, and/or microcontrollers, each of which can be a discrete chip or distributed amongst (and a portion of) a number of different chips.

A memory 163 is also included within ASIC 161 and can be shared by the various functional units present within ASIC 161, or can be distributed amongst two or more of them. Memory 163 can also be a separate chip. Memory 163 can be volatile and/or non-volatile memory. In this embodiment, ASIC 161 is coupled with power source 170, which can be a coin cell battery, or the like. AFE 162 interfaces with in vivo analyte sensor 104 and receives measurement data therefrom and outputs the data to processor 166 in digital form, which in turn processes the data to arrive at the end-result glucose discrete and trend values, etc. This data can then be provided to communication circuitry 168 for sending, by way of antenna 171, to reader device 120 (not shown), for example, where minimal further processing is needed by the resident software application to display the data. According to some embodiments, for example, a current glucose value can be transmitted from sensor control device 102 to reader device 120 every minute, and historical glucose values can be transmitted from sensor control device 102 to reader device 120 every five minutes.

As embodied herein, to conserve power and processing resources on sensor control device 102, digital data received from AFE 162 can be sent to reader device 120 (not shown) with minimal or no processing. In still other embodiments, processor 166 can be configured to generate certain predetermined data types (e.g., current glucose value, historical glucose values) either for storage in memory 163 or transmission to reader device 120 (not shown), and to ascertain certain alarm conditions (e.g., sensor fault conditions), while other processing and alarm functions (e.g., high/low glucose threshold alarms) can be performed on reader device 120. Those of skill in the art will understand that the methods, functions, and interfaces described herein can be performed—in whole or in part—by processing circuitry on sensor control device 102, reader device 120, local computer system 170, or trusted computer system 180.

FIG. 2C is similar to FIG. 2B but instead includes two discrete semiconductor chips 162 and 174, which can be packaged together or separately. Here, AFE 162 is resident on ASIC 161. Processor 166 is integrated with power management circuitry 164 and communication circuitry 168 on chip 174. AFE 162 can include memory 163 and chip 174 includes memory 165, which can be isolated or distributed within. In one example embodiment, AFE 162 is combined with power management circuitry 164 and processor 166 on one chip, while communication circuitry 168 is on a separate chip. In another example embodiment, both AFE 162 and communication circuitry 168 are on one chip, and processor 166 and power management circuitry 164 are on another chip. It should be noted that other chip combinations are possible, including three or more chips, each bearing responsibility for the separate functions described, or sharing one or more functions for fail-safe redundancy.

Example Embodiments of Graphical User Interfaces for Analyte Monitoring Systems

Described herein are example embodiments of GUIs for analyte monitoring systems. As an initial matter, it will be understood by those of skill in the art that the GUIs described herein comprise instructions stored in a memory of reader device 120, local computer system 170, trusted computer system 180, and/or any other device or system that is part of, or in communication with, analyte monitoring system 100. These instructions, when executed by one or more processors of the reader device 120, local computer system 170, trusted computer system 180, or other device or system of analyte monitoring system 100, cause the one or more processors to perform the method steps and/or output the GUIs described herein. Those of skill in the art will further recognize that the GUIs described herein can be stored as instructions in the memory of a single centralized device or, in the alternative, can be distributed across multiple discrete devices in geographically dispersed locations.

Example Embodiments of Sensor Results Interfaces

FIGS. 2D to 2I depict example embodiments of sensor results interfaces or GUIs for analyte monitoring systems. In accordance with the disclosed subject matter, the sensor results GUIs described herein are configured to display analyte data and other health information through a user interface application (e.g., software) installed on a reader device, such as a smart phone or a receiver, like those described with respect to FIG. 2B. Those of skill in the art will also appreciate that a user interface application with a sensor results interface or GUI can also be implemented on a local computer system or other computing device (e.g., wearable computing devices, smart watches, tablet computer, etc.).

Referring first to FIG. 2D, sensor results GUI 235 depicts an interface comprising a first portion 236 that can include a numeric representation of a current analyte concentration value (e.g., a current glucose value), a directional arrow to indicate an analyte trend direction, and a text description to provide contextual information such as, for example, whether the user's analyte level is in range (e.g., "Glucose in Range"). First portion 236 can also comprise a color or shade that is indicative of an analyte concentration or trend. For example, as shown in FIG. 2D, first portion 236 is a green shade, indicating that the user's analyte level is within a target range. According to some embodiments, for example, a red shade can indicate an analyte level below a low analyte level threshold, an orange shade can indicate an analyte level above a high analyte level threshold, and an yellow shade can indicate an analyte level outside a target range.

In addition, according to some embodiments, sensor results GUI 235 also includes a second portion 237 comprising a graphical representation of analyte data. In particular, second portion 237 includes an analyte trend graph reflecting an analyte concentration, as shown by the y-axis, over a predetermined time period, as shown by the x-axis. As embodied herein, the predetermined time period can be shown in five-minute increments, with a total of twelve hours of data. Those of skill in the art will appreciate, however, that other time increments and durations of analyte data can be utilized and are fully within the scope of this disclosure. Second portion 237 can also include a point 239 on the analyte trend graph to indicate the current analyte concentration value, a shaded green area 240 to indicate a target analyte range, and two dotted lines 238a and 238b to indicate, respectively, a high analyte threshold and a low analyte threshold. According to some embodiments, GUI 235 can also include a third portion 241 comprising a graphical indicator and textual information representative of a remaining amount of sensor life.

Referring next to FIG. 2E, another example embodiment of a sensor results GUI 245 is depicted. In accordance with the disclosed subject matter, first portion 236 is shown in a yellow shade to indicate that the user's current analyte concentration is not within a target range. In addition, second portion 237 includes: an analyte trend line 241 which can reflect historical analyte levels over time and a current analyte data point 239 to indicate the current analyte concentration value (shown in yellow to indicate that the current value is outside the target range).

According to another aspect of the embodiments, data on sensor results GUI 245 is automatically updated or refreshed according to an update interval (e.g., every second, every minute, every 5 minutes, etc.). For example, according to many of the embodiments, as analyte data is received by the reader device, sensor results GUI 245 will update: (1) the current analyte concentration value shown in first portion 236, and (2) the analyte trend line 241 and current analyte data point 239 show in second portion 237. Furthermore, As embodied herein, the automatically updating analyte data can cause older historical analyte data (e.g., in the left portion of analyte trend line 241) to no longer be displayed.

FIG. 2F is another example embodiment of a sensor results GUI 250. According to the depicted embodiment, sensor results GUI 250 includes first portion 236 which is shown in an orange shade to indicate that the user's analyte levels are above a high glucose threshold (e.g., greater than 250 mg/dL). Sensor results GUI 250 also depicts health information icons 251, such as an exercise icon or an apple icon, to reflect user logged entries indicating the times when the user had exercised or eaten a meal.

FIG. 2G is another example embodiment of a sensor results GUI 255. According to the depicted embodiments, sensor results GUI 255 includes first portion 236 which is also shown in an orange shade to indicate that the user's analyte levels are above a high glucose threshold. As can be seen in FIG. 2G, first portion 236 does not report a numeric value but instead displays the text "HI" to indicate that the current analyte concentration value is outside a glucose reporting range high limit. Although not depicted in FIG. 2G, those of skill in the art will understand that, conversely, an analyte concentration below a glucose reporting range low limit will cause first portion 236 not to display a numeric value, but instead, the text "LO".

FIG. 2H is another example embodiment of a sensor results GUI 260. According to the depicted embodiments, sensor results GUI 260 includes first portion 236 which is shown in a green shade to indicate that the user's current analyte level is within the target range. In addition, according to the depicted embodiments, first portion 236 of GUI 260 includes the text, "GLUCOSE GOING LOW," which can indicate to the user that his or her analyte concentration value is predicted to drop below a predicted low analyte level threshold within a predetermined amount of time (e.g., predicted glucose will fall below 75 mg/dL within 15 minutes). Those of skill in the art will understand that if a user's analyte level is predicted to rise above a predicted high analyte level threshold within a predetermined amount of time, sensor results GUI 260 can display a "GLUCOSE GOING HIGH" message.

FIG. 2I is another example embodiment of a sensor results GUI 265. According to the depicted embodiments, sensor results GUI 265 depicts first portion 236 when there is a sensor error. In accordance with the disclosed subject matter, first portion 236 includes three dashed lines 266 in place of the current analyte concentration value to indicate that a current analyte value is not available. As embodied herein, three dashed lines 266 can indicate one or more error conditions such as, for example, (1) a no signal condition; (2) a signal loss condition; (3) sensor too hot/cold condition; or (4) a glucose level unavailable condition. Furthermore, as can be seen in FIG. 2I, first portion 236 comprises a gray shading (instead of green, yellow, orange, or red) to indicate that no current analyte data is available. In addition, according to another aspect of the embodiments, second portion 237 can be configured to display the historical analyte data in the analyte trend graph, even though there is an error condition preventing the display of a numeric value for a current analyte concentration in first portion 236. However, as shown in FIG. 2I, no current analyte concentration value data point is shown on the analyte trend graph of second portion 237.

Example Embodiments of Time-in-Ranges Interfaces

FIGS. 3A to 3F depict example embodiments of GUIs for analyte monitoring systems. In particular, FIGS. 3A to 3F depict Time-in-Ranges (also referred to as Time-in-Range and/or Time-in-Target) GUIs, each of which comprise a plurality of bars or bar portions, wherein each bar or bar portion indicates an amount of time that a user's analyte level is within a predefined analyte range correlating with the bar or bar portion. As embodied herein, for example, the amount of time can be expressed as a percentage of a predefined amount of time.

Figure 3A:
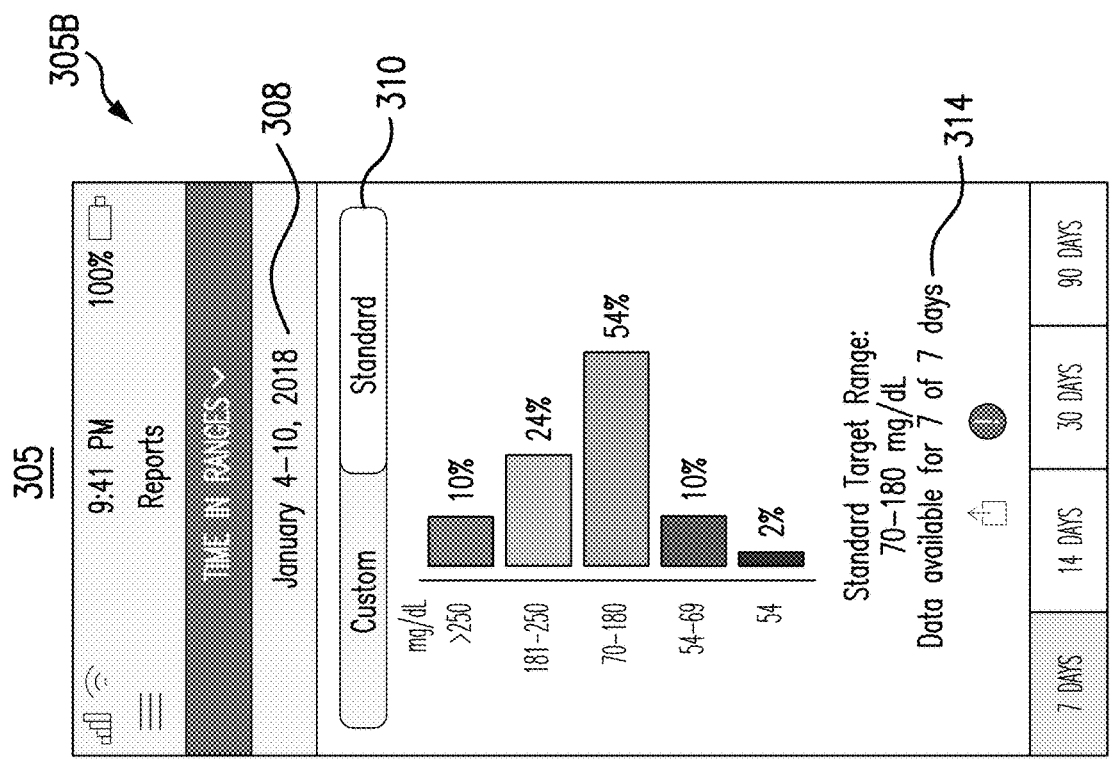
FIGS. 3A to 3F are example embodiments of GUIs comprising time-in-ranges interfaces.
Figure 3B:
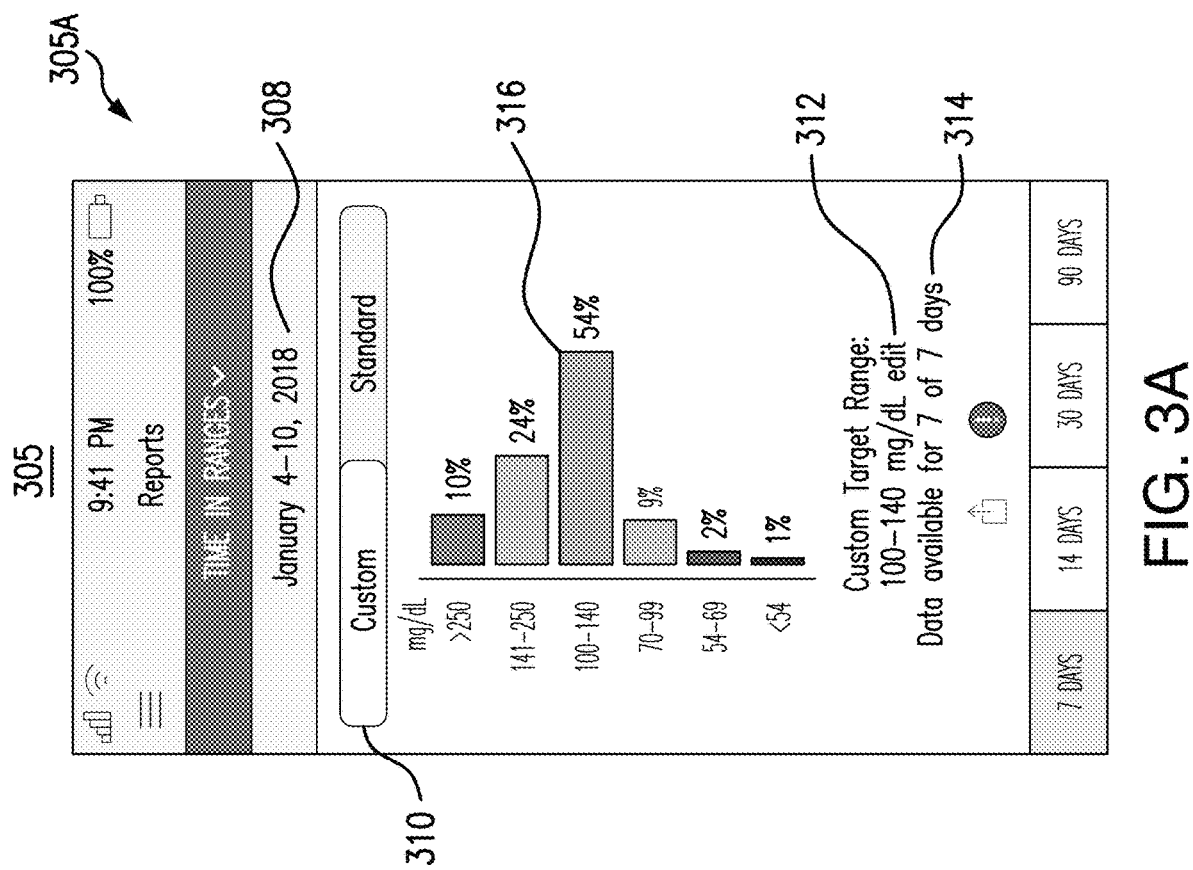

Turning to FIGS. 3A and 3B, an example embodiment of a Time-in-Ranges GUI 305 is shown, wherein Time-in-Ranges GUI 305 comprises a "Custom" Time-in-Ranges view 305A and a "Standard" Time-in-Ranges view 305B, with a slidable element 310 that allows the user to select between the two views. In accordance with the disclosed subject matter, Time-in-Ranges views 305A, 305B can each comprise multiple bars, wherein each bar indicates an amount of time that a user's analyte level is within a predefined analyte range correlating with the bar. As embodied herein, Time-in-Ranges views 305A, 305B further comprise a date range indicator 308, showing relevant dates associated with the displayed plurality of bars, and a data availability indicator 314, showing the period(s) of time in which analyte data is available for the displayed analyte data (e.g., "Data available for 7 of 7 days").

Referring to FIG. 3A, "Custom" Time-in-Ranges view 305A includes six bars comprising (from top to bottom): a first bar indicating that the user's glucose range is above 250 mg/dL for 10% of a predefined amount of time, a second bar indicating that the user's glucose range is between 141 and 250 mg/dL for 24% of the predefined amount of time, a third bar 316 indicating that the user's glucose range is between 100 and 140 mg/dL for 54% of the predefined amount of time, a fourth bar indicating that the user's glucose range is between 70 and 99 mg/dL for 9% of the predefined amount of time, a fifth bar indicating that the user's glucose range is between 54 and 69 mg/dL for 2% of the predefined amount of time, and a sixth bar indicating that the user's glucose range is less than 54 mg/dL for 1% of the predefined amount of time.

Those of skill in the art will recognize that the glucose ranges and percentages of time associated with each bar can vary depending on the ranges defined by the user and the available analyte data of the user. Furthermore, although FIGS. 3A and 3B show a predefined amount of time 314 equal to seven days, those of skill in the art will appreciate that other predefined amounts of time can be utilized (e.g., one day, three days, fourteen days, thirty days, ninety days, etc.), and are fully within the scope of this disclosure.

According to another aspect of the embodiments, "Custom" Time-in-Ranges view 305A also includes a user-definable custom target range 312 that includes an actionable "edit" link that allows a user to define and/or change the custom target range. As shown in "Custom" Time-in-Ranges view 305A, the custom target range 312 has been defined as a glucose range between 100 and 140 mg/dL and corresponds with third bar 316 of the plurality of bars. Those of skill in the art will also appreciate that, in other embodiments, more than one range can be adjustable by the user, and such embodiments are fully within the scope of this disclosure.

Referring to FIG. 3B, "Standard" Time-in-Ranges view 305B includes five bars comprising (from top to bottom): a first bar indicating that the user's glucose range is above 250 mg/dL for 10% of a predefined amount of time, a second bar indicating that the user's glucose range is between 181 and 250 mg/dL for 24% of the predefined amount of time, a third bar indicating that the user's glucose range is between 70 and 180 mg/dL for 54% of the predefined amount of time, a fourth bar indicating that the user's glucose range is between 54 and 69 mg/dL for 10% of the predefined amount of time, and a fifth bar indicating that the user's glucose range is less than 54 mg/dL for 2% of the predefined amount of time. As with the "Custom" Time-in-Ranges view 305A, those of skill in the art will recognize that the percentages of time associated with each bar can vary depending on the available analyte data of the user. Unlike the "Custom" Time-in-Ranges view 305A, however, the glucose ranges shown in "Standard" view 305B cannot be adjusted by the user.

Figures 3C, 3D:
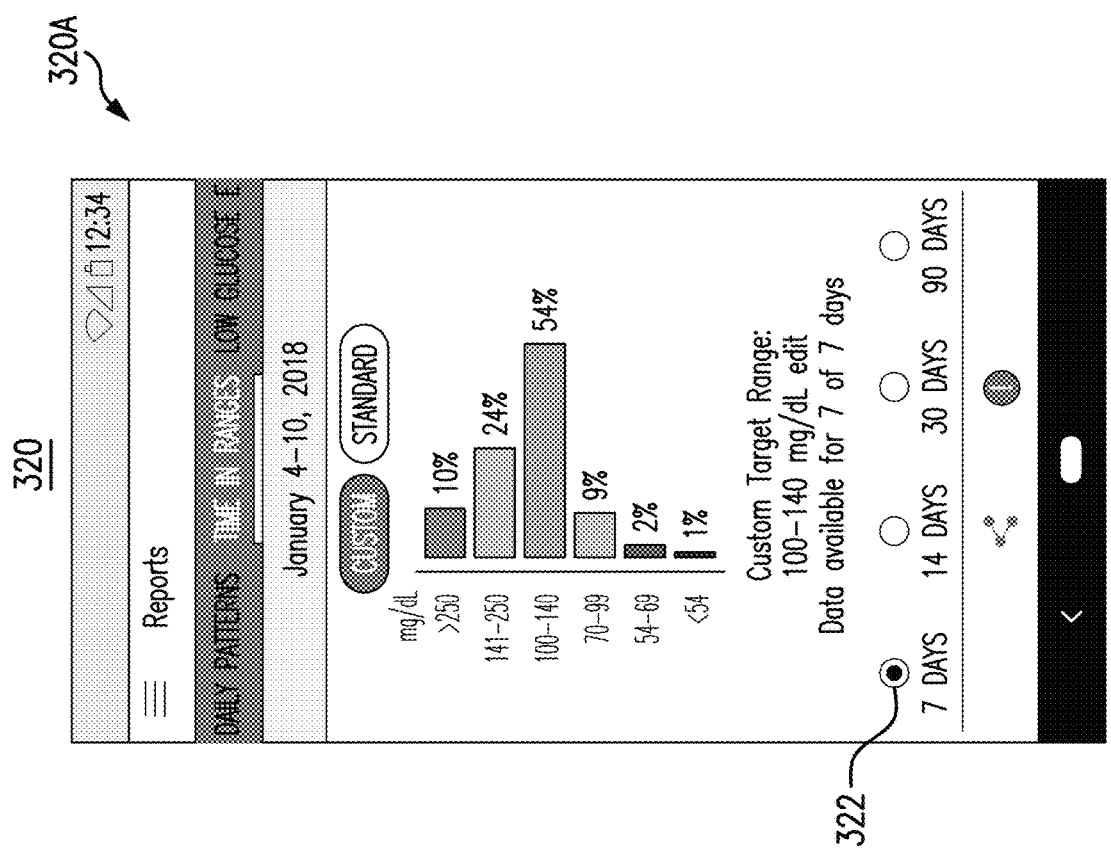

FIGS. 3C and 3D depict another example embodiment of Time-in-Ranges GUI 320 with multiple views, 320A and 320B, which are analogous to the views shown in FIGS. 3A and 3B, respectively. According to some embodiments, Time-in-Ranges GUI 320 can further include one or more selectable icons 322 (e.g., radio button, check box, slider, switch, etc.) that allow a user to select a predefined amount of time over which the user's analyte data will be shown in the Time-in-Range GUI 320. For example, as shown in FIGS. 3C and 3D, selectable icons 322 can be used to select a predefined amount of time of seven days, fourteen days, thirty days, or ninety days. Those of skill in the art will appreciate that other predefined amounts of time can be utilized and are fully within the scope of this disclosure.

Figures 3E, 3F:
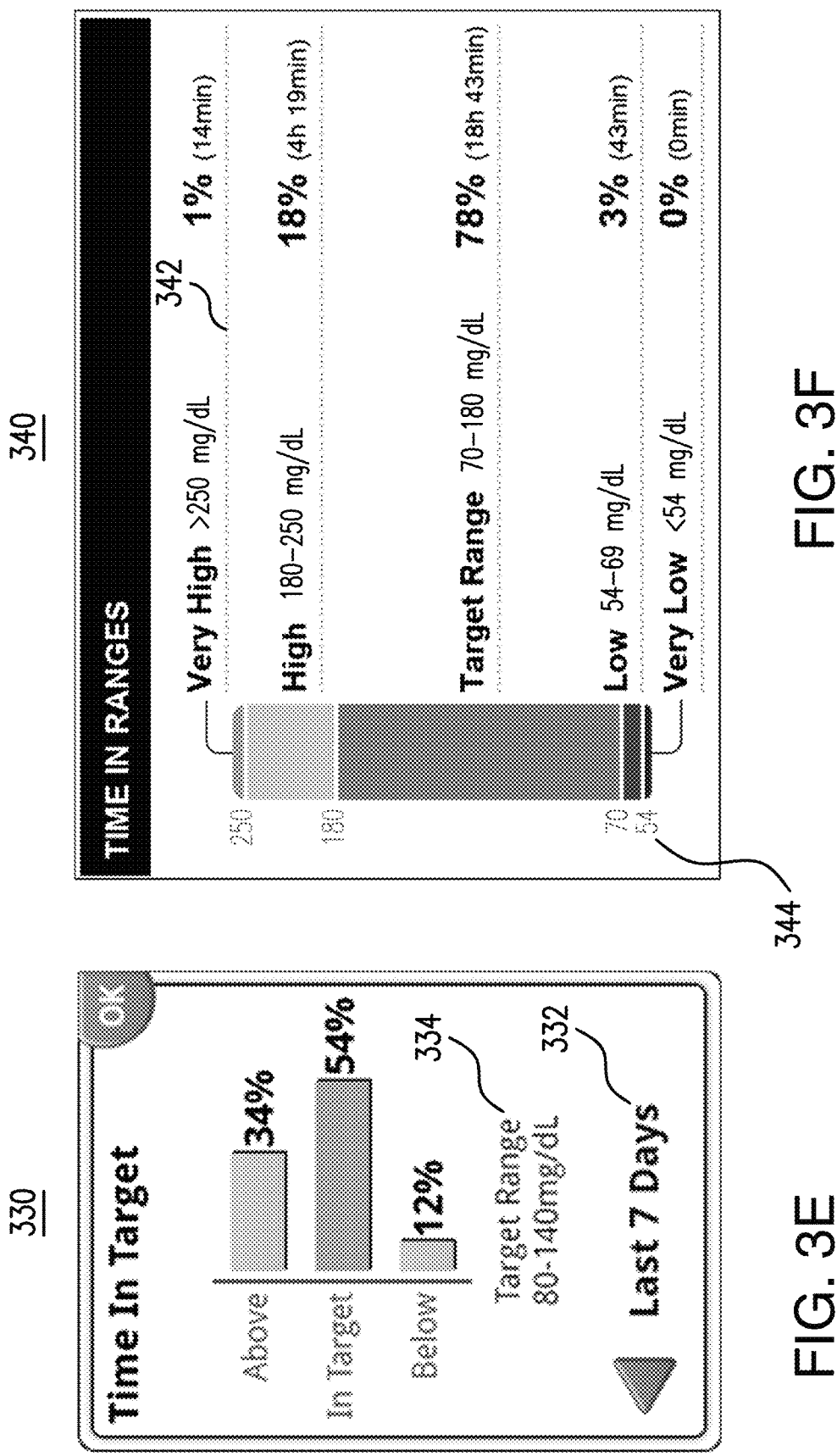

FIG. 3E depicts an example embodiment of a Time-in-Target GUI 330, which can be visually output to a display of a reader device (e.g., a dedicated reader device, a meter device, etc.). In accordance with the disclosed subject matter, Time-in-Target GUI 330 includes three bars comprising (from top to bottom): a first bar indicating that the user's glucose range is above a predefined target range for 34% of a predefined amount of time, a second bar indicating that the user's glucose range is within the predefined target range for 54% of the predefined amount of time, and a third bar indicating that the user's glucose range is below the predefined target range for 12% of the predefined amount of time. Those of skill in the art will recognize that the percentages of time associated with each bar can vary depending on the available analyte data of the user. Furthermore, although FIG. 3E shows a predefined amount of time 332 equal to the last seven days and a predefined target range 334 of 80 to 140 mg/dL, those of skill in the art will appreciate that other predefined amounts of time (e.g., one day, three days, fourteen days, thirty days, ninety days, etc.) and/or predefined target ranges (e.g., 70 to 180 mg/dL) can be utilized, and are fully within the scope of this disclosure.

FIG. 3F depicts another example embodiment of a Time-in-Ranges GUI 340, which includes a single bar comprising five bar portions including (from top to bottom): a first bar portion indicating that the user's glucose range is "Very High" or above 250 mg/dL for 1% (14 minutes) of a predefined amount of time, a second bar portion indicating that the user's glucose range is "High" or between 180 and 250 mg/dL for 18% (4 hours and 19 minutes) of the predefined amount of time, a third bar portion indicating that the user's glucose range is within a "Target Range" or between 70 and 180 mg/dL for 78% (18 hours and 43 minutes) of the predefined amount of time, a fourth bar portion indicating that the user's glucose range is "Low" or between 54 and 69 mg/dL for 3% (43 minutes) of the predefined amount of time, and a fifth bar portion indicating that the user's glucose range is "Very Low" or less than 54 mg/dL for 0% (0 minutes) of the predefined amount of time. As shown in FIG. 3F, according to some embodiments, Time-in-Ranges GUI 340 can display text adjacent to each bar portion indicating an actual amount of time, e.g., in hours and/or minutes.

According to one aspect of the embodiment shown in FIG. 3F, each bar portion of Time-in-Ranges GUI 340 can comprise a different color. As embodied herein, bar portions can be separated by dashed or dotted lines 342 and/or interlineated with numeric markers 344 to indicate the ranges reflected by the adjacent bar portions. As embodied herein, the time in ranges reflected by the bar portions can be further expressed as a percentage, an actual amount of time (e.g., 4 hours and 19 minutes), or, as shown in FIG. 3F, both. Furthermore, those of skill in the art will recognize that the percentages of time associated with each bar portion can vary depending on the analyte data of the user. In some embodiments of Time-in-Ranges GUI 340, the Target Range can be configured by the user. In other embodiments, the Target Range of Time-in-Ranges GUI 340 is not modifiable by the user.

Example Embodiments of Analyte Level and Trend Alert Interfaces

Figure 4C:
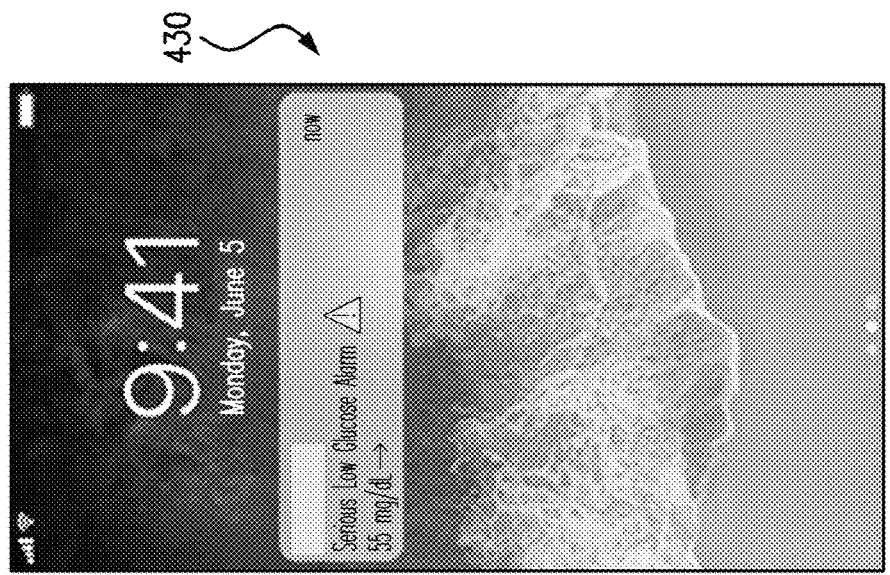
FIGS. 4A to 4O are example embodiments of GUIs comprising analyte level and trend alert interfaces.
Figure 4B:
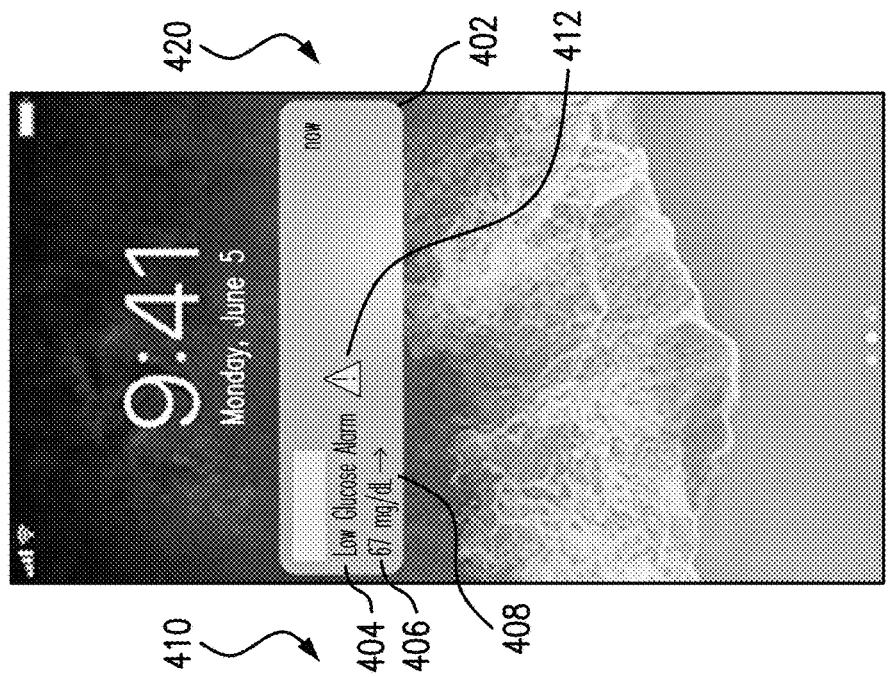
Figure 4A:
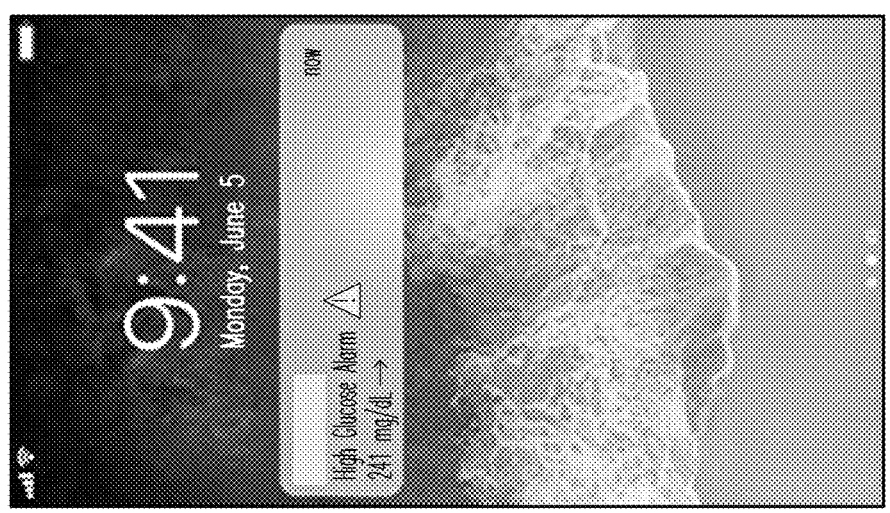
Figure 4E:
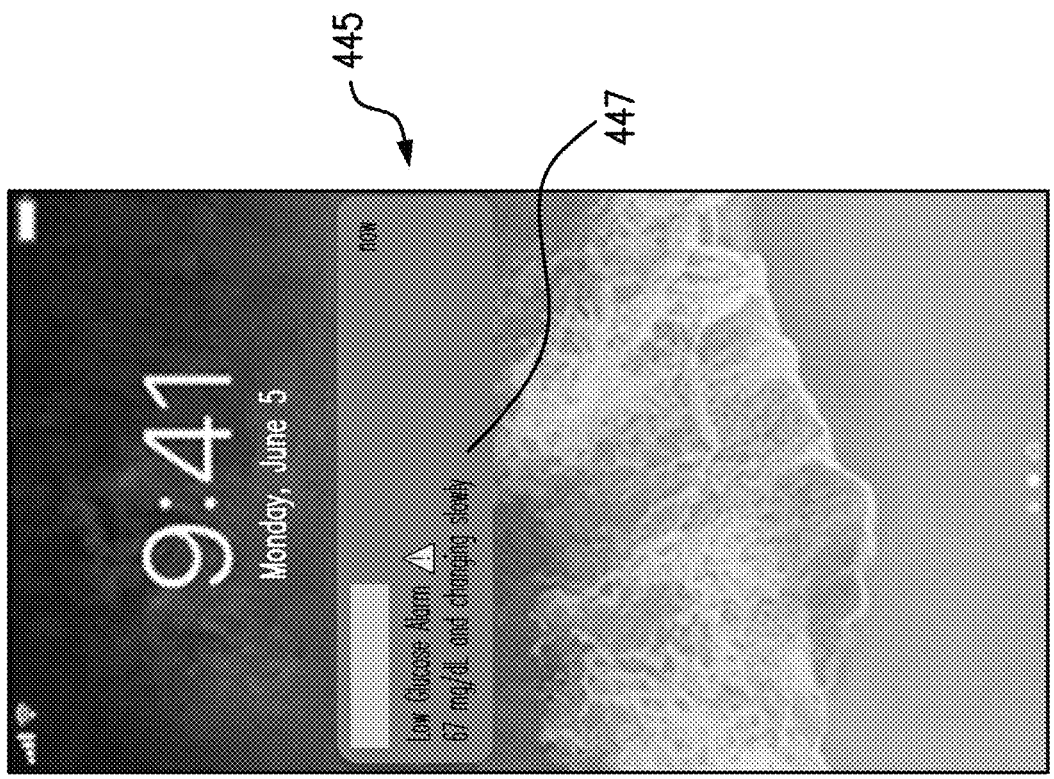

FIGS. 4A to 4O depict example embodiments of Analyte Level/Trend Alert GUIs for analyte monitoring systems. In accordance with the disclosed subject matter, the Analyte Level/Trend Alert GUIs comprise a visual notification (e.g., alert, alarm, pop-up window, banner notification, etc.), wherein the visual notification includes an alarm condition, an analyte level measurement associated with the alarm condition, and a trend indicator associated with the alarm condition.

Turning to FIGS. 4A to 4C, example embodiments of a High Glucose Alarm 410, Low Glucose Alarm 420, and a Serious Low Glucose Alarms 430 are depicted, respectively, wherein each alarm comprises a pop-up window 402 containing an alarm condition text 404 (e.g., "Low Glucose Alarm"), an analyte level measurement 406 (e.g., a current glucose level of 67 mg/dL) associated with the alarm condition, and a trend indicator 408 (e.g., a trend arrow or directional arrow) associated with the alarm condition. As embodied herein, an alarm icon 412 can be adjacent to the alarm condition text 404.

Figure 4D:
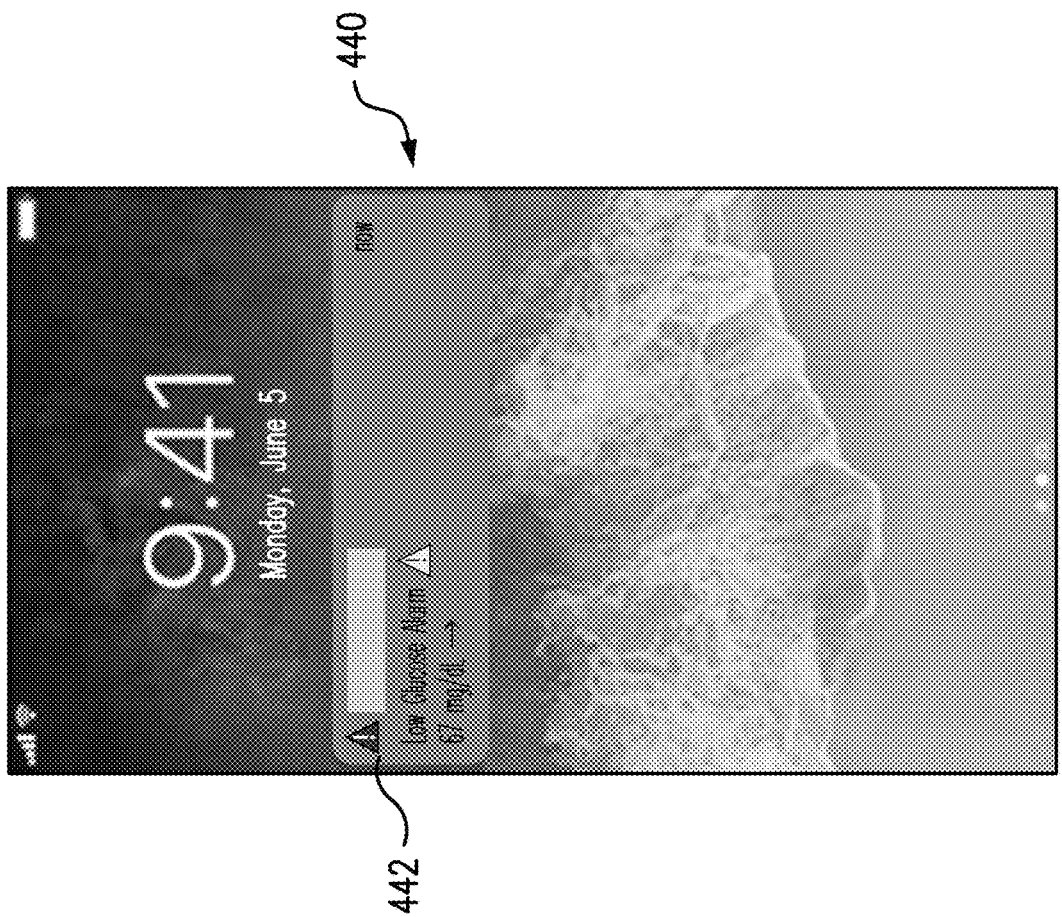
Figure 4G:
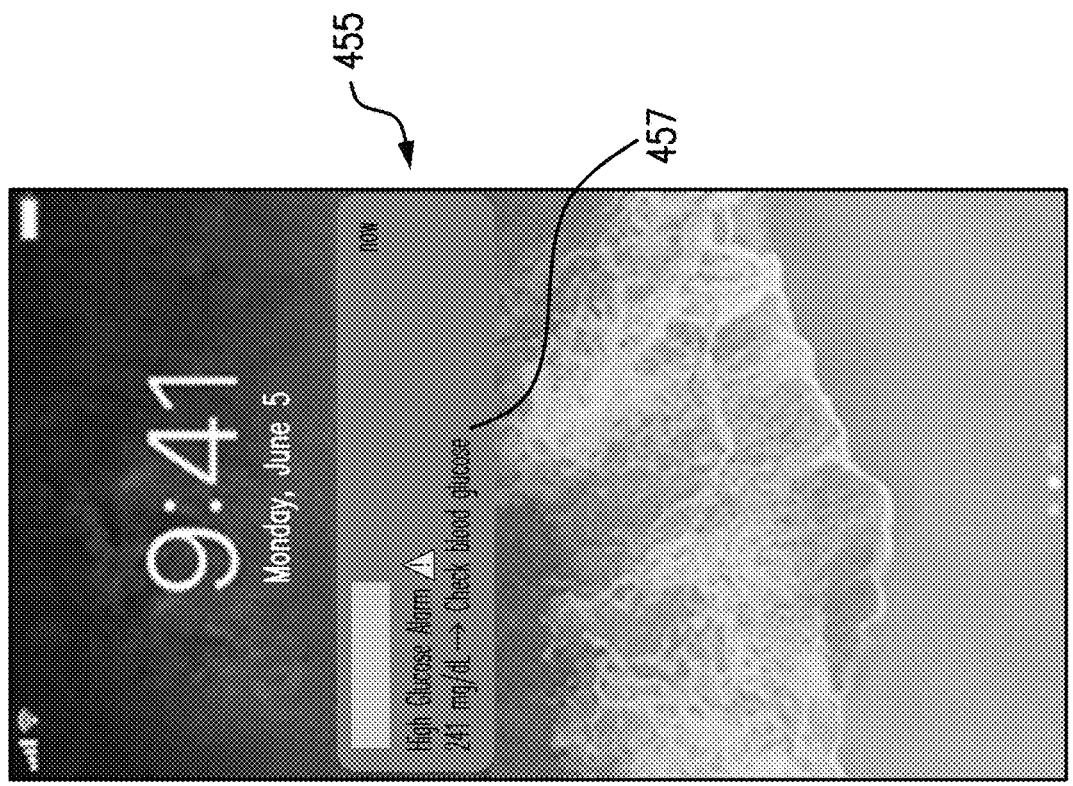

Referring next to FIGS. 4D to 4G, additional example embodiments of Low Glucose Alarms 440, 445, Serious Low Glucose Alarm 450, and High Glucose Alarm 455 are depicted, respectively. As shown in FIG. 4D, Low Glucose Alarm 440 is similar to the Low Glucose Alarm of FIG. 4B (e.g., comprises a pop-up window containing an alarm condition text, an analyte level measurement associated with the alarm condition, and a trend indicator associated with the alarm condition), but further includes an alert icon 442 to indicate that the alarm has been configured as an alert (e.g., will display, play a sound, vibrate, even if the device is locked or if the device's "Do Not Disturb" setting has been enabled). With respect to FIG. 4E, Low Glucose Alarm 445 is also similar to the Low Glucose Alarm of FIG. 4B, but instead of including a trend arrow, Log Glucose Alarm 445 includes a textual trend indicator 447. According to one aspect of some embodiments, textual trend indicator 447 can be enabled through a device's Accessibility settings such that the device will "read" the textual trend indicator 447 to the user via the device's text-to-speech feature (e.g., Voiceover for iOS or Select-to-Speak for Android).

Figure 4F:
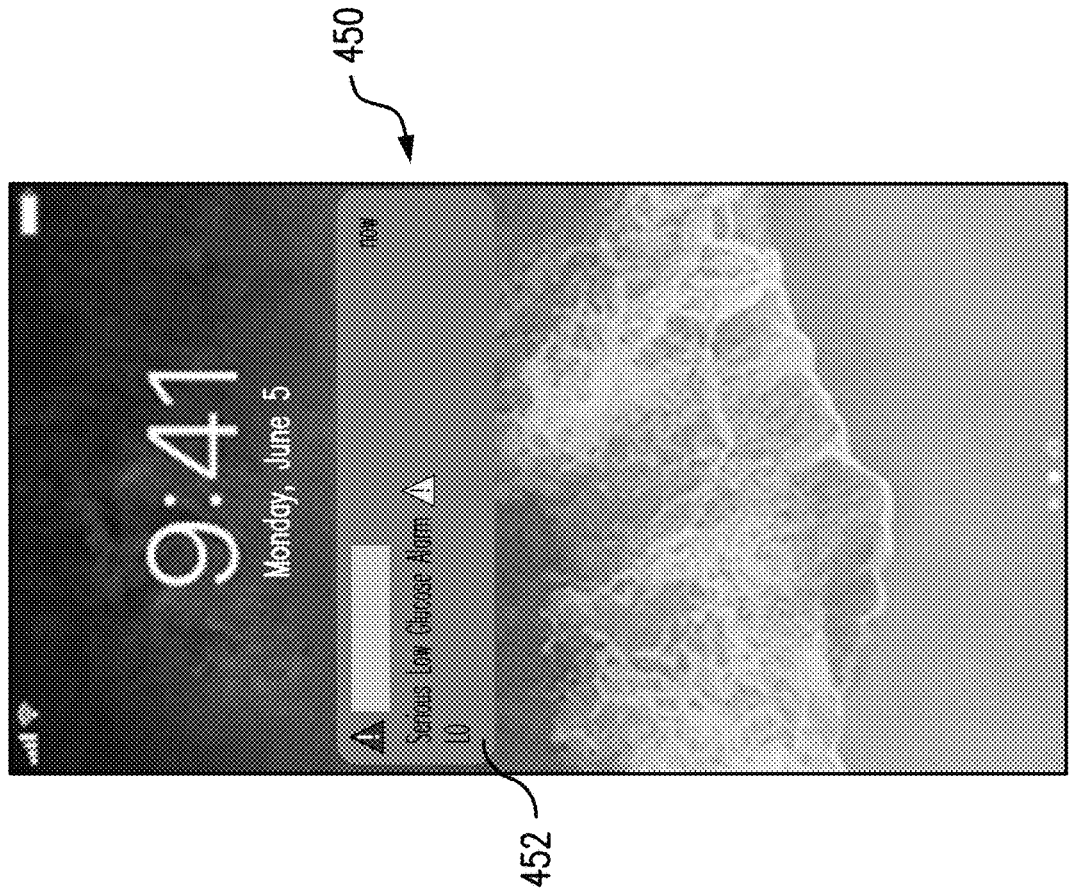

Referring next to FIG. 4F, Low Glucose Alarm 450 is similar to the Low Glucose Alarm of FIG. 4D (including the alert icon), but instead of displaying an analyte level measurement associated with an alarm condition and a trend indicator associated with the alarm condition, Low Glucose Alarm 450 displays a out-of-range indicator 452 to indicate that the current glucose level is either above or below a predetermined reportable analyte level range (e.g., "HI" or "LO"). With respect to FIG. 4G, High Glucose Alarm 455 is similar to the High Glucose Alarm of FIG. 4A (e.g., comprises a pop-up window containing an alarm condition text, an analyte level measurement associated with the alarm condition, and a trend indicator associated with the alarm condition), but further includes an instruction to the user 457. As embodied herein, for example, the instruction can be a prompt for the user to "Check blood glucose." Those of skill in the art will appreciate that other instructions or prompts can be implemented (e.g., administer a corrective bolus, eat a meal, etc.).

Figure 4J:
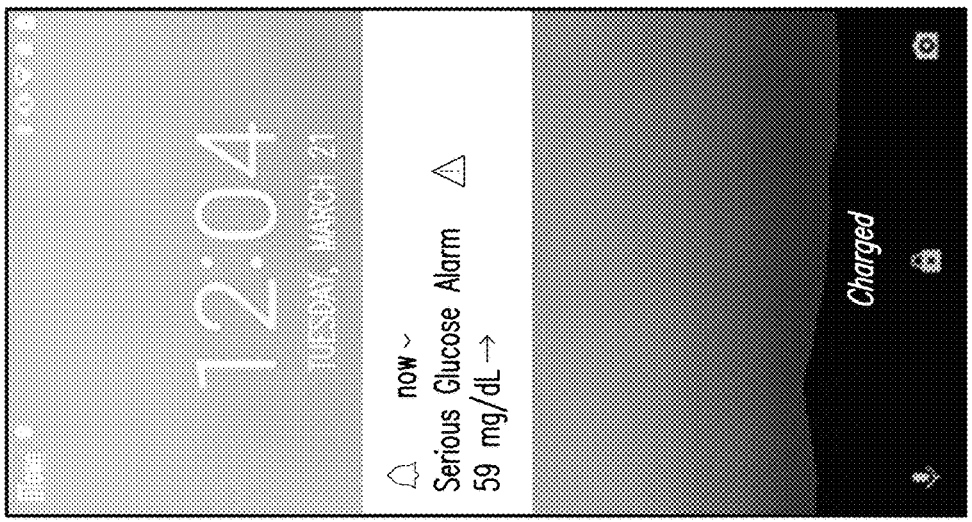
Figure 4I:
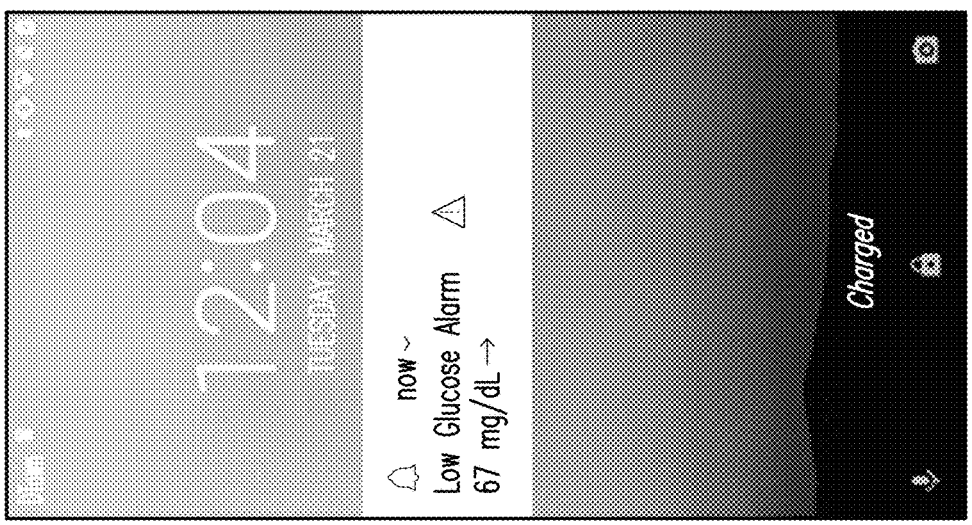
Figure 4H:
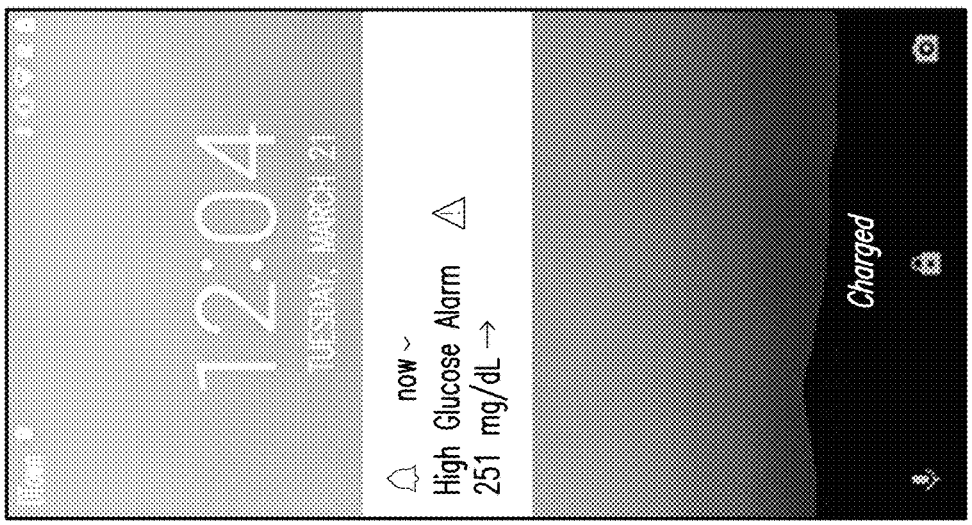
Figures 4K, 4L, 4M, 4N, 4O:
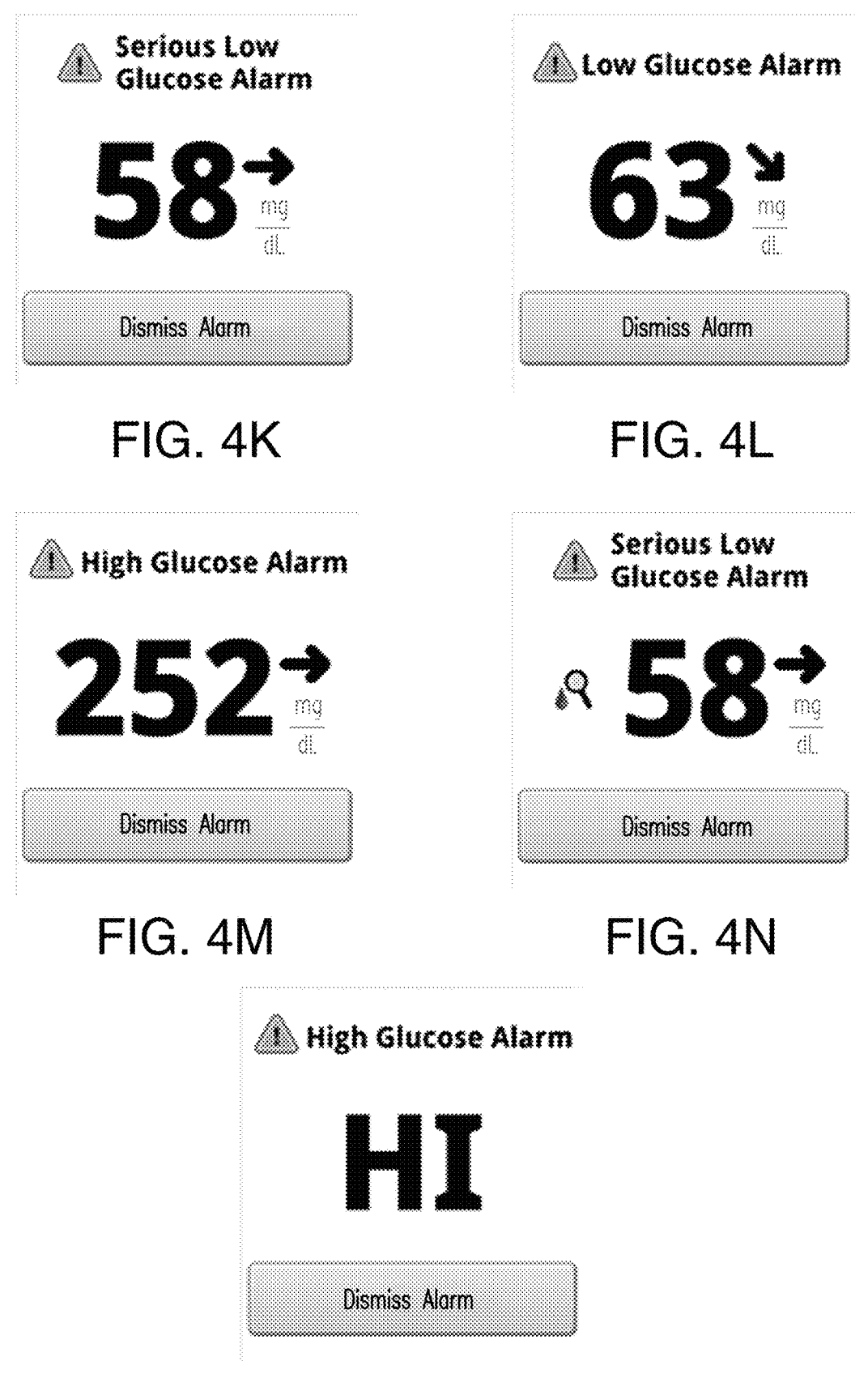

Furthermore, although FIGS. 4A to 4G depict example embodiments of Analyte Level/Trend Alert GUIs that are displayed on smart phones having an iOS operating system, those of skill in the art will also appreciate that the Analyte Level/Trend Alert GUIs can be implemented on other devices including, e.g., smart phones with other operating systems, smart watches, wearables, reader devices, tablet computing devices, blood glucose meters, laptops, desktops, and workstations, to name a few. FIGS. 4H to 4J, for example, depict example embodiments of a High Glucose Alarm, Low Glucose Alarm, and a Serious Low Glucose Alarm for a smart phone having an Android Operating System. Similarly, FIGS. 4K to 4O depict, respectively, example embodiments of a Serious Low Glucose Alarm, Low Glucose Alarm, High Glucose Alarm, Serious Low Glucose Alarm (with a Check Blood Glucose icon), and High Glucose Alarm (with an out-of-range indicator) for a reader device.

Example Embodiments of Sensor Usage Interfaces

FIGS. 5A to 5F depict example embodiments of sensor usage interfaces relating to GUIs for analyte monitoring systems. In accordance with the disclosed subject matter, sensor usage interfaces provide for technological improvements including the capability to quantify and promote user engagement with analyte monitoring systems. According to some embodiments, for example, a sensor usage interface can include the visual display of one or more "view" metrics, each of which can be indicative of a measure of user engagement with the analyte monitoring system. A "view" can comprise, for example, an instance in which a sensor results interface is rendered or brought into the foreground. According to other embodiments, a "view" can be defined as an instance when a user views a sensor results interface with a valid sensor reading for the first time in a sensor lifecount. As embodied herein, a sensor user interface can include a visual display of a "scan" metric indicative of another measure of user engagement with the analyte monitoring system. A "scan" can comprise, for example, an instance in which a user uses a reader device (e.g., smart phone, dedicated reader, etc.) to scan a sensor control device, such as, for example, in a Flash Analyte Monitoring system.

Figure 5B:
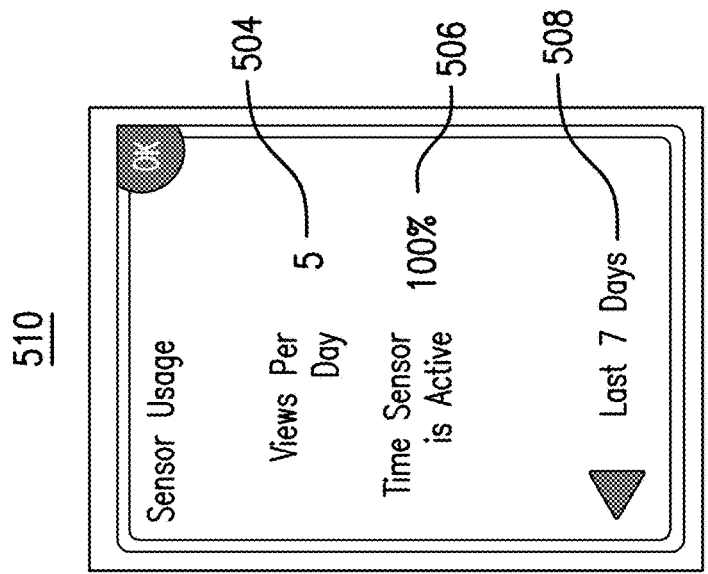
FIGS. 5A and 5B are example embodiments of GUIs comprising sensor usage interfaces.
Figure 5A:
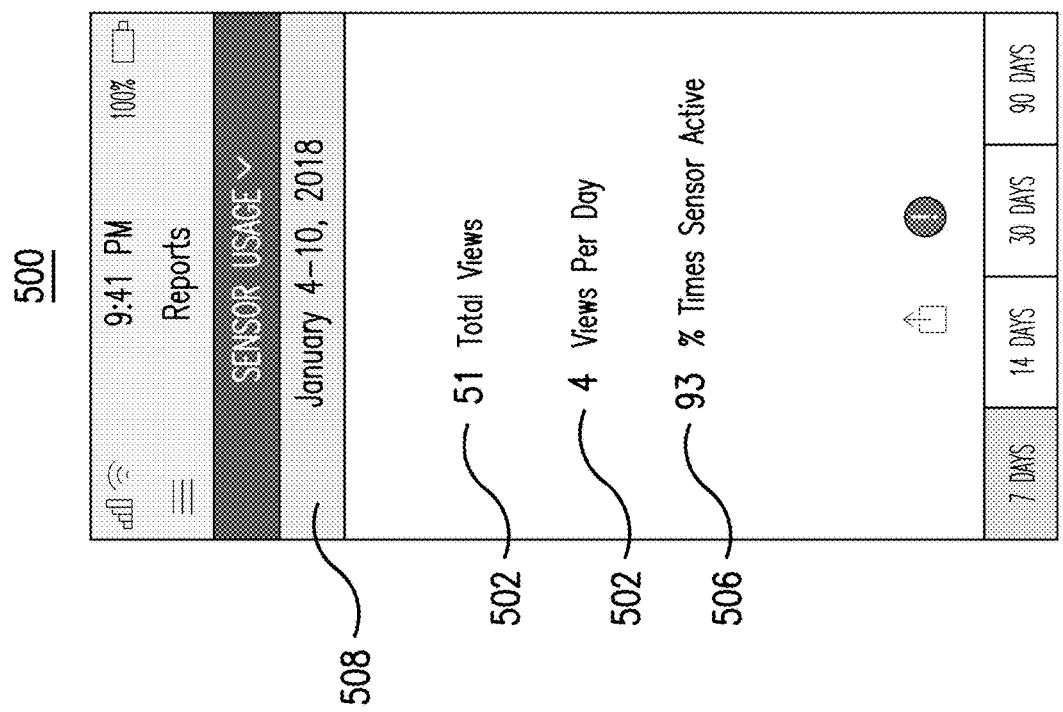

FIGS. 5A and 5B depict example embodiments of sensor usage interfaces 500 and 510, respectively. In accordance with the disclosed subject matter, sensor usage interfaces 500 and 510 can be rendered and displayed, for example, by a mobile app or software residing in non-transitory memory of reader device 120, such as those described with respect to FIGS. 1 and 2A. Referring to FIG. 5A, sensor user interface 500 can comprise: a predetermined time period interval 508 indicative of a time period (e.g., a date range) during which view metrics are measured, a Total Views metric 502, which is indicative of a total number of views over the predetermined time period 508; a Views Per Day metric 504, which is indicative of an average number of views per day over the predetermined time period 508; and a Percentage Time Sensor Active metric 506, which is indicative of the percentage of predetermined time period 508 that reader device 120 is in communication with sensor control device 102, such as those described with respect to FIGS. 1, 2B, and 2C. Referring to FIG. 5B, sensor user interface 510 can comprise a Views per Day metric 504 and a Percentage Time Sensor Active metric 508, each of which is measured for predetermined time period 508.

According to another aspect of the embodiments, although predetermined time period 508 is shown as one week, those of skill in the art will recognize that other predetermined time periods (e.g., 3 days, 14 days, 30 days) can be utilized. In addition, predetermined time period 508 can be a discrete period of time—with a start date and an end date—as shown in sensor usage interface 500 of FIG. 5A, or can be a time period relative to a current day or time (e.g., "Last 7 Days," "Last 14 Days," etc.), as shown in sensor usage interface 510 of FIG. 5B.

Figure 5C:
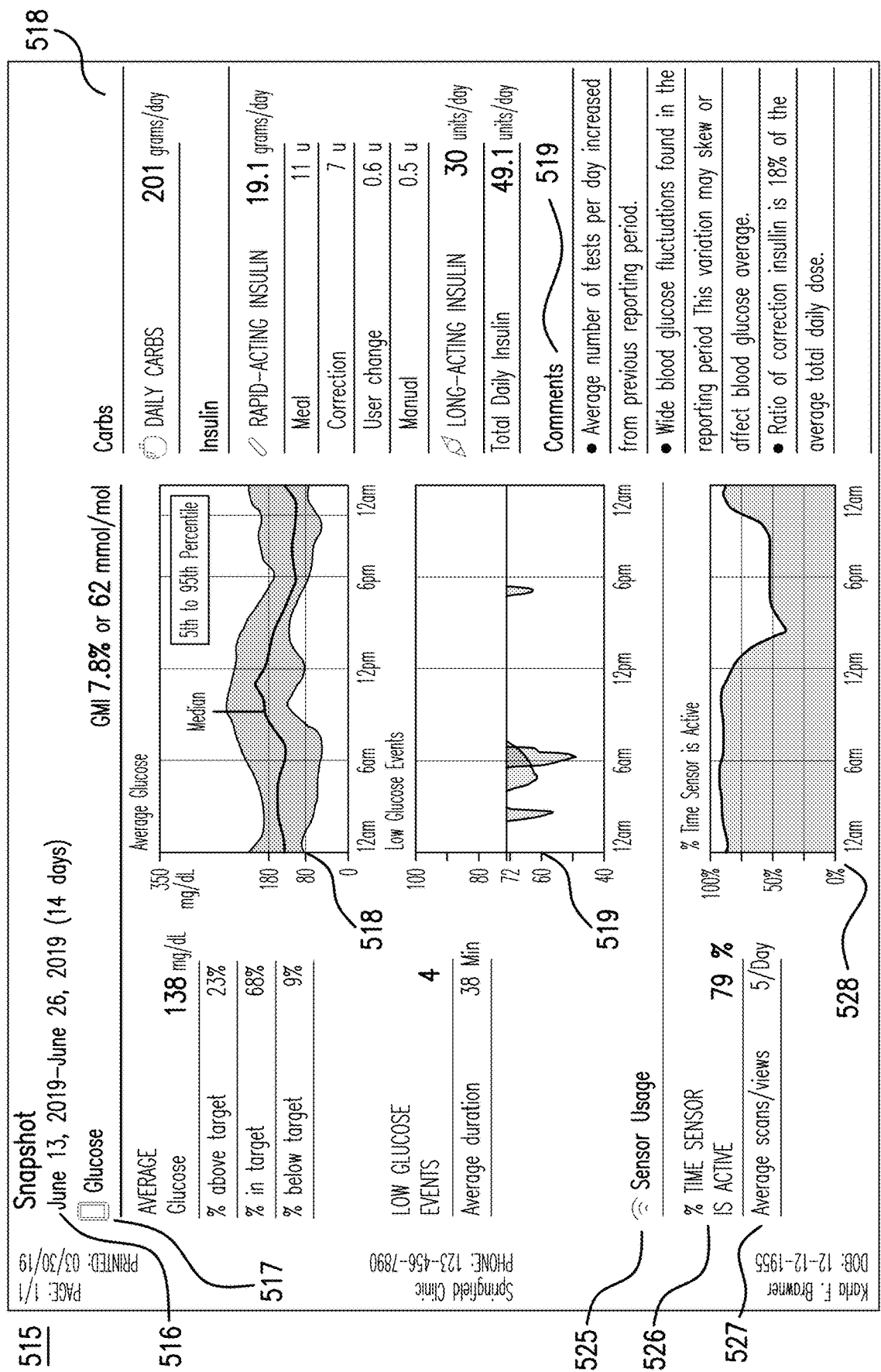
FIGS. 5C to 5F are example embodiments of report GUIs including sensor usage information.

FIG. 5C depicts an example embodiment of sensor usage interface 525, as part of analyte monitoring system report GUI 515. In accordance with the disclosed subject matter, GUI 515 is a snapshot report covering a predetermined time period 516 (e.g., 14 days), and comprising a plurality of report portions on a single report GUI, including: a sensor usage interface portion 525, a glucose trend interface 517, which can include an glucose trend graph, a low glucose events graph, and other related glucose metrics (e.g., Glucose Management Indicator); a health information interface 518, which can include information logged by the user about the user's average daily carbohydrate intake and medication dosages (e.g., insulin dosages); and a comments interface 519, which can include additional information about the user's analyte and medication patterns presented in a narrative format. According to another aspect of the embodiments, sensor usage interface 525 can comprise a Percentage Time Sensor Active metric 526, an Average Scans/Views metric 527 (e.g., indicative of an average sum of a number of scans and a number of views), and a Percentage Time Sensor Active graph 528. As can be seen in FIG. 5C, an axis of the Percentage Time Sensor Active graph can be aligned with a corresponding axis of one or more other graphs (e.g., average glucose trend graph, low glucose events graph), such that the user can visually correlate data between multiple graphs from two or more portions of the report GUI by the common units (e.g., time of day) from the aligned axes.

Figure 5D:
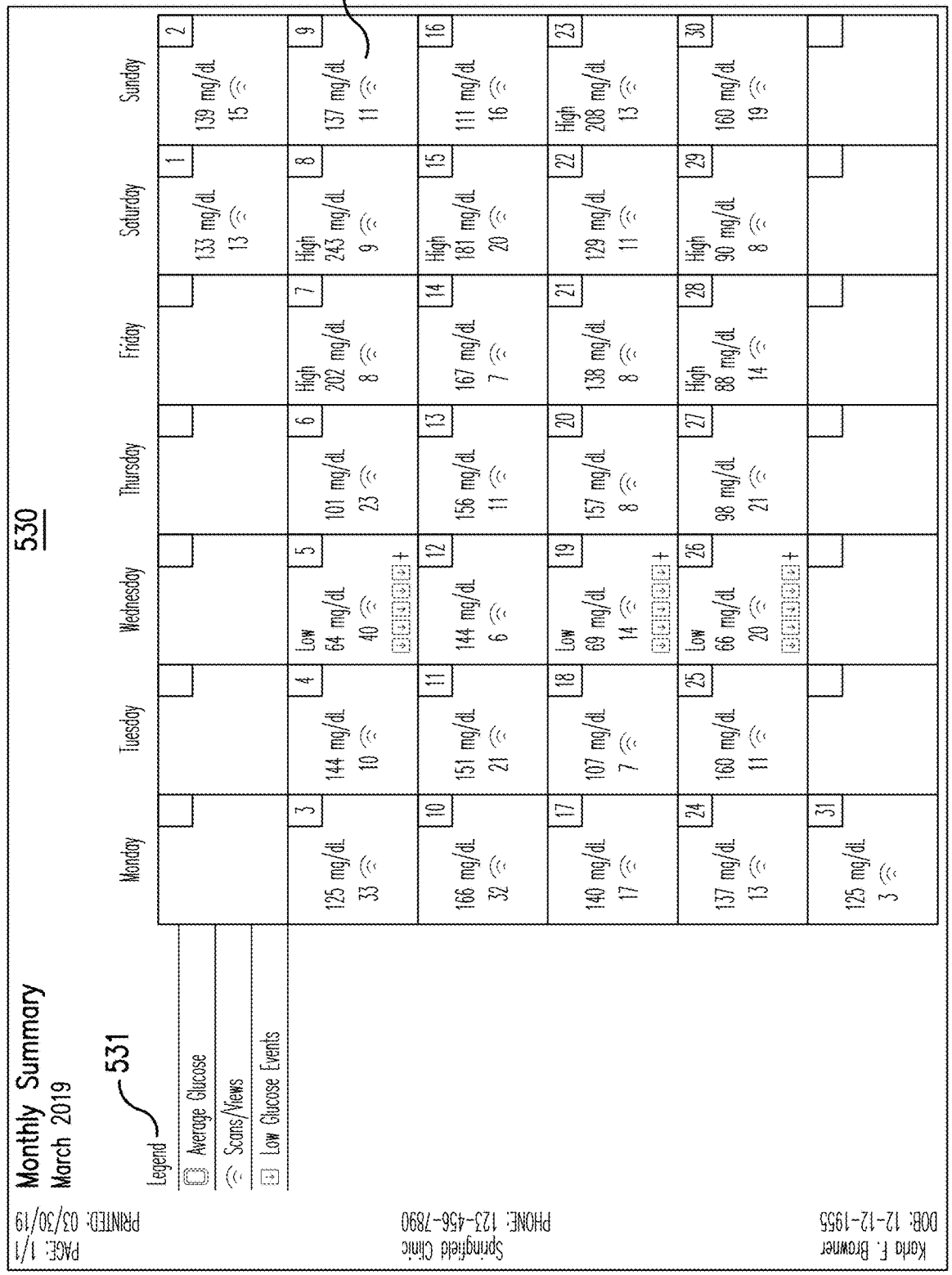

FIG. 5D depicts an example embodiment of another analyte monitoring system report GUI 530 including sensor usage information. In accordance with the disclosed subject matter, GUI 530 is a monthly summary report including a first portion comprising a legend 531, wherein legend 531 includes a plurality of graphical icons each of which is adjacent to a descriptive text. As shown in FIG. 5D, legend 531 includes an icon and descriptive text for "Average Glucose," an icon and descriptive text for "Scans/Views," and an icon and descriptive text for "Low Glucose Events." GUI 530 also includes a second portion comprising a calendar interface 532. For example, as shown in FIG. 5D, GUI 530 comprises a monthly calendar interface, wherein each day of the month can include one or more of an average glucose metric, low glucose event icons, and a sensor usage metric 532. As embodied herein, such as the one shown in FIG. 5D, the sensor usage metric ("scans/views") is indicative of a total sum of a number of scans and a number of views for each day.

Figure 5E:
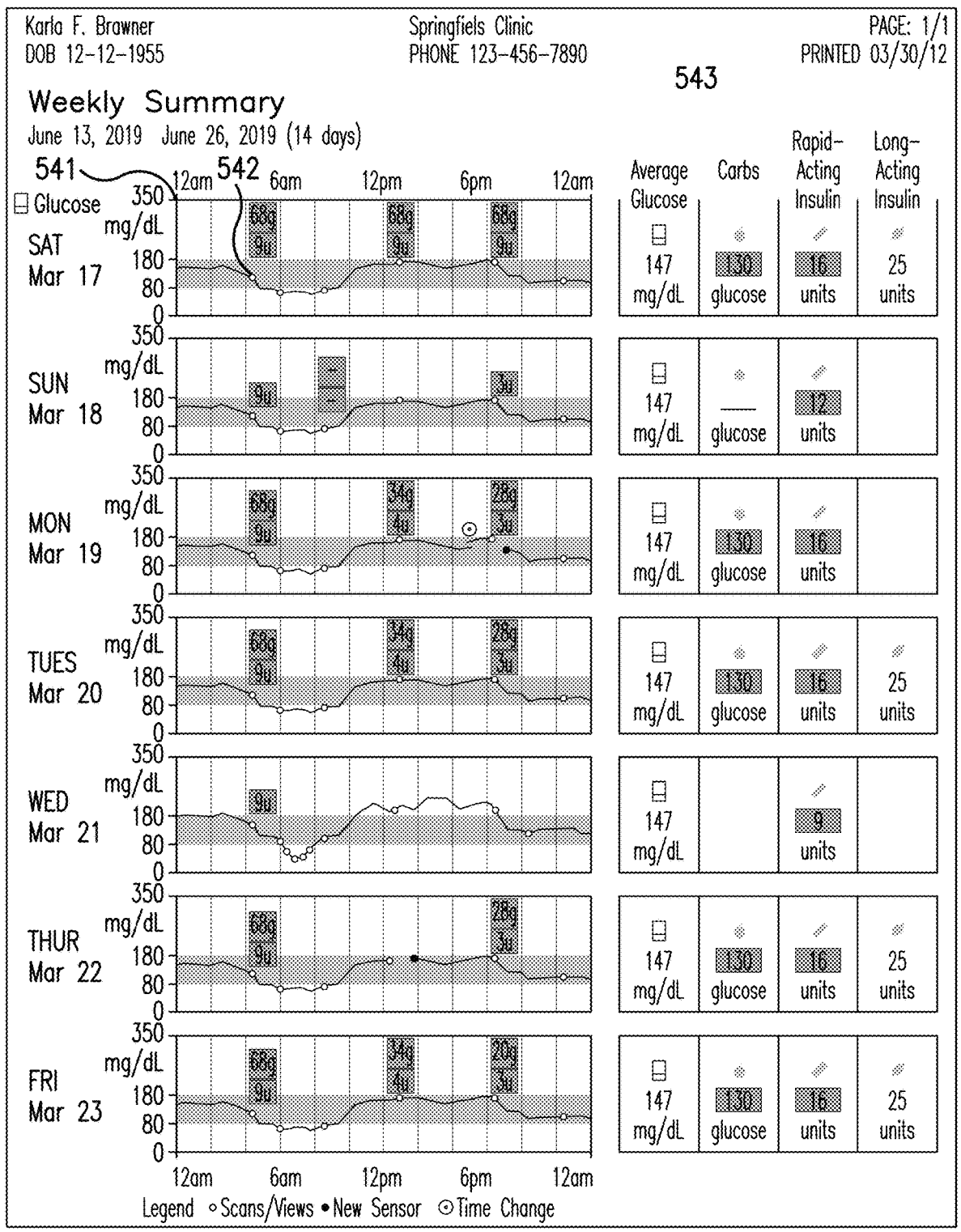

FIG. 5E depicts an example embodiment of another analyte monitoring system report GUI 540 including sensor usage information. In accordance with the disclosed subject matter, GUI 540 is a weekly summary report including a plurality of report portions, wherein each report portion is representative of a different day of the week, and wherein each report portion comprises a glucose trend graph 541, which can include the user's measured glucose levels over a twenty-four hour period, and a health information interface 543, which can include information about the user's average daily glucose, carbohydrate intake, and/or insulin dosages. As embodied herein, glucose trend graph 541 can include sensor usage markers 542 to indicate that a scan, a view, or both had occurred at a particular time during the twenty-four hour period.

Figure 5F:
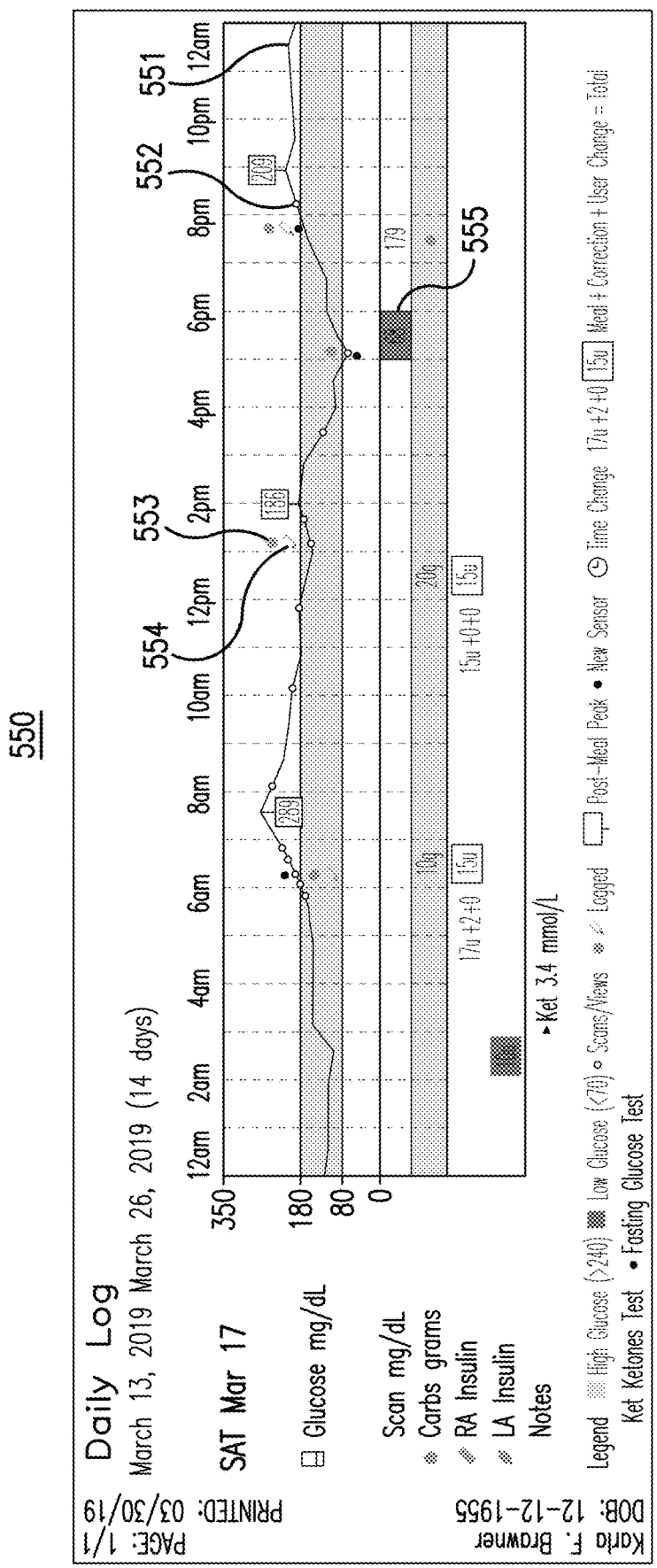

FIG. 5F depicts an example embodiment of another analyte monitoring system report GUI 550 including sensor usage information. In accordance with the disclosed subject matter, GUI 550 is a daily log report comprising a glucose trend graph 551, which can include the user's glucose levels over a twenty-four hour period. As embodied herein, glucose trend graph 551 can include sensor usage markers 552 to indicate that a scan, a view, or both had occurred at a particular time during the twenty-four hour period. Glucose trend graph 551 can also include logged event markers, such as logged carbohydrate intake markers 553 and logged insulin dosage markers 554, as well as glucose event markers, such as low glucose event markers 555.

FIGS. 5I to 5L depict various GUIs for improving usability and user privacy with respect to analyte monitoring software. FIG. 5G, GUI 5540 depicts a research consent interface 5540, which prompts the user to choose to either decline or opt in (through buttons 5542) with respect to permitting the user's analyte data and/or other product-related data to be used for research purposes. According to embodiments of the disclosed subject matter, the analyte data can be anonymized (de-identified) and stored in an international database for research purposes.

Figure 5H:
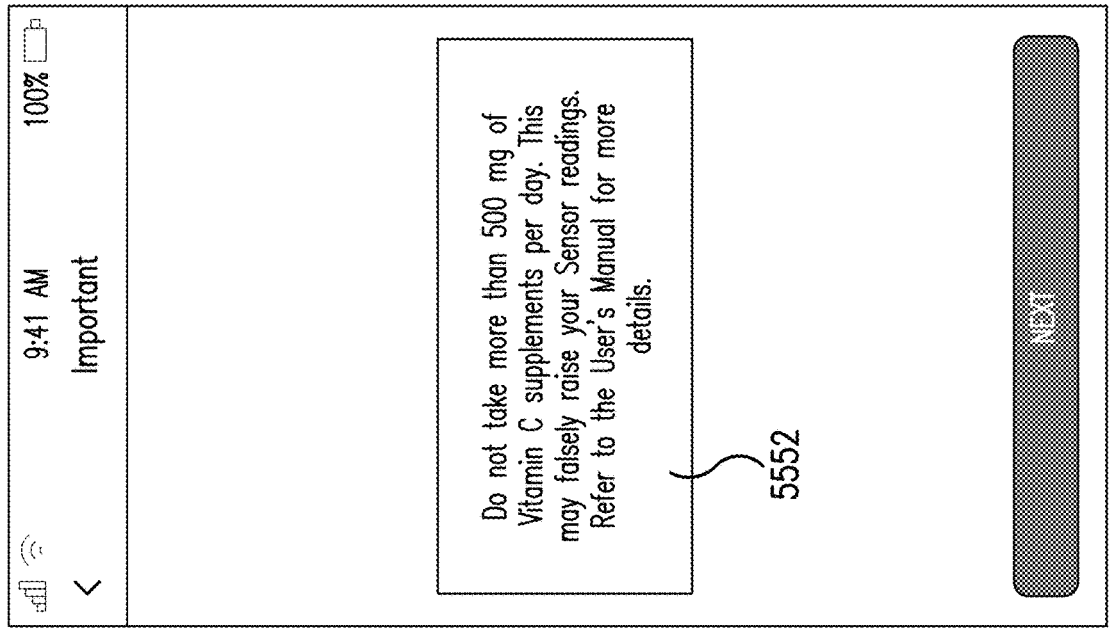
FIGS. 5G-5L are example embodiments of GUIs relating to an analyte monitoring software application.
Figure 5G:
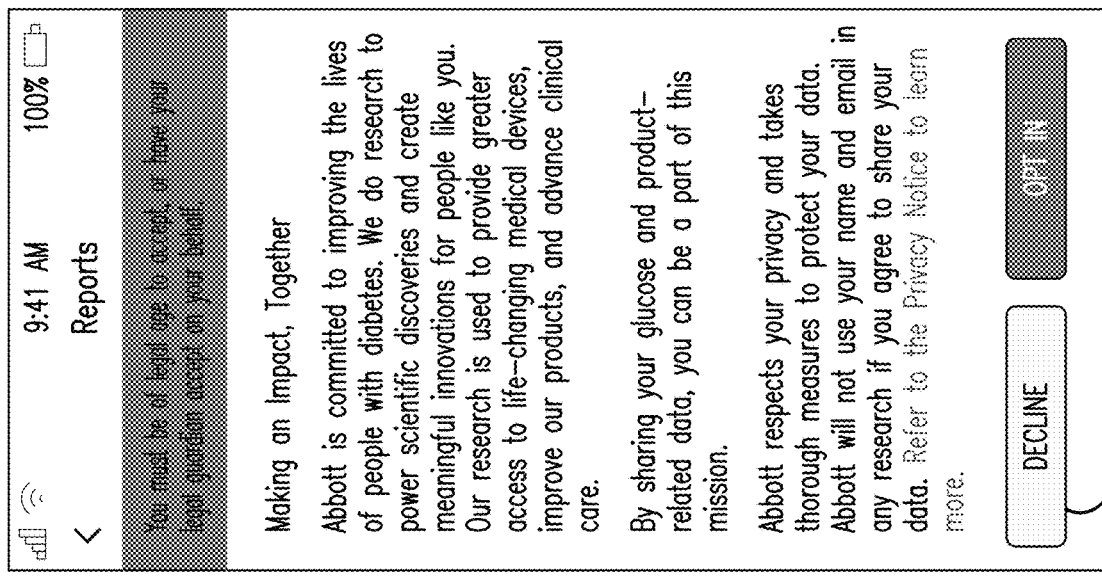

Referring next to FIG. 5H, GUI 5550 depicts a "Vitamin C" warning interface 5550 which displays a warning to the user that the daily use of more than 500 mg of Vitamin C supplements can result in falsely high sensor readings.

Figures 5I, 5J:
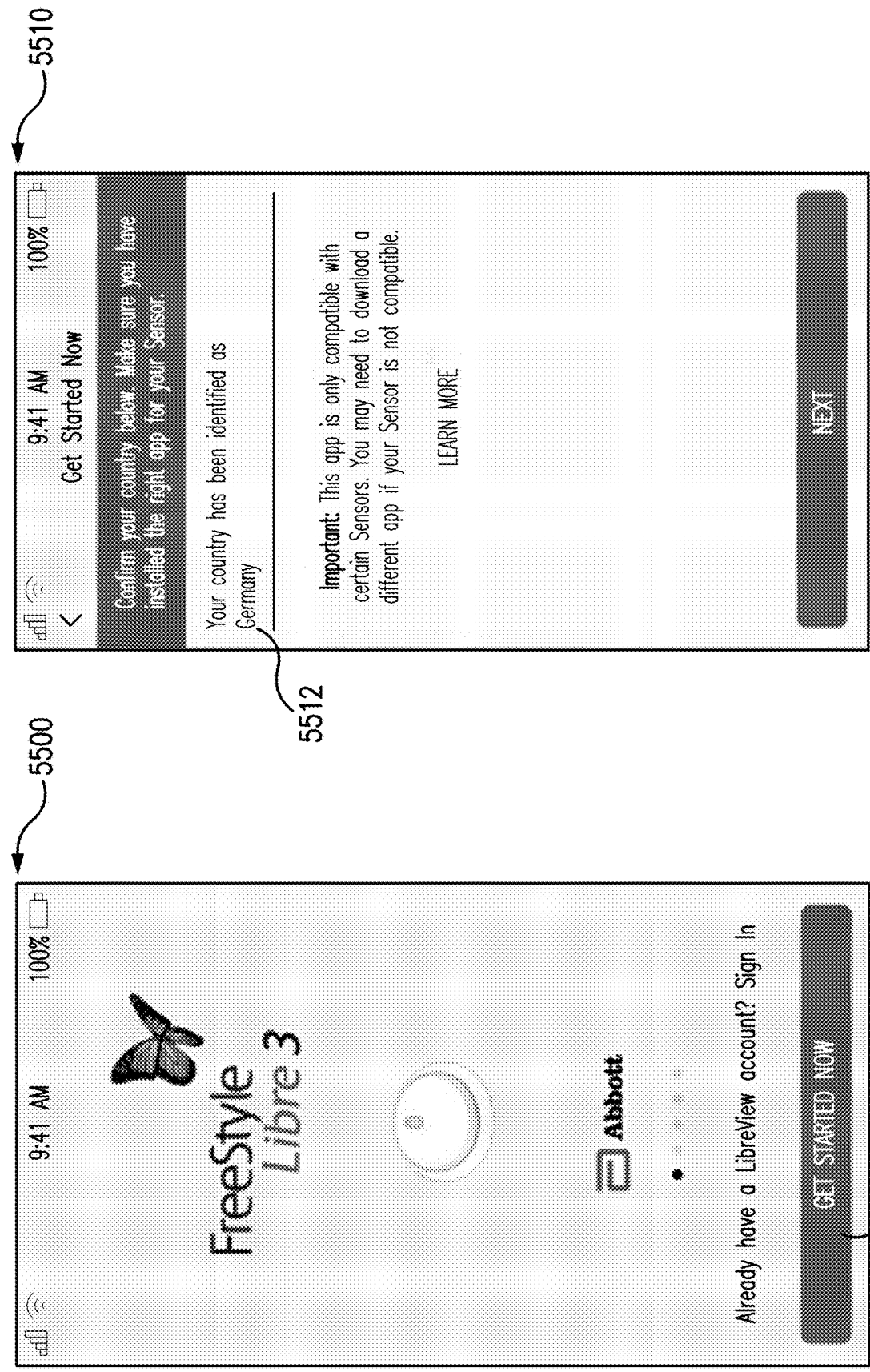

FIG. 5I is GUI 5500 depicting a first start interface which can be displayed to a user the first time the analyte monitoring software is started. In accordance with the disclosed subject matter, GUI 5500 can include a "Get Started Now" button 5502 that, when pressed, will navigate the user to GUI 5510 of FIG. 5J. GUI 5510 depicts a country confirmation interface 5512 that prompts the user to confirm the user's country. According to another aspect of the embodiments, the country selected can limit and/or enable certain interfaces within the analyte monitoring software application for regulatory compliance purposes.

Figure 5L:
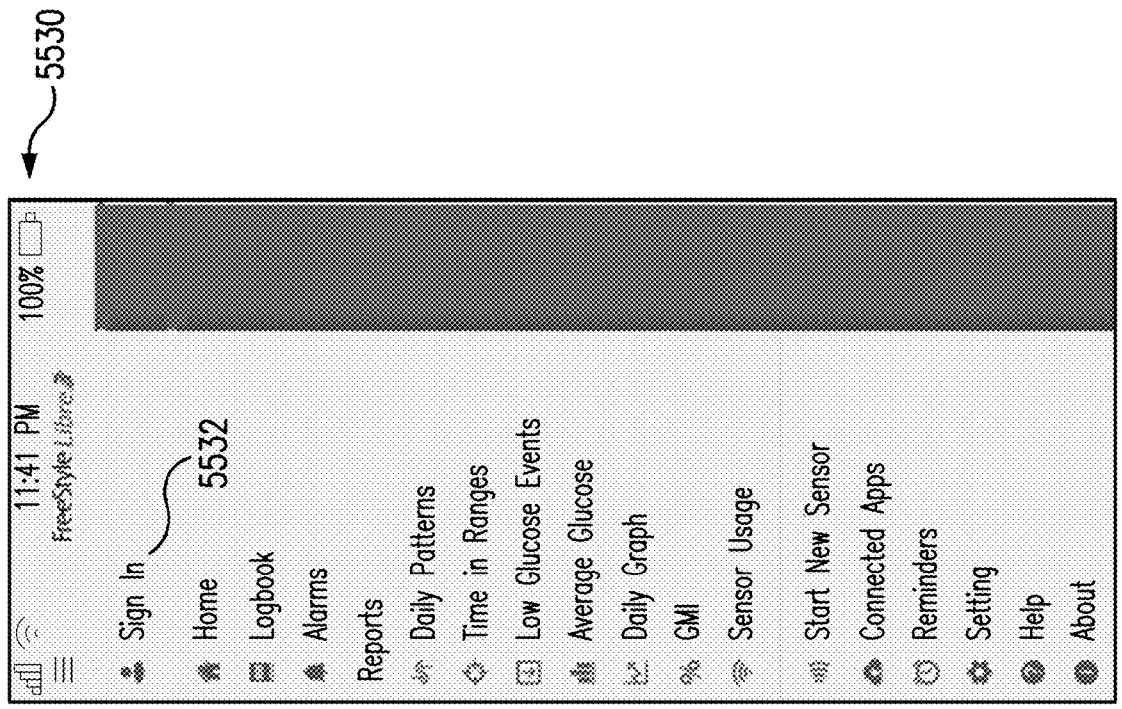
Figure 5K:
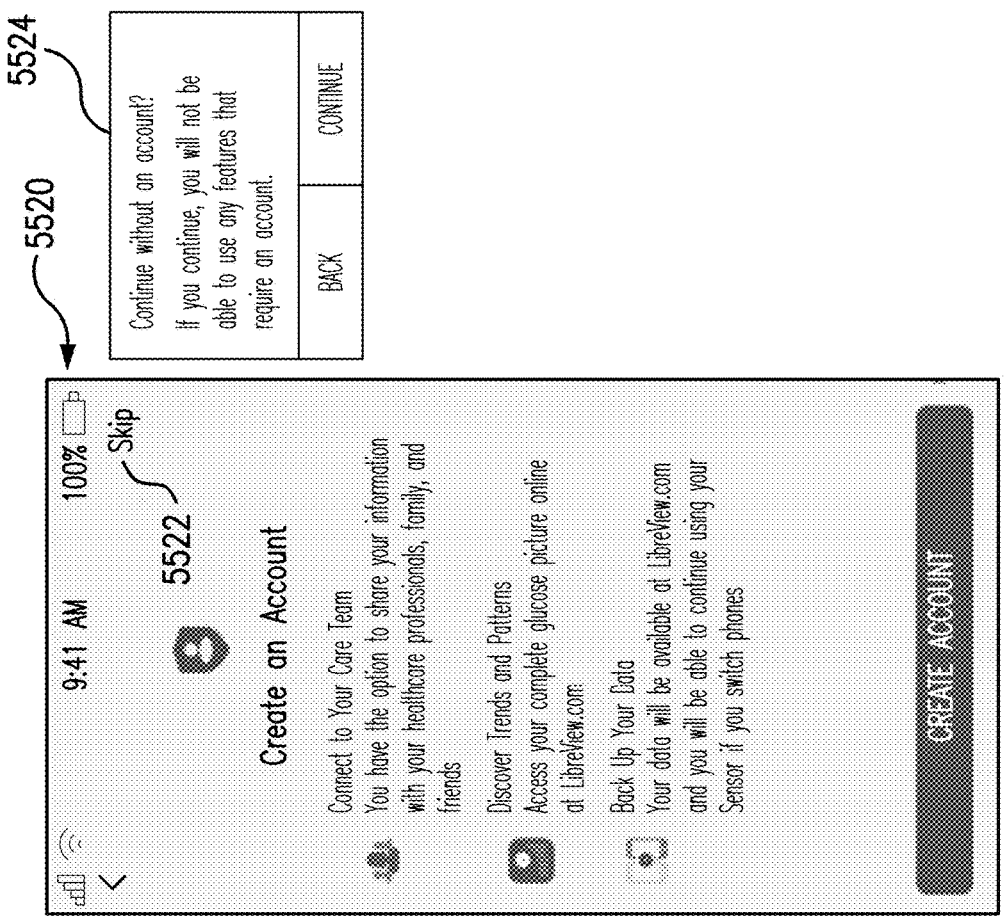

Turning next to FIG. 5K, GUI 5520 depicts a user account creation interface which allows the user to initiate a process to create a cloud-based user account. In accordance with the disclosed subject matter, a cloud-based user account can allow the user to share information with healthcare professionals, family and friends; utilize a cloud-based reporting platform to review more sophisticated analyte reports; and back up the user's historical sensor readings to a cloud-based server. As embodied herein, GUI 5520 can also include a "Skip" link 5522 that allows a user to utilize the analyte monitoring software application in an "accountless mode" (e.g., without creating or linking to a cloud-based account). Upon selecting the "Skip" link 5522, an information window 5524 can be displayed to inform that certain features are not available in "accountless mode." Information window 5524 can further prompt the user to return to GUI 5520 or proceed without account creation.

FIG. 5L is GUI 5530 depicting a menu interface displayed within an analyte monitoring software application while the user is in "accountless mode." In accordance with the disclosed subject matter, GUI 5530 includes a "Sign in" link 5532 that allows the user to leave "accountless mode" and either create a cloud-based user account or sign-in with an existing cloud-based user account from within the analyte monitoring software application.

It will be understood by those of skill in the art that any of the GUIs, reports interfaces, or portions thereof, as described herein, are meant to be illustrative only, and that the individual elements, or any combination of elements, depicted and/or described for a particular embodiment or figure are freely combinable with any elements, or any combination of elements, depicted and/or described with respect to any of the other embodiments.

Example Embodiments of Digital Interfaces for Analyte Monitoring Systems

Described herein are example embodiments of digital interfaces for analyte monitoring systems. In accordance with the disclosed subject matter, a digital interface can comprise a series of instructions, routines, subroutines, and/or algorithms, such as software and/or firmware stored in a non-transitory memory, executed by one or more processors of one or more devices in an analyte monitoring system, wherein the instructions, routines, subroutines, or algorithms are configured to enable certain functions and inter-device communications. As an initial matter, it will be understood by those of skill in the art that the digital interfaces described herein can comprise instructions stored in a non-transitory memory of a sensor control device 102, reader device 120, local computer system 170, trusted computer system 180, and/or any other device or system that is part of, or in communication with, analyte monitoring system 100, as described with respect to FIGS. 1, 2A, and 2B. These instructions, when executed by one or more processors of the sensor control device 102, reader device 120, local computer system 170, trusted computer system 180, or other device or system of analyte monitoring system 100, cause the one or more processors to perform the method steps described herein. Those of skill in the art will further recognize that the digital interfaces described herein can be stored as instructions in the memory of a single centralized device or, in the alternative, can be distributed across multiple discrete devices in geographically dispersed locations.

Example Embodiments of Methods for Data Backfilling

Example embodiments of methods for data backfilling in an analyte monitoring system will now be described. In accordance with the disclosed subject matter, gaps in analyte data and other information can result from interruptions to communication links between various devices in an analyte monitoring system 100. These interruptions can occur, for example, from a device being powered off (e.g., a user's smart phone runs out of battery), or a first device temporarily moving out of a wireless communication range from a second device (e.g., a user wearing sensor control device 102 inadvertently leaves her smart phone at home when she goes to work). As a result of these interruptions, reader device 120 may not receive analyte data and other information from sensor control device 102. It would thus be beneficial to have a robust and flexible method for data backfilling in an analyte monitoring system to ensure that once a communication link is re-established, each analyte monitoring device can receive a complete set of data, as intended.

Figure 6A:
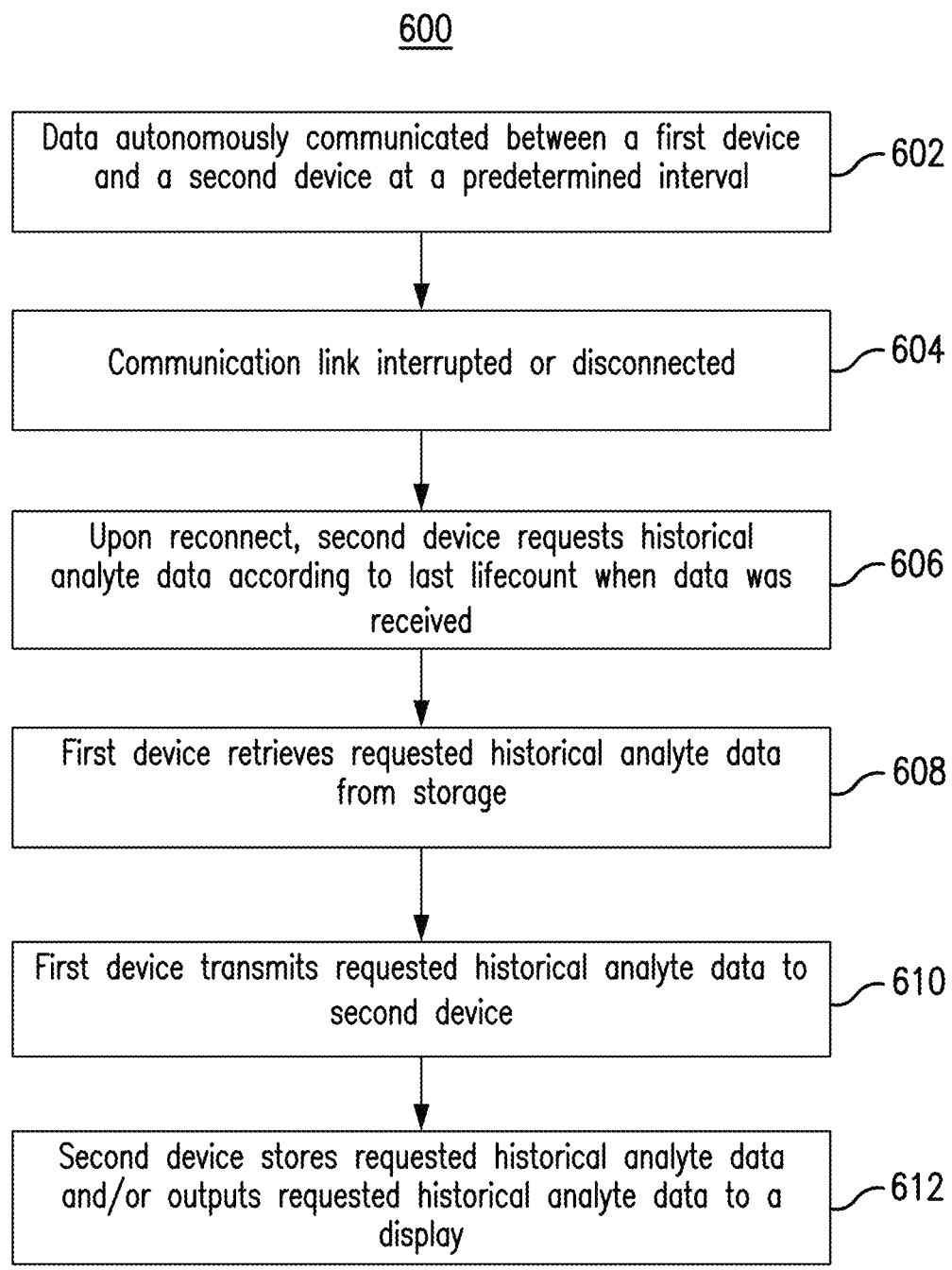
FIGS. 6A and 6B are flow diagrams depicting example embodiments of methods for data backfilling in an analyte monitoring system.

FIG. 6A is a flow diagram depicting an example embodiment of a method 600 for data backfilling in an analyte monitoring system. In accordance with the disclosed subject matter, method 600 can be implemented to provide data backfilling between a sensor control device 102 and a reader device 120. At Step 602, analyte data and other information is autonomously communicated between a first device and a second device at a predetermined interval. As embodied herein, the first device can be a sensor control device 102, and the second device can be a reader device 120, as described with respect to FIGS. 1, 2A, and 2B. In accordance with the disclosed subject matter, analyte data and other information can include, but is not limited to, one or more of: data indicative of an analyte level in a bodily fluid, a rate-of-change of an analyte level, a predicted analyte level, a low or a high analyte level alert condition, a sensor fault condition, or a communication link event. According to another aspect of the embodiments, autonomous communications at a predetermined interval can comprise streaming analyte data and other information according to a standard wireless communication network protocol, such as a Bluetooth or Bluetooth Low Energy protocol, at one or more predetermined rates (e.g., every minute, every five minutes, every fifteen minutes, etc.). As embodied herein, different types of analyte data or other information can be autonomously communicated between the first and second devices at different predetermined rates (e.g., historical glucose data every 5 minutes, current glucose value every minute, etc.).

At Step 604, a disconnection event or condition occurs that causes an interruption to the communication link between the first device and the second device. As described above, the disconnection event can result from the second device (e.g., reader device 120, smart phone, etc.) running out of battery power or being powered off manually by a user. A disconnection event can also result from the first device being moved outside a wireless communication range of the second device, from the presence of a physical barrier that obstructs the first device and/or the second device, or from anything that otherwise prevents wireless communications from occurring between the first and second devices.

At Step 606, the communication link is re-established between the first device and the second device (e.g., the first device comes back into the wireless communication range of the second device). Upon reconnection, the second device requests historical analyte data according to a last lifecount metric for which data was received. In accordance with the disclosed subject matter, the lifecount metric can be a numeric value that is incremented and tracked on the second device in units of time (e.g., minutes), and is indicative of an amount of time elapsed since the sensor control device was activated. For example, As embodied herein, after the second device (e.g., reader device 120, smart phone, etc.) re-establishes a Bluetooth wireless communication link with the first device (e.g., sensor control device 120), the second device can determine the last lifecount metric for which data was received. Then, according to some embodiments, the second device can send to the first device a request for historical analyte data and other information having a lifecount metric greater than the determined last lifecount metric for which data was received.

As embodied herein, the second device can send a request to the first device for historical analyte data or other information associated with a specific lifecount range, instead of requesting historical analyte data associated with a lifecount metric greater than a determined last lifecount metric for which data was received.

At Step 608, upon receiving the request, the first device retrieves the requested historical analyte data from storage (e.g., non-transitory memory of sensor control device 102), and subsequently transmits the requested historical analyte data to the second device at Step 610. At Step 612, upon receiving the requested historical analyte data, the second device stores the requested historical analyte data in storage (e.g., non-transitory memory of reader device 120). In accordance with the disclosed subject matter, when the requested historical analyte data is stored by the second device, it can be stored along with the associated lifecount metric. As embodied herein, the second device can also output the requested historical analyte data to a display of the second device, such as, for example to a glucose trend graph of a sensor results GUI, such as those described with respect to FIGS. 2D to 2I. For example, As embodied herein, the requested historical analyte data can be used to fill in gaps in a glucose trend graph by displaying the requested historical analyte data along with previously received analyte data.

Furthermore, those of skill in the art will appreciate that the method of data backfilling can be implemented between multiple and various devices in an analyte monitoring system, wherein the devices are in wired or wireless communication with each other.

Figure 6B:
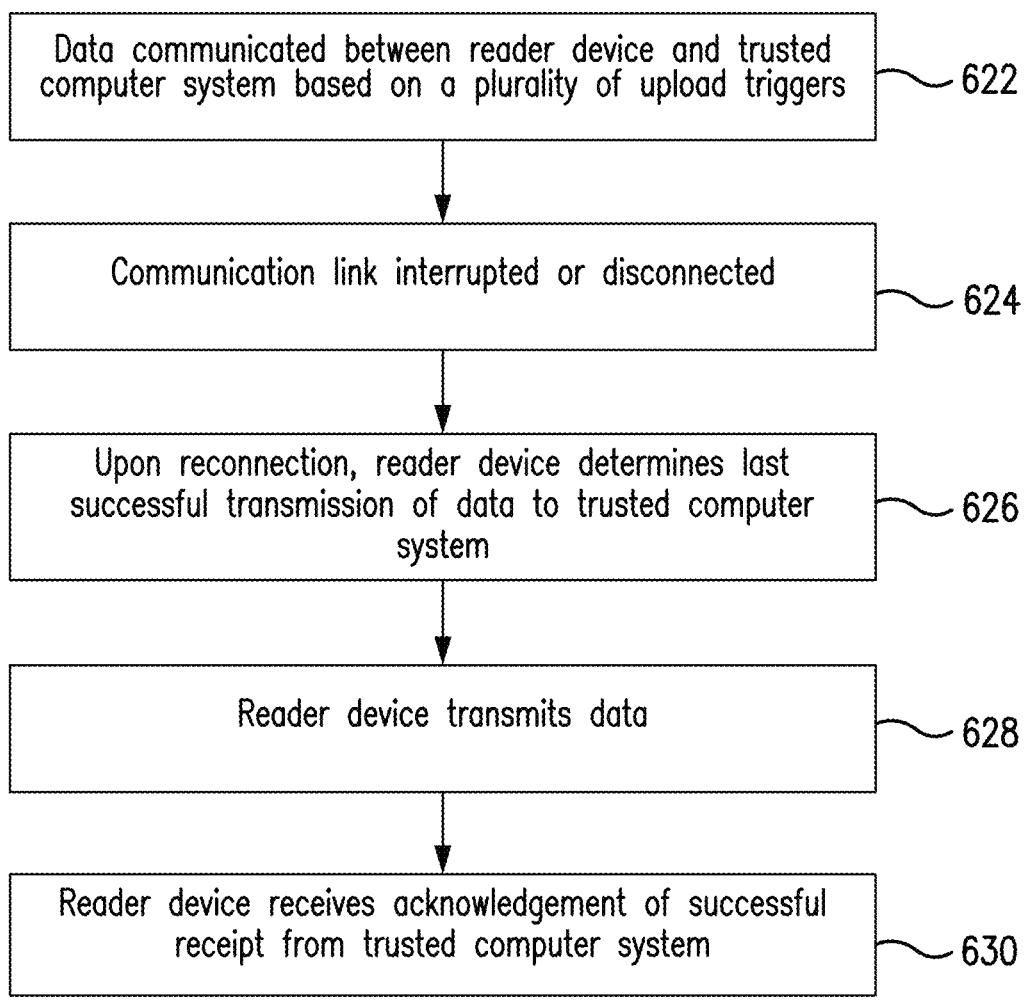

FIG. 6B is a flow diagram depicting another example embodiment of a method 620 for data backfilling in an analyte monitoring system. In accordance with the disclosed subject matter, method 620 can be implemented to provide data backfilling between a reader device 120 (e.g., smart phone, dedicated reader) and a trusted computer system 180, such as, for example, a cloud-based platform for generating reports. At Step 622, analyte data and other information is communicated between reader device 120 and trusted computer system 180 based on a plurality of upload triggers. In accordance with the disclosed subject matter, analyte data and other information can include, but are not limited to, one or more of: data indicative of an analyte level in a bodily fluid (e.g., current glucose level, historical glucose data), a rate-of-change of an analyte level, a predicted analyte level, a low or a high analyte level alert condition, information logged by the user, information relating to sensor control device 102, alarm information (e.g., alarm settings), wireless connection events, and reader device settings, to name a few. According to another aspect of the embodiments, the plurality of upload triggers can include (but is not limited to) one or more of the following: activation of sensor control device 102; user entry or deletion of a note or log entry; a wireless communication link (e.g., Bluetooth) reestablished between reader device 120 and sensor control device 102; alarm threshold changed; alarm presentation, update, or dismissal; internet connection re-established; reader device 120 restarted; a receipt of one or more current glucose readings from sensor control device 102; sensor control device 120 terminated; signal loss alarm presentation, update, or dismissal; signal loss alarm is toggled on/off; view of sensor results screen GUI; or user sign-in into cloud-based platform.

According to another aspect of the embodiments, in order to track the transmission and receipt of data between devices, reader device 120 can "mark" analyte data and other information that is to be transmitted to trusted computer system 180. As embodied herein, for example, upon receipt of the analyte data and other information, trusted computer system 180 can send a return response to reader device 120, to acknowledge that the analyte data and other information has been successfully received. Subsequently, reader device 120 can mark the data as successfully sent. As embodied herein, the analyte data and other information can be marked by reader device 120 both prior to being sent and after receipt of the return response. In other embodiments, the analyte data and other information can be marked by reader device 120 only after receipt of the return response from trusted computer system 180.

Referring to FIG. 6B, at Step 624, a disconnection event occurs that causes an interruption to the communication link between reader device 120 and trusted computer system 180. For example, the disconnection event can result from the user placing the reader device 120 into "airplane mode" (e.g., disabling of the wireless communication modules), from the user powering off the reader device 120, or from the reader device 120 moving outside of a wireless communication range.

At Step 626, the communication link between reader device 120 and trusted computer system 180 (as well as the internet) is re-established, which is one of the plurality of upload triggers. Subsequently, reader device 120 determines the last successful transmission of data to trusted computer system 180 based on the previously marked analyte data and other information sent. Then, at Step 628, reader device 120 can transmit analyte data and other information not yet received by trusted computer system 180. At Step 630, reader device 120 receives acknowledgement of successful receipt of analyte data and other information from trusted computer system 180.

Although FIG. 6B is described above with respect to a reader in communication with a trusted computer system, those of skill in the art will appreciate that the data backfilling method can be applied between other devices and computer systems in an analyte monitoring system (e.g., between a reader and a local computer system, between a reader and a medical delivery device, between a reader and a wearable computing device, etc.). These embodiments, along with their variations and permutations, are fully within the scope of this disclosure.

In addition to data backfilling, example embodiments of methods for aggregating disconnect and reconnect events for wireless communication links in an analyte monitoring system are described. In accordance with the disclosed subject matter, there can be numerous and wide-ranging causes for interruptions to wireless communication links between various devices in an analyte monitoring system. Some causes can be technical in nature (e.g., a reader device is outside a sensor control device's wireless communication range), while other causes can relate to user behavior (e.g., a user leaving his or her reader device at home). In order to improve connectivity and data integrity in analyte monitoring systems, it would therefore be beneficial to gather information regarding the disconnect and reconnect events between various devices in an analyte monitoring system.

Figure 6C:
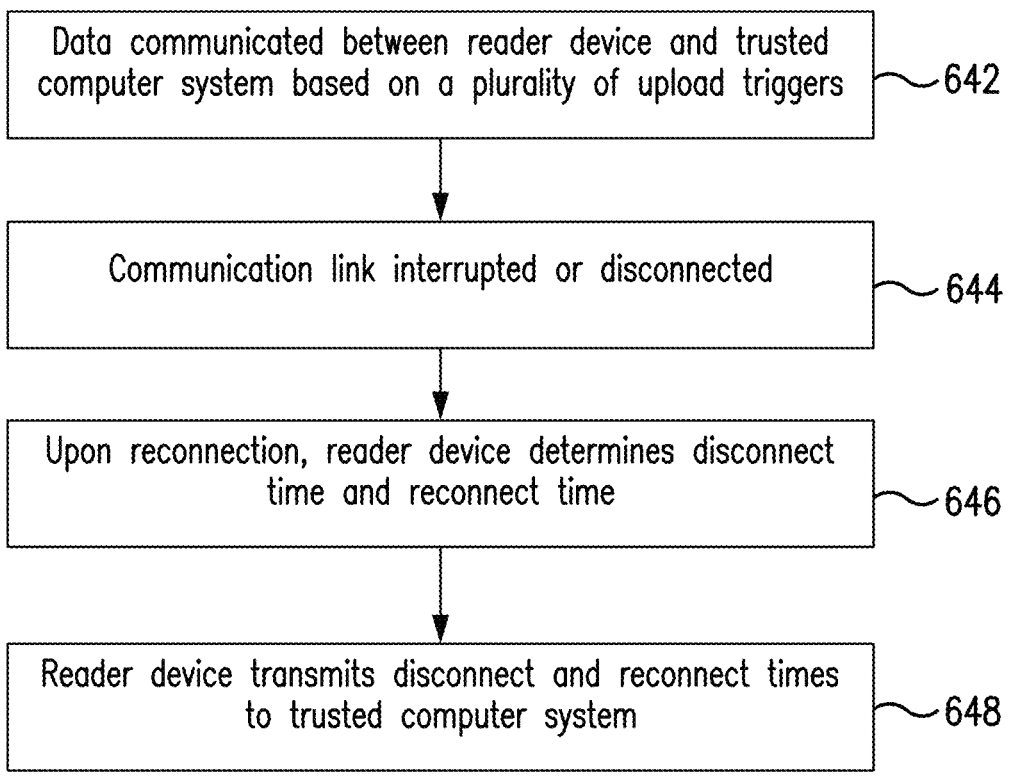
FIG. 6C is a flow diagram depicting an example embodiment of a method for aggregating disconnect and reconnect events in an analyte monitoring system.

FIG. 6C is a flow diagram depicting an example embodiment of a method 640 for aggregating disconnect and reconnect events for wireless communication links in an analyte monitoring system. As embodied herein, for example, method 640 can be used to detect, log, and upload to trusted computer system 180, Bluetooth or Bluetooth Low Energy disconnect and reconnect events between a sensor control device 102 and a reader device 120. In accordance with the disclosed subject matter, trusted computer system 180 can aggregate disconnect and reconnect events transmitted from a plurality of analyte monitoring systems. The aggregated data can then by analyzed to determine whether any conclusions can be made about how to improve connectivity and data integrity in analyte monitoring systems.

At Step 642, analyte data and other information are communicated between reader device 120 and trusted computer system 180 based on a plurality of upload triggers, such as those previously described with respect to method 620 of FIG. 6B. At Step 644, a disconnection event occurs that causes an interruption to the wireless communication link between sensor control device 102 and reader device 120. Example disconnection events can include, but are not limited to, a user placing the reader device 120 into "airplane mode," the user powering off the reader device 120, the reader device 120 running out of power, the sensor control device 102 moving outside a wireless communication range of the reader devices 120, or a physical barrier obstructing the sensor control device 102 and/or the reader device 120, to name only a few.

Referring still to FIG. 6C, at Step 646, the wireless communication link between the sensor control device 102 and reader device 120 is re-established, which is one of the plurality of upload triggers. Subsequently, reader device 120 determines a disconnect time and a reconnect time, wherein the disconnect time is the time that the interruption to the wireless communication link began, and the reconnect time is the time that the wireless communication link between the sensor control device 102 and reader device 120 is re-established. According to some embodiments, the disconnection and reconnection times can also be stored locally in an event log on reader device 120. At Step 648, reader device 120 transmits the disconnect and reconnect times to trusted computer system 180.

According to some embodiments, the disconnect and reconnect times can be stored in non-transitory memory of trusted computer system 180, such as in a database, and aggregated with the disconnect and reconnect times collected from other analyte monitoring systems. As embodied herein, the disconnect and reconnect times can also be transmitted to and stored on a different cloud-based platform or server from trusted computer system 180 that stores analyte data. In still other embodiments, the disconnect and reconnect times can be anonymized.

In addition, those of skill in the art will recognize that method 640 can be utilized to collect disconnect and reconnect times between other devices in an analyte monitoring system, including, for example: between reader device 120 and trusted computer system 180; between reader device 120 and a wearable computing device (e.g., smart watch, smart glasses); between reader device 120 and a medication delivery device (e.g., insulin pump, insulin pen); between sensor control device 102 and a wearable computing device; between sensor control device 102 and a medication delivery device; and any other combination of devices within an analyte monitoring system. Those of skill in the art will further appreciate that method 640 can be utilized to analyze disconnect and reconnect times for different wireless communication protocols, such as, for example, Bluetooth or Bluetooth Low Energy, NFC, 802.11x, UHF, cellular connectivity, or any other standard or proprietary wireless communication protocol.

Example Embodiments of Improved Expired/Failed Sensor Transmissions

Example embodiments of methods for improved expired and/or failed sensor transmissions in an analyte monitoring system will now be described. In accordance with the disclosed subject matter, expired or failed sensor conditions detected by a sensor control device 102 can trigger alerts on reader device 120. However, if the reader device 120 is in "airplane mode," powered off, outside a wireless communication range of sensor control device 102, or otherwise unable to wirelessly communicate with the sensor control device 102, then the reader device 120 may not receive these alerts. This can cause the user to miss information such as, for example, the need to replace a sensor control device 102. Failure to take action on a detected sensor fault can also lead to the user being unaware of adverse glucose conditions (e.g., hypoglycemia and/or hyperglycemia) due to a terminated sensor.

Figure 7:
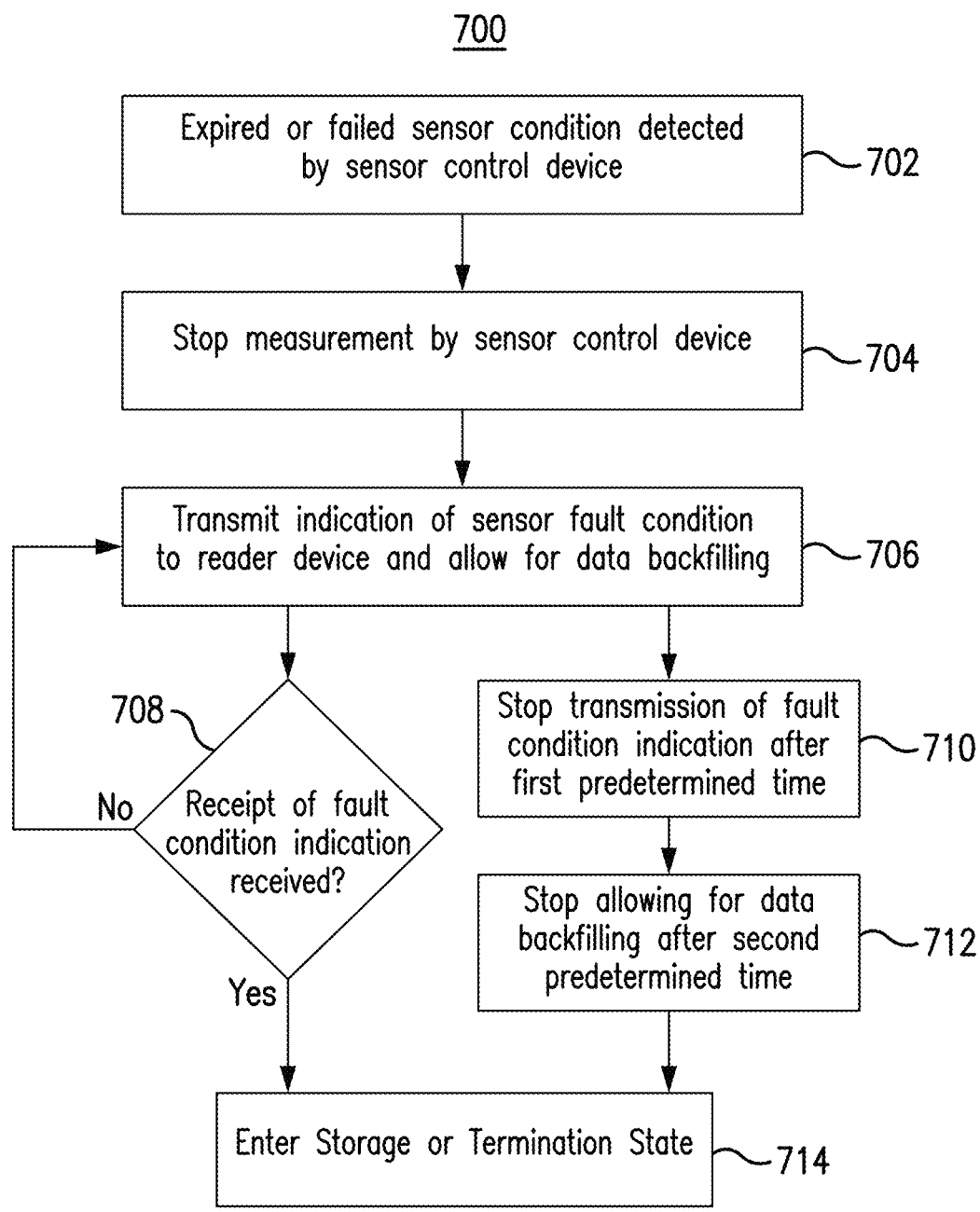
FIG. 7 is a flow diagram depicting an example embodiment of a method for failed or expired sensor transmissions in an analyte monitoring system.

FIG. 7 is a flow diagram depicting an example embodiment of a method 700 for improved expired or failed sensor transmissions in an analyte monitoring system. In accordance with the disclosed subject matter, method 700 can be implemented to provide for improved sensor transmissions by a sensor control device 102 after an expired or failed sensor condition has been detected. At Step 702, an expired or failed sensor condition is detected by sensor control device 102. As embodied herein, the sensor fault condition can comprise one or both of a sensor insertion failure condition or a sensor termination condition. According to some embodiments, for example, a sensor insertion failure condition or a sensor termination condition can include, but is not limited to, one or more of the following: a FIFO overflow condition detected, a sensor signal below a predetermined insertion failure threshold, moisture ingress detected, an electrode voltage exceeding a predetermined diagnostic voltage threshold, an early signal attenuation (ESA) condition, or a late signal attenuation (LSA) condition, to name a few.

Referring again to FIG. 7, at Step 704, sensor control device 102 stops acquiring measurements of analyte levels from the analyte sensor in response to the detection of the sensor fault condition. At Step 706, sensor control device 102 begins transmitting an indication of a sensor fault condition to reader device 120, while also allowing for the reader device 120 to connect to the sensor control device 102 for purposes of data backfilling. In accordance with the disclosed subject matter, the transmission of the indication of the sensor fault condition can comprise transmitting a plurality of Bluetooth or Bluetooth Low Energy advertising packets, each of which can include the indication of the sensor fault condition. As embodied herein, the plurality of Bluetooth or BLE advertising packets can be transmitted repeatedly, continuously, or intermittently. Those of skill in the art will recognize that other modes of wirelessly broadcasting or multicasting the indication of the sensor fault condition can be implemented. According to another aspect of the embodiments, in response to receiving the indication of the sensor fault condition, reader device 120 can visually display an alert or prompt for a confirmation by the user.

At Step 708, sensor control device 102 can be configured to monitor for a return response or acknowledgment of receipt of the indication of the sensor fault condition from reader device 120. As embodied herein, for example, a return response or acknowledgement of receipt can be generated by reader device 120 when a user dismisses an alert on the reader device 120 relating to the indication of the sensor fault condition, or otherwise responds to a prompt for confirmation of the indication of the sensor fault condition. If a return response or acknowledgement of receipt of the indication of the sensor fault condition is received by sensor control device 102, then at Step 714, sensor control device 102 can enter either a storage state or a termination state. According to some embodiments, in the storage state, the sensor control device 102 is placed in a low-power mode, and the sensor control device 102 is capable of being re-activated by a reader device 120. By contrast, in the termination state, the sensor control device 102 cannot be re-activated and must be removed and replaced.

If a receipt of the fault condition indication is not received by sensor control device 102, then at Step 710, the sensor control device 102 will stop transmitting the fault condition indication after a first predetermined time period. As embodied herein, for example, the first predetermined time period can be one of: one hour, two hours, five hours, etc. Subsequently, at Step 712, if a receipt of the fault condition indication is still not received by sensor control device 102, then at Step 712, the sensor control device 102 will also stop allowing for data backfilling after a second predetermined time period. As embodied herein, for example, the second predetermined time period can be one of: twenty-four hours, forty-eight hours, etc. Sensor control device 102 then enters a storage state or a termination state at Step 714.

By allowing sensor control device 102 to continue transmissions of sensor fault conditions for a predetermined time period, the embodiments of this disclosure mitigate the risk of unreceived sensor fault alerts. In addition, although the embodiments described above are in reference to a sensor control device 102 in communication with a reader device 120, those of skill in the art will recognize that indications of sensor fault conditions can also be transmitted between a sensor control device 102 and other types of mobile computing devices, such as, for example, wearable computing devices (e.g., smart watches, smart glasses) or tablet computing devices.

Example Embodiments of Data Merging in Analyte Monitoring Systems

Example embodiments of methods for merging data received from one or more analyte monitoring systems will now be described. As described earlier with respect to FIG. 1, a trusted computer system 180, such as a cloud-based platform, can be configured to generate various reports based on received analyte data and other information from a plurality of reader devices 120 and sensor control devices 102. A large and diverse population of reader devices and sensor control devices, however, can give rise to complexities and challenges in generating reports based on the received analyte data and other information. For example, a single user can have multiple reader devices and/or sensor control devices, either simultaneously or serially over time, each of which can comprise different versions. This can lead to further complications in that, for each user, there may be sets of duplicative and/or overlapping data. It would therefore be beneficial to have methods for merging data at a trusted computer system for purposes of report generation.

Figure 8A:
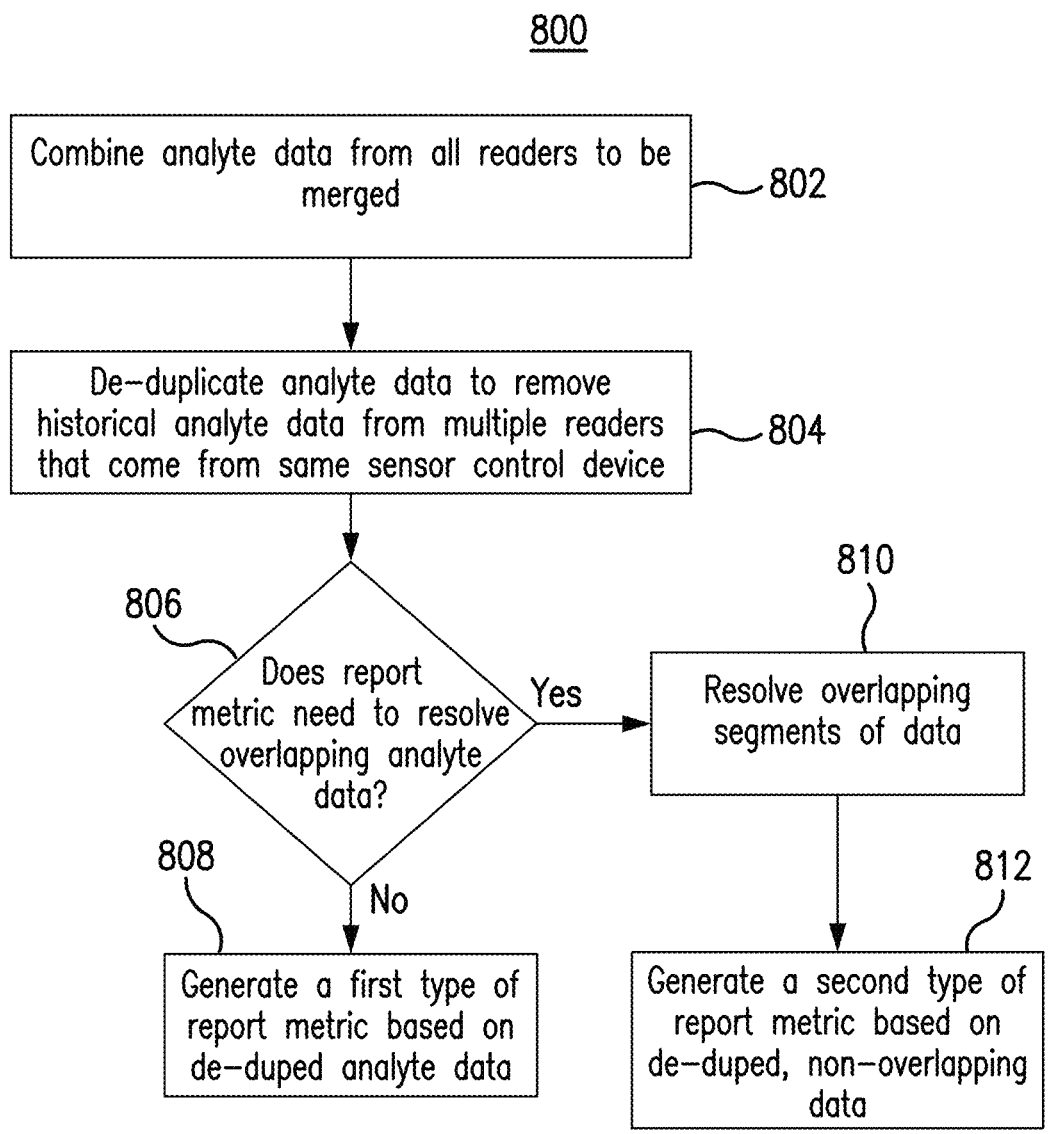
FIGS. 8A and 8B are flow diagrams depicting example embodiments of methods for data merging in an analyte monitoring system.

FIG. 8A is a flow diagram depicting an example embodiment of a method 800 for merging data associated with a user and generating one or more report metrics, wherein the data originates from multiple reader devices and multiple sensor control devices. In accordance with the disclosed subject matter, method 800 can be implemented to merge analyte data in order to generate different types of report metrics utilized in various reports. At Step 802, data is received from one or more reader devices 120 and combined for purposes of merging. At Step 804, the combined data is then de-duplicated to remove historical data from multiple readers originating from the same sensor control device. In accordance with the disclosed subject matter, the process of de-duplicating data can include (1) identifying or assigning a priority associated with each reader device from which analyte data is received, and (2) in the case where there is "duplicate" data, preserving the data associated with the reader device with a higher priority. As embodied herein, for example, a newer reader device (e.g., newer model, having a more recent version of software installed) is assigned a higher priority than an older reader device (e.g., older model, having an older version of software installed). As embodied herein, priority can be assigned by device type (e.g., smart phone having a higher priority over a dedicated reader).

Referring still to FIG. 8A, at Step 806, a determination is made as to whether one or more of the report metrics to be generated requires resolution of overlapping data. If not, at Step 808, a first type of report metric can be generated based on de-duplicated data without further processing. As embodied herein, for example, the first type of report metric can include average glucose levels used in reports, such as a snapshot or monthly summary report (as described with respect to FIGS. 5C and 5D). If it is determined that one or more of the report metrics to be generated requires resolution of overlapping data, then at Step 810, a method for resolving overlapping regions of data is performed. An example embodiment method for resolving overlapping regions of data is described below with respect to FIG. 8B. Subsequently, at Step 812, a second type of report metric based on data that has been de-duplicated and processed to resolve overlapping data segments, is generated. As embodied herein, for example, the second type of report metric can include low glucose event calculations used in reports, such as the daily log report (as described with respect to FIG. 5F).

Figure 8B:
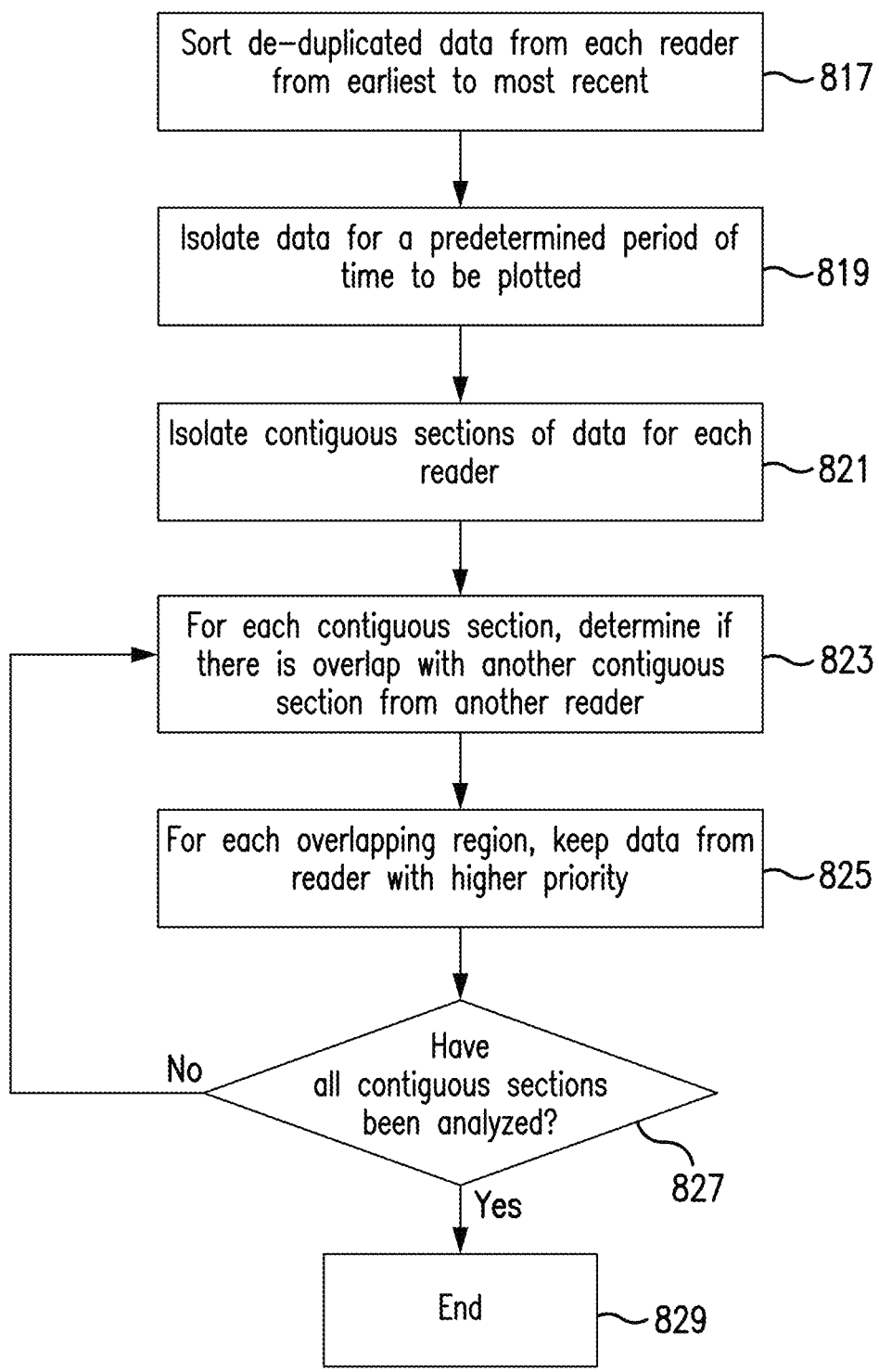

FIG. 8B is a flow diagram depicting an example embodiment of a method 815 for resolving overlapping regions of analyte data, which can be implemented, for example, in Step 810 of method 800, as described with respect to FIG. 8A. At Step 817, the de-duplicated data from each reader (resulting from Step 804 of method 800, as described with respect to FIG. 8A) can be sorted from earliest to most recent. At Step 819, based on the report metric to be generated, the de-duplicated and sorted data is then isolated according to a predetermined period of time. As embodied herein, for example, if the report metric is a graph reflecting glucose values over a specific day, then the de-duplicated and sorted data can be isolated for that specific day. Next, at Step 821, contiguous sections of the de-duplicated and sorted data for each reader device are isolated. In accordance with the disclosed subject matter, non-contiguous data points can be discarded or disregarded (e.g., not used) for purposes of generating report metrics. At Step 823, for each contiguous section of de-duplicated and sorted data of a reader device, a determination is made as to whether there are any overlapping regions with other contiguous sections of de-duplicated and sorted data from other reader devices. At Step 825, for each overlapping region identified, the de-duplicated and sorted data from the reader device with the higher priority is preserved. At Step 827, if it is determined that all contiguous sections have been analyzed according to the previous steps, then method 815 ends at Step 829. Otherwise, method 815 then returns to Step 823 to continue identifying and resolving any overlapping regions between contiguous sections of de-duplicated and sorted data for different reader devices.

FIGS. 8C to 8E are graphs (840, 850, 860) depicting various stages of de-duplicated and sorted data from multiple reader devices, as the data is processed according to method 815 for resolving overlapping regions of data. Referring first to FIG. 8C, graph 840 depicts de-duplicated and sorted data from three different reader devices: a first reader 841 (as reflected by the circular data points), a second reader 842 (as reflected by diamond-shaped data points), and a third reader 843 (as reflected by the square-shaped data points). According to one aspect of graph 840, the data is depicted at Step 821 of method 815, after it has been de-duplicated, sorted, and isolated to a predetermined time period. As can be seen in FIG. 8C, a contiguous section of data for each of the three reader devices (841, 842, and 843) has been identified, and three traces are shown. According to another aspect of the graph 840, non-contiguous points 844 are not included in the three traces.

Referring next to FIG. 8D, graph 850 depicts the data from readers 841, 842, 843 at Step 823 of method 815, wherein three overlapping regions between the contiguous sections of data have been identified: a first overlapping region 851 between all three contiguous sections of data; a second overlapping region 852 between two contiguous sections of data (from reader device 842 and reader device 843); and a third overlapping region 853 between two contiguous sections of data (also from reader device 842 and reader device 843).

FIG. 8E is a graph 860 depicting data at Step 825 of method 815, wherein a single trace 861 indicates the merged, de-duplicated, and sorted data from three reader devices 841, 842, 843 after overlapping regions 851, 852, and 853 have been resolved by using the priority of each reader device. According to graph 860, the order of priority from highest to lowest is: reader device 843, reader device 842, and reader device 841.

Although FIGS. 8C, 8D, and 8E depict three contiguous sections of data with three discrete overlapping regions identified, those of skill in the art will understand that either fewer or more contiguous sections of data (and non-contiguous data points) and overlapping regions are possible. For example, those of skill in the art will recognize that where a user has only two reader devices, there may be fewer contiguous sections of data and overlapping regions, if any at all. Conversely, if a user has five reader devices, those of skill in the art will understand that there may be five contiguous sections of data with three or more overlapping regions.

Example Embodiments of Sensor Transitioning

Example embodiments of methods for sensor transitioning will now be described. In accordance with the disclosed subject matter, as mobile computing and wearable technologies continue to advance at a rapid pace and become more ubiquitous, users are more likely to replace or upgrade their smart phones more frequently. In the context of analyte monitoring systems, it would therefore be beneficial to have sensor transitioning methods to allow a user to continue using a previously activated sensor control device with a new smart phone. In addition, it would also be beneficial to ensure that historical analyte data from the sensor control device could be backfilled to the new smart phone (and subsequently uploaded to the trusted computer system) in a user-friendly and secure manner.

Figure 9A:
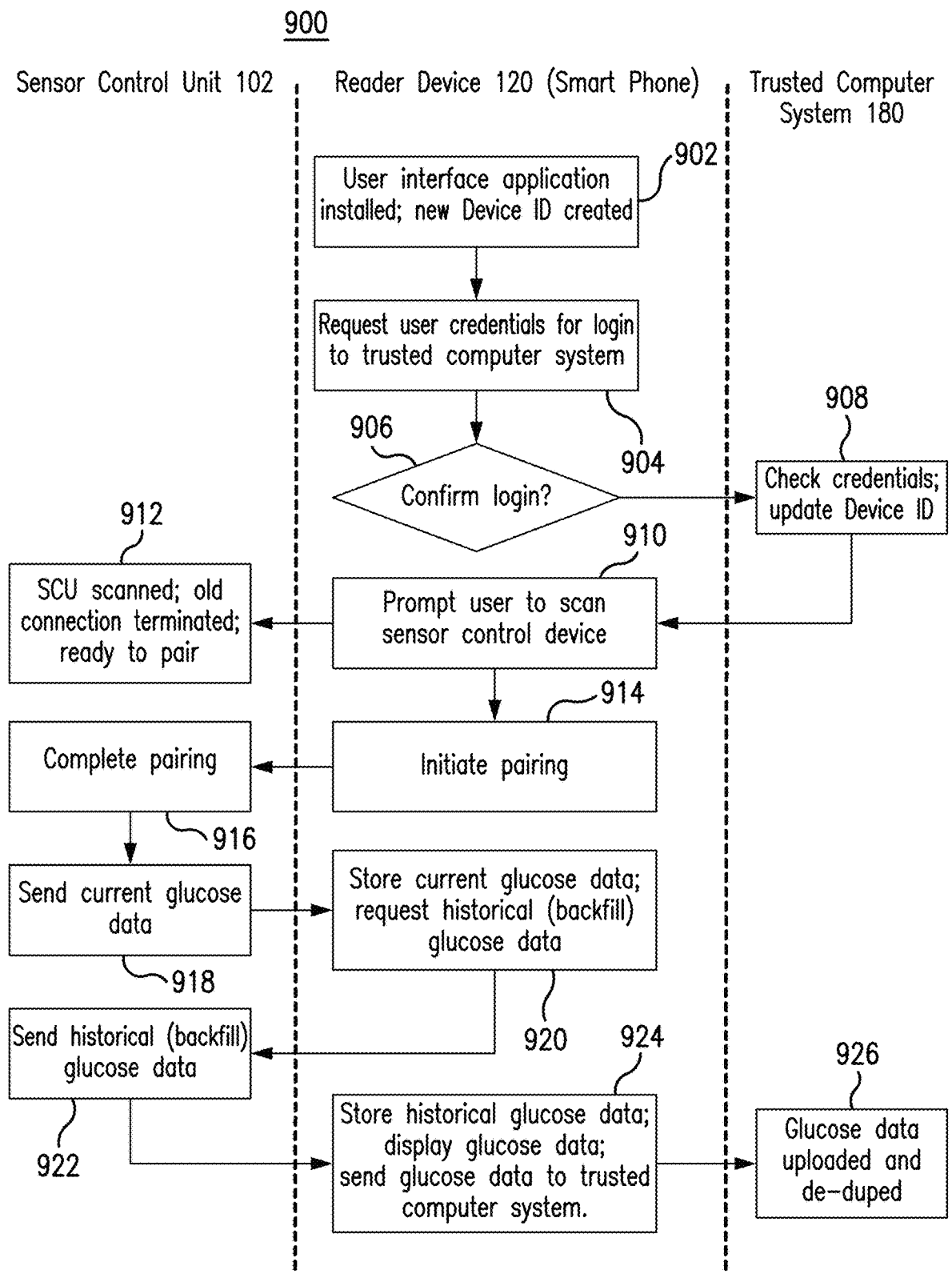
FIG. 9A is a flow diagram depicting an example embodiment of a method for sensor transitioning in an analyte monitoring system.
Figure 9D:
FIGS. 9B to 9D are example embodiments of GUIs to be displayed according to an example embodiment of a method for sensor transitioning in an analyte monitoring system.
Figure 9C:
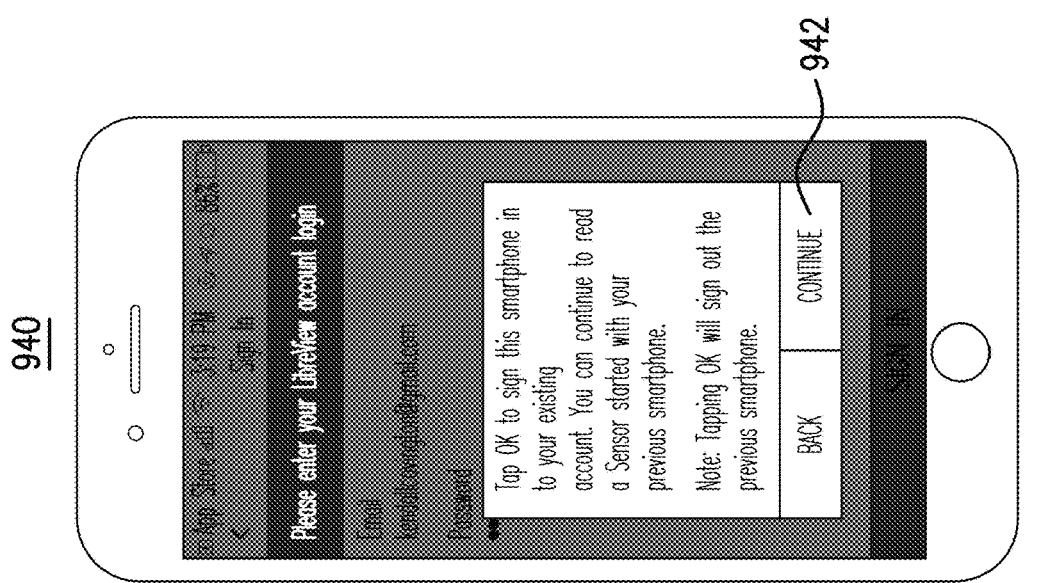
Figure 9B:
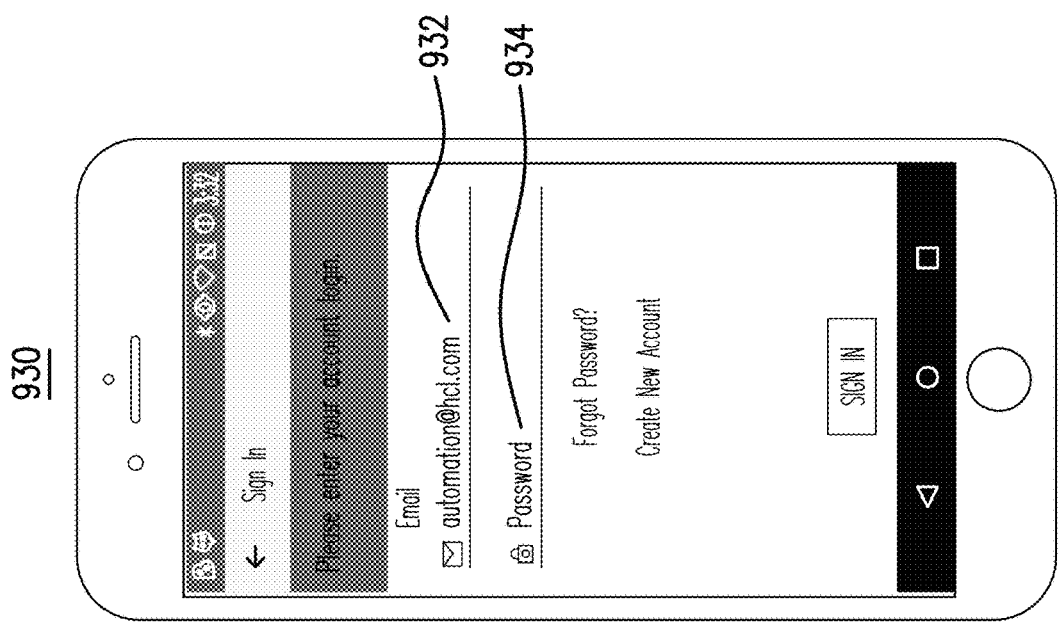

FIG. 9A is a flow diagram depicting an example embodiment of a method 900 for transitioning a sensor control device. In accordance with the disclosed subject matter, method 900 can be implemented in an analyte monitoring system to allow a user to continue using a previously activated sensor control device with a new reader device (e.g., smart phone). At Step 902, a user interface application (e.g., mobile software application or app) is installed on reader device 120 (e.g., smart phone), which causes a new unique device identifier, or "device ID," to be created and stored on reader device 120. At Step 904, after installing and launching the app, the user is prompted to enter their user credentials for purposes of logging into trusted computer system 180 (e.g., cloud-based platform or server). An example embodiment of a GUI 930 for prompting the user to enter their user credentials is shown in FIG. 9B. In accordance with the disclosed subject matter, GUI 930 can include a username field 932, which can comprise a unique username or an e-mail address, and a masked or unmasked password field 934, to allow the user to enter their password.

Referring again to FIG. 9A, at Step 906, after user credentials are entered into the app, a prompt is displayed requesting user confirmation to login to trusted computer system 180. An example embodiment of GUI 940 for requesting user confirmation to login to trusted computer system 180 is shown in FIG. 9D. In accordance with the disclosed subject matter, GUI 940 can also include a warning, such as the one shown in FIG. 9D, that confirming the login will cause the user to be logged off from other reader devices (e.g., the user's old smart phone).

If the user confirms login, then at Step 908, the user's credentials are sent to trusted computer system 180 and subsequently verified. In addition, according to some embodiments, the device ID can also be transmitted from the reader device 120 to trusted computer system 180 and stored in a non-transitory memory of trusted computer system 180. According to some embodiments, for example, in response to receiving the device ID, trusted computer system 180 can update a device ID field associated with the user's record in a database.

After the user credentials are verified by trusted computer system 180, at Step 910, the user is prompted by the app to scan the already-activated sensor control device 102. In accordance with the disclosed subject matter, the scan can comprise bringing the reader device 120 in close proximity to sensor control device 102, and causing the reader device 120 to transmit one or more wireless interrogation signals according to a first wireless communication protocol. As embodied herein, for example, the first wireless communication protocol can be a Near Field Communication (NFC) wireless communication protocol. Those of skill in the art, however, will recognize that other wireless communication protocols can be implemented (e.g., infrared, UHF, 802.11x, etc.). An example embodiment of GUI 950 for prompting the user to scan the already-activated sensor control device 102 is shown in FIG. 9D.

Referring still to FIG. 9A, at Step 912, scanning of sensor control device 102 by reader device 120 causes sensor control device 102 to terminate an existing wireless communication link with the user's previous reader device, if there is currently one established. In accordance with the disclosed subject matter, the existing wireless communication link can comprise a link established according to a second wireless communication protocol that is different from the first wireless communication protocol. As embodied herein, for example, the second wireless communication protocol can be a Bluetooth or Bluetooth Low Energy protocol. Subsequently, sensor control device 102 enters into a "ready to pair" state, in which sensor control device 102 is available to establish a wireless communication link with reader device 120 according to the second wireless communication protocol.

At Step 914, reader device 120 initiates a pairing sequence via the second wireless communication protocol (e.g., Bluetooth or Bluetooth Low Energy) with sensor control device 102. Subsequently, at Step 916, sensor control device 102 completes the pairing sequence with reader device 120. At Step 918, sensor control device 102 can begin sending current glucose data to reader device 120 according to the second wireless communication protocol. As embodied herein, for example, current glucose data can be wirelessly transmitted to reader device 120 at a predetermined interval (e.g., every minute, every two minutes, every five minutes).

Referring still to FIG. 9A, at Step 920, reader device 120 receives and stores current glucose data received from sensor control device 102 in a non-transitory memory of reader device 120. In addition, according to some embodiments, reader device 120 can request historical glucose data from sensor control device 102 for backfilling purposes. According to some embodiments, for example, reader device 120 can request historical glucose data from sensor control device 102 for the full wear duration, which is stored in a non-transitory memory of sensor control device 102. In other embodiments, reader device 120 can request historical glucose data for a specific predetermined time range (e.g., from day 3 to present, from day 5 to present, last 3 days, last 5 days, lifecount >0, etc.). Those of skill will appreciate that other backfilling schemes can be implemented (such as those described with respect to FIGS. 6A and 6B), and are fully within the scope of this disclosure.

Upon receipt of the request at Step 922, sensor control device 102 can retrieve historical glucose data from a non-transitory memory and transmit it to reader device 120. In turn, at Step 924, reader device 120 can store the received historical glucose data in a non-transitory memory. In addition, according to some embodiments, reader device 120 can also display the current and/or historical glucose data in the app (e.g., on a sensor results screen). In this regard, a new reader can display all available analyte data for the full wear duration of a sensor control device. As embodied herein, reader device 120 can also transmit the current and/or historical glucose data to trusted computer system 180. At Step 926, the received glucose data can be stored in a non-transitory memory (e.g., a database) of trusted computer system 180.

As embodied herein, the received glucose data can also be de-duplicated prior to storage in non-transitory memory.

Example Embodiments of Check Sensor and Replace Sensor System Alarms

Example embodiments of autonomous check sensor and replace sensor system alarms, and methods relating thereto, will now be described. In accordance with the disclosed subject matter, certain adverse conditions affecting the operation of the analyte sensor and sensor electronics can be detectable by the sensor control device. For example, an improperly inserted analyte sensor can be detected if an average glucose level measurement over a predetermined period of time is determined to be below an insertion failure threshold. Due to its small form factor and a limited power capacity, however, the sensor control device may not have sufficient alarming capabilities. As such, it would be advantageous for the sensor control device to transmit indications of adverse conditions to another device, such as a reader device (e.g., smart phone), to alert the user of those conditions.

Figure 10A:
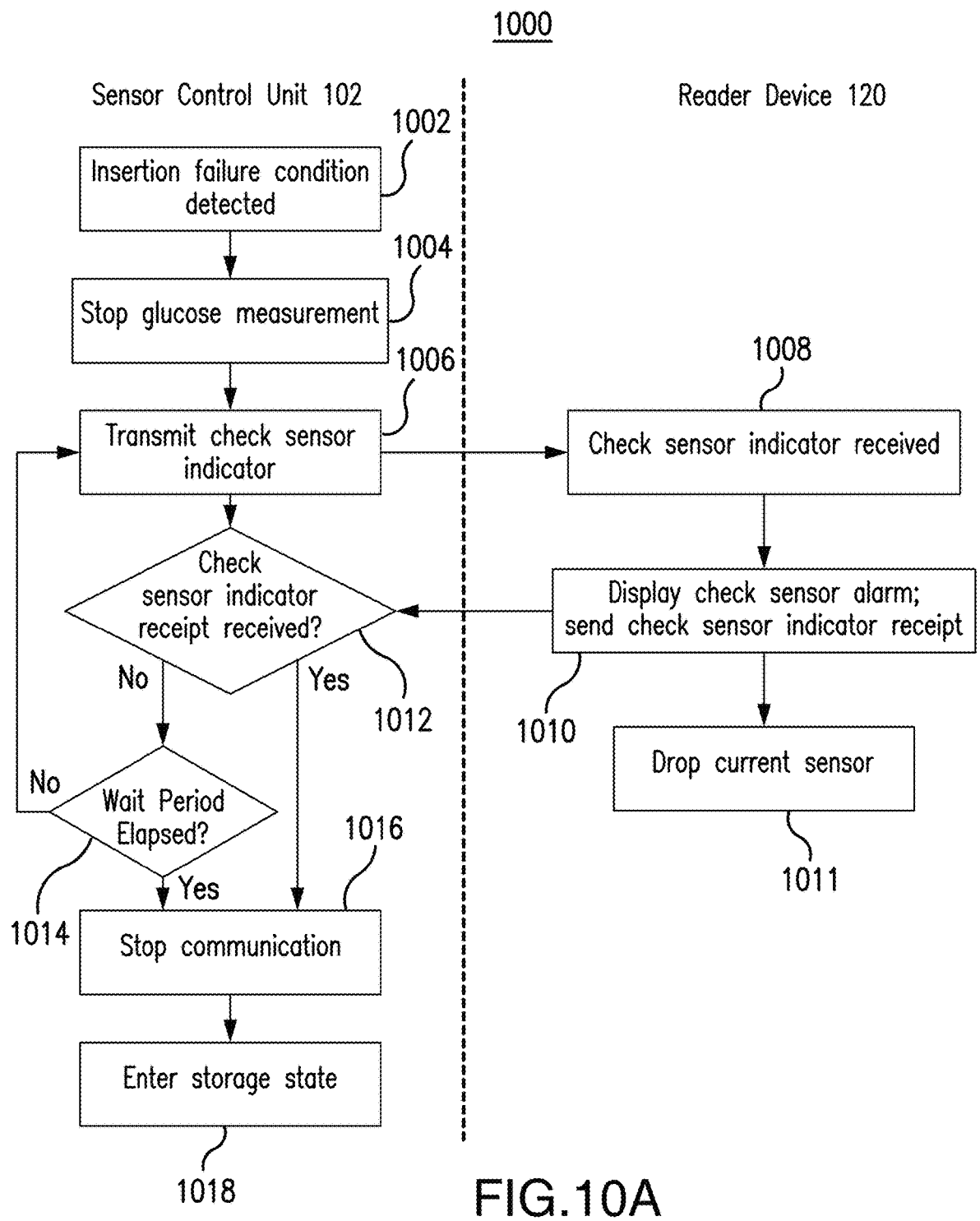
FIG. 10A is a flow diagram depicting an example embodiment of a method for generating a sensor insertion failure system alarm.

FIG. 10A is a flow diagram depicting an example embodiment of a method 1000 for generating a sensor insertion failure system alarm (also referred to as a "check sensor" system alarm). At Step 1002, a sensor insertion failure condition is detected by sensor control device 102. As embodied herein, for example, a sensor insertion failure condition can be detected when an average glucose value during a predetermined time period (e.g., average glucose value over five minutes, eight minutes, 15 minutes, etc.) is below an insertion failure glucose level threshold. At Step 1004, in response to the detection of the insertion failure condition, sensor control device 102 stops taking glucose measurements. At Step 1006, sensor control device 102 generates a check sensor indicator and transmits it via wireless communication circuitry to reader device 120. Subsequently, as shown at Steps 1012 and 1014, sensor control device 102 will continue to transmit the check sensor indicator until either: (1) a receipt of the indicator is received from reader device 120 (step 1012); or (2) a predetermined waiting period has elapsed (Step 1014), whichever occurs first.

Figure 10D:
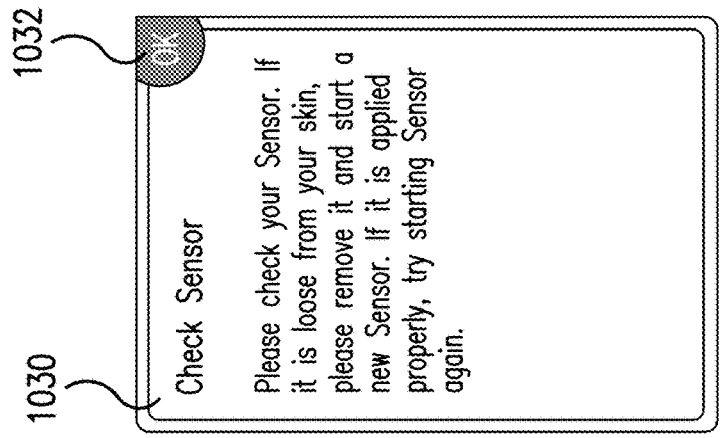
FIGS. 10B to 10D are example embodiments of GUIs to be displayed according to an example embodiment of a method for generating a sensor insertion failure system alarm.
Figure 10C:
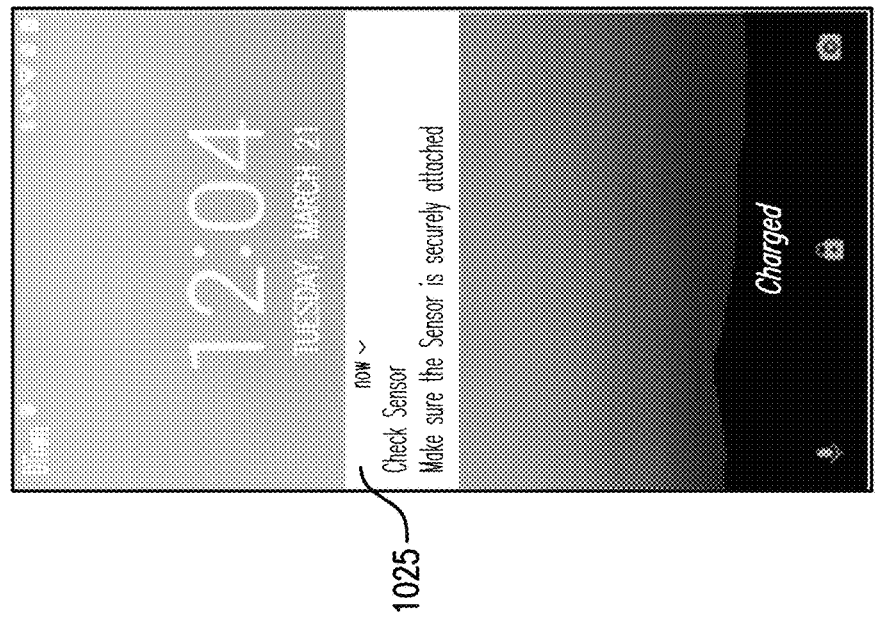
Figure 10B:
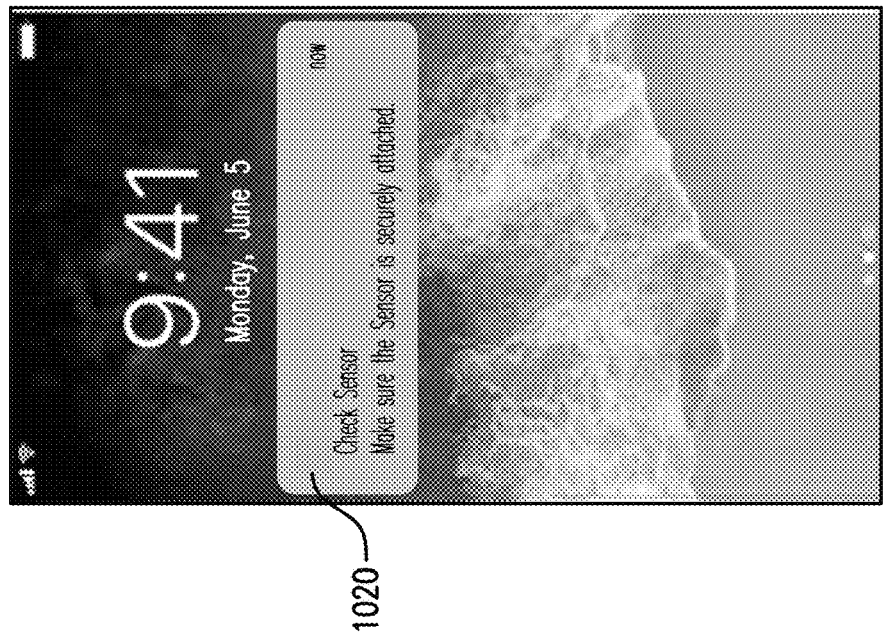

According to another aspect of the embodiments, if a wireless communication link is established between sensor control device 102 and reader device 120, then reader device 120 will receive the check sensor indicator at Step 1008. In response to receiving the check sensor indicator, reader device 120 will display a check sensor system alarm at Step 1010. FIGS. 10B to 10D are example embodiments of check sensor system alarm interfaces, as displayed on reader device 120. As embodied herein, for example, the check sensor system alarm can be a notification box, banner, or pop-up window that is output to a display of a smart phone, such as interfaces 1020 and 1025 of FIGS. 10B and 10C. As embodied herein, the check sensor alarm can be output to a display on a reader device 120, such as a glucose meter or a receiver device, such as interface 1030 of FIG. 10D. According to the embodiments, reader device 120 can also transmit a check sensor indicator receipt back to sensor control device 102. As embodied herein, for example, the check sensor indicator receipt can be automatically generated and sent upon successful display of the check sensor system alarm 1020, 1025, or 1030. In other embodiments, the check sensor indicator receipt is generated and/or transmitted in response to a predetermined user input (e.g., dismissing the check sensor system alarm, pressing a confirmation 'OK' button 1032, etc.).

Subsequently, at Step 1011, reader device 120 drops sensor control device 102. In accordance with the disclosed subject matter, for example, Step 1011 can comprise one or more of: terminating an existing wireless communication link with sensor control device 102; unpairing from sensor control device 102; revoking an authorization or digital certificate associated with sensor control device 102; creating or modifying a record stored on reader device 120 to indicate that sensor control device 102 is in a storage state; or transmitting an update to trusted computer system 180 to indicate that sensor control device 102 is in a storage state.

Referring back to FIG. 10A, if either the check sensor indicator receipt is received (at Step 1012) by sensor control device 102 or the predetermined wait period has elapsed (Step 1014), then at Step 1016, sensor control device 102 stops the transmission of check sensor indicators. Subsequently, at Step 1018, sensor control device 102 enters a storage state in which sensor control device 102 does not take glucose measurements and the wireless communication circuitry is either de-activated or transitioned into a dormant mode. According to one aspect, while in a 'storage state,' sensor control device 102 can be re-activated by reader device 120.

Although method 1000 of FIG. 10A is described with respect to glucose measurements, those of skill in the art will appreciate that sensor control device 102 can be configured to measure other analytes (e.g., lactate, ketone, etc.) as well. In addition, although method 1000 of FIG. 10A describes certain method steps performed by reader device 120 (e.g., receiving check sensor indicator, displaying a check sensor system alarm, and sending a check sensor indicator receipt), those of skill in the art will understand that any or all of these method steps can be performed by other devices in an analyte monitoring system, such as, for example, a local computer system, a wearable computing device, or a medication delivery device. It will also be understood by those of skill in the art that method 1000 of FIG. 10A can combined with any of the other methods described herein, including but not limited to method 700 of FIG. 7, relating to expired and or failed sensor transmissions.

Figure 11A:
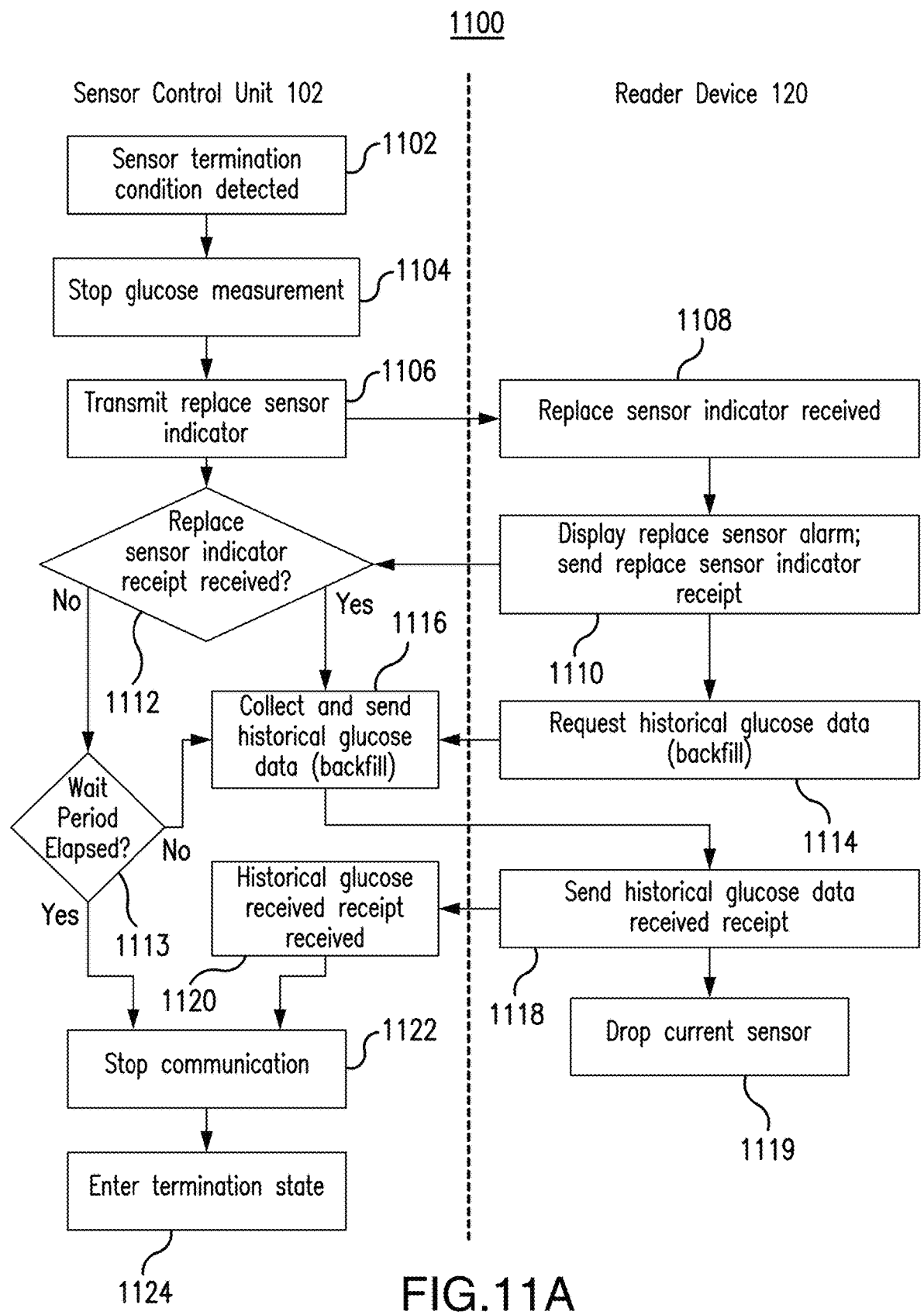
FIG. 11A is a flow diagram depicting an example embodiment of a method for generating a sensor termination system alarm.

FIG. 11A is a flow diagram depicting an example embodiment of a method 1100 for generating a sensor termination system alarm (also referred to as a "replace sensor" system alarm). At Step 1102, a sensor termination condition is detected by sensor control device 102. As described earlier, a sensor termination condition can include, but is not limited to, one or more of the following: a FIFO overflow condition detected, a sensor signal below a predetermined insertion failure threshold, moisture ingress detected, an electrode voltage exceeding a predetermined diagnostic voltage threshold, an early signal attenuation (ESA) condition, or a late signal attenuation (LSA) condition, to name a few.

At Step 1104, in response to the detection of a sensor termination condition, sensor control device 102 stops taking glucose measurements. At Step 1106, sensor control device 102 generates a replace sensor indicator and transmits it via wireless communication circuitry to reader device 120. Subsequently, at Step 1112, sensor control device 102 will continue to transmit the replace sensor indicator while determining whether a replace sensor indicator receipt has been received from reader device 102. In accordance with the disclosed subject matter, sensor control device 102 can continue to transmit the replace sensor indicator until either: (1) a predetermined waiting period has elapsed (Step 1113), or (2) a receipt of the replace sensor indicator is received (Step 1112) and sensor control device 102 has successfully transmitted backfill data (Steps 1116, 1120) to reader device 120.

Referring still to FIG. 11A, if a wireless communication link is established between sensor control device 102 and reader device 120, then reader device 120 will receive the replace sensor indicator at Step 1108. In response to receiving the replace sensor indicator, reader device 120 will display a replace sensor system alarm at Step 1110. FIGS. 11B to 11D are example embodiments of replace sensor system alarm interfaces, as displayed on reader device 120. As embodied herein, for example, the replace sensor system alarm can be a notification box, banner, or pop-up window that is output to a display of a smart phone, such as interfaces 1130 and 1135 of FIGS. 11B and 11C. As embodied herein, the check sensor alarm can be output to a display on a reader device 120, such as a glucose meter or a receiver device, such as interface 1140 of FIG. 11D. According to the embodiments, to acknowledge receipt of the indicator, reader device 120 can also transmit a replace sensor indicator receipt back to sensor control device 102. As embodied herein, for example, the replace sensor indicator receipt can be automatically generated and sent upon successful display of the replace sensor system alarm 1130, 1135, or 1140. In other embodiments, the replace sensor indicator is generated and/or transmitted in response to a predetermined user input (e.g., dismissing the check sensor system alarm, pressing a confirmation 'OK' button 1142, etc.).

At Step 1114, after displaying the replace sensor system alarm and transmitting the replace sensor indicator receipt, reader device 120 can then request historical glucose data from sensor control device 102. At Step 1116, sensor control device 102 can collect and send to reader device 120 the requested historical glucose data. In accordance with the disclosed subject matter, the step of requesting, collecting, and communicating historical glucose data can comprise a data backfilling routine, such as the methods described with respect to FIGS. 6A and 6B.

Referring again to FIG. 11A, in response to receiving the requested historical glucose data, reader device 120 can send a historical glucose data received receipt to sensor control device 102 at Step 1118. Subsequently, at Step 1119, reader device 120 drops sensor control device 102. In accordance with the disclosed subject matter, for example, Step 1119 can comprise one or more of: terminating an existing wireless communication link with sensor control device 102; unpairing from sensor control device 102; revoking an authorization or digital certificate associated with sensor control device 102; creating or modifying a record stored on reader device 120 to indicate that sensor control device 102 has been terminated; or transmitting an update to trusted computer system 180 to indicate that sensor control device 102 has been terminated.

At Step 1120, sensor control device 102 receives the historical glucose data received receipt. Subsequently, at Step 1122, sensor control device 102 stops the transmission of the replace sensor indicator and, at Step 1124, sensor control device 102 can enter into a termination state in which sensor control device 102 does not take glucose measurements and the wireless communication circuitry is either de-activated or in a dormant mode. In accordance with the disclosed subject matter, when in a termination state, sensor control device 102 cannot be re-activated by reader device 120.

Although method 1100 of FIG. 11A is described with respect to glucose measurements, those of skill in the art will appreciate that sensor control device 102 can be configured to measure other analytes (e.g., lactate, ketone, etc.) as well. In addition, although method 1100 of FIG. 11A describes certain method steps performed by reader device 120 (e.g., receiving replace sensor indicator, displaying a replace sensor system alarm, and sending a replace sensor indicator receipt), those of skill in the art will understand that any or all of these method steps can be performed by other devices in an analyte monitoring system, such as, for example, a local computer system, a wearable computing device, or a medication delivery device. It will also be understood by those of skill in the art that method 1100 of FIG. 11A can combined with any of the other methods described herein, including but not limited to method 700 of FIG. 7, relating to expired and or failed sensor transmissions.

Examples of Improved Clinical Outcomes Based on Continuous Glucose Monitoring

Described herein are example embodiments of improved clinical outcomes based on analyte monitoring systems as described herein. In accordance with disclosed subject matter, a continuous glucose monitor regimen can include standard approved use of an analyte monitoring system. For example, and not limitation, continuous glucose monitor can be available by prescription and a regimen can be prescribed by a health care professional or as otherwise approved by a regulatory authority. In an exemplary embodiment, a regimen can include using a reader device (e.g., smart phone, dedicated reader, etc.) to scan a sensor control device, such as, for example, in a Flash Analyte Monitoring system. In an exemplary embodiment, a regimen can include rendering or brining into the foreground a sensor results interface as described herein.

The presently disclosed subject matter will be better understood by reference to the following Examples. These Examples are merely illustrative of the presently disclosed subject matter and should not be considered as limiting the scope of the subject matter in any way.

Effects of User Engagement on Clinical Outcomes

In diabetes treatment, strict glycemic control can have an effect on preventing the development of microvascular complications as well as on the development and progression of long-term macrovascular complications.

Therefore, being aware of glycemic variability in everyday life facilitates high-quality self-management and helps the patient aim toward stricter glycemic control. Self-monitoring of blood glucose (SMBG) by finger-stick measurement is the most common monitoring method, and the Japanese Clinical Practice Guideline for Diabetes 2019 states that SMBG is effective in glycemic control in patients with type 1 diabetes and insulin-treated patients with type 2 diabetes and recommends it as Grade A. Although the recommended timing and frequency of SMBG depend on the disease type and treatment goals, the American Diabetes Association (ADA) requires testing 6-10 times daily, although individual needs may vary, for patients using intensive insulin regimens. Further, with SMBG it can be difficult to detect nocturnal/early morning hypoglycemia or hyperglycemia immediately after meals and impossible to monitor glucose fluctuations.

Continuous glucose monitoring (CGM), as disclosed in embodiments of the disclosed subject matter, which periodically displays data (e.g., every 1-5 minutes), was shown to significantly reduce HbA1c levels compared with SMBG in a systematic review and meta-analysis. According to embodiments disclosed herein, the CGM can be a CGM with 10, 14, 21, or 30 day wear. In some embodiments, the CGM can be a 14-day in-vivo CGM, for example, not limitation, a CGM using a redox mediator and flux limiting membrane as described in U.S. Pat. Nos. 6,605,200, 6,932,894, 8,280, 474. This is one way to describe Libre without mentioning it by name.

According to a report by Bailey et al., *The Performance and Usability of a Factory-Calibrated Flash Glucose Monitoring System*, Diabetes Tech. Ther., 2015, 17(11): p. 787-794 which is herein incorporated by reference in its entirety, the mean absolute relative difference (MARD) can be 11.4% for flash glucose monitoring sensor glucose levels against capillary blood glucose reference values, with accuracy remaining stable over 14 days of wear and unaffected by patient characteristics such as body mass index (BMI), age, clinical site, insulin administration, or HbA1c. Other studies comparing flash glucose monitoring with different methods (arterial blood glucose, venous Yellow Springs Instrument (YSI) reference, laboratory random blood sugar) reported MARD within the range of 9.56-15.4%, and this accuracy was considered clinically acceptable.

In one exemplary embodiment, thirteen clinical studies investigating the efficacy of flash glucose monitoring and discussed in this exemplary embodiment are summarized in FIGS. 23A-23B. Each of these clinical studies is herein incorporated by reference in its entirety.

SHIFT, by Ogawa et al., *Effect of the FreeStyle Libre™ Flash Glucose Monitoring System on Glycemic Control in Subjects with Type 2 Diabetes Treated with Basal-Bolus Insulin Therapy: An Open Label, Prospective, Multicenter Trial in Japan*, J. Diabetes Investigation, 2021, 12(1): p. 82-90, which is herein incorporated by reference in its entirety, was a multicenter, single-arm, prospective study to evaluate the effect of flash glucose monitoring on glycemic control in 94 Japanese patients with type 2 diabetes treated with basal-bolus insulin therapy, in which a 2-week baseline phase was followed by an 11-week flash glucose monitoring intervention. One endpoint was the change from baseline of time in hypoglycemia at 2.5 months. Other studies in Japanese patients include a randomized controlled trial (RCT) by Wada et al., *Flash glucose monitoring helps achieve better glycemic control than conventional self-monitoring of blood glucose in non-insulin-treated type 2 diabetes: a randomized controlled trial*, BMJ Open Diabetes Res. Care, 2020, 8(1), which is herein incorporated by reference in its entirety, that compared the effects of flash glucose monitoring and SMBG on glycemic control in 100 patients with non-insulin-treated type 2 diabetes and an observational study by Ida et al., *Effects of Flash Glucose Monitoring on Dietary Variety, Physical Activity, and Self-Care Behaviors in Patients with Diabetes*, J. Diabetes Res., 2020, which is herein incorporated by reference in its entirety that evaluated the effects of flash glucose monitoring on dietary variety, physical activity, and self-care behavior in 90 patients with type 1 and type 2 diabetes.

IMPACT, a study by Bolinder et al., *Novel glucose-sensing technology and hypoglycaemia in type 1 diabetes: a multicentre, non-masked, randomised controlled trial*, Lancet, 2016, 388(10057): p. 2254-63, which is herein incorporated by reference in its entirety, was a non-masked RCT in patients with type 1 diabetes, in which 239 type 1 diabetes patients with HbA1c≤7.5% from 23 European centers were enrolled and randomly assigned to the flash glucose monitoring group and the SMBG group in a 1:1 ratio. With an outcome of change in time in hypoglycemia from baseline to 6 months, the trial compared the effectiveness of flash glucose monitoring for glycemic control with that of SMBG.

In the REPLACE study, by Haak et al, *Use of Flash Glucose-Sensing Technology for* 12 *months as a Replacement for Blood Glucose Monitoring in Insulin-treated Type* 2 *Diabetes*, Diabeter Therapy, 2017, 8(3): p. 573-586, which is herein incorporated by reference in its entirety, an open-label RCT in patients with type 2 diabetes, 224 type 2 diabetes patients with HbA1c between 7.5 and 12.0% from 26 European centers were enrolled and randomly assigned to the flash glucose monitoring group and the SMBG group in a 2:1 ratio. One outcome was change in HbA1c from baseline to 6 months. Then, 139 flash glucose monitoring patients who completed the 6-month treatment phase of this study continued into an additional 6-month prospective observational study (open-access phase). In both RCTs, participants had a review of their glycemic control during their visits.

Kröger et al., *Three European Retrospective Real-World Chart Review Studies to Determine the Effectiveness of Flash Glucose Monitoring on HbA1c in Adults with Type 2*, Diabetes Therapy, 2020, 11: p. 279-291, which is herein incorporated by reference in its entirety reported a retrospective chart review of patients with type 2 diabetes using flash glucose monitoring in 18 centers in France, Austria, and Germany. The 363 patients included in the review had switched from SMBG to flash glucose monitoring at least 3 months before the start of the study and had a baseline HbA1c (measurement within 3 months prior to starting flash glucose monitoring use) between 8.0 and 12.0%. One outcome was change in HbA1c from baseline at 3-6 months after starting flash glucose monitoring use.

An open-label RCT reported by Yaron et al., *Effect of Flash Glucose Monitoring Technology on Glycemic Control and Treatment Satisfaction in Patients With Type 2 Diabetes*, Diabetes Care, 2019, 42(7), which is herein incorporated by reference in its entirety, was conducted in 101 patients with type 2 diabetes (baseline HbA1c 7.5-10.0%) from 2 centers in Israel. Patients were randomly assigned to the flash glucose monitoring group and the SMBG group in a 1:1 ratio and treated for 10 weeks. Patients in the flash glucose monitoring group were instructed to perform a scan at least every 8 hours, and all patients were frequently instructed to adjust their insulin doses. One outcome was satisfaction with treatment; other measures including quality of life (QOL), HbA1c, comfort using flash glucose monitoring, and frequency of hypoglycemic events were also evaluated.

Evans et al., *The Impact of Flash Glucose Monitoring on Glycaemic Control as Measured by HbA1c: A Meta-analysis of Clinical Trials and Real-World Observational Studies*, Diabetes Therapy, 2020, 11(1): p. 83-95, which is herein incorporated by reference in its entirety, reported a meta-analysis of 25 studies (n=1,723) that reported change in HbA1c in adult and pediatric patients with type 1 or type 2 diabetes using flash glucose monitoring. A meta-analysis was performed using a random effects model on the 21 studies where HbA1c levels at baseline and 2-4 months after starting flash glucose monitoring use were available, and random effects meta-regression of change in HbA1c was performed versus baseline HbA1c. In addition, a longitudinal analysis was performed in 1,276 adult patients with type 1 and type 2 diabetes whose HbA1c was continuously measured 1-12 months after starting flash glucose monitoring use.

FLARE-NL4, by Fokkert et al, *Improved well-being and decreased disease burden after 1-year use of flash glucose monitoring (FLARE-NL4)*, BMJ Open Diabetes Research & Care, 2020, 7(1), which is herein incorporated by reference in its entirety, was a 1-year prospective registry study that included 1,277 patients with type 1 and type 2 diabetes using flash glucose monitoring in the Netherlands. One endpoint was change in HbA1c; other endpoints evaluated included frequency and severity of hypoglycemia, health-related QOL, and disease burden including hospital admission and work absenteeism.

Dunn et al., *Real-world flash glucose monitoring patterns and associations between self-monitoring frequency and glycaemic measures: A European analysis of over 60 million glucose tests*, Diabetes Res. & Clinical Practice, 2017, 137: p. 37-46, which is herein incorporated by reference in its entirety, analyzed real-world data of flash glucose monitoring use from 50,831 readers in Europe stored in a cloud database between September 2014 and May 2016. Patients were grouped by scan frequency, and the relationship between scan frequency and estimated HbA1c (eA1c) was evaluated. Other studies that used real-world data include a report investigating the relationship between scan frequency and CGM measures in clinical practice in Spain, and a report investigating the use of flash glucose monitoring in Brazil.

The HbA1c test can be used for the diagnosis and management of diabetes. Although HbA1c does not detect glucose variability or hypoglycemic events, it is known to reflect the average blood glucose levels over the previous 2 to 3 months, and equations have been described to calculate the estimated average glucose levels from the HbA1c levels or the eA1c from the average glucose levels. In addition, HbA1c correlates with the risk of long-term diabetes complications and is considered a reliable biomarker for diagnosing and evaluating the long-term prognosis of diabetes.

IMPACT and REPLACE did not show a significant difference in the mean change in HbA1c from baseline between the flash glucose monitoring group and the SMBG group at 6 months after the start of the study (IMPACT, difference in mean HbA1c between the 2 groups at 6 months after the start of the study: 0.00, p=0.9556; REPLACE, change in HbA1c at 6 months after the start of the study, SMBG group: —0.31, flash glucose monitoring group: −0.29, p=0.8222).

Figure 23C:
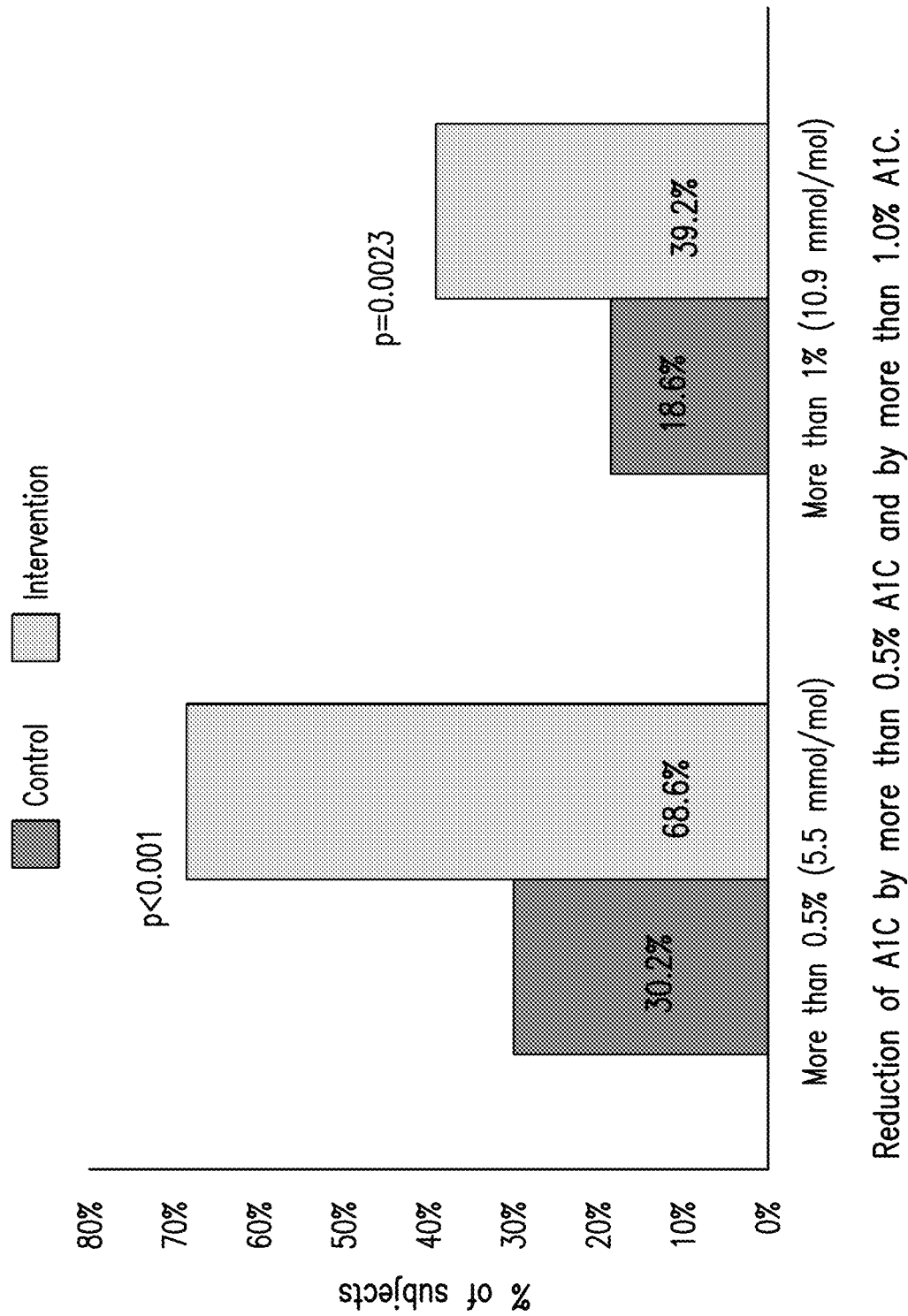

In FIG. 23C, as observed by Yaron et al.'s RCT, the mean change (standard deviation [SD]) in HbA1c from baseline at 10 weeks after the start of the study was significantly lower at −0.82 (0.84)% in the flash glucose monitoring group compared with −0.33 (0.78)% in the SMBG group (p=0.005). In a non-prespecified post hoc analysis, the proportion of patients whose HbA1c was reduced by ≥0.5% was 68.6% in the flash glucose monitoring group compared with 30.2% in the SMBG group, showing a significant difference (p<0.001); a significant difference was similarly seen in the proportion of patients whose HbA1c was reduced by ≥1% (SMBG group: 18.6%, flash glucose monitoring group: 39.2%, p=0.0023).

As illustrated in FIG. 23D, in Kröger et al.'s chart review, HbA1c levels significantly decreased from baseline with the mean (standard error) change of −0.9 (0.05)% in patients with type 2 diabetes who used flash glucose monitoring continuously for 3-6 months (p<0.0001), and this pattern was consistent across the 3 countries in the study.

Figure 23E:
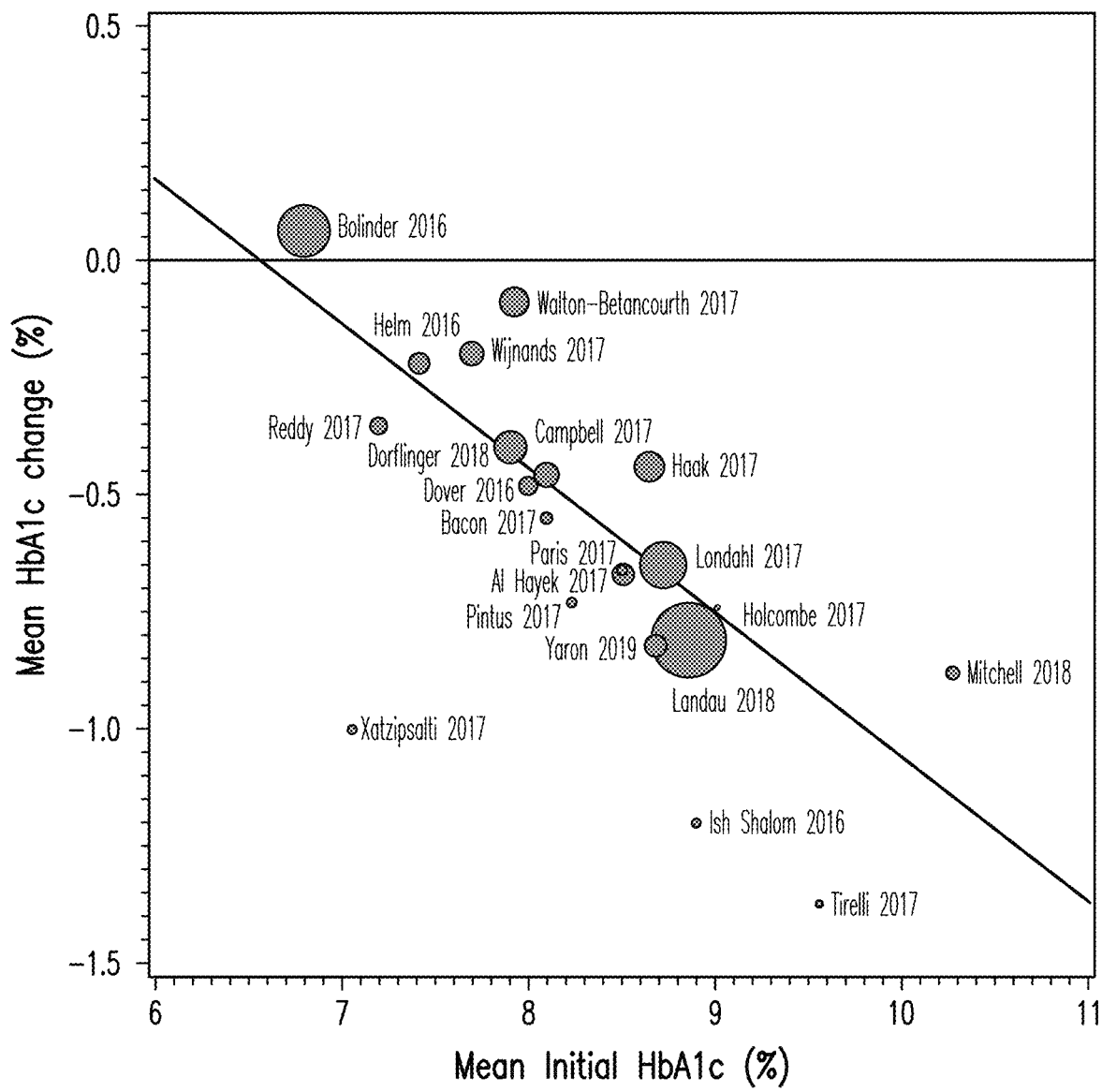

As illustrated in FIG. 23E, Evans et al.'s meta-regression analysis demonstrated that the higher the baseline HbA1c, the greater the reduction in HbA1c after treatment using flash glucose monitoring. A longitudinal analysis in 1,276 adults showed that HbA1c fell markedly within 2 months of starting flash glucose monitoring use and the changes were sustained up to 12 months. Although mostly studied in type 1 diabetes patients, flash glucose monitoring is shown to improve and maintain HbA1c in many studies.

In the SHIFT study conducted in Japanese patients, a significant improvement was observed in eA1c at the end of the study (11 weeks) when compared with baseline (−0.39±0.81%, p<0.0001). According to Ida et al.'s report, no significant changes in HbA1c were observed at the end of the study (12 weeks) when compared with baseline in patients with type 1 diabetes (7.7±1.2 vs. 7.7±1.3, p=0.921), but a significant improvement was observed in patients with type 2 diabetes (7.4±0.8 vs. 7.7±1.2, p=0.025). 20). Wada et al. reported that HbA1c was significantly improved compared with baseline in both the flash glucose monitoring group (−0.43%, p<0.001) and the SMBG group (−0.30%, p=0.001).

Beyond a change a HbA1c, certain studies analyzed according to this embodiment also indicate time in hypoglycemia for the subjects studied. Hypoglycemia is an emergency that occurs during diabetes treatment, and it has been suggested that severe hypoglycemia or hypoglycemia unawareness may become risk factors for macroangiopathy and dementia. Flash glucose monitoring incorporates an ambulatory glucose profile (AGP), and patients can graphically see the trends in their glucose level over a day. In addition, sensor glucose levels <70 mg/dL persisting for >15 minutes are recorded as hypoglycemic events.

Figure 23F:
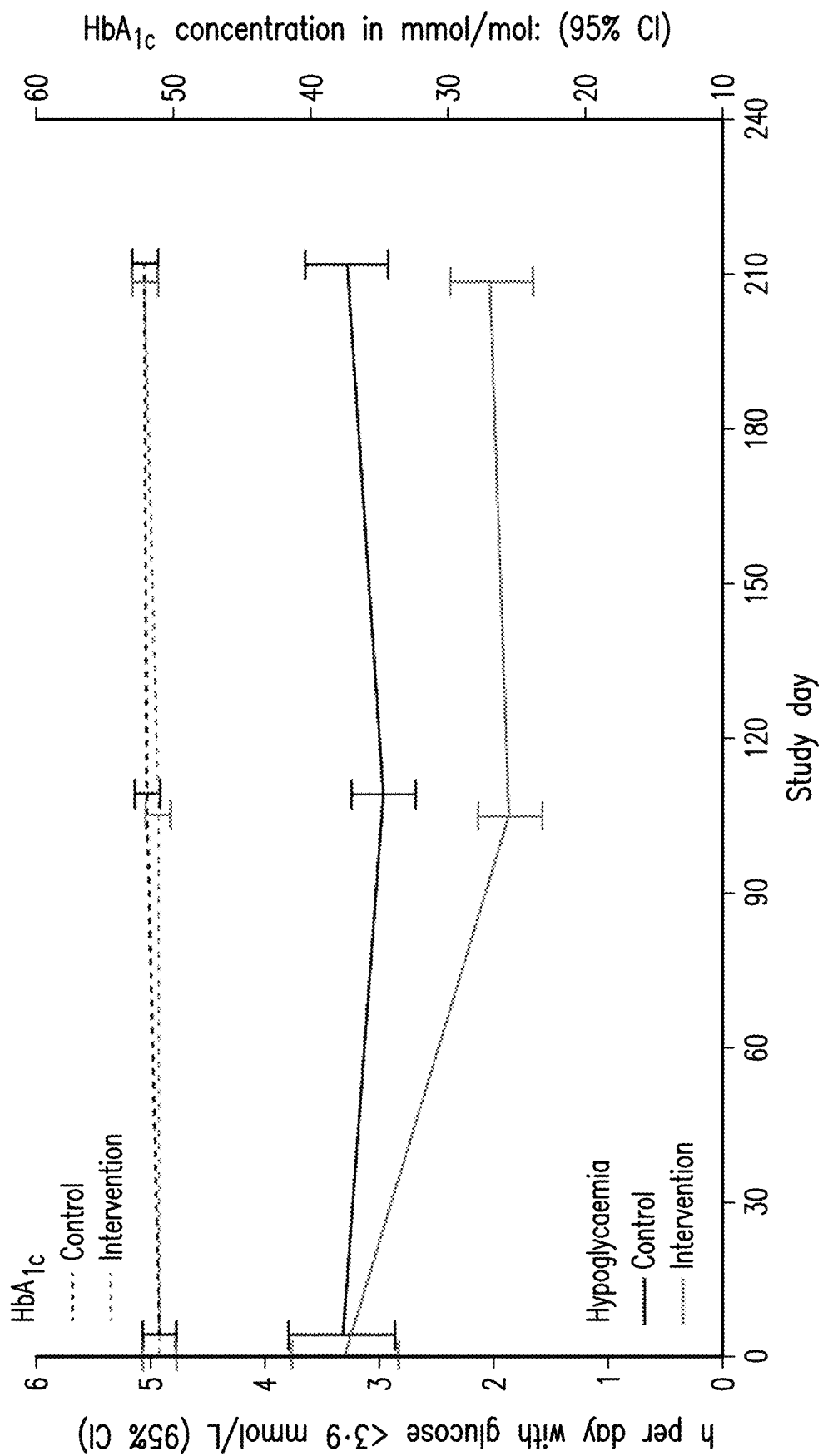

As illustrated in FIG. 23F, in the IMPACT study, conducted in patients with type 1 diabetes, one outcome of mean time in hypoglycemia (<70 mg/dL) at 6 months was 2.03 h/day (−1.39 h/day from baseline) in the flash glucose monitoring group, which was 38% lower than 3.27 h/day (−0.14 h/day from baseline) in the SMBG group (p<0.0001).

In the REPLACE study conducted in patients with type 2 diabetes, although there was no difference in at least outcome of change in HbA1c from baseline at 6 months between the flash glucose monitoring group and the SMBG group, mean time in hypoglycemia (<70 mg/dL) at 6 months was reduced by 43% in the flash glucose monitoring group compared with the SMBG group (p=0.0006). During the open-access extension phase of REPLACE, mean time in hypoglycemia at 12 months was reduced by 50% compared with baseline for the flash glucose monitoring group (p=0.0002).

In SHIFT, time in hypoglycemia at the end of the study (11 weeks) was not significantly different compared with baseline (p=0.6354), but eA1c was significantly decreased (p<0.0001). Overall, it was suggested that the use of flash glucose monitoring can improve eA1c without increasing time in hypoglycemia and can improve time in range (TIR) and reduce time above range (TAR).

In IMPACT and REPLACE, with target sensor glucose levels of 70-180 mg/dL, TIR at 6 months was compared between the flash glucose monitoring group and the SMBG group. As a result, the IMPACT study in patients with type 1 diabetes showed a significant increase in TIR compared with the SMBG group, but the REPLACE study in patients with type 2 diabetes did not show a difference in TIR between the groups (p=0.7925). 21), 22) In the SHIFT study, with a treatment target range of 70-180 mg/dL, TIR at 11 weeks was 16.7±3.7 h/day (mean±SD), showing a significant improvement from baseline (15.0±4.0 h/day) (p<0.0001).

Analysis according to the above outlined studies show certain benefits of flash glucose monitoring within a clinical setting, specifically, results from certain RCTs such as IMPACT and REPLACE support the clinical benefits of flash glucose monitoring in glycemic control. Here, further studies are reviewed that used real-world data from Europe, Spain, and Brazil.

Figure 23G:
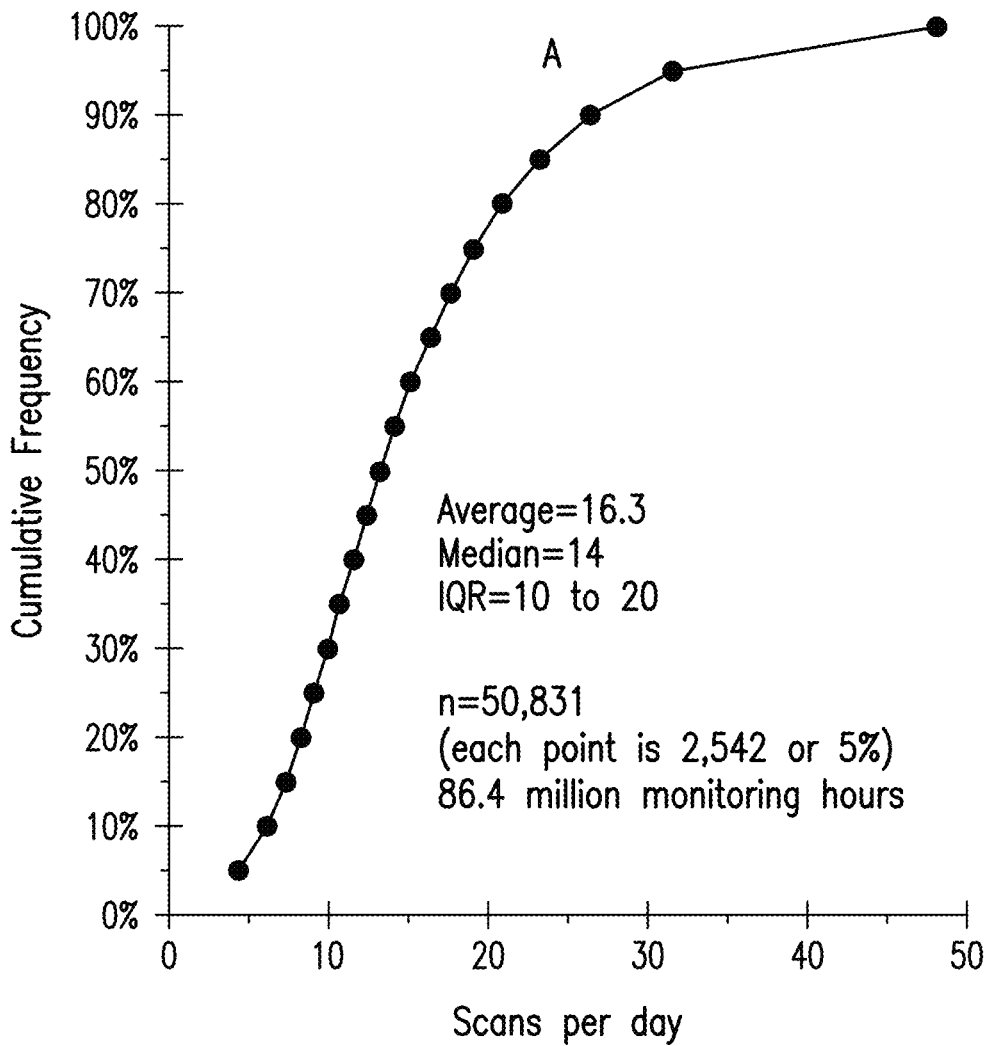

As illustrated in FIG. 23G, the use and clinical benefits of flash glucose monitoring from the real-world data of 50,831 readers in Europe, users performed a total of 86.4 million hours of readings, 345.6 million automatically stored readings, and 63.8 million scans, with a median of 14 scans (interquartile range: 10-20 scans).

Figure 23H:
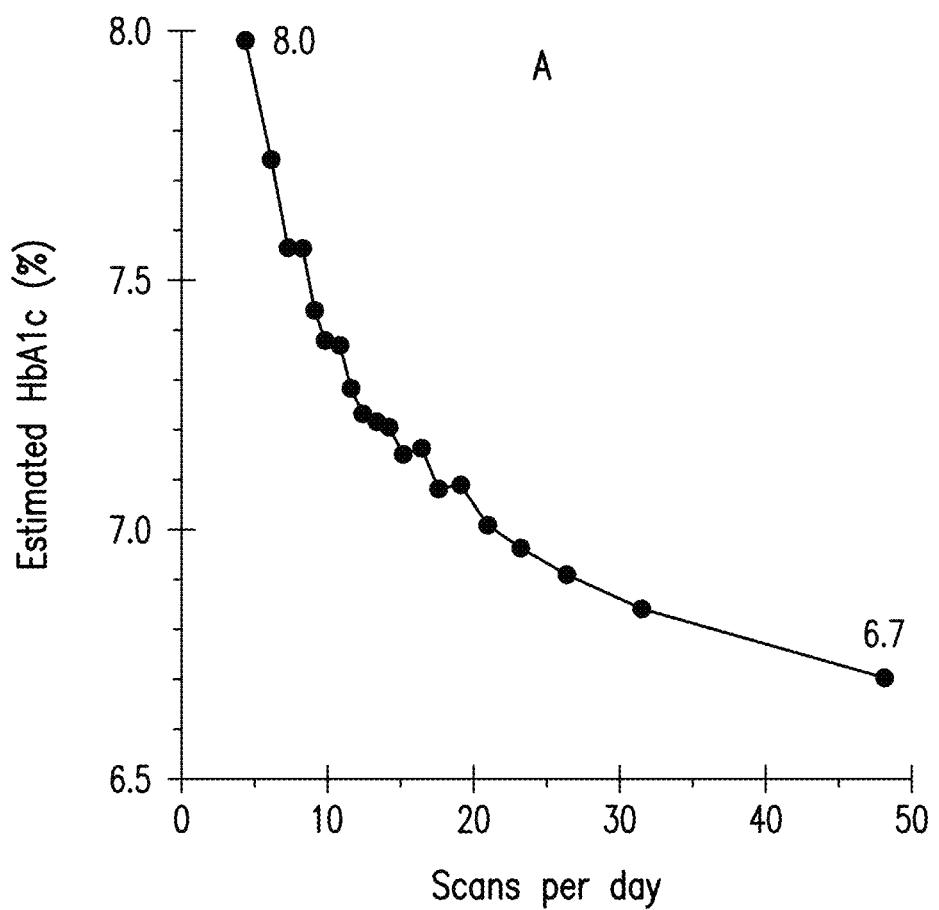

FIG. 23H illustrates an analysis wherein the readers were allocated to 20 equally sized groups by scan frequency, the lowest scan rate group (mean, 4.4 times/day) had an eA1c of 8.0%, while the highest scan rate group (mean, 48.1 times/day) had an eA1c of 6.7%, showing a reduction in eA1c with increasing number of scans. TIR (sensor glucose levels 70-180 mg/dL) significantly increased from 12.0 h/day to 16.8 h/day when comparing the lowest with the highest scan rate groups (p<0.001). Both TAR and TBR significantly decreased in the highest scan rate group compared with the lowest scan rate group (p<0.001 each). These patterns can be consistent across different countries.

Similar results were obtained from the real-world data of 22,949 readers in Spain: eA1c was significantly lower at 6.9% (95% CI: 6.9-7.0%) in the highest scan rate group (mean, 39.6 scans/day) compared with 8.0% (95% CI: 8.0-8.1%) in the lowest scan rate group (3.9 scans/day; p<0.001); and TIR (sensor glucose levels 70-180 mg/dL) significantly increased from 11.5 h/day in the lowest scan rate group to 15.6 h/day in the highest scan rate group (p<0.001). 29) A real-world data study in Brazil also showed that eA1c was significantly lower at 6.71% (95% CI: 6.63-6.80%) in the highest scan rate group (mean, 43.1 times/day) compared with 7.56% (95% CI: 7.44-7.68%) in the lowest scan rate group (mean, 3.56 times/day; p<0.01), and TIR (sensor glucose levels 70-180 mg/dL) increased in the highest rate group compared with the lowest rate group (p<0.01).

These results suggest that increased scan frequency with flash glucose monitoring can improve glycemic control conditions including HbA1c and CGM metrics.

Figure 23I:
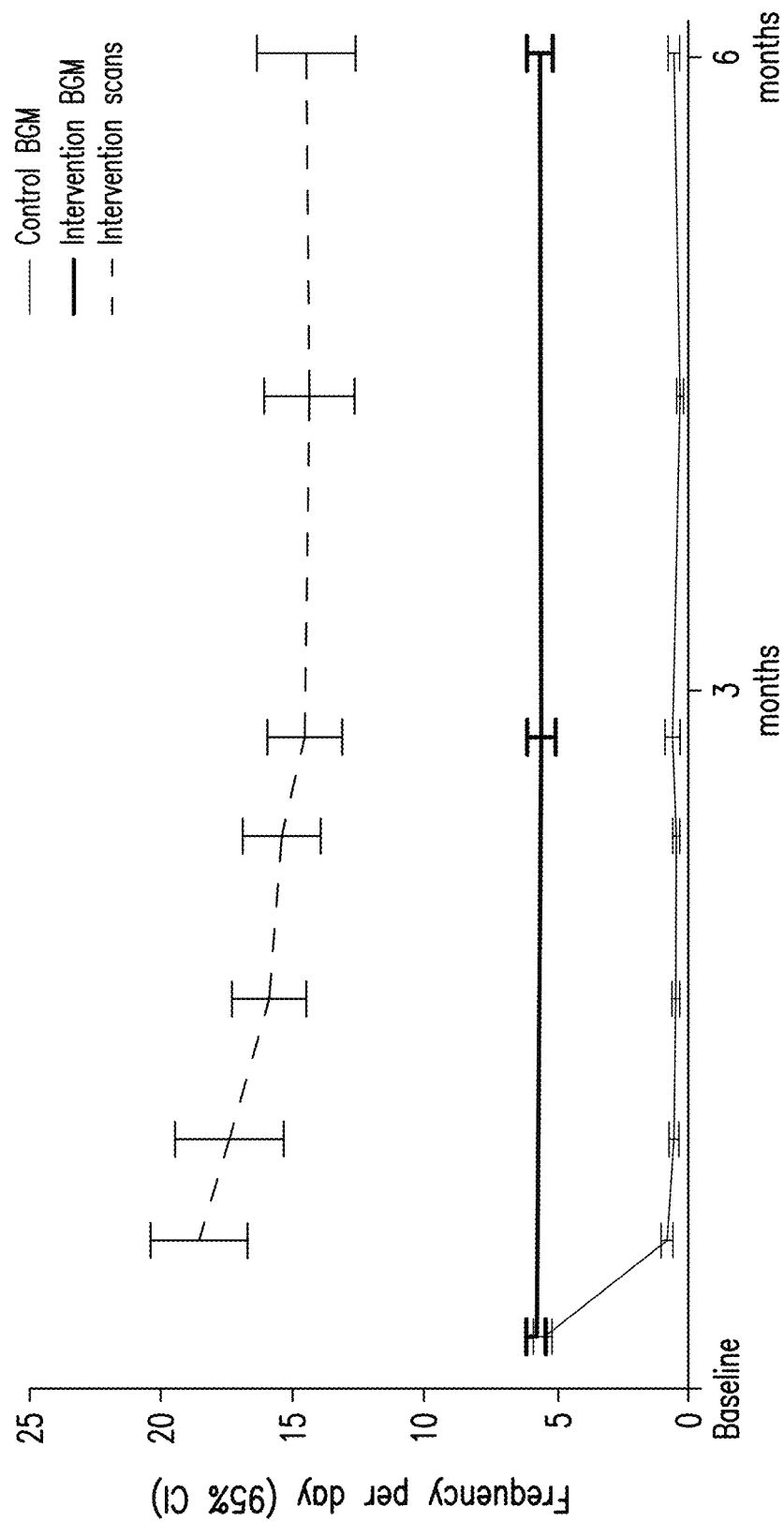
Figure 23J:
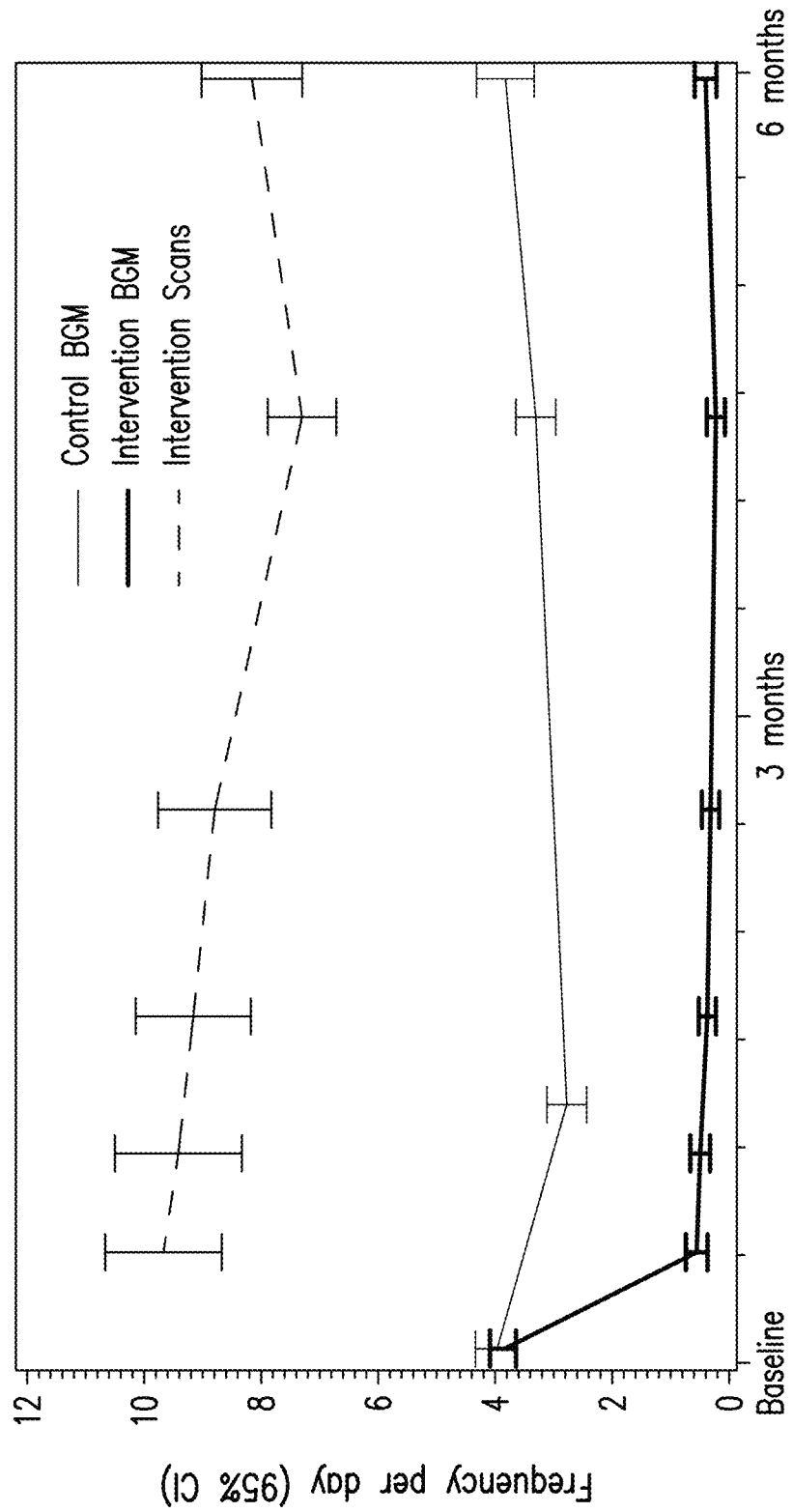

Glycemic control using flash glucose monitoring can reduce the daily burden for patients with diabetes by reducing the frequency of SMBG with finger-stick measurement. As illustrated in FIG. 23I, according to the IMPACT study, the mean (SD) number of SMBG tests performed in the flash glucose monitoring group decreased from 5.5 (2.0) tests/day at baseline to 0.5 (0.7) tests/day at 6 months. No change was seen in the SMBG group, with 5.8 (1.7) tests/day at baseline and 5.6 (2.2) tests/day at 6 months. Further, as illustrated in FIG. 23J, during the 6-month study period of REPLACE, the mean (SD) SMBG frequency for the flash glucose monitoring group also fell from 3.8 (1.4) tests/day to 0.3 (0.7) tests/day, whereas no change was seen for the SMBG group (3.9 [1.5] tests/day to 3.8 [1.9] tests/day). The average scan frequency (SD) for the flash glucose monitoring group was 15.1 (6.9) times/day in IMPACT and 8.3 (4.4) times/day in REPLACE, and the flash glucose monitoring group tended to perform more frequent monitoring than the SMBG group. REPLACE showed no significant difference in the number of scans performed by those <65 years and ≥65 years of age.

Patient reported outcome measures (PROMs), which contain both QOL and treatment satisfaction, are also a common metric and the goals of diabetes treatment include maintaining the same everyday QOL as healthy people and improvements of treatment satisfaction. One of the typical measures used to assess QOL in the treatment of diabetes is the Diabetes Quality of Life (DQoL) Questionnaire, which was developed by the Diabetes Control and Complications Trial (DCCT) Research Group, can assess the impact of disease on the lifestyle and daily lives of patients with insulin-dependent diabetes mellitus.

Diabetes Treatment Satisfaction Questionnaire (DTSQ) was developed in the UK and can be used globally as a tool to quantify treatment satisfaction. It can be applied to all patients with diabetes and is useful for comparison between treatments. The DTSQ change version (DTSQc), which can be used to assess changes in satisfaction pre- and post-intervention, has also been developed.

In IMPACT and REPLACE, the DTSQ score was improved significantly in the flash glucose monitoring group compared with the SMBG group (both p<0.0001); however, there was no difference in the DQoL score between the groups in IMPACT. Yaron et al.'s RCT showed significant differences between the SMBG and flash glucose monitoring groups in the DTSQc score items flexibility of treatment and willingness to recommend treatment to someone else (p=0.019, 0.023). A 1-year registry study, FLARE-NL4, used non-diabetes-specific QOL measures; the 12-Item Short Form Health Surveyv2 (SF-12v2) mental component summary score of QOL and the 3-level version of EuroQol (EQ-5D-3L) showed significant improvement from baseline to the end of the study (95% CIs for each difference: 2.1-4.4, 0.01-0.05), whereas the SF-12v2 physical component summary score of QOL showed no significant change. The percentage of patients with diabetes-related hospital admissions in the past 12 months decreased significantly from 13.7% at baseline to 4.7% (p<0.01), and the work absenteeism rate in the past 6 months also decreased significantly from 18.5% to 7.7% (p<0.05) (Table 3). 27)

In SHIFT, scores for the DTSQ, including treatment satisfaction, significantly improved from baseline to the end of the study (p<0.0001), and participants' perception of episodes of hypoglycemia and hyperglycemia also significantly improved (p=0.0062 and p=0.0310, respectively).

Overall, although different PROMs were used, flash glucose monitoring use was shown to have favorable effects on patient QOL and treatment satisfaction.

Beyond the different objective analysis outline above, safety related to actual device use is also a factor in technique uptake and effectiveness of treatment. The most common device-related adverse events on flash glucose monitoring include sensor insertion site reactions (e.g., pain, hemorrhage, swelling, induration, bruise) and sensor-wear reactions (e.g., erythema, itching, rash). In IMPACT, 13 device-related adverse events were reported by 10 participants in the flash glucose monitoring group, including 4 events each of allergic reaction and insertion site reaction, 2 events of erythema, and 1 event each of itching, rash, and edema. In addition, 248 sensor insertion/wear-related findings or symptoms were observed in 65 participants in both groups. Seven participants discontinued the study due to device-related adverse events or repetitive occurrences of sensor insertion-related symptoms. During the 6-month treatment phase of REPLACE, 6 participants in the flash glucose monitoring group reported 9 sensor-wear reactions as device-related adverse events, all of which were resolved at the end of the study. In addition, 50 participants from both groups reported 158 symptoms associated with sensor insertion/wear or finger-stick measurement, and 63% of these symptoms were due to the sensor adhesive. These symptoms resolved without medical intervention. In SHIFT, a total of 273 adverse events were experienced by 60 of 94 participants (63.8%), including serious adverse events reported for 5 participants. Of these, 257 adverse events were related to symptomatic hypoglycemia. No episodes of diabetic ketoacidosis (DKA) or hyperosmolar hyperglycemic state (HHS) were reported.

Serious acute complications of diabetes can also occur, including DKA and HHS, but there were no reported events of DKA or HHS in IMPACT, REPLACE, or SHIFT. As discussed above, information displayed on the flash glucose monitoring reader includes the glucose level trend arrow, which indicates the direction and velocity of changing glucose levels over the previous 15 minutes; it is expected that determination of the timing and the dose of insulin based on this information will lead to prevention of acute complications.

At the American Diabetes Association's 80th Scientific Sessions held in June 2020 (ADA 2020), results were reported from a large clinical trial in patients with type 1 and type 2 diabetes on intensive insulin therapy in countries including the US, Sweden, and France, showing in particular an improvement in rates of acute diabetes events and hospitalizations.

Clinical studies of flash glucose monitoring reviewed in this embodiment investigated the efficacy of flash glucose monitoring in glycemic control of insulin-treated diabetic patients using various outcome measures including change in HbA1c, time in hypoglycemia, and PROMs. IMPACT and REPLACE showed a significant decrease in time in hypoglycemia, but did not show any significant changes in HbA1c. On the other hand, Yaron et al.'s RCT and Kröger et al.'s chart review demonstrated a significant reduction in HbA1c; the SHIFT study, which was conducted in Japanese patients, demonstrated a significant reduction in eA1c, although no significant change was observed in time in hypoglycemia.

A report from the Committee on a Survey of Severe Hypoglycemia in the Japan Diabetes Society indicates that as long as HbA1c is not extremely low, hypoglycemia is inversely correlated with HbA1c; therefore, the fact that either the decrease in time in hypoglycemia or the reduction in HbA1c was significant suggests that flash glucose monitoring has generally contributed to the stabilization of glucose control. Baseline characteristics and number of scans can affect the efficacy of flash glucose monitoring. Discussions are needed in the future on creating standard protocols in order to increase the clinical efficacy of flash glucose monitoring.

With regard to the assessment of QOL, in Yaron et al.'s RCT with an outcome measure of DTSQ, although there was no significant improvement in the overall DTSQc score, significant improvement was seen in scores for the items flexibility of treatment and willingness to recommend treatment to someone else for the flash glucose monitoring group compared with the SMBG group. Although the DTSQ score was not the primary outcome measure for IMPACT and REPLACE, it improved significantly in the flash glucose monitoring group compared with the SMBG group. These results suggest that the use of flash glucose monitoring may contribute more to the improvement of QOL in diabetes treatment than SMBG.

Reduction in Acute Diabetic Events and All-Cause Hospitalizations

Hospitalizations and unplanned readmissions are prevalent among individuals with type 2 diabetes, who account for 90% to 95% of all diabetes cases. Adults with type 2 diabetes can be hospitalized and readmitted for numerous health conditions. Among these conditions, emergency department utilizations and hospitalizations for severe hyperglycemia and hypoglycemia can be common and associated with high readmission rates, particularly among patients with large fluctuations in glycated hemoglobin (HbA1c) and very high or very low average HbA1c levels.

According to an embodiment, a continuous glucose monitor regimen as described herein can be used to reduce the rate of hospitalization in select type 2 diabetic patients. The examples provided below further demonstrate benefits of methods and systems as described herein.

Example 1

In accordance with an embodiment as described herein, the effects of continuous glucose analyte monitoring system regimen on inpatient and emergency outpatient acute diabetes-related event (ADE) and all-cause hospitalization (ACH) rates, in a large population of patients with type 2 diabetes who were treated with basal-bolus insulin therapy was studied. Additional details of this embodiment are disclosed in *Flash CGM Is Associated With Reduced Diabetes Events and Hospitalizations in Insulin-Treated Type 2 Diabetes*, which was originally published in the Journal of the Endocrine Society, Volume 5, Issue 4, Pages 1-9, 2021, Oxford University Press and can be accessed at the website https://academic.oup.com/jes/article/5/4/bvab013/6126709, and is incorporated by reference herein in its entirety.

Patient data can be obtained, for example, from the IBM Watson Health MarketScan® Commercial Claims and Medicare Supplemental databases, which capture paid and adjudicated billing claims from inpatient hospital stays, outpatient encounters, and pharmacy prescriptions for privately insured and Medicare Supplemental patients throughout the United States. This nationally-representative database can be used to support publications in the field of diabetes research.

Patients can be included if they had a diagnosis of type 2 diabetes, were ≥18 years old, received a prescription for short- or rapid-acting insulin, were naïve to CGM, and acquired either the 10-day or 14-day sensor system between November 2017 and September 2018. In addition, patients were continuously enrolled in the inpatient, outpatient, and pharmacy databases for at least 6 months prior to system regimen. In total, a cohort of 2,463 type 2 diabetes patients was identified for assessment. Most patients were over the age of 50. The majority of patients had hypertension and dyslipidemia, and over half were obese. Patient characteristics are presented in FIG. 12A.

Diabetes type can be determined from the closest relevant diagnosis claim prior to flash CGM regimen, as shown in FIG. 12F. In exemplary cases wherein the closest claim had billing codes related to both type 1 and type 2 diabetes, the patient was not included. In addition, patients with a gestational diabetes diagnosis in the six months prior to flash CGM regimen were excluded.

International Classification of Diseases, 9th and 10th Revision (ICD-10) codes were used to identify patients with diagnosed type 2 diabetes. ICD-9 and ICD-10 codes were used to identify prevalence of co-morbidities within the study cohort, as shown in FIGS. 12G-12L. As embodied herein, existence of a comorbidity was defined by the presence of a related diagnosis code in either inpatient or outpatient claims at any time from beginning of each patient's data availability through the day of flash CGM regimen. Within the identified population, National Drug Code (NDC) data can be used to identify patients who acquired a flash CGM system during the required observation period. Patients who were treated with basal-bolus insulin therapy can be identified, for example, by short- or rapid-acting insulin regimen in the NDC data within 6-months prior to system regimen, as shown in FIGS. 12M-12P. Basal insulin was not specifically identified because patients with a record of short- or rapid-acting insulin regimen were likely treated with basal-bolus therapy.

To ensure that patients were naïve to CGM, patients with evidence of prior CGM purchase can be excluded, for example, by identifying users with sensor, transmitter, or receiver according to either NDC codes or Healthcare Common Procedure Coding System (HCPCS) codes, which are illustrated in FIGS. 12M-12P.

One outcome measure was change in ADE during the 6 months following system regimen compared with 6 months prior to use. Acute events included: hypoglycemia, hypoglycemic coma, clinical hyperglycemia, diabetic ketoacidosis (DKA), and hyperosmolarity. These were identified as either inpatient events with the associated ICD-10 code as a diagnosis code or emergency outpatient events, which included emergency department services, urgent care, or ambulance services with the associated ICD-10 code in any position. For each patient, medical billing codes associated with the same service or admit date were counted as a single event, as illustrated in FIGS. 12M-12P. The change in ACH rates was assessed as a secondary outcome.

In this exemplary embodiment, the analysis can be structured as patient-as-own-control. Rates for all primary and secondary measures were calculated in the 6-month windows pre- and post-system purchase but are reported in units of events per patient year (ev/pt-yr). Rates can be adjusted for variable follow-up after system purchase. In this example, cumulative events figures are based on Nelson-Aalen estimator, though the use of other estimators known in the art is contemplated. Hazard ratios, 95% confidence bounds, and p-values can be based on Cox regression with Andersen-Gill extension for repeated events. All p-values are reported without correction for multiple comparisons. RStudio version 1.0.153 (Boston, MA, USA) with R version 3.4.0 was used in this example for statistical analysis.

Figure 12B:
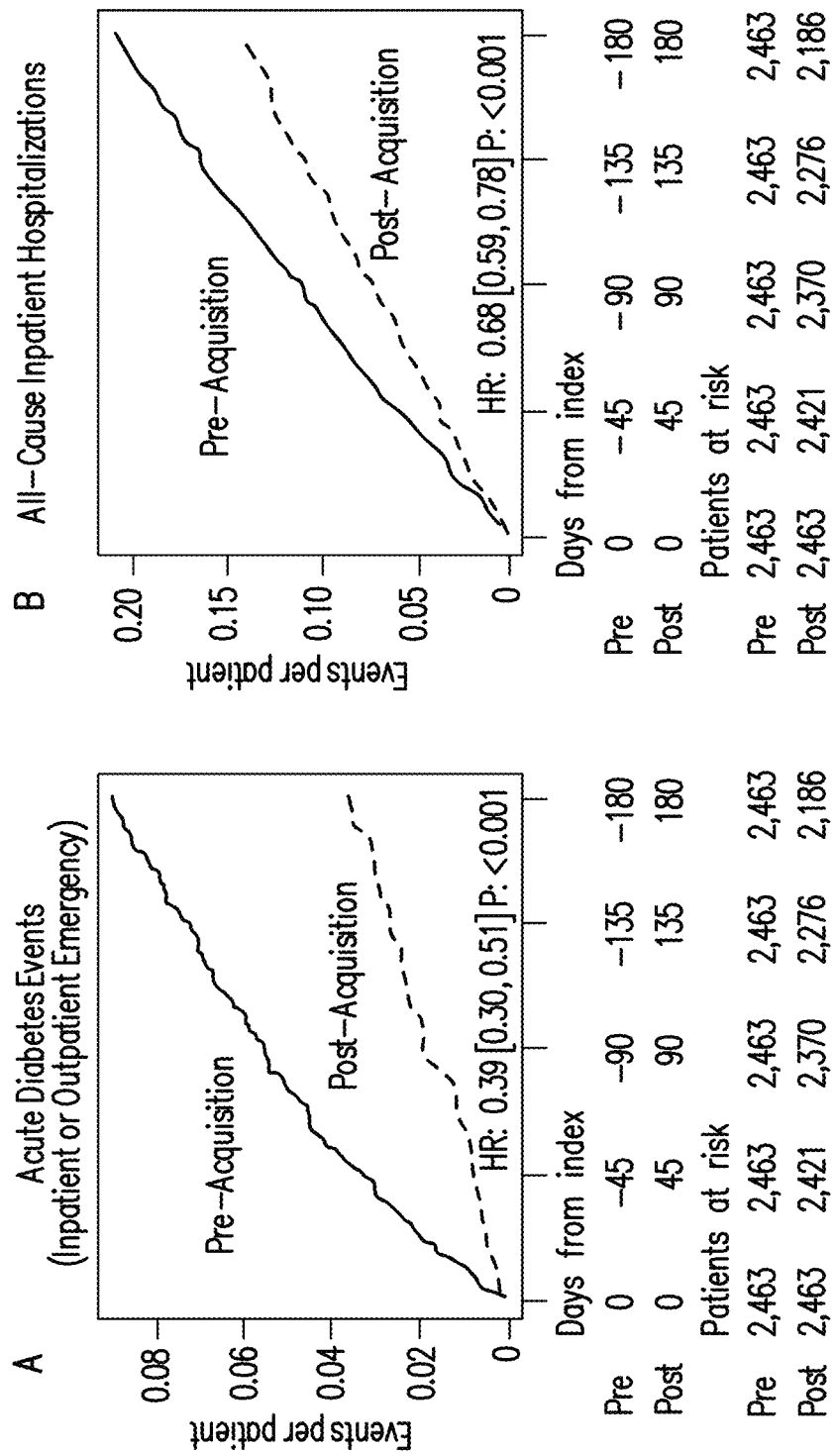
FIGS. 12A-12Q show the results of an exemplary study demonstrating reduction in acute diabetes events and all cause hospitalizations associated with continuous glucose monitoring.

Reductions in ACH can also be observed, from 0.420 to 0.283 events/patient-year (HR: 0.67 [0.58, 0.77]; P<0.001), as shown in FIG. 12B. As illustrated in FIG. 12C, the number of ADE, ACH, and patients experiencing these events dropped during the 6-month post-regimen period. Circulatory system disorders can be a cause of ACH after flash CGM regimen. However, Endocrine, Nutritional and Metabolic system disorders, which a category related to diabetes, fell from the second to fifth most common major diagnostic category. Substantial decreases in infectious and parasitic diseases, respiratory system events, and kidney and urinary tract conditions were also observed.

As embodied herein, a notable reduction in ADE and ACH within the first 45 days of the flash CGM post-regimen period was found. Results from the current analysis showed an association between a regimen of flash CGM and reductions in ADE requiring emergency outpatient/inpatient hospital services and all-cause events requiring inpatient hospitalization. During the six-month assessment period, a reduction in ADE from 0.180 to 0.072 events/patient-year (HR: 0.40 [0.31, 0.51]; P<0.001) can be observed, as illustrated in FIG. 12B. Illustrated in FIG. 12C, the change in the number of events per patient, particularly in ADE, suggests a corresponding reduction in readmissions. Moreover, although the rate of hypoglycemic ADE was extremely low prior to the flash CGM regimen, the reduction in hyperglycemic ADE with reductions in hypoglycemia is a strong indicator of overall improved glycemic control. Both of these findings hold clinical and financial implications. For example, extreme hyperglycemia at hospital admission can be a predictor of poor clinical outcomes for coronary artery bypass graft and ischemic stroke. Each hypoglycemic event is statistically significant (p<0.001) associated with increased risk for poor cardiovascular outcomes and all-cause mortality.

Figure 12D:
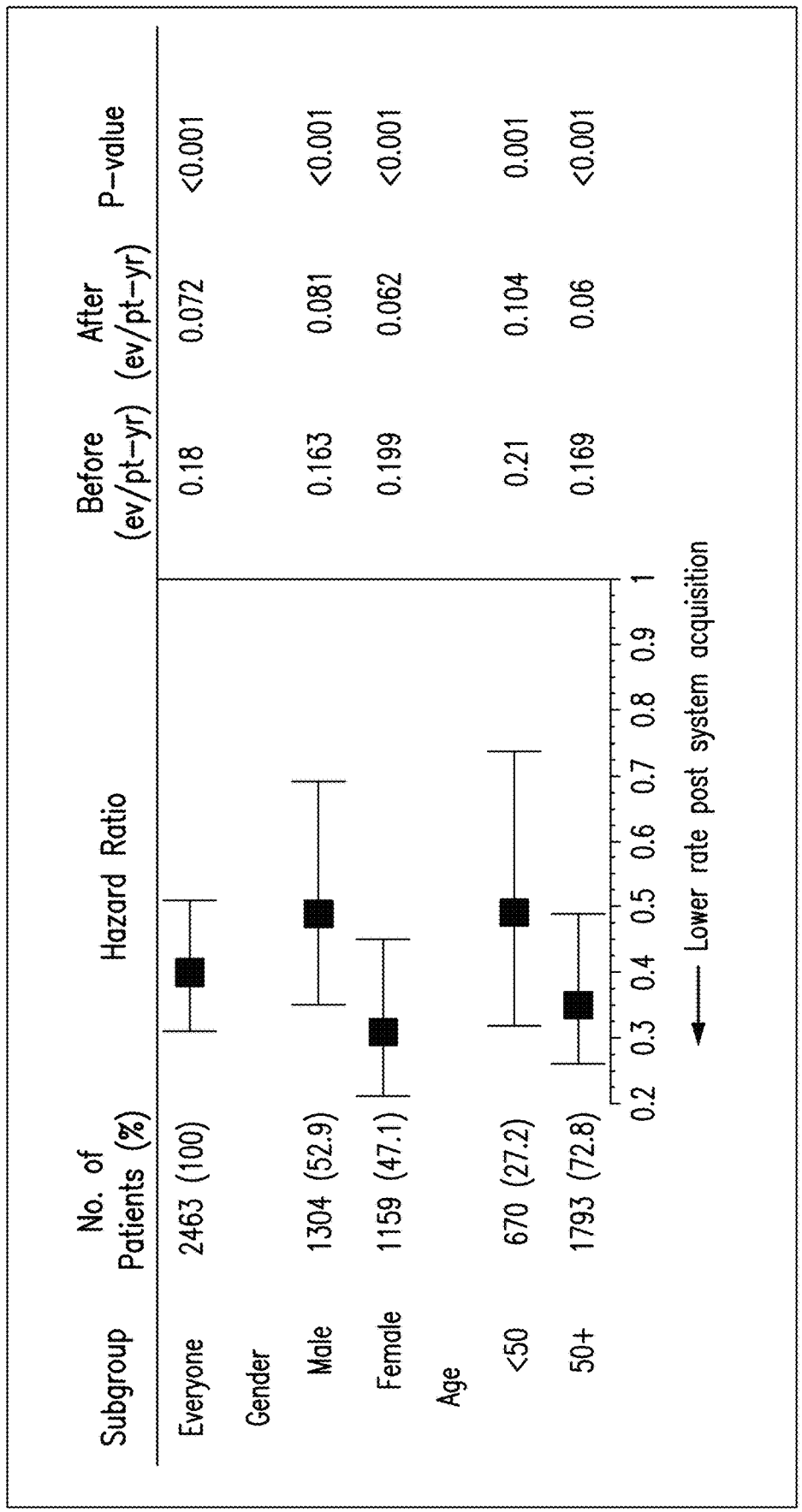

As illustrated in FIG. 12D, risk reductions can be significant regardless of gender or age, but most notable among female patients (HR 0.31 [0.21 0.45], p<0.001) and patients age ≥50 years (HR 0.35 [0.26 0.49], p<0.001).

Because surveillance of hypoglycemia in the United States can rely on data from electronic health records (EHR) or administrative claims from hospital admissions and emergency department utilization, the actual incidence of severe hypoglycemia may be substantially underreported. In a recent survey of 13,359 individuals with diabetes who were treated with glucose-lowering medications, 11.7% reported having one or more severe hypoglycemic events requiring third-party assistance in the previous 12 months; however, 0.8% had a documented hypoglycemia-related emergency department or hospital utilization during the same time period.

Apart from acute clinical outcomes, episodes of severe hypoglycemia can impact patient adherence to therapy, which can lead to poor glycemic control and increased risk of long-term complications. An international survey of 27,585 diabetes patients found that 25.8% to 46.7% of people with type 2 diabetes reduced their insulin dosages in response to hypoglycemia.

Results also highlight a desire to reduce hyperglycemia without increasing the incidence and severity of hypoglycemia. Although recent data show similar rates for hypoglycemic- and hyperglycemic ADE in the general diabetes population (8.8 vs. 9.7 per/1,000 patients, respectively), the substantially larger number of hyperglycemic vs. hypoglycemic ADE prior to flash CGM regimen suggests that many study patients historically maintained elevated glucose levels.

As shown in FIG. 12E, notable decreases in hospitalizations for selected predetermined comorbidities are provided by a CGM regimen in accordance with the disclosed subject matter. For example, hospitalization decreased more than expected for infections (41.7%), renal disease (48.5%) and liver disease (41.7). In an embodiment, as can be in seen in FIG. 12E, the overall (or "baseline") rate of hospitalizations among all type 2 diabetic patients on basal-bolus therapy irrespective in, for example, the infectious and parasitic disease major diagnostic category (MDC), for six months prior to initiation of continuous glucose monitor regimen was 4.8 events per 100 patient-years and 2.8 events per 100 patient-years for six months after initiation of continuous glucose monitor regime. Accordingly, the rate of hospitalization for infectious and parasitic diseases in type 2 diabetic patients on basal-bolus therapy with continuous glucose monitor regimen after six months unexpectedly reduced by approximately 41.67% relative to an average rate of hospitalization for infectious and parasitic diseases of type 2 diabetic patients on basal bolus therapy without continuous glucose monitor regimen.

One advantage of analysis according to this subject matter is use of claims data from a large dataset, which can provide reliable information about flash CGM system regimen over time in 2,463 patients with insulin-treated type 2 diabetes. Similarly, assessments of complications and utilization of healthcare resources (e.g., emergency room visits, inpatient hospitalizations) based on ICD-10 codes allows accurate quantification of actual events and utilization without reliance on patient-reported data.

Other exemplary embodiments show reductions in time spent with glucose levels <70 mg/dL (<3.9 mmol/L) among flash CGM users compared with controls.

These exemplary findings provide support for the potential of using flash CGM in insulin-treated type 2 diabetes to both improve clinical outcomes and reduce the financial costs associated with hospitalizations and emergency department utilization due to ADE. Moreover, wider use of flash CGM can address the changing trends of increasing all-cause hospitalizations among younger and middle-age adults and the newly emerging trends of increased mortality due to infections, respiratory illness and renal and hepatic complications.

Example 2

In accordance with an embodiment as described herein, the effects of a flash CGM system regimen on inpatient and emergency outpatient acute diabetes-related event (ADE) and all-cause hospitalization (ACH) rates, in a large population of patients with type 2 diabetes who were treated with non-MDI therapy were examined.

Patient data can be obtained from the IBM MarketScan™ administrative claims database, which captures paid and adjudicated billing claims from inpatient hospital stays, outpatient encounters, and pharmacy prescriptions for over 30 million privately insured and Medicare Supplemental patients throughout the United States. This nationally-representative database has been used to support publications in the field of diabetes research. The database allows for longitudinal patient follow-up, but patients can be lost to follow-up for a variety of reasons including switching employers, switching insurance, losing a job, or death. The dataset does not need to contain information on why a patient is no longer under observation.

Patients were included who had a diagnosis of T2D, age ≥18 years, were naïve to continuous glucose monitoring, and who acquired their flash CGM system during the period between October 2017 and March 2019. To select patients on non-MDI insulin or non-insulin therapy, the cohort was further limited to those without a purchase of short- or rapid-acting insulin in the 6 months prior to flash CGM regimen. Patients without observed diabetes medications can be included in the non-insulin therapy subgroup. Patients were excluded if they did not have at least 6 months of database enrollment prior to the flash CGM system purchase or had gestational diabetes in the same time frame. Using the above outline criteria, a cohort of 10,282 adult T2D patients were identified for assessment. In this exemplary embodiment, the majority of patients were under age 65, had hypertension, and over half were obese. Patient characteristics are illustrated in FIG. 13A.

International Classification of Diseases, 9th and 10th Revision (ICD-10) codes can be used to identify patients with diagnosed T2D. In the rare case the closest claim had billing codes related to both T1D and T2D, the patient was not included. ICD-9 and ICD-10 codes were also used to identify prevalence of co-morbidities within the study cohort.

Within the selected population, National Drug Code (NDC) data can be used to identify patients who acquired a flash CGM system and to exclude patients who were treated with short- or rapid-acting insulin therapy within 6-months prior to system regimen. Patients with evidence of prior CGM purchase, including sensor, transmitter, or receiver, were excluded. NDC code sets compiled through medical expert review were also used to estimate non-insulin diabetes medication usage in the same time window.

One outcome measure was change in ADE during the 6 months following CMG regimen compared with 6 months prior to use. Acute events can include: hypoglycemia, hypoglycemic coma, clinical hyperglycemia, diabetic ketoacidosis (DKA), and hyperosmolarity. These were identified as either inpatient events with the associated ICD-10 code as a diagnosis code or emergency outpatient events, which included emergency department services, urgent care, or ambulance services with the associated ICD-10 code in any position. For each patient, medical billing codes associated with the same service or admit date were counted as a single event. The change in ACH rates was assessed as a secondary outcome. Event rates were calculated by dividing the number of observed events by the total observation time.

In this exemplary embodiment, the analysis was structured as patient-as-own-control. Rates for all primary and secondary measures were calculated in the 6-month windows pre- and post-system purchase but are reported in units of events per patient year (ev/pt-yr). Rates adjust for variable follow-up after system purchase. Cumulative events figures are based on the Nelson-Aalen estimator. All hazard ratios, 95% confidence bounds, and p-values are based on weighted Cox regression with Andersen-Gill extension for repeated events, adjusted for all comorbidities and insulin usage status listed in FIG. 13A. Weighted Cox regression is used to account for non-proportionality of hazards, as tested via Schoenfeld residuals. All p-values are reported without correction for multiple comparisons. RStudio version 1.0.153 (Boston, MA, USA) with R version 3.4.0 was used for statistical analysis.

Results from the analysis showed an association between flash CGM regimen and reductions in acute diabetes-related events requiring emergency outpatient/inpatient hospital services and all-cause events requiring inpatient hospitalization. These results are particularly noteworthy given that patients treated with non-MDI therapies tend to have lower rates of microvascular and macrovascular complications than patients treated with intensive insulin therapy.

Figure 13D:
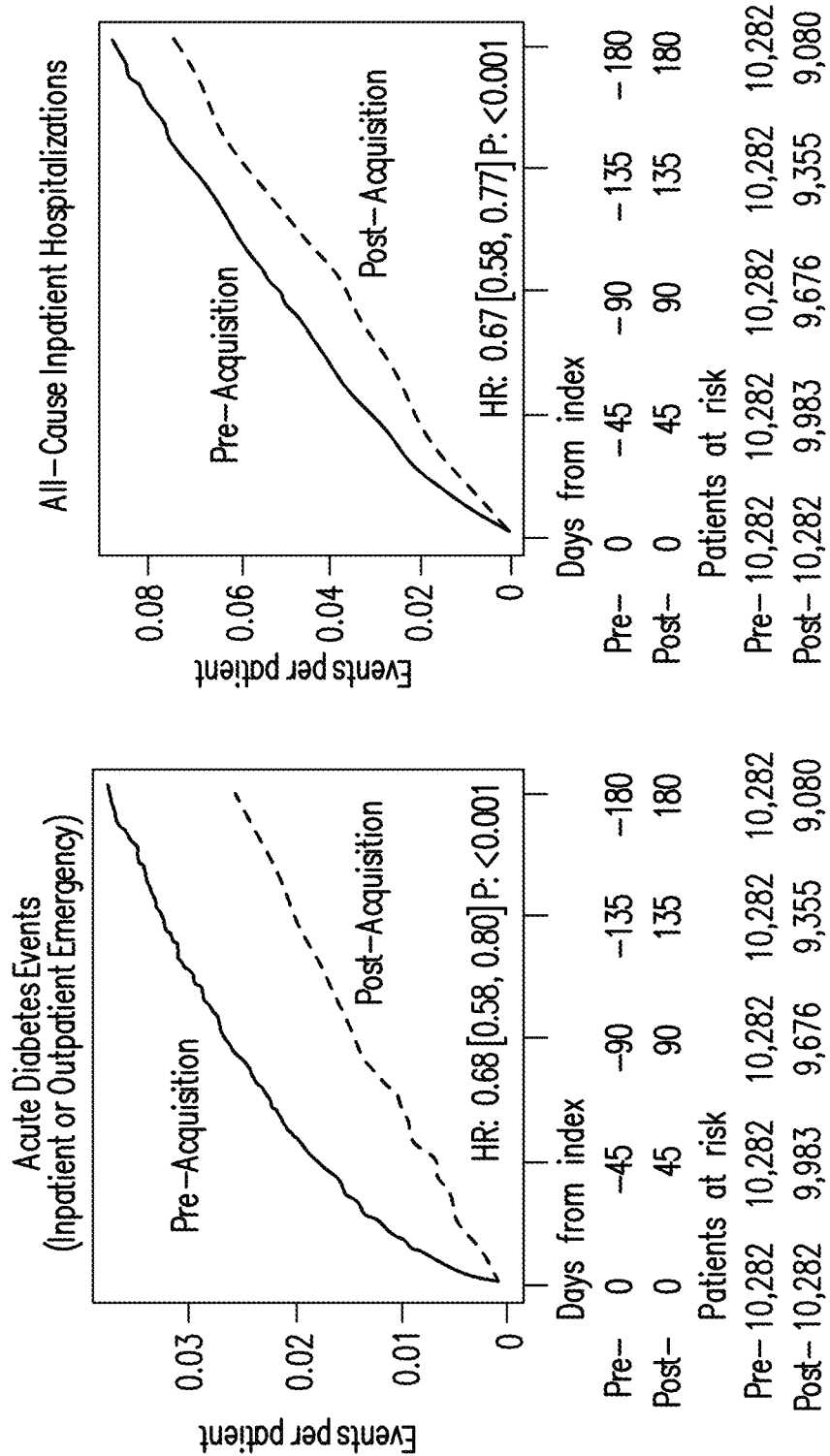

As illustrated in FIG. 13D, during the post-CGM regimen period (171 days average follow-up) the rate of ADE decreased from 0.076 to 0.052 events/pt-yr (HR: 0.68 [0.58 0.80]; P<0.001). As illustrated in FIG. 13D, ACH decreased from 0.177 to 0.151 events/pt-yr (HR: 0.85 [0.77 0.94]; P=0.002).

The majority of ADEs were outpatient emergency events as shown in FIG. 13B. In addition, an examination of the unique patients impacted by these events indicates that repeated events need not dominate. In this exemplary embodiment, less than 0.7% of patients experienced more than one acute diabetes event in a given pre- or post-CGM regimen period.

A further exploratory analysis of all-cause inpatient hospitalizations subdivided by major diagnostic category (MDC) is presented in descending order of frequency in FIG. 13C. There are small decreases in the rates of circulatory system, nervous system, infectious disease, and kidney/urinary tract hospitalizations. The biggest drop is in the endocrine, nutritional, and metabolic system category (MDC 10), the one most closely associated with diabetes. Surgical procedures for obesity increased from <11 to 22 events.

As shown in FIG. 13C, notable decreases in hospitalizations for selected predetermined comorbidities are provided by a CGM regimen in accordance with the disclosed subject matter, for example, hospitalizations decreased more than expected for infections (33.33%) and renal disease (30.8%). In an embodiment, as can be seen in FIG. 13C, the overall (or "baseline") rate of hospitalizations among all type 2 diabetic patients on non-MDI therapy in, for example, the infectious and parasitic disease major diagnostic category, for six months prior to initiation of continuous glucose monitor regimen is 1.8 events per 100 patient-years and 1.2 events per 100 patient-years for six months after initiation of continuous glucose monitor regimen. Accordingly, the rate of hospitalization for infectious and parasitic diseases in type 2 diabetic patients on non-MDI therapy after six months is reduced by approximately 33.33% relative to an average rate of hospitalization for infectious and parasitic diseases of type 2 diabetic patients on non-MDI therapy without CGM regimen.

Figure 13E:
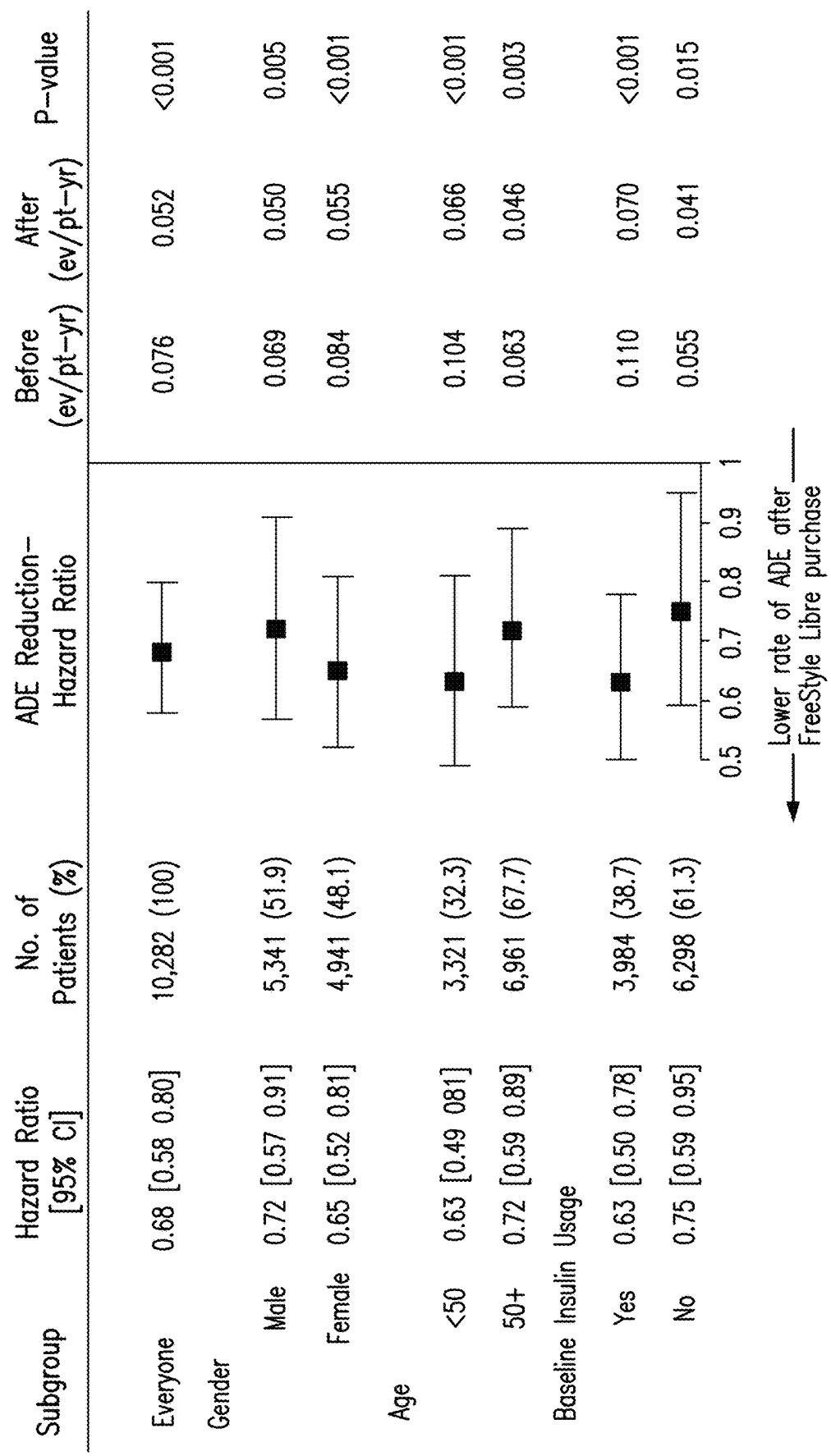

Further analyses by gender, age, and insulin usage show a reduction in ADEs across all sub-groups, as shown in FIG. 13E. Interaction terms with treatment were not significant for all three sub-groups. Baseline rates of ADEs trended higher for both patients under 50 years old and insulin users.

Acute diabetes events and hospitalizations can be reduced according to the disclosed subject matter. According to the Centers for Disease Control and Prevention (CDC), approximately 460,000 emergency department visits for hyperglycemic crises (n=224,000) and severe hypoglycemia (n=235,000) were reported in 2016. One advantage of analysis according to the present subject matter is use of claims data from a large dataset, which included 10,282 T2D patients treated with non-MDI insulin and non-insulin therapy. Moreover, the dataset provided reliable information about flash CGM system regimen over time with 4,817 years of patient follow-up post-flash CGM system regimen. Use of ICD-10 codes allowed accurate quantification of complications and utilization of healthcare resources (e.g., emergency room visits, inpatient hospitalizations) without reliance on patient-reported data.

Example 3

In accordance with embodiments disclosed here, a method of treatment of type 2 diabetic patient can include selecting a type 2 diabetic patient having a predetermined comorbidity for treatment, initiating a continuous glucose monitor regimen for the selected type 2 diabetic patient, wherein after six months of initiation of the continuous glucose monitor regimen, a rate of hospitalization for a predetermined diagnostic category of the selected patient having the predetermined comorbidity can be unexpectedly reduced by at least 12% relative to an average rate of hospitalization for the predetermined diagnostic category of selected patients having the predetermined comorbidity without the continuous glucose monitor regimen.

For example, as can be seen in FIG. 25D, in the infectious and parasitic diseases major diagnostic category, 30 hospitalizations were reported among anemic type 2 diabetic patients on basal-bolus therapy in the six months prior to the CGM regimen versus 14 hospitalizations in the six months after CGM regimen. As can be seen in FIG. 25D, this corresponds to a hospitalization rate, as measured in events per 100 patient-years, of 9.5 and 4.7, respectively. Accordingly, as can be seen in FIG. 25D, the rate of hospitalization for infectious and parasitic diseases of type 2 diabetic patients on basal-bolus therapy having anemia with CGM regimen after six months unexpectedly reduced by approximately 51% relative to an average rate of hospitalization for infectious and parasitic diseases of type 2 diabetic patients on basal-bolus therapy having anemia but without CGM regimen.

As can be seen in FIG. 24D, in the infectious and parasitic diseases major diagnostic category, 51 hospitalizations were reported among anemic type 2 diabetic patients on non-multiple daily insulin injection (non-MDI) therapy in the six months prior to CGM regimen versus 25 hospitalizations in the six months after CGM regimen. As can be seen in FIG. 24D, this corresponds to a hospitalization rate, as measured in events per 100 patient-years, of 5.2 and 2.7, respectively. Accordingly, as can be seen in FIG. 24D, the rate of hospitalization for infectious and parasitic diseases of type 2 diabetic patients on non-MDI therapy having anemia with CGM regimen after six months is unexpectedly reduced by approximately 48% relative to an average rate of hospitalization for infectious and parasitic diseases of patients on non-MDI therapy having anemia without CGM regimen.

According to embodiments, the predetermined comorbidity can be anemia. As embodied herein, the anemic patient can receive basal-bolus insulin therapy. As can be seen in FIG. 25D, the predetermined diagnostic category can be infectious and parasitic diseases, and the rate of hospitalization for infectious and parasitic diseases of the selected patient after six months can be unexpectedly reduced by 51% relative to an average rate of hospitalization for infectious and parasitic diseases of selected patients having anemia without the continuous glucose monitor regimen. As can be seen in FIG. 25E, the predetermined diagnostic category can be respiratory diseases, and the rate of hospitalization for respiratory diseases of the selected patient after six months can be unexpectedly reduced by 38% relative to an average rate of hospitalization for respiratory diseases of selected patients having anemia without the continuous glucose monitor regimen. As can be seen in FIG. 25E, the predetermined diagnostic category can be kidney and urinary tract diseases, and the rate of hospitalization for kidney and urinary tract diseases of the selected patient after six months can be unexpectedly reduced by 57% relative to an average rate of hospitalization for kidney and urinary tract diseases of selected patients having anemia without the continuous glucose monitor regimen. As can be seen in FIG. 25G, the predetermined diagnostic category can be hepatobiliary and pancreatic diseases, and the rate of hospitalization for hepatobiliary and pancreatic diseases of the selected patient after six months can be unexpectedly reduced by 55% relative to an average rate of hospitalization for hepatobiliary and pancreatic diseases of selected patients having anemia without the continuous glucose monitor regimen.

As embodied herein, the anemic patient can be receiving non-multiple daily insulin injection therapy. As can be seen in FIG. 24D, the predetermined diagnostic category is infectious and parasitic diseases, and the rate of hospitalization for infectious and parasitic diseases of the selected patient after six months can be unexpectedly reduced by 48% relative to an average rate of hospitalization for infectious and parasitic diseases of selected patients having anemia without the continuous glucose monitor regimen. As can be seen in FIG. 24D, the predetermined diagnostic category is respiratory diseases, and the rate of hospitalization for respiratory diseases of the selected patient after six months can be unexpectedly reduced by 59% relative to an average rate of hospitalization for respiratory diseases of selected patients having anemia without the continuous glucose monitor regimen. As can be seen in FIG. 24E, the predetermined diagnostic category is kidney and urinary tract diseases, and the rate of hospitalization for kidney and urinary tract diseases of the selected patient after six months can be unexpectedly reduced by 51% relative to an average rate of hospitalization for kidney and urinary tract diseases of selected patients having anemia without the continuous glucose monitor regimen. As can be seen in FIG. 24F, the predetermined diagnostic category is hepatobiliary and pancreatic diseases, and the rate of hospitalization for hepatobiliary and pancreatic diseases of the selected patient after six months can be unexpectedly reduced by 44% relative to an average rate of hospitalization for hepatobiliary and pancreatic diseases of selected patients having anemia without the continuous glucose monitor regimen.

As can be seen in FIGS. 12E and 13C, the predetermined diagnostic category can be infectious and parasitic diseases, and the rate of hospitalization for infectious and parasitic diseases of the selected patient after six months can be unexpectedly reduced by at least 33% relative to an average rate of hospitalization for infectious and parasitic diseases of selected patients having the predetermined comorbidity without the continuous glucose monitor regimen.

As embodied herein, the selected patient can be receiving basal-bolus insulin therapy. As can be seen in FIG. 25D, the predetermined comorbidity is a fluid and electrolyte disorder, and the rate of hospitalization for infectious and parasitic diseases of the selected patient having fluid and electrolyte disorder after six months can be unexpectedly reduced by at least 59% relative to an average rate of hospitalization for infectious and parasitic diseases of selected patients having fluid and electrolyte disorder without the continuous glucose monitor regimen. As can be seen in FIG. 25D, the predetermined comorbidity is a valvular disorder, and the rate of hospitalization for infectious and parasitic diseases of the selected patient having a valvular disorder after six months can be unexpectedly reduced at least by 58% relative to an average rate of hospitalization for infectious and parasitic diseases of selected patients having a valvular disorder without the continuous glucose monitor regimen. As can be seen in FIG. 25D, the predetermined comorbidity is liver disease, and the rate of hospitalization for infectious and parasitic diseases of the selected patient having liver disease after six months can be unexpectedly reduced by at least 50% relative to an average rate of hospitalization for infectious and parasitic diseases of selected patients having liver disease without the continuous glucose monitor regimen.

As embodied herein, the selected patient can be receiving non-multiple daily insulin injection therapy. As can be seen in FIG. 24D, the predetermined comorbidity is a fluid or electrolyte disorder, and the rate of hospitalization for infectious and parasitic diseases of the selected patient having a fluid or electrolyte disorder after six months can be unexpectedly reduced by at least 68% relative to an average rate of hospitalization for infectious and parasitic diseases of selected patients having fluid or electrolyte disorders without the continuous glucose monitor regimen. As can be seen in FIG. 24D, the predetermined comorbidity is a valvular disorder, and the rate of hospitalization for infectious and parasitic diseases of the selected patient having a valvular disorder after six months can be unexpectedly reduced by at least 53% relative to an average rate of hospitalization for infectious and parasitic diseases of selected patients having valvular disorders without the continuous glucose monitor regimen. As can be seen in FIG. 24D, the predetermined comorbidity is liver disease, and the rate of hospitalization for infectious and parasitic diseases of the selected patient having liver disease after six months can be unexpectedly reduced by at least 54% relative to an average rate of hospitalization for infectious and parasitic diseases of selected patients having liver disease without the continuous glucose monitor regimen.

In accordance with the disclosed subject matter, a system to establish an analyte monitor regimen is also provided. The system includes a sensor control device comprising an analyte sensor coupled with sensor electronics, the sensor control device configured to transmit data indicative of an analyte level, and, a reader device comprising a display, wireless communication circuitry configured to receive the data indicative of the analyte level, and one or more processors coupled with a memory, the memory configured to store instructions that, when executed by the one or more processors, cause the one or more processors to output to the display an analyte level measurement, wherein after six months of initiating an analyte monitor regimen using the system for a type 2 diabetic patient having a predetermined comorbidity, a rate of hospitalization for a predetermined diagnostic category of the selected patient having the predetermined comorbidity can be unexpectedly reduced by at least 12% relative to an average rate of hospitalization for a predetermined diagnostic category of selected patients having the predetermined comorbidity without the continuous glucose monitor regimen. The system can include any of the features described hereinabove for the method of treatment.

In accordance with the disclosed subject matter, a method of treatment of a type 2 diabetic patient can include selecting a type 2 diabetic patient having a predetermined comorbidity for treatment, initiating a continuous glucose monitor regimen for the selected type 2 diabetic patient, wherein after six months of initiation of the continuous glucose monitor regimen, an average rate of hospitalization for a predetermined diagnostic category of the selected patient having the predetermined comorbidity can be unexpectedly reduced by at least 12% relative to an average rate of hospitalization for the predetermined diagnostic category of the selected patient having the predetermined comorbidity during a period of six months prior to initiating the continuous glucose monitor regimen.

According to embodiments, the predetermined comorbidity can be anemia. As embodied herein, the anemic patient can receive basal-bolus insulin therapy. As can be seen in FIG. 25D, the predetermined diagnostic category is infectious and parasitic diseases, and the average rate of hospitalization for infectious and parasitic diseases of the selected patient after six months can be unexpectedly reduced by 51% relative to an average rate of hospitalization for infectious and parasitic diseases of the selected patient having anemia during a period of six months prior to initiating the continuous glucose monitor regimen. As can be seen in FIG. 25E, the predetermined diagnostic category is respiratory diseases, and the average rate of hospitalization for respiratory diseases of the selected patient after six months can be unexpectedly reduced by 38% relative to an average rate of hospitalization for respiratory diseases of the selected patient having anemia during a period of six months prior to initiating the continuous glucose monitor regimen. As can be seen in FIG. 25E, the predetermined diagnostic category is kidney and urinary tract diseases, and the average rate of hospitalization for kidney and urinary tract diseases of the selected patient after six months can be unexpectedly reduced by 57% relative to an average rate of hospitalization for kidney and urinary tract diseases of the selected patient having anemia during a period of six months prior to initiating the continuous glucose monitor regimen. As can be seen in FIG. 25G, the predetermined diagnostic category is hepatobiliary and pancreatic diseases, and the average rate of hospitalization for hepatobiliary and pancreatic diseases of the selected patient after six months can be unexpectedly reduced by 55% relative to an average rate of hospitalization for hepatobiliary and pancreatic diseases of the selected patient having anemia during a period of six months prior to initiating the continuous glucose monitor regimen.

As embodied herein, the anemic patient can be receiving non-multiple daily insulin injection therapy. As can be seen in FIG. 24D, the predetermined diagnostic category is infectious and parasitic diseases, and the average rate of hospitalization for infectious and parasitic diseases of the selected patient after six months can be unexpectedly reduced by 48% relative to an average rate of hospitalization for infectious and parasitic diseases of the selected patient having anemia during a period of six months prior to initiating the continuous glucose monitor regimen. As can be seen in FIG. 24D, the predetermined diagnostic category is respiratory diseases, and the average rate of hospitalization for respiratory diseases of the selected patient after six months can be unexpectedly reduced by 59% relative to an average rate of hospitalization for respiratory diseases of the selected patient having anemia during a period of six months prior to initiating the continuous glucose monitor regimen. As can be seen in FIG. 24E, the predetermined diagnostic category is kidney and urinary tract diseases, and the average rate of hospitalization for kidney and urinary tract diseases of the selected patient after six months can be unexpectedly reduced by 51% relative to an average rate of hospitalization for kidney and urinary tract diseases of the selected patient having anemia during a period of six months prior to initiating the continuous glucose monitor regimen. As can be seen in FIG. 24F, the predetermined diagnostic category is hepatobiliary and pancreatic diseases, and the average rate of hospitalization for hepatobiliary and pancreatic diseases of the selected patient after six months can be unexpectedly reduced by 44% relative to an average rate of hospitalization for hepatobiliary and pancreatic diseases of the selected patient having anemia during a period of six months prior to initiating the continuous glucose monitor regimen.

As can be seen in FIGS. 12E and 13C, the predetermined diagnostic category is infectious and parasitic diseases, and the average rate of hospitalization for infectious and parasitic diseases of the selected patient after six months can be unexpectedly reduced by at least 33% relative to an average rate of hospitalization for infectious and parasitic diseases of the selected patient having the predetermined comorbidity during a period of six months prior to initiating the continuous glucose monitor regimen.

As embodied herein, the selected patient can be receiving basal-bolus insulin therapy. As can be seen in FIG. 25D, the predetermined comorbidity is a fluid and electrolyte disorder, and the average rate of hospitalization for infectious and parasitic diseases of the selected patient having fluid and electrolyte disorder after six months can be unexpectedly reduced by at least 59% relative to an average rate of hospitalization for infectious and parasitic diseases of the selected patient having fluid and electrolyte disorder during a period of six months prior to initiating the continuous glucose monitor regimen. As can be seen in FIG. 25D, the predetermined comorbidity is a valvular disorder, and the average rate of hospitalization for infectious and parasitic diseases of the selected patient having a valvular disorder after six months can be unexpectedly reduced at least by 58% relative to an average rate of hospitalization for infectious and parasitic diseases of the selected patient having a valvular disorder during a period of six months prior to initiating the continuous glucose monitor regimen. As can be seen in FIG. 25D, the predetermined comorbidity is liver disease, and the average rate of hospitalization for infectious and parasitic diseases of the selected patient having liver disease after six months can be unexpectedly reduced by at least 50% relative to an average rate of hospitalization for infectious and parasitic diseases of the selected patient having liver disease during a period of six months prior to initiating the continuous glucose monitor regimen.

As embodied herein, the selected patient can be receiving non-multiple daily insulin injection therapy. As can be seen in FIG. 24D, the predetermined comorbidity is a fluid or electrolyte disorder, and the average rate of hospitalization for infectious and parasitic diseases of the selected patient having a fluid or electrolyte disorder after six months can be unexpectedly reduced by at least 68% relative to an average rate of hospitalization for infectious and parasitic diseases of the selected patient having fluid or electrolyte disorders during a period of six months prior to initiating the continuous glucose monitor regimen. As can be seen in FIG. 24D, the predetermined comorbidity is a valvular disorder, and the average rate of hospitalization for infectious and parasitic diseases of the selected patient having a valvular disorder after six months can be unexpectedly reduced by at least 53% relative to an average rate of hospitalization for infectious and parasitic diseases of the selected patient having valvular disorders during a period of six months prior to initiating the continuous glucose monitor regimen. As can be seen in FIG. 24D, the predetermined comorbidity is liver disease, and the average rate of hospitalization for infectious and parasitic diseases of the selected patient having liver disease after six months can be unexpectedly reduced by at least 54% relative to an average rate of hospitalization for infectious and parasitic diseases of the selected patient having liver disease during a period of six months prior to initiating the continuous glucose monitor regimen.

As can be seen in FIGS. 24B-S and 25B-V, the same analysis can be performed for any of the disclosed major diagnostic categories using any of the disclosed sub-groups (e.g., comorbidities, age, gender, non-insulin diabetes medications, medication therapy group, or other diabetic therapy) for type 2 diabetic patients on basal-bolus therapy and non-MDI therapy.

All percentage reductions in rate of hospitalizations shown in FIGS. 24B-S and 25B-V illustrate minimum percentage reduction (i.e., at least a reduction of the percentage shown in FIGS. 24B-S and 25B-V). For example, and not limitation, the rate of hospitalization for infectious and parasitic diseases of type 2 diabetic patients on basal-bolus therapy having anemia with CGM regimen after six months unexpectedly reduced by at least 51% (i.e., reduction in rate of hospitalization could be greater than 51%) relative to an average rate of hospitalization for infectious and parasitic diseases of type 2 diabetic patients on basal-bolus therapy having anemia but without CGM regimen. Additionally, reductions in rate of hospitalization could be achieved earlier than 6 months (e.g., 12 weeks, 3 months, 4 months, or any other period of time reasonably understood by a person of skill in the art) in all percentage reductions in rate of hospitalizations shown in FIGS. 24B-S and 25B-V.

Example 4

In accordance with an embodiment as described herein, risk of hospitalization for acute diabetes events ("ADE") 12 months-before and 12 months-after access to a CGM in accordance with the disclosed subject matter herein above (e.g., in certain embodiments, the FreeStyle Libre system) was studied. In this exemplary embodiment, the analysis was done upon a cohort of persons in France, wherein each person had been diagnosed with either Type-1 or Type-2 diabetes.

In selecting the persons to be included in the analysis, inclusion criteria can be defined. For example, an inclusion period can be defined, such as Aug. 1, 2017 to Dec. 31, 2017, within which a person who has used a CGM system can be included. Further inclusion criteria can include whether persons have at least 1 full year of follow up data available. In this exemplary embodiment, within France, 74,076 persons were identified as fitting the inclusion criteria. Further, of that group, 33,165 were diagnosed with Type-1 diabetes and 40,486 were diagnosed with Type-2 diabetes. Further, within that group, 88% were treated with MDS or CSII, while 12% were treated with basal only therapy, OAD, or did not received treatment.

Figure 20A:
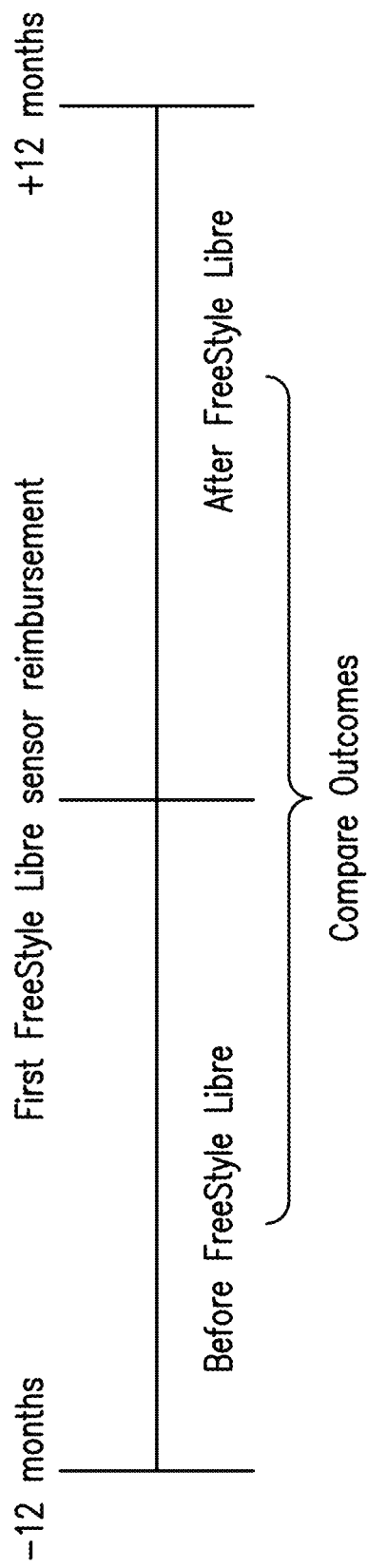
FIGS. 20A-20C show the results of a study which examined the effects of a continuous glucose monitor on acute diabetes events and all cause hospitalizations.
Figure 20B:
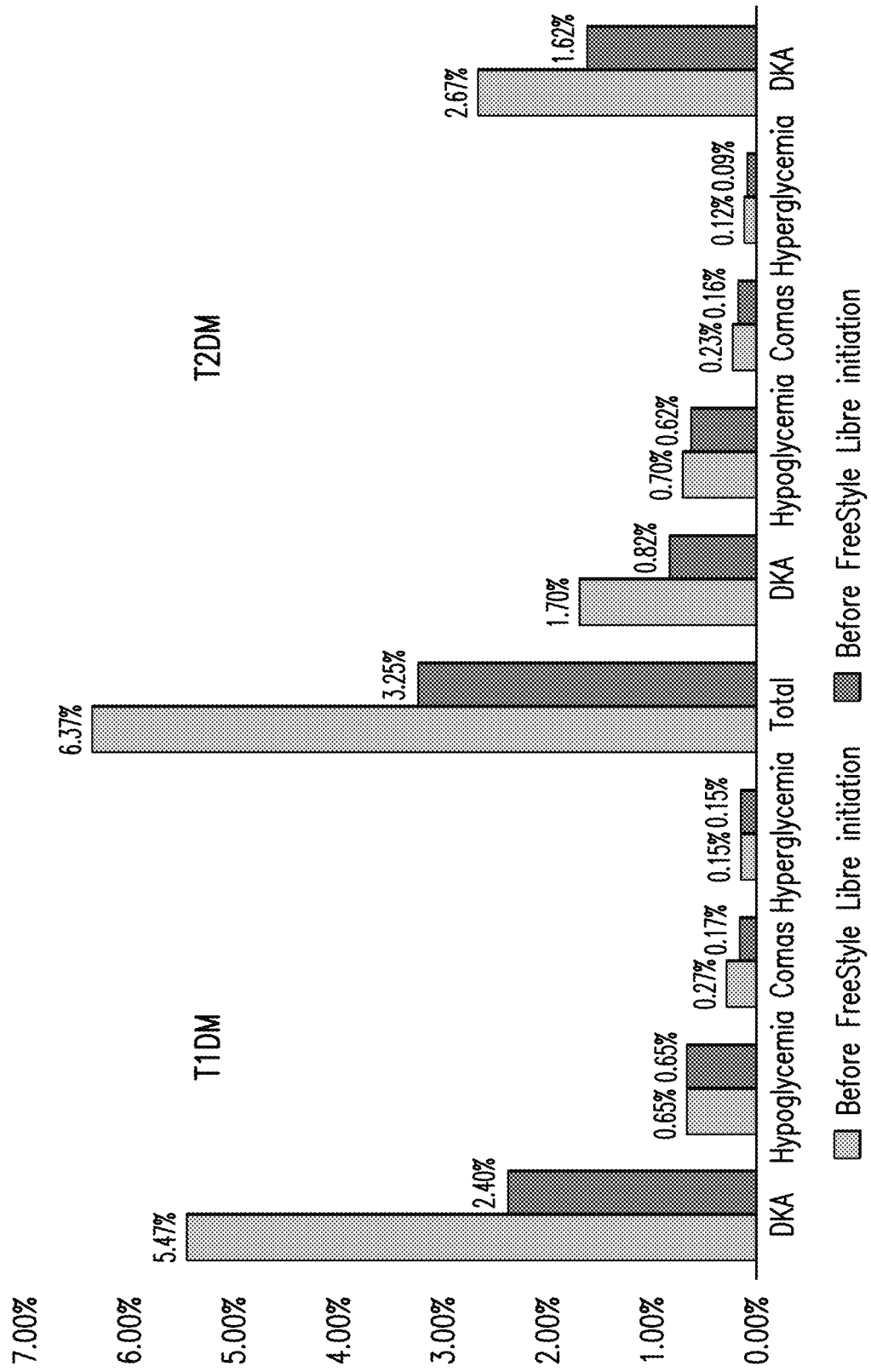

As illustrated in FIG. 20B, 6.4% of persons in the cohort with Type-1 diabetes and 2.7% of persons in the cohort with Type-2 diabetes experienced at least one hospitalization for any ADE in the year prior to prescription of the CGM system. In contrast, 3.3% of persons in the cohort with Type-1 diabetes and 1.6% of persons in the cohort with Type-2 diabetes experienced at least one hospitalization for any ADE in the year after prescription (and use) of the CGM system. In this exemplary embodiment, the decrease is largely driven by a decrease in DKA related hospitalization (excluding comas) for both Type-1 and Type-2 diabetes. A decrease can also be observed for diabetes related comas in both group. Further, a decrease can also be observed in subgroups of CSII and MDI patients.

Figure 20C:
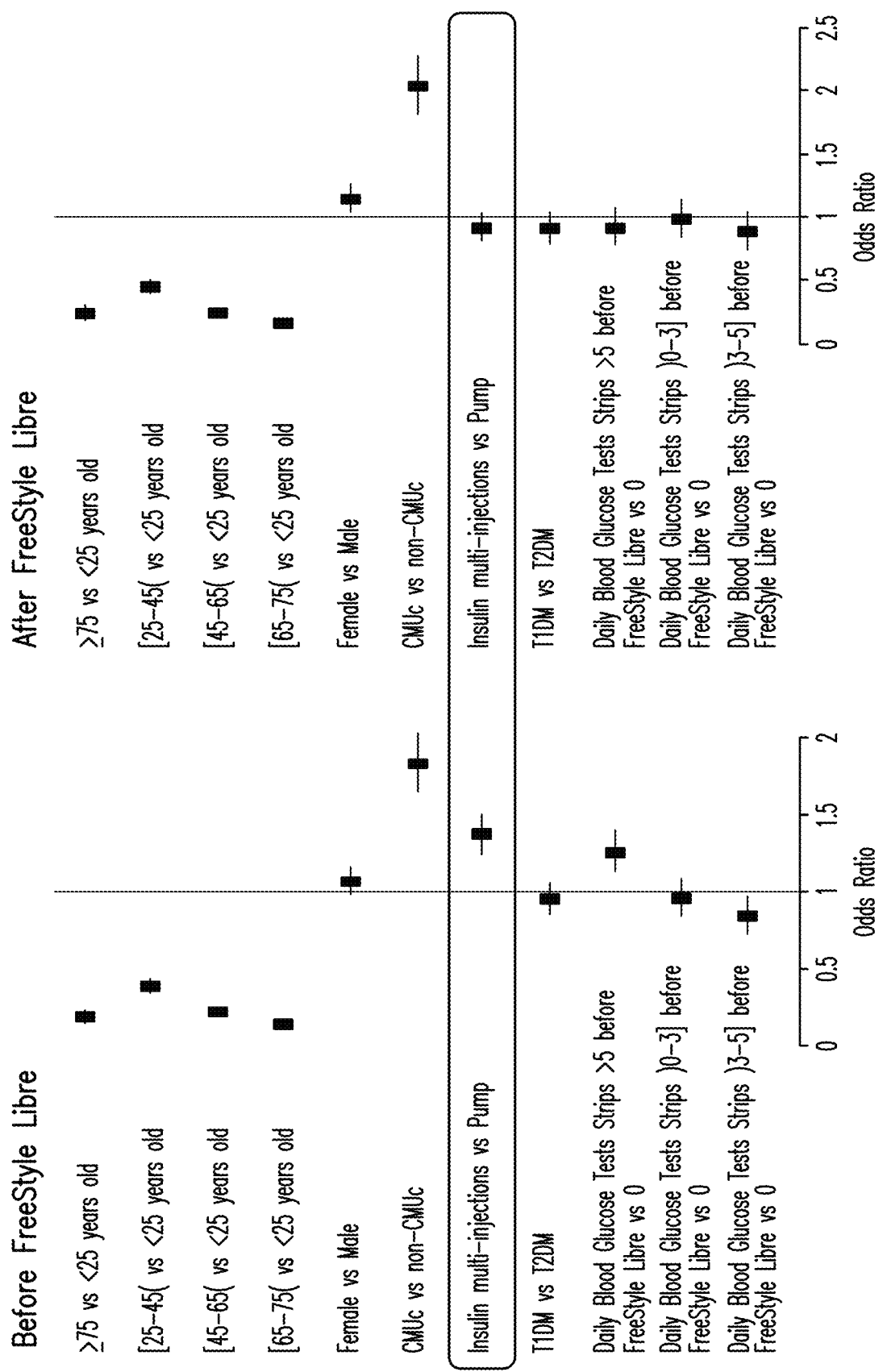

As illustrated in FIG. 20C, in the subgroup of CSII and MDI patients (88% of total population), this exemplary analysis can show that before initiation of a CGM system (e.g., in certain embodiments, the FreeStyle Libre system), the variables age (<25 years old), universal health coverage for people with low socioeconomic status and type of insulin therapy (pens vs pump) were independently associated with higher rates of hospitalizations for acute complications. After initiation, only age and universal health coverage remained independent risk factors.

Reduction in HbA1c Levels

According to an embodiment, a continuous glucose monitor regimen as described herein can reduce levels of HbA1c in patients with diabetes. In preferred embodiments, a CGM regimen can help reduce levels of HbA1c in patients with Type-2 diabetes. The examples provided below further demonstrate benefits of methods and systems as described herein.

Hemoglobin A1C, also known as "glycated hemoglobin" and "HbA1c," refers to hemoglobin that has been joined with glucose within the blood stream. It can be used to provide an average value for glucose levels in a patient's blood, as the amount of HbA1c within a blood stream is directly proportional to the total amount of sugar in a patient's blood. Further, given that the lifetime of red blood cells within a human body (which contain hemoglobin) is approximately 8-12 weeks, the measure of HbA1c also gives an indication of glucose values over these periods. While the specific ideal level of HbA1c a patient should aim for can vary, generally levels under 6.5% are a goal for patients with diabetes. As discussed below, higher levels of HbA1c can pose greater risk of ADEs as well as hospitalization due to other causes.

Example 1

In accordance with an embodiment as described herein, outcome measures include: (a) assessing the data collected within the NDR, regarding both the incident and prevalent users of FreeStyle Libre system in Sweden since mid-2016, stratified by type of diabetes, type of diabetes treatment and method of administering insulin; (b) analyzing changes in recorded HbA1c levels in people with T1DM or T2DM before and after initiating a CGM system (e.g., in certain embodiments, the FreeStyle Libre system), including subgroup analyses according to prior metabolic control, gender and age.

In Sweden, approximately 5.5% of the population have diabetes, the majority of whom have type 2 diabetes (T2DM). The Swedish National Diabetes Register (NDR), covering both primary and secondary care, aims to monitor and improve diabetes care, reducing diabetes-related morbidity and enabling comparisons between a number of clinical outcome measures. Nationwide registration of people with diabetes in Sweden is encouraged at least once a year. By January 2019, the register covered 435,093 adults recorded as having diabetes during the preceding 12 months, constituting 90-95% of all people with diabetes in Sweden. Children up to 18 years of age with diabetes are registered in the SWEDIABKIDS Swedish Childhood Diabetes Registry. In June 2016, the NDR initiated documentation of the usage of sensor-based continuous glucose monitoring (CGM) including the FreeStyle Libre system (Abbott Diabetes Care, Witney, Oxon, UK) amongst adults with diabetes and thus created the opportunity to systematically investigate the impact of a CGM system (e.g., in certain embodiments, the FreeStyle Libre system) in Sweden.

Data can be extracted from the NDR covering the period from 1st January 2014 to the 25th June 2019. In an embodiment, the study population included adults (≥18 years old) with T1DM or with T2DM with a diabetes clinic visit recorded in the NDR after 1st January 2014 and recorded use of the FreeStyle Libre system with an index date of June 2016 or later. The Index date is the date of the first registration where the FreeStyle Libre system use is recorded in the NDR for a person with diabetes. There need not be any specific exclusion criteria.

One focus of this embodiment is understanding the association between new incident users of the FreeStyle Libre system and three distinct variables within the NDR: type of diabetes; HbA1c values; prior use of CGM. Data was collected in line with international consensus standards on HbA1c reporting in mmol/mol and converted into % units according to the IFCC reference system for national standardization. As with all registries, missing values in each of these categories will occur if the information is unknown, or if the assessment was not conducted or recorded by the responsible healthcare professional. Within the NDR cohort of interest the relevant data completeness is provided in FIG. 14I.

Figure 14F:
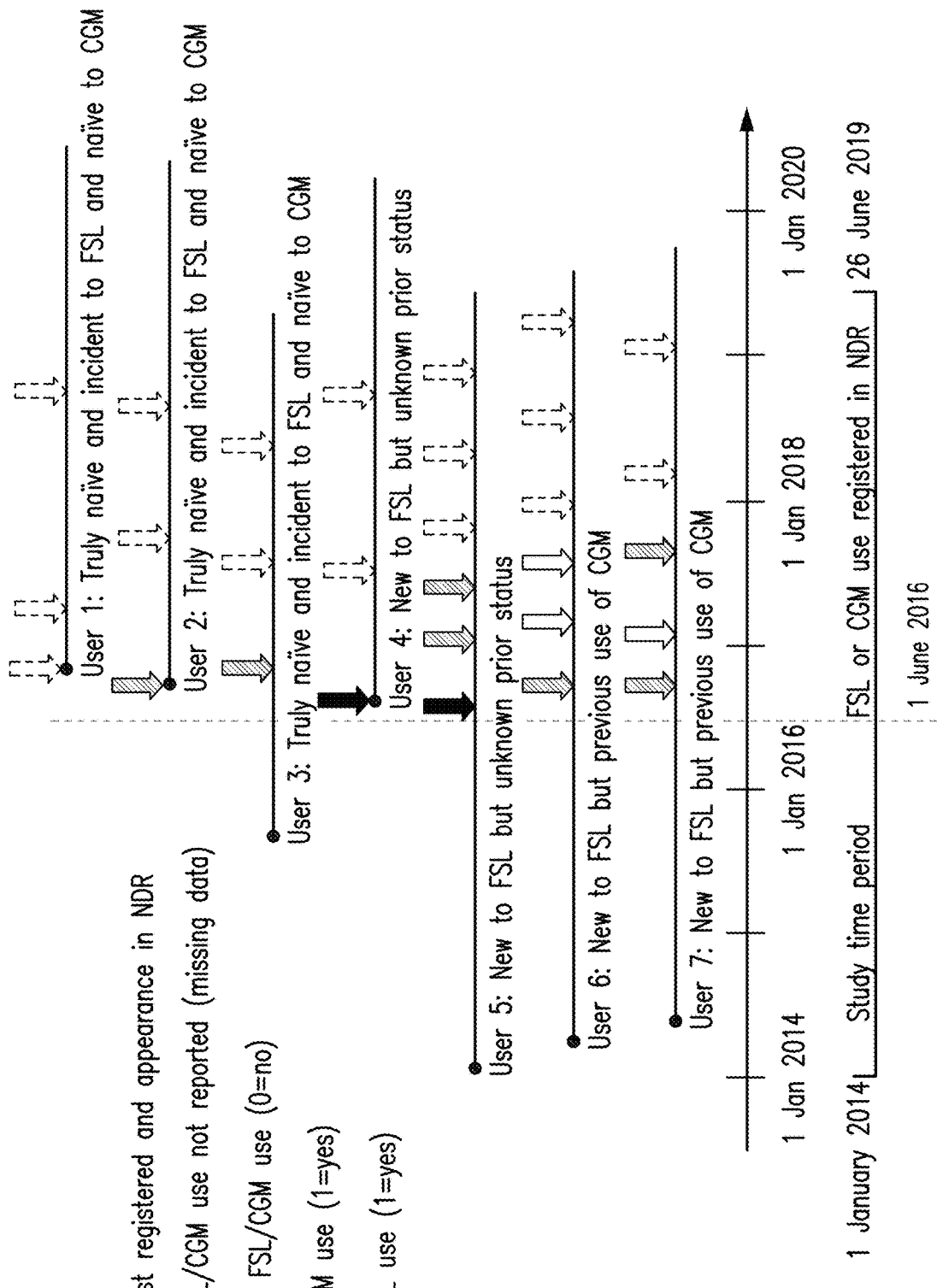

Certain individuals with an NDR index date from June 2016 to June 2019 can be identified within each calendar year. These new incident users were then categorized based on their known or possible use of CGM (other than FreeStyle Libre) prior to their FreeStyle Libre index date. These categories can include: (a) truly naïve, with confirmed absence of use of CGM prior to the index date; (b) new incident users with unknown prior status; (c) new incident users with documented use of CGM prior to the index date. The identification and selection process for new incident users is illustrated in FIG. 14F.

FreeStyle Libre users can be considered to be new incident users for the first 12 months after their initial index date. Thereafter they can be deemed as prevalent users and not included in further analysis. This study is focused on new incident users of the FreeStyle Libre system within the 12 months following their index date. Individuals were deemed to be naïve to use of a CGM device if they were recorded on the registry as not exposed to CGM prior to their first registration with the FreeStyle Libre system in the NDR. Individuals were deemed to have prior use of CGM if the relevant variable within the NDR regarding CGM experience was selected. All other new incident users were classified as prior use unknown. Based on this identification and selection criteria the number of incident new users and prevalent users for FreeStyle Libre during the study period is illustrated in FIG. 14A.

HbA1c can be a recorded variable for people with diabetes in the NDR. The latest laboratory measured HbA1c value within 6 months prior to index date per person can be compared with the HbA1c value recorded between day 91—day 272 after the index date that was closest to the 6-month timepoint (day 181.5) and also between day 272-day 455 after the Index date that was closest to the 12 month timepoint (day 363.5). HbA1c measurements were available within the defined before and after periods for a subset of the total study population who were incident FreeStyle Libre users. Based on these criteria, change in HbA1c can be evaluated for all new incident users based on, for example: type of diabetes; baseline HbA1c prior to the index date; and age. Data for change in HbA1c are presented as absolute mean change in % HbA1c units from baseline at 6 months, not % change as a proportion of baseline.

Figure 14I:
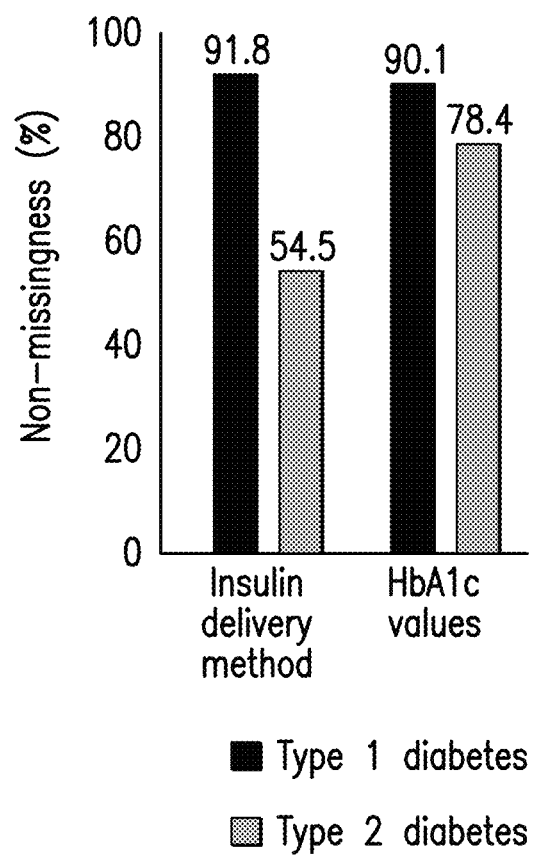

During the period of this embodiment, 36,352 individuals with Type 1 diabetes (T1DM) and 3,202 adults with Type 2 diabetes (T2DM) were identified as having at least one registration of FreeStyle Libre use. HbA1c measurements were available for a subset (n=9,898) of the total population of these incident FreeStyle Libre users. The relevant medication status for the total population of new incident users of the FreeStyle Libre system are provided in FIG. 14H. Certain subjects can have been diagnosed with T1DM or T2DM before or during 2013. Data completeness for the variables under consideration was high for the variables under consideration, especially for T1DM, as shown in FIG. 14I, and intra-patient coherence for type of diabetes was 100%, such that interpretation of our study outcomes is not confounded by errors in classification of diabetes type.

As illustrated in FIG. 14A, in the T1DM category, there were 9481 (26% of incident users) truly naïve adults identified with no prior use of FreeStyle Libre or CGM, as defined by the selection process in FIG. 14F. In the T2DM category there were 827 (26%) truly naïve adults. The most common profile for people with an index date in the NDR was as new to FreeStyle Libre but with unknown prior status, both in T1DM (n=25540, 70%) and in T2DM (n=2243, 72%). The number of users who were new to FreeStyle Libre but with prior experience of CGM was 1328 (4%) in T1DM and 60 (2%) in T2DM.

Figure 14J:
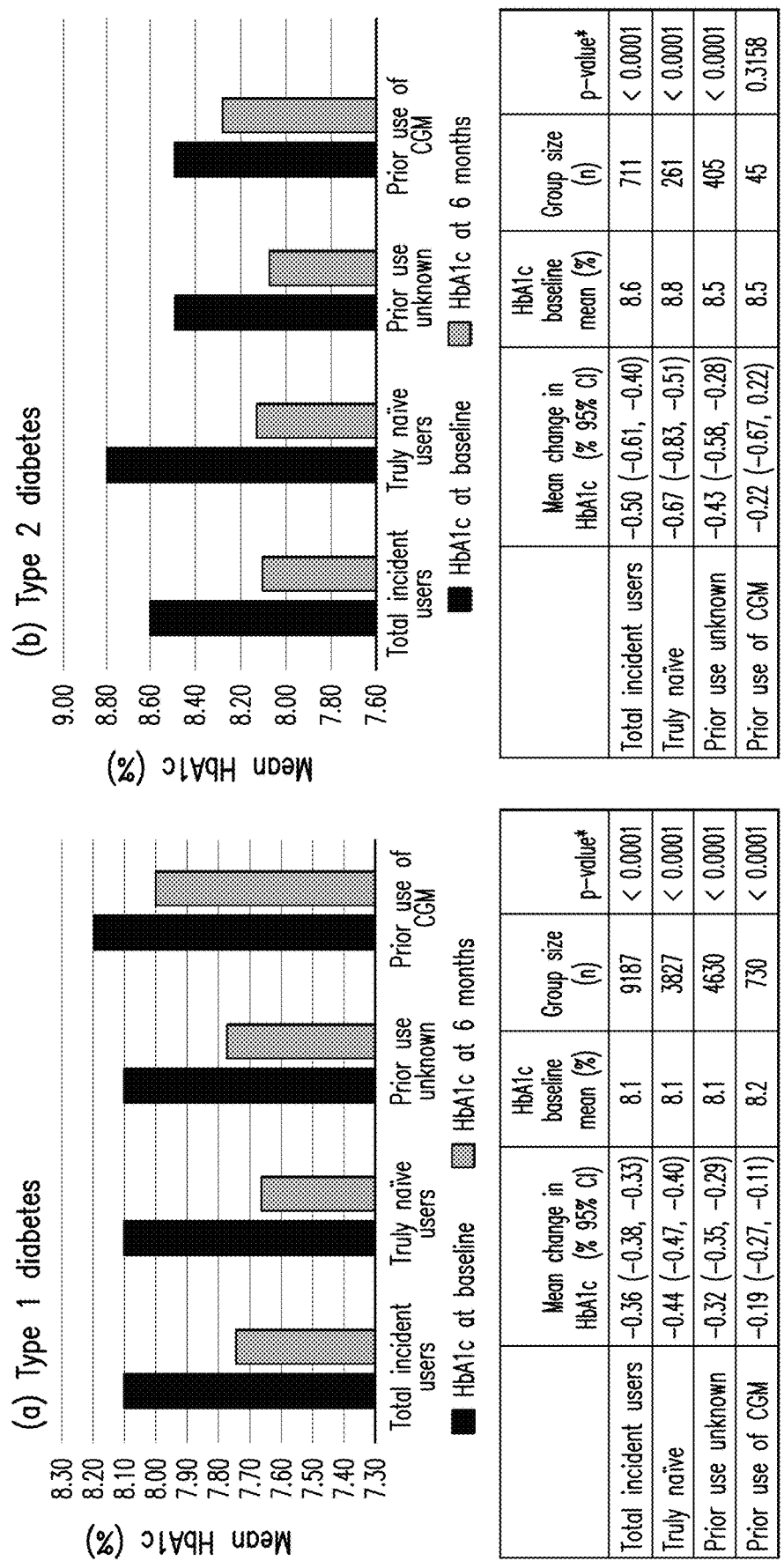

As illustrated in FIG. 14B, based on the definitions above, this embodiment can identify 9187 (25%) incident users with T1DM who had HbA1c measurements registered in NDR that aligned with the 6-month post-index timepoint and 8316 (23%) with HbA1c readings at the 12-month timepoint. For incident users with T2D, there were 711 (22%) and 538 (17%) incident users with 6-month and 12-month post-index HbA1c values, respectively. In this embodiment, analysis of the 9187 incident T1DM users with recorded HbA1c before and after the index date shows a reduction in HbA1c following first registration of the FreeStyle System in the NDR, as illustrated in FIG. 14G. Amongst the total incident users, there was a −0.33% (95% CI −0.36, −0.31) reduction at 12 months (p<0.0001). The fall was most notable for truly naïve users, with a reduction in HbA1c of −0.44% (95% CI −0.48, −0.41; p<0.0001). The users with prior use of CGM also observed a decrease in HbA1c at 12 months using the FreeStyle Libre system (−0.18%; p<0.0001). Observed falls in HbA1c across all incident users with T1DM were evident at 6 months, as shown in FIG. 14J and sustained to the 12-month end point.

In this embodiment, amongst the 711 incident users with T2DM a reduction in HbA1c at 12 months after initiating the FreeStyle Libre system was also shown, as can be seen in FIG. 14G. The fall across the total incident users, was −0.52% (95% CI −0.63, −0.40; p<0.0001). As in T1DM, the fall was greatest for truly naïve users, with a reduction in HbA1c of −0.66% (95% CI −0.84, −0.49; p<0.0001). In common with T1DM, the observed falls in HbA1c across all incident users with T2DM were evident at 6 months, as illustrated in FIG. 14J, and sustained to the 12-month end point.

Figure 15A:
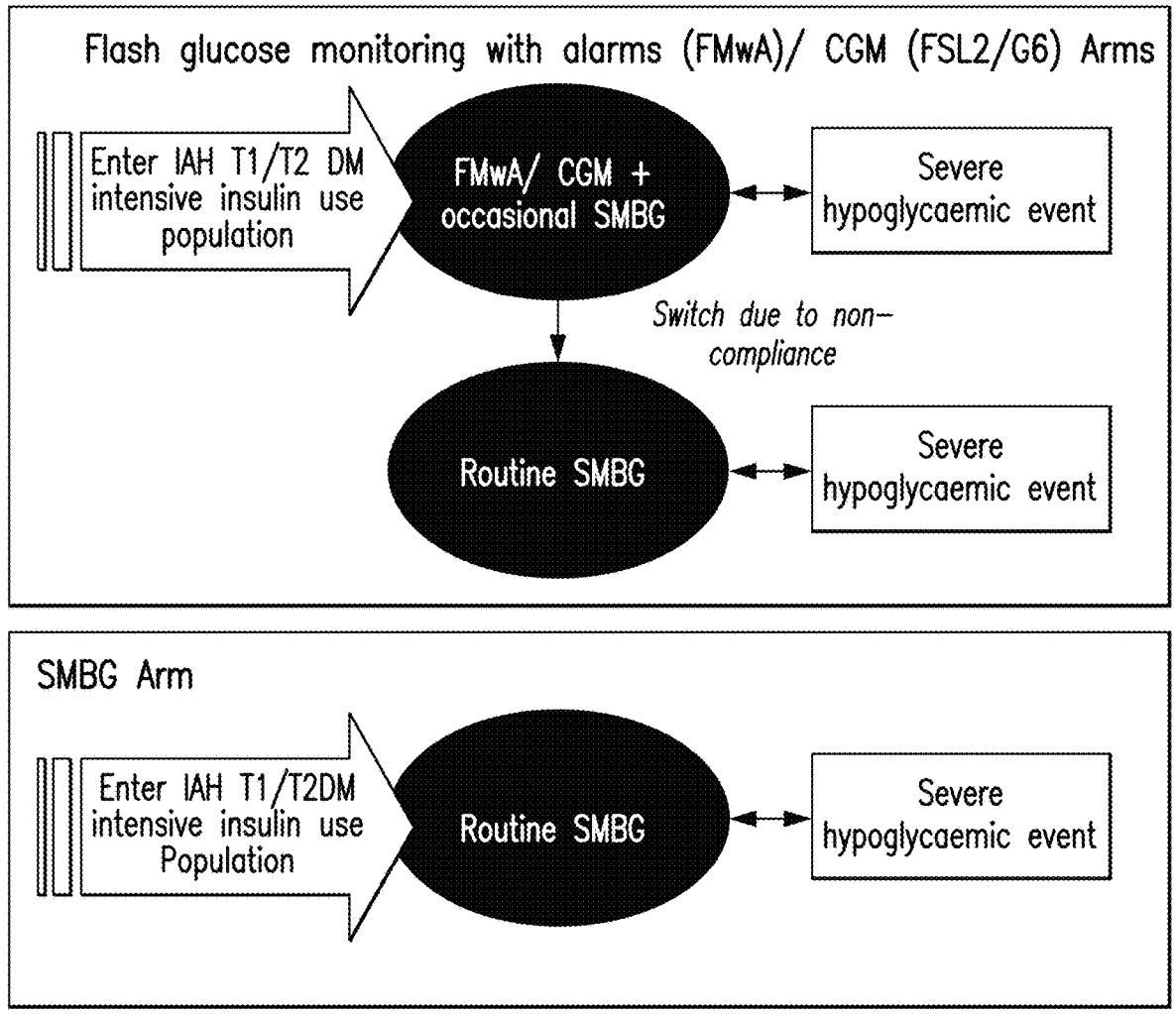
Figure 15B:
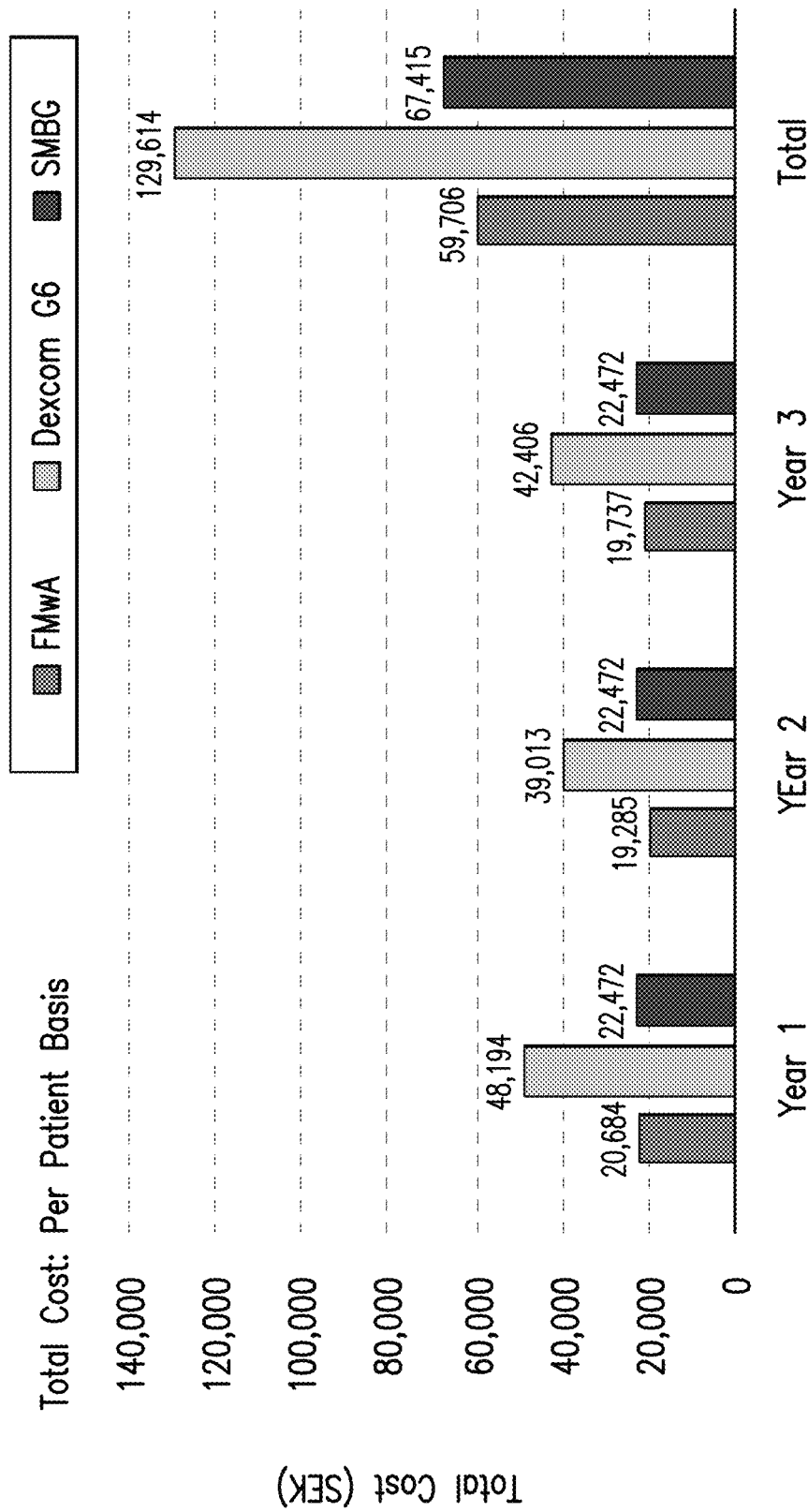
Figure 15C:
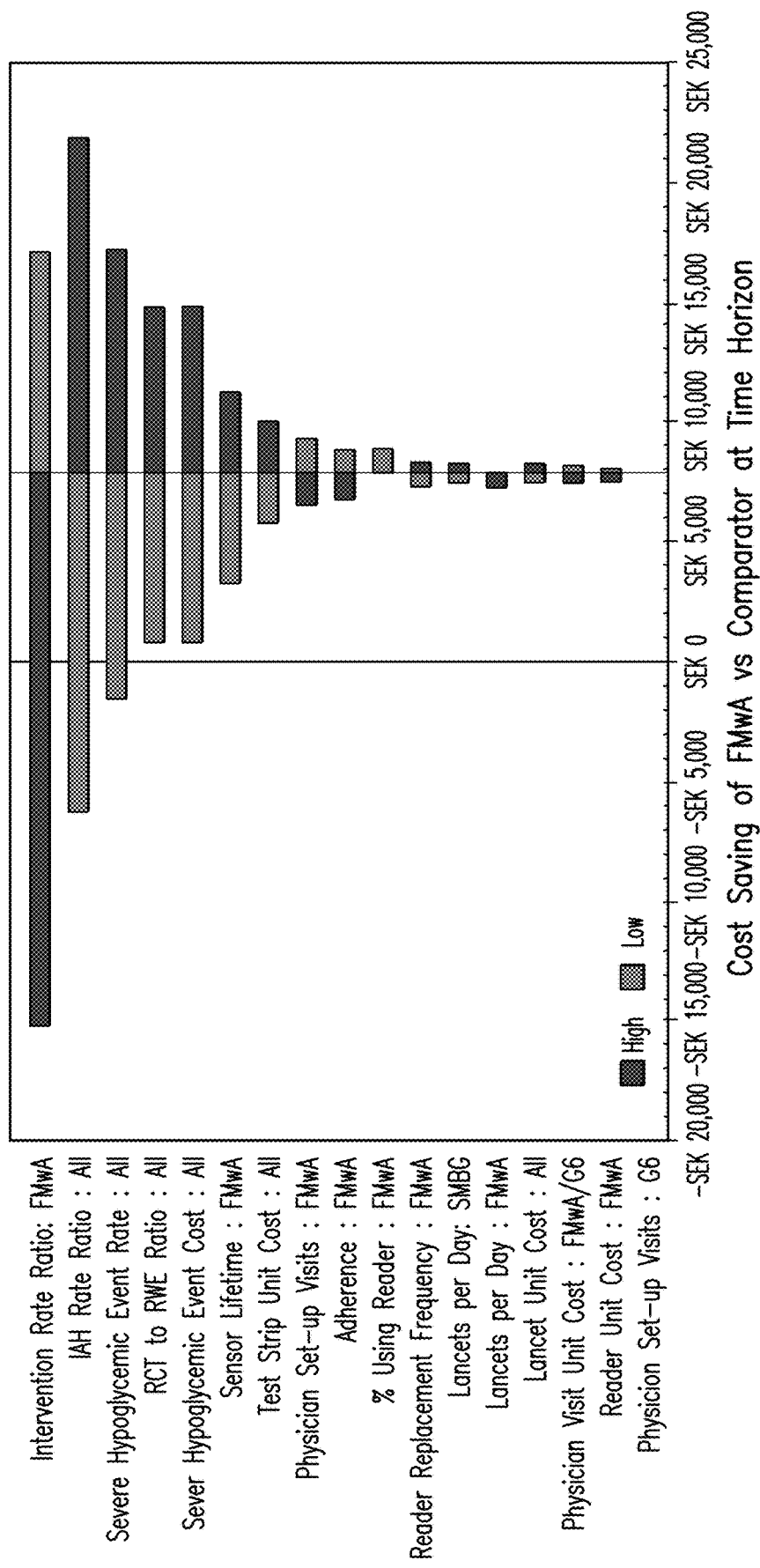
Figure 15D:
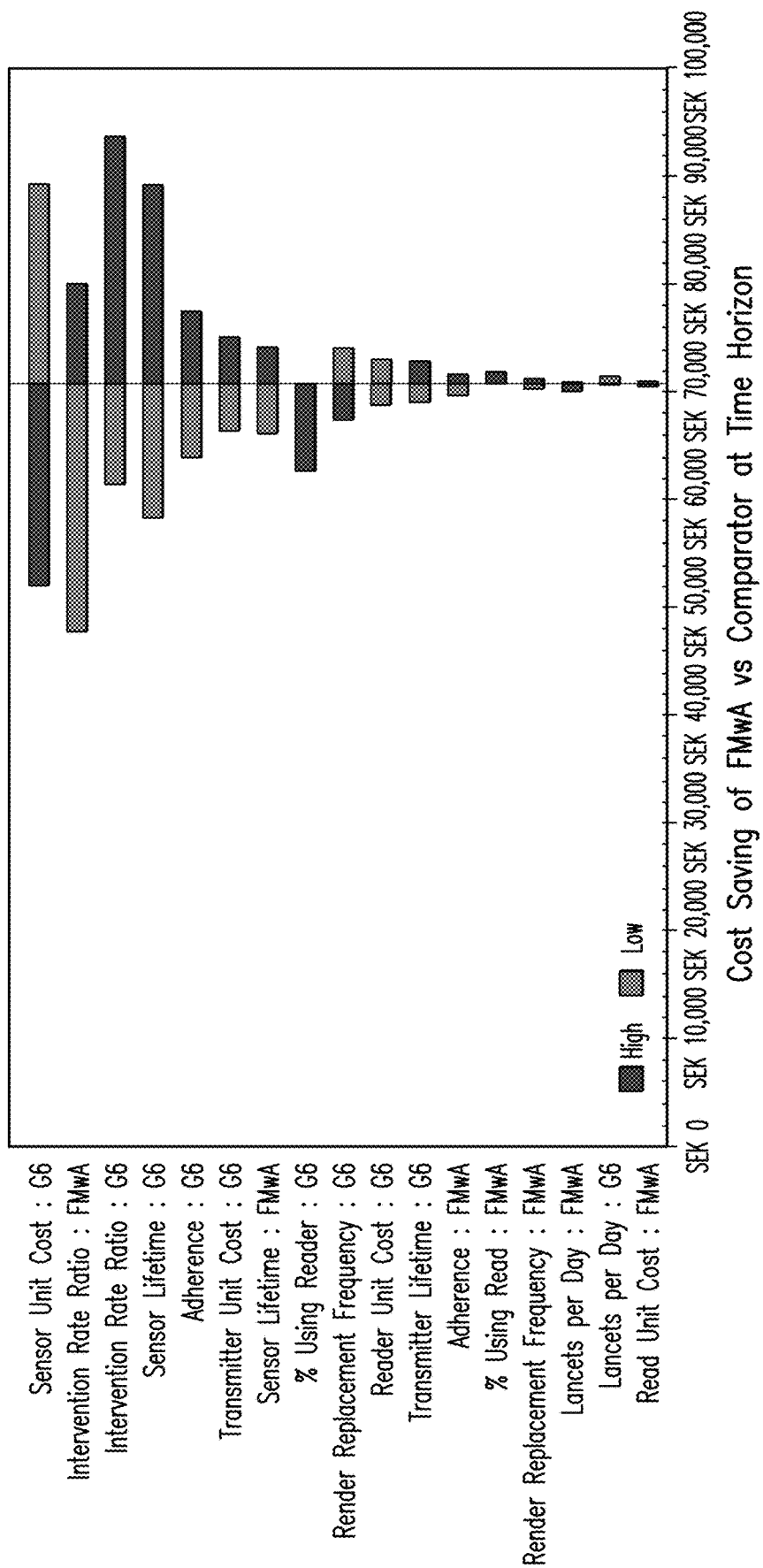

Both in the T1DM and in the T2DM categories, illustrated in FIGS. 14C and 15D, respectively, the benefits of FreeStyle Libre at 6 months after the index date were greatest in the subset of users who had the highest baseline HbA1c measurements. In the T1DM category, for the subgroup with baseline HbA1c<8.0%, there was a small but statistically significant fall of −0.05% (95% CI −0.08, −0.02; p=0.0017) only amongst truly naïve users. As shown in FIG. 14C, reductions in HbA1c were evident in T1DM for all incident users with HbA1c ≥8.0%, after initiation of FreeStyle Libre. These were largest amongst users with baseline HbA1c ≥12.0%, with a fall of −3.1% (95% CI −3.5, −2.7) across all users, but reductions were also present for those with baseline HbA1c 9.0-<12% (−0.98%, 95% CI −1.00, −0.92) and 8.0-<9.0% (−0.42%, 95% CI −0.45, −0.39; Table 3). These falls in T1DM can be seen for all incident users, including truly naïve users, those with unknown prior status and also for subjects with prior use of CGM.

As illustrated in FIG. 14D, no significant change in HbA1c was observed in the T2DM category for users with baseline HbA1c<8.0%, whereas reductions were observed for naïve users and users with unknown prior status with baseline HbA1c 8.0% or above. As with T1DM, falls in HbA1c were evident as baseline HbA1c increased, with reductions of −3.4% (95% CI −4.4, −2.5) for all incident users with HbA1c ≥12.0%.

As illustrated in FIG. 14E, in the T1DM category reductions for incident users aged 18-24 years (−0.37%, 95% CI −0.45, −0.30; p<0.0001) or aged 25-65 years (−0.39%, 95% CI −0.42, −0.37; p<0.0001), who together comprised 82% of the incident group with T1DM, can be observed. People aged 66-74 years and those >74 years each achieved smaller reductions (−0.20% and −0.19% respectively, p<0.0001 in each case. In T2DM, observed reductions in HbA1c at 6 months were skewed towards older subjects, such that no significant change in HbA1c was noted for the 18-24 year age group. The subgroup aged 25-65 years recorded a −0.70% fall in HbA1c at 6 months after the index date (p<0.0001) and those aged 66-74 years had a −0.34% reduction (p<0.0001). No change was observed for adults with T2DM aged >74 years.

As illustrated in FIG. 14G, for incident users of FreeStyle Libre, a correlation can be observed between FreeStyle Libre use after the index date and reductions in HbA1c. For people with T1DM, there was an observed fall in HbA1c across the total incident population of −0.33% at 12 months. Reductions in HbA1c at 12 months after the FreeStyle Libre index date were also evident for incident users with T2DM, who achieved a −0.52% reduction. The greater reduction observed in T2DM may be explained by the higher baseline mean HbA1c of this group, which was 8.6% for all incident users with T2DM prior to the index date, compared to a mean HbA1c of 8.1% in T1DM. Both in T1DM and in T2DM, the reductions in HbA1c were observed at 6 months, as shown in FIG. 14J, and sustained to 12 months.

As illustrated in FIG. 14G, within the incident user groups, those truly naïve to prior use of CGM experienced the most benefit from initiating FreeStyle Libre, with reductions in HbA1c of −0.44% in T1DM and −0.66% in T2DM at 12 months. People with unknown prior use of CGM can achieve reductions, both in T1DM (−0.28%) and in T2DM (−0.49%). An observation of note was that people with T1DM who were registered as prior users of CGM also experienced reductions in HbA1c at 12 months after the index date (−0.18%, p<0.0001).

The value of good glucose-control behaviors independent of the application of FreeStyle Libre can be supported by the data on HbA1c change observed for the separate groups of users stratified by baseline HbA1c prior to the index date, as shown by FIGS. 14C and 15D. Incident users of the FreeStyle Libre system with better initial control, as evidenced by baseline HbA1c <8.0%, achieved reductions 6 months after the index date and not at all in T2DM. Both in T1DM and in T2DM, reductions in HbA1c at 6 months after the index date were more notable for incident users with higher starting baseline values ≥8.0% and greatest for those with HbA1c ≥12.0%. The data according to this embodiment supports that reductions in HbA1c across the total population of incident users at 6 months after the FreeStyle Libre index date are driven by those individuals with higher baseline HbA1c measurements.

Analysis of the data from the NDR can also confirm that the benefits of reduced HbA1c after initiating the FreeStyle Libre system can be extended across all age groups with T1DM and in the majority of those with T2DM. The reduction observed in young adults (aged 18-24 years) with T1DM following intervention with FreeStyle Libre is worthy of note, since this age group can be identified as having the poorest glycemic control as measured by HbA1c as a consequence of psychosocial factors and poor adherence with insulin therapy. This embodiment did show a reduction in HbA1c for the 18-24 years old study group in T2DM, though the population size was small (n=12). Another outcome from this embodiment is that improvements in glycemic control amongst adults with T1DM or T2DM, aged 66-74 years and older, are achievable using the FreeStyle Libre system. This extends previous studies reporting reductions in HbA1c using CGM in subjects with a mean age of 67 years with T1DM or T2DM. This embodiment also shows reductions in HbA1c in T1DM for people aged 74 year or more, in a sizeable study group (n=463) starting from a mean baseline of 8.1%. Use of sensor-based glucose monitoring systems in older and elderly people with diabetes has focused on reducing the risk of hypoglycemia and severe hypoglycemia in this high-risk population rather than directly reducing HbA1c. The data indicates that improvements in long-term glycemic control are possible for older people with T1DM or T2DM.

Example 2

In accordance with an embodiment as described herein, the experience of two treatment centres in Germany, where the FreeStyle Libre system was introduced to patients with either T1D or T2D on insulin as part of standard care, and HbA1c values recorded over 12 months following initiation was analyzed. According to this embodiment, the retrospective observational analysis of diabetes management in a real-world setting shows that there can be a reduction in HbA1c in patients with either T1D or T2D on insulin following the introduction of the FreeStyle Libre system to their standard care. Additional details of this embodiment are disclosed in *Improving HbA1c Control in Type 1 or Type 2 Diabetes Using Flash Glucose Monitoring: A Retrospective Observational Analysis in Two German Centres*, which was originally published in Diabetes Therapy, Volume 12, Pages 363-72, 2021, Springer and can be accessed at the website https://link.springer.com/article/10.1007/s13300-020-00978-9, and is incorporated by reference herein in its entirety.

Patient data can be obtained from two German clinical centers, the Gemeinschaftspraxis Drs. Klausmann in Aschaffenburg and Zentrum für Diabetes and Gefäßerkrankungen Münster. Both centers are established in delivering standard outpatient care for people with diabetes within the German healthcare system. De-identified patient records were examined to select subjects with either T1D or T2D on insulin who were initiated on the FreeStyle Libre system as part of standard care. No selection criteria were applied other than treatment with FreeStyle Libre as part of standard care. The data reflect consecutive adult patients started on FreeStyle Libre between November 2015 and September 2018. Laboratory tested HbA1c values were recorded for all patients prior to the start of FreeStyle Libre using standard clinical laboratory reference analyzers, with at least one HbA1c value that was established after starting. Not all subjects had data recorded at each interval across the 12-month analysis period, as a consequence of the time of their start of FreeStyle Libre or a missed attendance. A total of 131 patients with T1D and 176 patients with T2D on insulin met the inclusion criteria and were included in the analysis. The age of patient ranged from 24-92 years. All patients were recorded as being on insulin therapy for the duration of the analysis, either on multiple daily doses of insulin (MDI), mealtime insulin only or continuous subcutaneous insulin infusion (CSII). The baseline characteristics of the study population are illustrated in FIG. 16A.

Matched paired data can be analyzed using both the data analysis tools in Microsoft Excel 2016 and the R Project for Statistical Computing (www.r-project.org) software version 3.6.2. The level of significance was set at 0.05 or better. A linear model can be used to investigate the trend of mean HbA1c values across the measurement time points from baseline onwards. Student's t-test was used to compare means of matched paired data and unmatched data as appropriate to the analysis. Tukey's contrast analysis was used to compare the means of every outcome timepoint from 3 months onwards. Linear regression was used to identify the predicted change in HbA1c given the input baseline HbA1c.

Figure 16B:
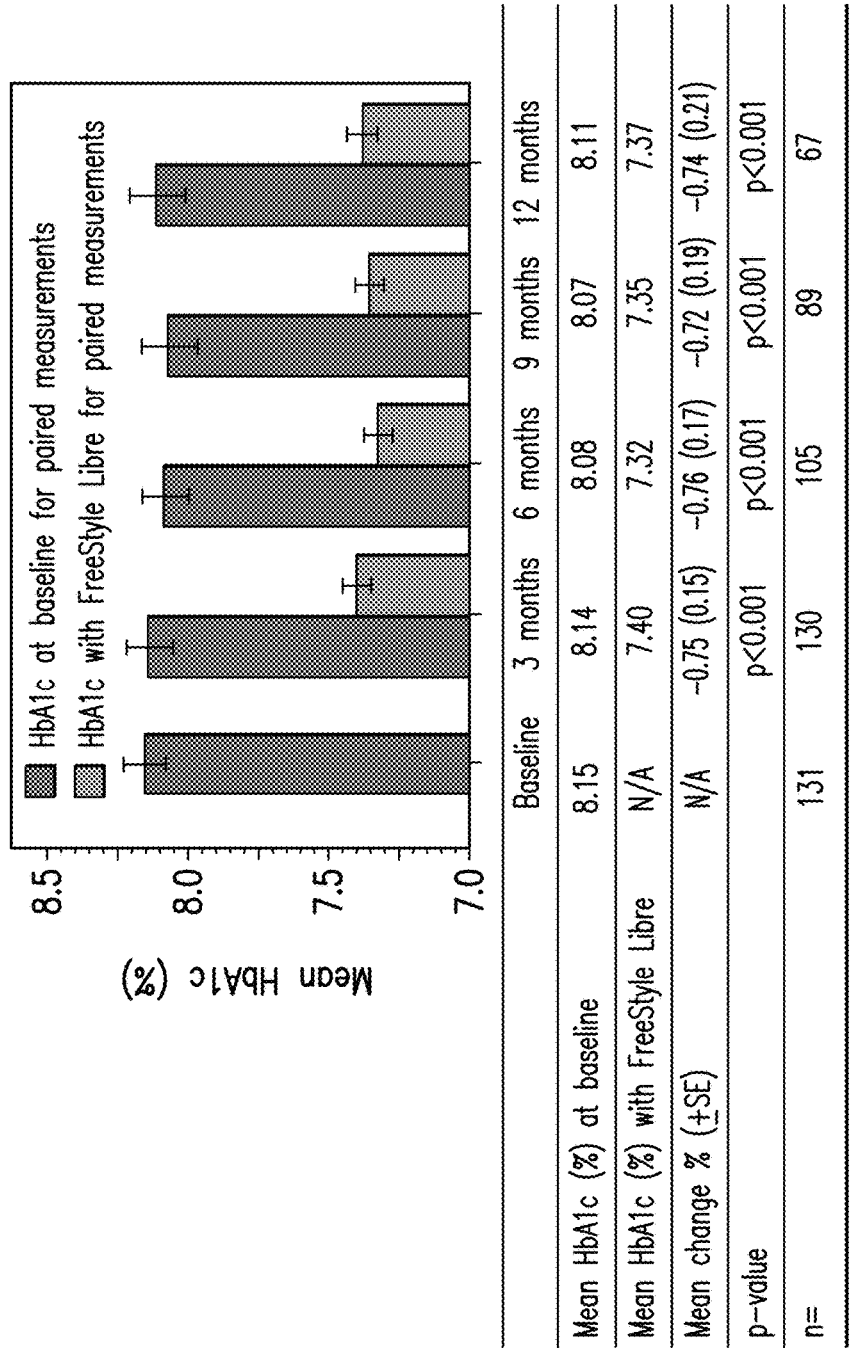
Figure 16C:
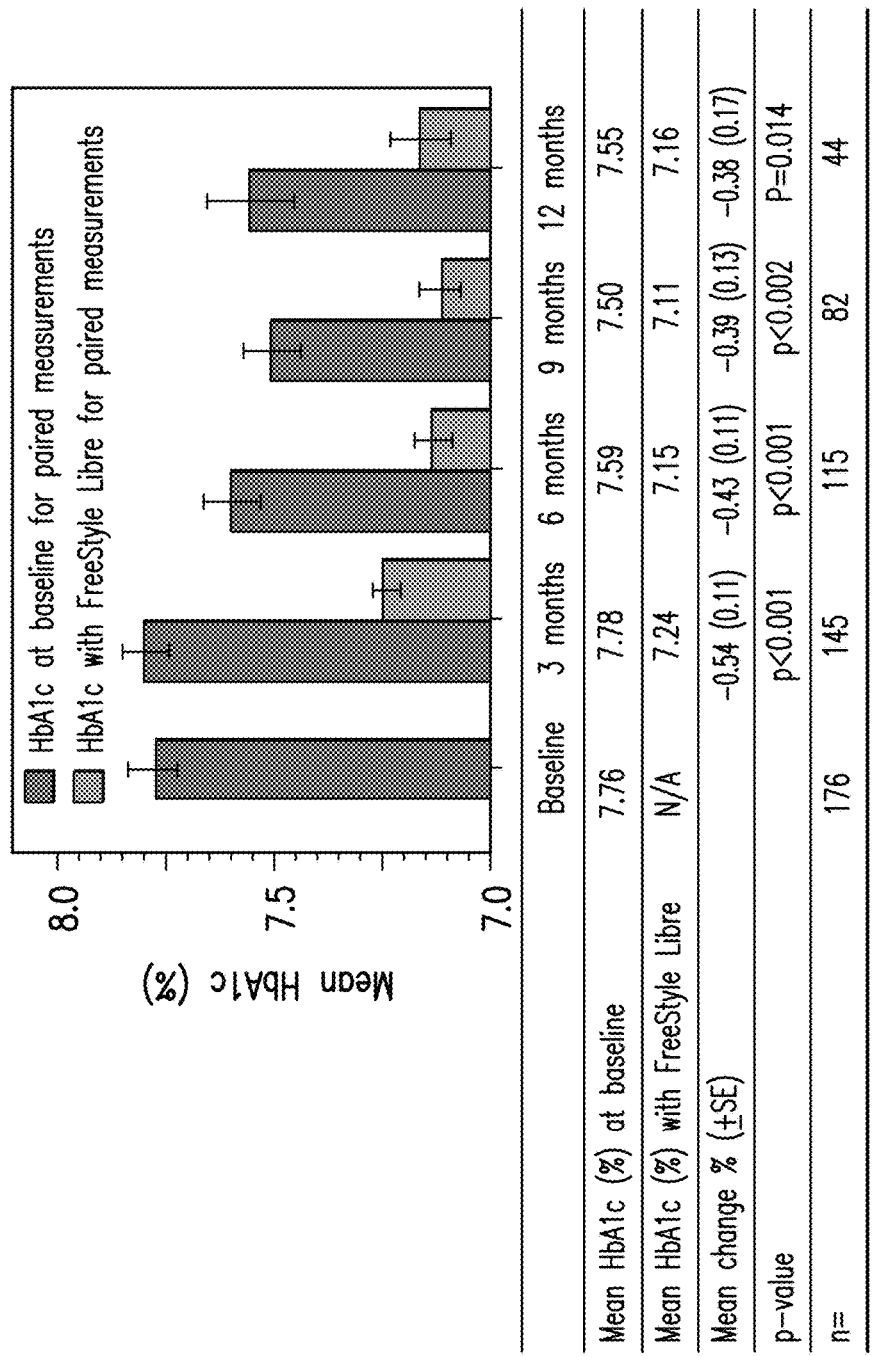

A statistically significant reduction in mean HbA1c from baseline was detected at all timepoints in 131 patients with T1D, as shown in FIG. 16B. Mean starting baseline (±SE), was 8.15% (±0.15%). HbA1c values decreased by −0.75% (±0.15%) at 3 months, by −0.76% (±0.17%) at 6 months, by −0.72% (±0.19%) at 9 months and by 0.74% (±0.21%) at 12 months ($p<0.001$ in all cases). A similar trend was seen in 176 patients with T2D on insulin, as shown in FIG. 16C, with a mean baseline HbA1c of 7.76% (±0.12%). HbA1c was reduced by −0.54% (±0.11%) at 3 months, by 0.43% (±0.11%) at 6 months, by −0.39% (±0.13%) at 9 months and by −0.38% (±0.17%) at 12 months ($P<0.001$ at 3, 6 months, $P<0.002$ at 9 months; $P=0.014$ at 12 months).

Tukey contrast analysis both in T1D and T2D can show a difference between timepoints after 3 months that was not significant, indicating that the greatest impact on HbA1c values was observed within the first 3 months of use of the FreeStyle Libre system and sustained for 12 months.

Figure 16D:
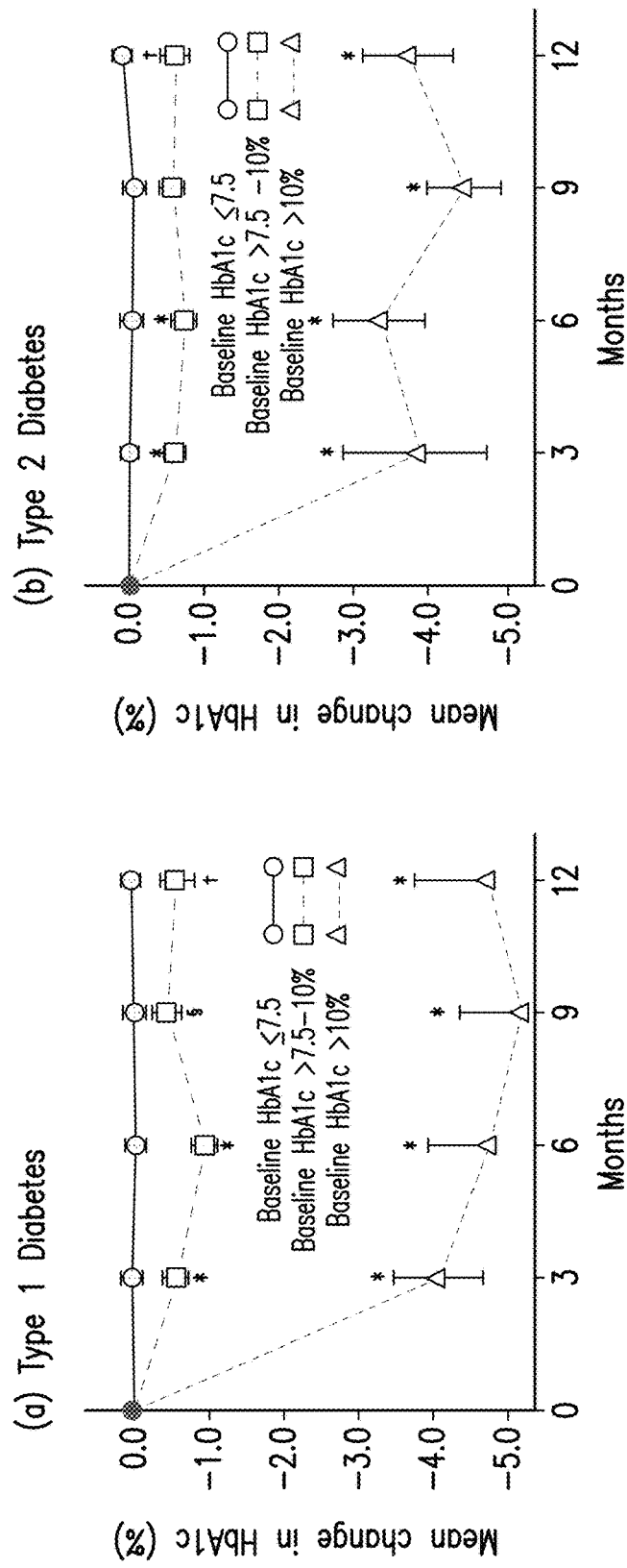

As illustrated in FIG. 16D, in an exemplary subgroup analysis centered on metabolic control, patients can be stratified into those with baseline HbA1c≤7.5% (58 mmol/mol), those with baseline HbA1c >7.5-10% (>58-86 mmol/mol) and those with HbA1c >10% (>86 mmol/mol). This can show that patients with T1D or T2D on insulin, with a baseline HbA1c >7.5% (>58 mmol/mol), can achieve a reduction in HbA1c over time with FreeStyle Libre whereas those with HbA1c levels ≤7.5% (58 mmol/mol) did not. For all patients with HbA1c in the range >7.5-10% (>58-86 mmol/mol) the change at 12 months was significant but was considerably greater amongst patients with HbA1c >10% (86 mmol/mol). For people with T1D, those with mean HbA1c >7.5-10% (>58-86 mmol/mol) achieved a clinically significant reduction of 0.59% (±0.19%) after 12 months, from a mean HbA1c from 8.49% to 7.90% (FIG. 3a; $p<0.01$). For those with a baseline HbA1c >10% (86 mmol/mol) there was a mean 4.66% (±0.87%) reduction, from 11.83% to 7.17% (FIG. 3a; $p<0.001$). In people with T2D on insulin and HbA1c >7.5-10% (>58-86 mmol/mol), the reduction in mean HbA1c 12 months after starting FreeStyle Libre was 0.62% (±0.22%), from 8.43% to 7.81% (FIG. 3b; $p<0.01$) and for patients with HbA1c >10% (86 mmol/mol) the reduction at 12 months was 3.73% (from 11.4% to 7.67%; $p<0.01$).

Linear regression can be used to predict a change in HbA1c at 3 months, given the input baseline HbA1c. Therefore, baseline HbA1c can be strongly negatively correlated with subsequent change in HbA1c, both in T1D ($R2=0.602$, $p<0.001$) as shown in FIG. 16E, and in T2D ($R2=0.698$, $p<0.001$), as also shown in FIG. 16E. In T1D, on average, for each percentage increase in mean initial HbA1c, the mean change in final HbA1c at 3 months falls by an additional 0.72% (95% CI −0.83 to −0.62). In T2D, for each percentage increase in mean initial HbA1c, the mean change in final HbA1c falls by an additional 0.71% (95% CI −0.79 to −0.64).

The outcomes from data collected by two German diabetes treatment centers show improvements in HbA1c for patients with either T1D or T2D on insulin. The reductions in HbA1c occur within the first 3 months and are sustained over a 12-month period. Linear regression can show that a predictor of a reduction in HbA1c after starting the FreeStyle Libre system is HbA1c at baseline. For each percentage increase in mean initial HbA1c, the mean change in final HbA1c at 3 months in T1D falls by an additional 0.72%, and by 0.71% in T2D on insulin. As illustrated in FIG. 16D, the subgroup analysis of subjects based in prior metabolic control can show that a reduction in HbA1c from baseline is achievable for people with T1D or T2D on insulin with mean HbA1c >7.5-10% (>58-86 mmol/mol) after starting the FreeStyle Libre system, with greater reductions for patients with HbA1c above 10% (>86 mmol/mol). People with T1D or T2D on insulin and good prior glucose control (mean HbA1c≤7.5% at baseline) do not see a significant change in their HbA1c over 3-12 months.

Those patients with tighter long-term glucose control, as evidenced by a starting HbA1c level below 7.5%, are likely to be improving their metabolic control using the FreeStyle Libre system, but not by reducing the HbA1c.

One consequence of immediate access for users of the FreeStyle Libre system to a range of glycemic information that can improve their decision making during daily diabetes self-care. These can include their glucose status in real time, the trend arrows that indicate the direction and speed of change in their glucose status and the summary reports that are available to them via the readers or smartphone apps that they use to scan and collect glucose data. This information can facilitate an in-depth awareness of their daily life and allows for effective treatment decisions that are not possible with SMBG testing. The intuitive nature of CGM systems mean that this improvement in self-care behavior starts following the application of the first glucose sensor and is sufficient for a change in long-term HbA1c to be evident after 3 months. Persons with T2D on insulin therapy can see a considerable benefit in long-term HbA1c when managed with flash glucose monitoring.

The results according to the disclosed embodiment support improved glucose control, as measured by HbA1c, using flash glucose monitoring in patients with either T1D or T2D on insulin. The retrospective observational analysis, according to this embodiment, shows that the introduction of the FreeStyle Libre system is associated with a reduction in HbA1c levels in people with diabetes on insulin within 3 months of initiation and the results are sustainable over 12 months. Furthermore, patients whose baseline HbA1c levels are above 7.5% (58 mmol/mol) can see an HbA1c reduction. These improvements in glucose control can contribute to a reduction in the long-term risk of microvascular and macrovascular complications and the consequent costs of morbidity and mortality associated with diabetes.

Example 3

In accordance with an embodiment as described herein, a kinetic model is disclosed which can incorporate the patient-specific parameters of red blood cell production, elimination (i.e. RBC lifespan) and the apparent hemoglobin glycation rate governed by the glucose transport across red blood cell ("RBC") membrane and glycation of the hemoglobin molecule intracellularly. The model has been developed and validated with data from European clinical trial cohorts and one specific continuous glucose monitor (CGM) technology (FreeStyle Libre®, Abbott Diabetes Care). Additional details of this embodiment are disclosed in *Accurate prediction of HbA1c by continuous glucose monitoring using a kinetic model with patient-specific parameters for red blood cell lifespan and glucose uptake*, which was originally published in Diabetes and Vascular Disease Research, Volume 18, Issue 3, 2021, Sage Journals and can be accessed at the website https://journals.sagepub.com/doi/full/10.1177/14791641211013734, and is incorporated by reference herein in its entirety.

RBC production and removal are in balance during homeostasis, with the production in the bone marrow stimulated by erythropoietin released by the kidney in response to detected oxygen levels. Removal and recycling of RBCs are primarily performed by macrophages in the spleen, with a selectivity for damaged and aged RBCs that have decreased motility and flexibility, necessary to traverse across the capillary bed. In addition, there is a variable and dynamic response available in the liver by monocytes to remove RBCs under conditions of degraded RBC integrity. These complex mechanisms can result in varying RBC survival, and thus their exposure to circulating glucose levels that drive the intracellular hemoglobin glycation detected by the HbA1c assay. Certain experimental evidence has shown there is a variation of mean RBC lifespan between hematologically normal individuals, but accurate assessment of RBC lifespan is both difficult and time-consuming, and therefore beyond the capability of routine diabetes management. Further, besides individual variation, there are growing indications that there are consistent differences in RBC survival across ethnic groups, making further understanding and elucidation imperative in order to deliver effective care for all individuals.

Beyond RBC survival, a second variable factor in determining HbA1c is the facilitated cross-membrane transport of glucose into RBCs by GLUT1 transporters. The majority of glucose is consumed by the Embden-Meyerhof-Parnas pathway to support energy requirements of the RBC. The fraction of glucose that binds irreversibly to hemoglobin, resulting in "glycated hemoglobin", is detected via the HbA1c assay.

Figure 17A:
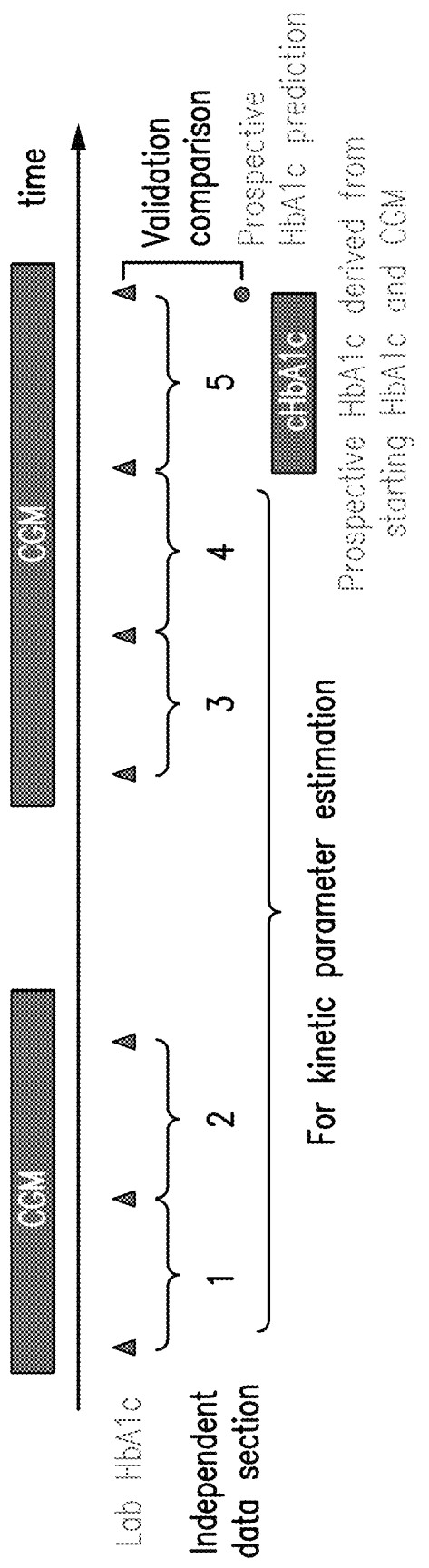

The kinetic model according to this exemplary embodiment can take one or more data sections to estimate the patient-specific kinetic parameters. Each data section consists of a frequent glucose trace (at least every 15 minutes) between two lab HbA1c values at least two weeks apart. To ensure acceptable accuracy of estimates, it can be required that at least 80% of CGM data points be present, and any continuous gap be less than 24-hours within a data section. The final data section of each subject was excluded from the parameter estimation. The parameters can then be fixed and used to prospectively calculate an HbA1c value (termed "cHbA1c") for comparison to the final lab HbA1c. It can be required that each subject had a total of three or more data-sections, therefore at least two for parameter estimation. FIG. 17A is an example of data sections and prospective evaluation for an individual.

In this exemplary embodiment, all selected subjects had type 1 diabetes treated with the sensor-augmented pump (SAP) from Kobe University Hospital in Japan. All glucose readings were collected by a fingerstick-calibrated CGM sensor (Enlite™, Metronic). HbA1c values were measured by a central laboratory (Kobe University Hospital, HPLC with Arkray HA8181). Within available data collected by Kobe University, 51 subjects met the quality and sufficiency criteria for analysis, as shown in FIG. 17B.

For each individual, two kinetic parameters can be calculated using the kinetic model with all data sections except the last. These parameters are RBC turnover rate kage (or RBC lifespan=1/kage) and the apparent hemoglobin glycation rate kgly (dominated by cross-membrane glucose uptake). As illustrated in FIG. 17A, the prospective use of the model with the kinetic parameters on the final data section produced cHbA1c throughout the data section and comparison was at the end value that aligned with the lab HbA1c. Both kinetic parameter estimation and prospective cHbA1c calculations were performed with equation 8 reported previously, which is listed below for convenience.

$$A1c_z = EA_z(1 - D_z) + \sum_{i=1}^{z-1}\left[EA_i(1 - D_i)\prod_{j=i+1}^{z} D_j\right] + A1c_0 \prod_{j=1}^{z} D_j$$

Where $D_i$ can represent $e^{-(k_{gly}*g_i + k_{age})t_i}$ and $EA_i$ can represent $g_i/(k_{age}/k_{gly}+g_i)$. The value $A1c_z$ is equivalent to cHbA1c at the end of time interval $t_z$. And the intra-RBC glucose level $g_i$ can represent $(K_M*G_i)/(K_M+G_i)$ depends on the blood glucose level Gi and glucose binding affinity to GLUT1, wherein $K_M$ can equal approximately 26.2 mM.

For comparison to the final lab HbA1c, the corresponding estimated HbA1c (eHbA1c) and glucose management indicator GMI values were determined by 14-day average CGM glucose (AG). The performances of these methods were compared by the agreements between the estimated and lab HbA1c values. Specifically, the absolute deviation distributions and R2 values from Pearson's correlation of linear regression can be compared. Estimated HbA1c (eHbA1c) and Glucose Management Indicator (GMI) can be calculated from average glucose with the following regression equations:

$$GMI_\% = AG_{mg/dL} * 0.02392 + 3.31$$

$$eHbA1c_\% = (AG_{mg/dL} + 46.7)/28.7$$

Distributions can be further characterized by the mean and standard deviation for normally distributed data and by median and interquartile range for non-normally distributed data. Any glucose trace gaps less than 45 minutes had missing values imputed with the nearest observation or average of nearest observations if both were available (the observations immediately before or after the gap). For a longer gap, each missing value was imputed with the average of the observations at the same time in previous and next days. Python/SciPy can used for all analyses, though other known programming languages are contemplated.

Based on the exemplary model, HbA1c is sensitive to $k_{gly}$ and $k_{age}$ during or after a day-to-day glucose change. In a period of steady day-to-day glucose, HbA1c is sensitive to the ratio of $k_{gly}$ or $k_{age}$. For this reason, it can be more difficult to estimate kinetic parameters than their ratio. As a consequence, a reasonable HbA1c prediction, for steady state, can be provided when only the ratio of $k_{gly}$ and $k_{age}$ is available. Therefore, less data sections can be required for HbA1c prediction than RBC lifespan (or $k_{age}$) estimation.

Since the exemplary model also assumes no $k_{gly}$ and $k_{age}$ change during the study period, a higher confidence group was defined for subjects with more day-to-day glucose change (top ⅔ or between-day glucose CV >17%), and no major life/therapeutic changes that can affect RBC metabolism. These changes can include, but are not limited to, childbirth, iron deficiency treatment, hospitalization, and major drug changes. From the higher confidence group, those with more than 10 data sections were evaluated further to examine the effect of increasing the number of data sections to improve the accuracy of kinetic parameter and HbA1c estimations. By sequentially including additional data sections, the mean absolute deviations to the final RBC lifespan and lab HbA1c for each individual can be calculated. This can set an expectation on the numbers of data section one will need to collect for good estimations on the RBC lifespan and HbA1c.

Prospective use of the exemplary model according to this embodiment with patient-specific kinetic constants produced more accurate predictions of the lab HbA1c compared to eHbA1c and GMI. FIG. 17C illustrates the comparison metrics of HbA1c estimation using the kinetic model, eHbA1c and GMI. The kinetic model can have the smallest median and mean absolute deviation of 0.10% and 0.11% (1.1 and 1.2 mmol/mol). The mean absolute deviations from eHbA1c and GMI were larger (p<0.001), approximately four to five times as large. As an HbA1c difference of 0.5% (5.5 mmol/mol) is usually considered clinically relevant, the rates of correspondence within this range was evaluated. The cHbA1c has minimal clinically relevant deviation with 92.3% within 0.5% (5.5 mmol/mol), compared to eHbA1c and GMI at 65.5% and 73.1%, respectively.

Figure 17D:
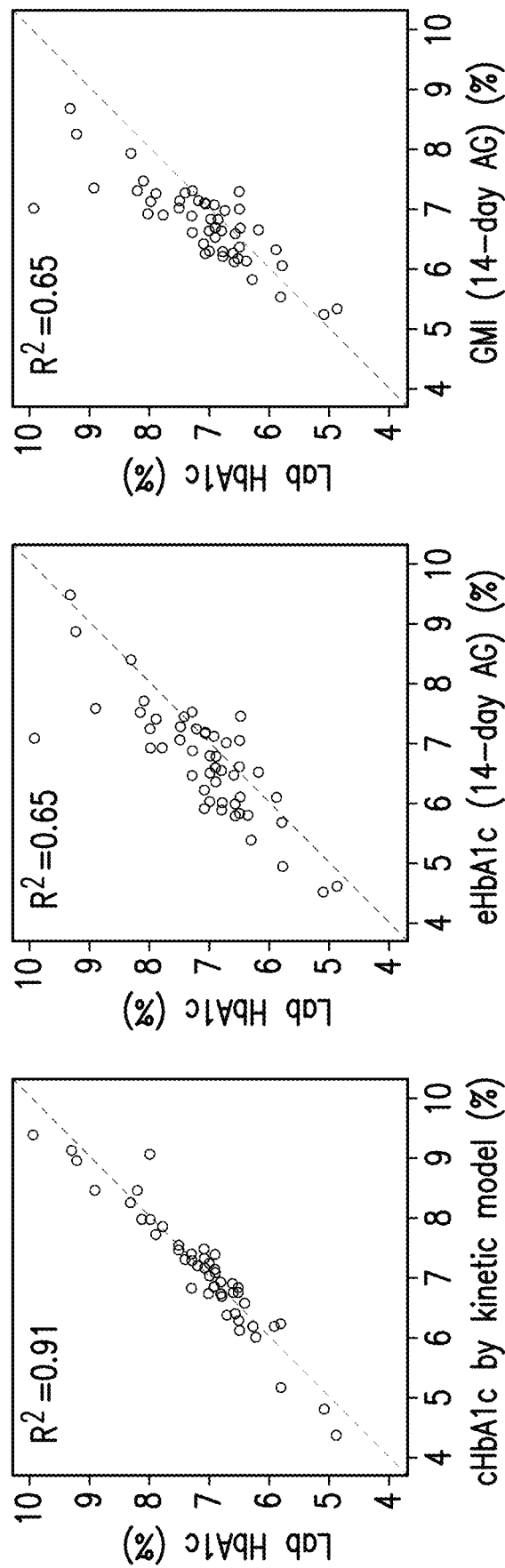

FIG. 17D illustrates the improved agreement between cHbA1c and laboratory HbA1c, compared to eHbA1c and GMI. The cHbA1c had no overall bias, whereas the eHbA1c and GMI had biases of −0.4% and −0.3%, respectively. The superior accuracy of cHbA1c was also indicated by a tighter association with the laboratory HbA1c, with coefficient of determination (R2) of 0.91 compared to 0.65 for both eHbA1c and GMI. Laboratory HbA1c ranged from 4.9% to 9.9% (30 to 85 mmol/mol), with a mean value of 7.1% (54 mmol/mol). At this mean value, cHbA1c had a 95% prediction confidence interval range from 6.9% to 7.3% (52 to 56 mmol/mol), which is a 78% reduction compared to eHbA1c (6.5% to 8.3% or 48 to 67 mmol/mol) and GMI (6.5% to 8.3% or 48 to 67 mmol/mol).

According to this exemplary model, RBC lifespans in the higher confidence group of 26 subjects can be calculated. This subgroup has a similar age distribution to the overall study cohort with a median (IQR) of 44 (37-55) years and a range of 10-70 years. The gender distribution was also similar, with 7 males and 19 females. In the subgroup of this embodiment, the median (IQR) RBC lifespan was 74 (66-88) days with a range of 56-120 days. Two subjects had compromised kidney function measured by eGFR less than 44, and one pediatric subject less than 20 years old. All three individuals showed short RBC lifespans less than 70 days.

Figure 17E:
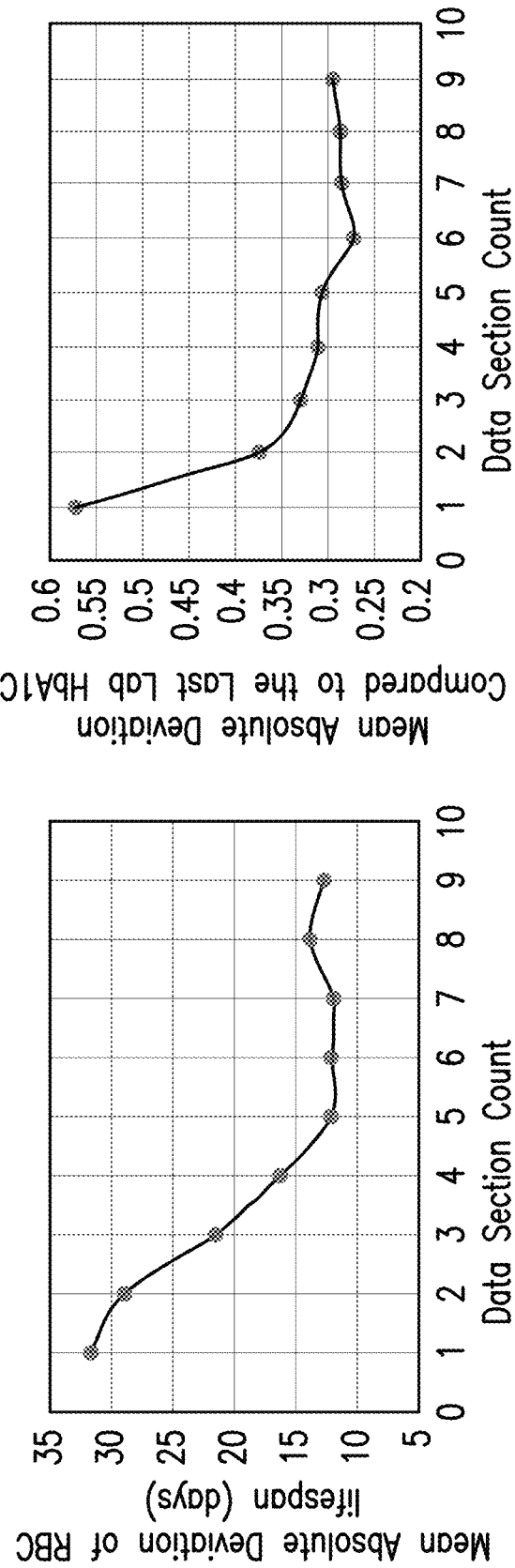

Within the 26 higher confidence subjects with relatively larger day-to-day glucose variability and without major life/therapeutic changes during the data collection, there were 12 subjects that have at least 10 data sections. FIG. 17E illustrates the prospective absolute deviations of cHbA1c with the last lab HbA1c as well as the absolute deviations of RBC lifespan compared to the final RBC lifespan estimated with all data sections. The average absolute deviations of the cHbA1c predictions decrease sharply and then stabilize after the third data section. The absolute deviations of RBC lifespan also decreased longitudinally, reaching stability after the fifth data section.

Within this cohort, RBC lifespans in the higher confidence group of 26 subjects can be calculated. This subgroup has a similar age distribution to the overall study cohort with a median (IQR) of 44 (37-55) years and a range of 10-70 years. The gender distribution was also similar, with 7 males and 19 females. In this subgroup, the median (IQR) RBC lifespan was 74 (66-88) days with a range of 56-120 days. Two subjects had compromised kidney function measured by eGFR less than 44, and one pediatric subject less than 20 years old. All three individuals showed short RBC lifespans less than 70 days.

Within the 26 higher confidence subjects with relatively larger day-to-day glucose variability and without major life/therapeutic changes during the data collection, there were 12 subjects that have at least 10 data sections. FIG. 17E shows the prospective absolute deviations of cHbA1c with the last lab HbA1c as well as the absolute deviations of RBC lifespan compared to the final RBC lifespan estimated with all data sections. The average absolute deviations of the cHbA1c predictions decrease sharply and then stabilize after the third data section. The absolute deviations of RBC lifespan also decreased longitudinally, reaching stability after the fifth data section.

The exemplary model can provide estimates for the kinetic parameters associated with RBC lifespan and RBC glucose uptake rate. The longitudinal analysis disclosed above shows that the kinetic parameter estimation usually converges after 5 data sections. The median RBC lifespan in this cohort was relatively short, around 74 days. In a previous study with a European cohort, a similar median RBC lifespan of 78 days (or RBC turnover rate $k_{age}$=1.29%/day) was observed. These medium RBC lifespans are within or lower than the reported range of mean RBC age by Cohen and colleague, who are herein incorporated by reference in their entireties. In that exemplary study, a mean RBC age range of 38 to 56 days, or RBC lifespans of 76 to 112 days, was found in six people with diabetes. The observed short RBC lifespans might be related to the disease stage of both Japan and European cohorts. In this embodiment, the three subjects expected to have shortened RBC lifespans (either pediatric or with kidney disease) had the lowest RBC lifespans of 55-68 days. Having a routine manner of monitoring RBC lifespan and glucose uptake has the promise of aiding in documenting risk for development and progression of complications due to diabetes and other conditions.

This model identifies underlying variation of RBC lifespan in those without identified conditions which could impact the clinical interpretation of HbA1c. Those with reduced RBC lifespan may be at risk of hyperglycemic damage in those tissues sensitive to elevated circulating glucose levels, as the HbA1c could underreport mean hyperglycemia exposure. Conversely, those with extended RBC lifespan may be at risk of hypoglycemia if treatment decisions are escalated to reduce HbA1c that is elevated due to extended exposure time (rather than glucose level) to circulating glucose. This embodiment has several points of interest. First, it has a consistent and high-quality laboratory HbA1c data. The precision of the laboratory HbA1c is a factor in the accuracy of the model. Second, each individual had long term CGM and several concurrent laboratory HbA1c measurements. These longitudinal data were able to confirm the role of additional measurements to improve the accuracy of the personal glycation factors. Third, the results of this analysis are complementary to those previously studied, and further introduce new advantages and unexpected results.

Example 4

Figure 18A:
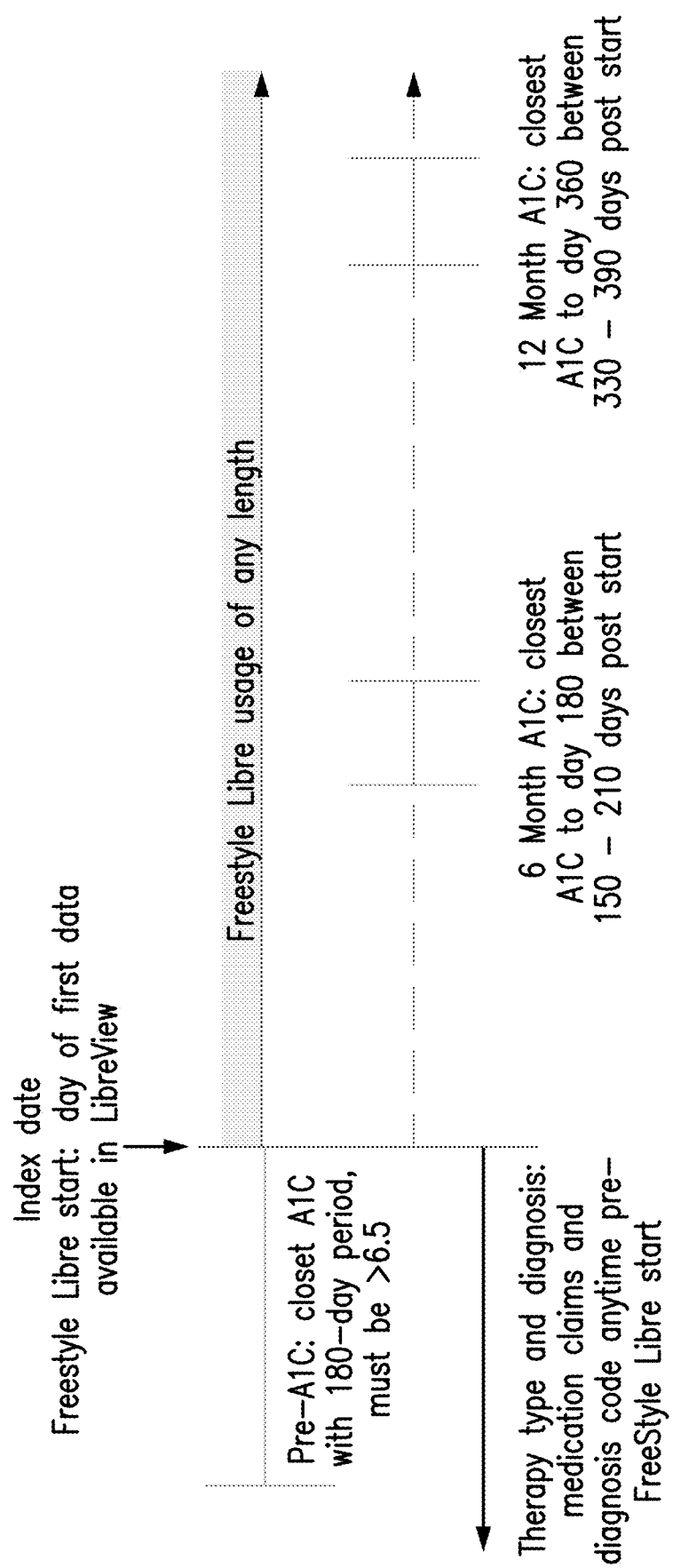
Figure 18B:
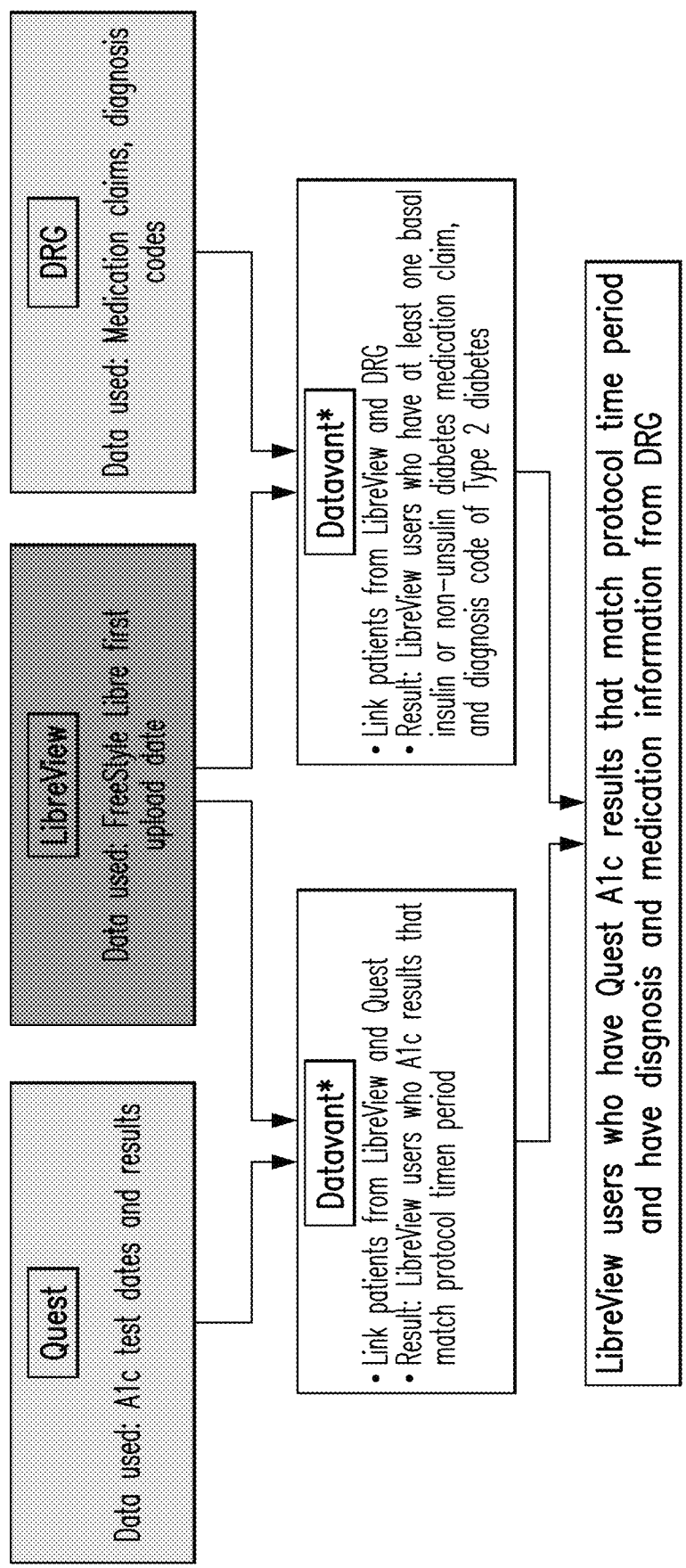

In accordance with an embodiment as described herein, data from three different data sets may be collected and linked together to study Hb1A1c reduction after initiating use of a continuous glucose monitor in Type 2 diabetes patients on long-acting insulin or non-insulin therapy. According to some embodiments, data can be collected from LibreView, Quest Diagnositcs, and/or Decision Resources group. These data sources can then be linked, as shown in FIG. 18B, for example by the use of any suitable linking methodology, such as Datavant. The study can be designed according to the template illustrated in FIG. 18A.

The data included information glucose data from patients, HbA1c test dates and results, and medication claims and diagnosis codes from medical and pharmaceutical claims. After use of a continuous glucose monitor, patients with Type-2 diabetes on basal insulin or non-insulin therapy (including GLP-1) had reduction in HbA1c levels from baseline to 6 months of use and for baseline to 12 months of use.

For example, as illustrated in FIG. 18C use of the flash continuous glucose monitor among users of long-acting insulin can result in a mean change in HbA1c of −0.6% after 6 months of use and of −0.5% after 12 months of use. Similarly, use of the flash continuous glucose monitor among non-insulin patients resulted in a mean change in HbA1c of −0.9% after 6 months of use and of −0.7% after 12 months of use.

Example 5

In accordance with an embodiment as described herein, data can be collected from IBM Explorys databases according to the inclusion criteria shown in FIG. 19A. For example, the analysis can be performed on a cohort of persons who have been prescribed a CGM monitor (for example, a FreeStyle Libre CGM) between a predetermined timeframe, such as between November 2017 and February 2020; who have Type 2 diabetes; who are under the age of 65 years old; who have not been treated with short or rapid-acting insulin (such as, bolus insulin); for whom HbA1c data is available; who have a baseline HbA1c level of 8 or more; for whom at least 6 months of pre-prescription database enrollment is available.

Further, persons can be excluded according to certain exclusion criteria, some of which are also shown in FIG. 19A. These criteria include, but are not limited to, persons who have a history of CGM purchase outside a predetermined time frame; who have gestational diabetes; and/or who have both Type 1 and Type 2 codes on latest encounters with health records.

Figure 19B:
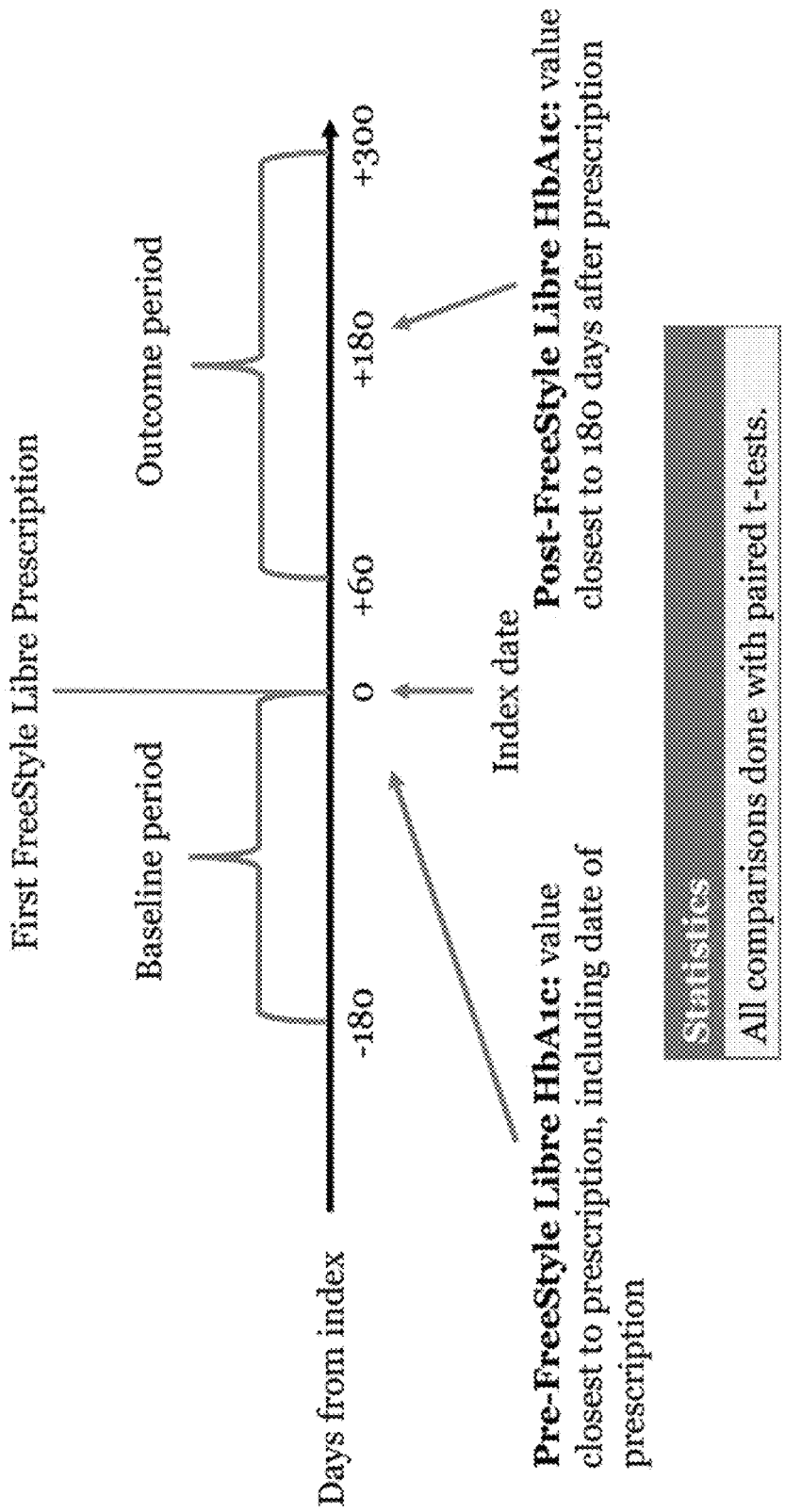

The exemplary study design is illustrated in FIG. 19B, which shows determination of a baseline period, which is up to 180 days before an index data, wherein the index data can be the date on which a person is first prescribed a CGM monitor, for example, and not limitation, a FreeStyle Libre CGM. Further, the study can designate an outcome period, during which HbA1c levels can be measured at a plurality of times after the index date, including, for example but not limitation, 60 days, 180 days, and 300 days after the index date.

Figure 19C:
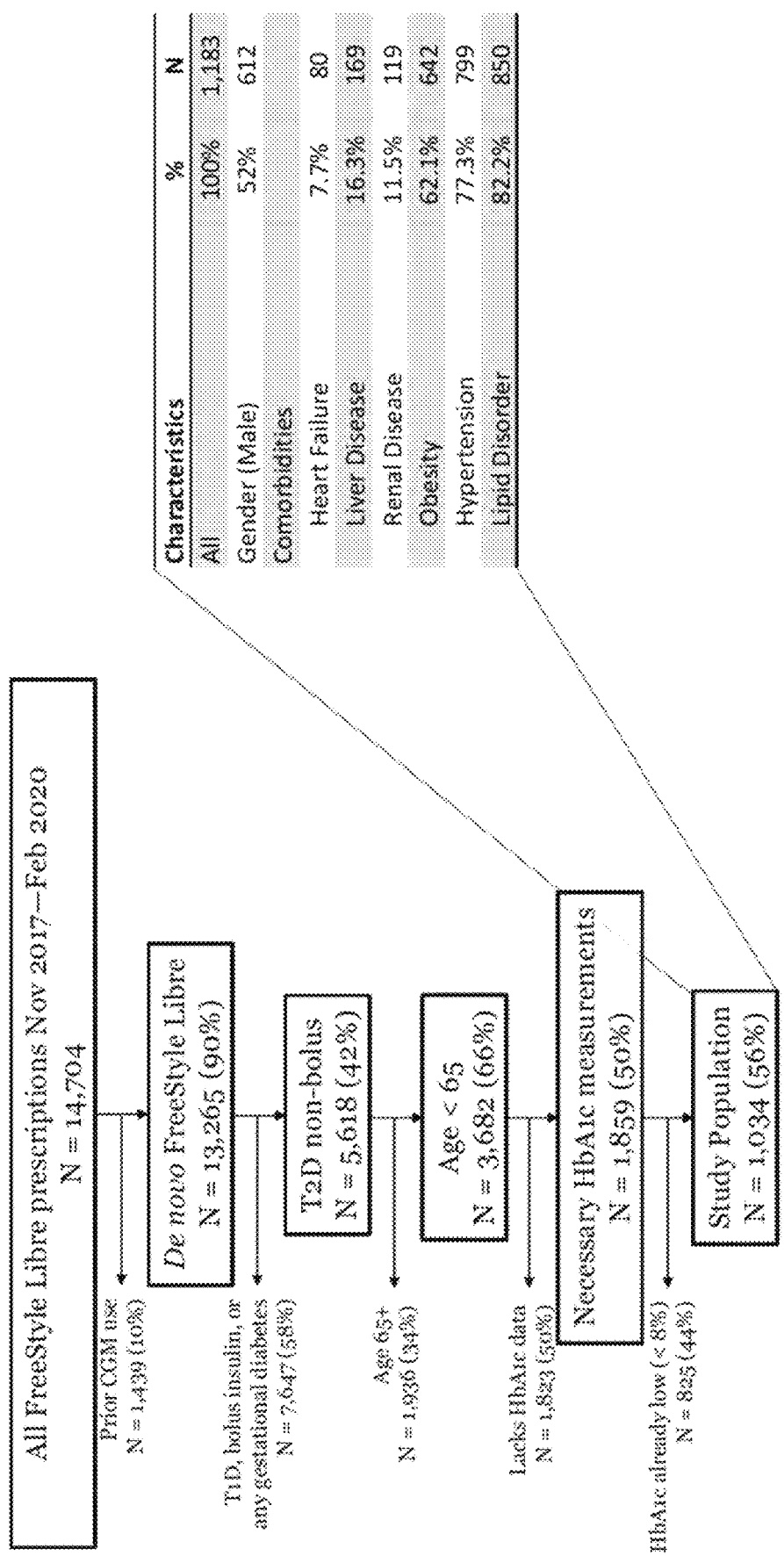

FIG. 19C shows selection of an exemplary cohort, and the resultant characteristics of members of that cohort. In this exemplary selection, beginning with 14,704 persons prescribed with a CGM monitor in a predetermined time period (November 2017—February 2020), the number was reduced to 13,265 for those for whom the prescription was their first, then to 5,618 for those who had Type 2 Diabetes and were treated with a non-bolus method, then to 3,682 persons who were under the age of 65, then to 1,859 who had HbA1c levels available, and, finally, to 1,034 persons who had the predetermined HbA1c level (in this case, >8).

Figure 19D:
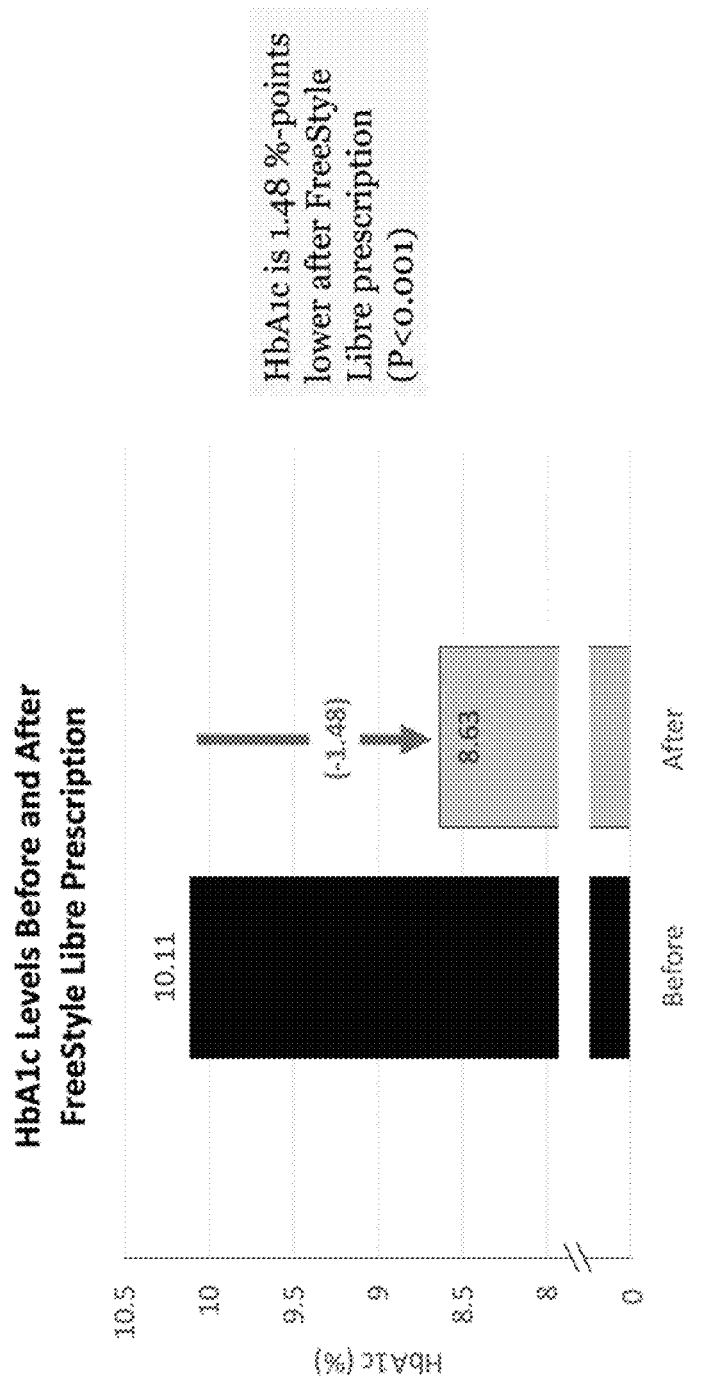
Figure 19E:
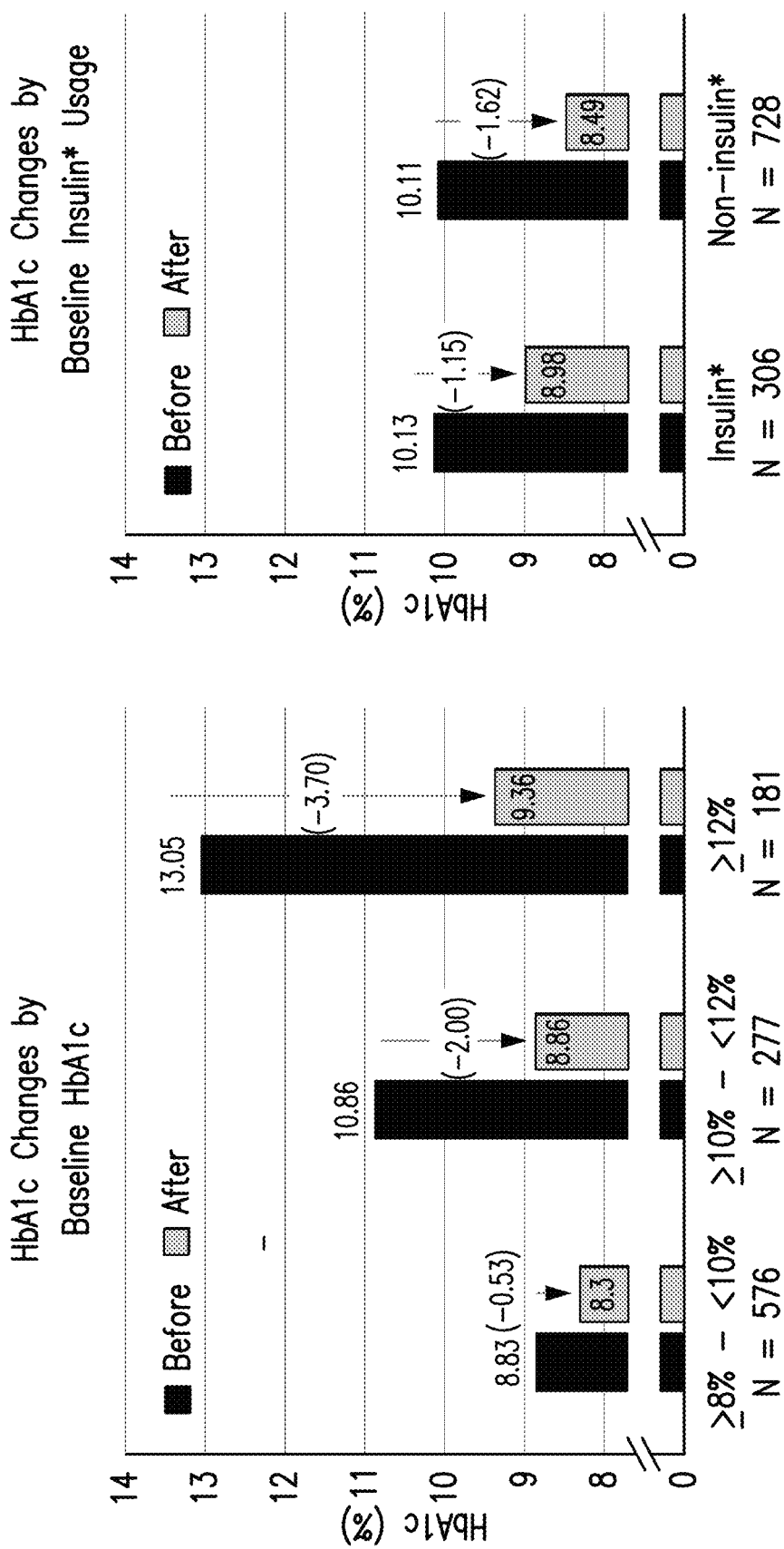

FIG. 19D illustrates a reduction in HbA1c levels for persons in the exemplary cohort. In this example, on average, HbA1c levels were reduced by 1.48 percentage points after prescription of a CGM (in this exemplary embodiment, a FreeStyle Libre CGM). Further reductions observed across different subgroups are illustrated in FIG. 19E. As can be seen, persons having higher baseline HbA1c levels had larger decreases in HbA1c. Further, persons who are not treated with insulin (e.g. basal, premix, NPH) therapy showed a larger HbA1c decrease than patients who are treated with insulin therapy.

Budgetary and Economic Impact

According to an embodiment, the positive budgetary and economic impact of continuous glucose monitor regimen vis a vis public health systems is described.

Example 1

In accordance with an embodiment as described herein, an analysis estimates the potential costs associated with using flash glucose monitoring with optional alarms compared with either real time continuous glucose monitors (rtCGM) or routine SMBG. In the absence of direct evidence for flash monitoring with optional alarms, a set of clinical and resource-based assumptions are applied. The analysis can be focused on adults with diabetes and IAH who use an intensified insulin regimen, from a Swedish payer perspective.

Sweden has one of the highest prevalence rates of diabetes in Europe and is currently estimated to be 7%. Impaired awareness of hypoglycemia (IAH), can refer to the absence or diminished ability to perceive the onset of hypoglycemia amongst diabetes patients who are users of an intensified insulin regimen. IAH caused by recurrent, untreated and non-severe hypoglycemic events makes patients less aware and able to respond to onset hypoglycemia, putting them at higher risk of suffering severe hypoglycemic events. Prevalence estimates of IAH range between 20%-32% in adults with insulin-treated type 1 diabetes mellitus (T1DM) and 10% in adults with insulin-treated type 2 diabetes mellitus (T2DM) and increases with age and duration of diabetes.

Certain people with IAH can be disproportionally high healthcare users, due to an increase in the risk of severe hypoglycemia. In addition to the high cost burden, hypoglycemia is associated with a lower quality of life, increased anxiety and reduced productivity. Maintaining glucose levels within a recommended range reduces the risk of developing hypoglycemia associated with an intensified insulin regimen. The Tandvårds-Läkemedelförmånsverket (TLV), a national health authority in Sweden, recommends that adults with insulin treated diabetes test at least four and up to ten times per day however recognize that adherence is poor as finger prick testing can be both time consuming, painful and inconvenient.

rtCGM automatically tracks glucose in interstitial fluid and in certain embodiment can be used in combination with occasional self-monitoring of blood glucose (SMBG) and features alarms to notify patients when their glucose is outside of a pre-defined range. This facilitates improved glycemic control by allowing patients or their caregivers to monitor and respond to changes. While rtCGM has been demonstrated to be effective in improving glycaemic control, adherence is variable. Of 1,662 participants reporting rtCGM use at enrolment into the T1DM Exchange registry, 675 (41%) reported discontinuing rtCGM use at the 1-year data collection. Alarm fatigue can also contribute to non-adherence.

The clinical benefits of flash glucose monitoring in comparison to routine SMBG have been demonstrated in two randomized controlled trials (RCTs) in people with T1DM and T2DM using an intensified insulin regimen. Both RCTs reported differences in the number of patients experiencing severe hypoglycaemic events in favour of rtCGM. In real-world studies flash monitoring has shown reductions from baseline in HbA1c and hypoglycaemia. The economic case for flash glucose monitoring has also been demonstrated in published economic analyses, demonstrating cost-effectiveness of flash monitoring compared to routine SMBG in people with T1DM and in intensified insulin regimen users with T2DM from a Swedish payer perspective. A key differentiator of the newer model of flash glucose monitoring is that the optional alarms empower patients by providing a choice about how they want to use alarms. The efficacy of flash monitoring with optional alarms for people with diabetes and IAH who are using an intensified insulin regimen is expected to be similar to rtCGM because both alert patients in real-time of hypoglycaemia or hyperglycaemia. However, as the notification feature is optional it may reduce the risk of non-adherence due to alarm fatigue.

The analysis according to this embodiment can calculate the cost per patient treated over a three-year period, applying a set of clinical and resource use assumptions to simulate a hypothetical base-case scenario. Flash monitoring with optional alarms, was compared to two alternatives: routine SMBG, or rtCGM, based on the Dexcom G6 rtCGM system. Costs were estimated from a Swedish national health service payer perspective and are reported in 2018 SEK. The costs considered in the model include glucose monitoring costs and resource use to treat severe hypoglycaemic events.

A simple two state cohort Markov model can be built in Microsoft Excel® in Office 365® which can be configured account for risk of severe hypoglycaemic events requiring medical assistance and non-adherence over a three-year time horizon using quarterly Markov cycles (T1DM, type 1; T2DM, type 2), as illustrated in FIG. 15A. In the flash monitoring with optional alarms and rtCGM, patients enter the first health state where they use flash monitoring with optional alarms or rtCGM respectively, with occasional SMBG. Patients may discontinue flash monitoring with optional alarms or rtCGM due to non-compliance and move to a state where they are on routine SMBG. In both states, patients can experience severe hypoglycaemic events for which they accrue the medical costs associated with the event. In the routine SMBG arm, the model consists of only one state from which the patient may experience severe hypoglycaemic events.

The cost inputs, as illustrated in FIG. 15E, can be sourced from Swedish price lists, manufacturer data and resource use reported in the control arm of the HypoDE study, an RCT comparing rtCGM to routine SMBG in a population predominantly of people with IAH. The unit cost for a physician visit was sourced from a prior Swedish cost-effectiveness study. The cost of a severe hypoglycaemic event was calculated using inflated unit costs reported in Jonsson et al., which is herein incorporated in its entirety by reference and the resource use reported in Heller et al., which is herein incorporated in its entirety by reference. For the purposes of this embodiment, a severe hypoglycaemic event is one that requires third party medical assistance, including ambulance call outs, emergency room visits or hospital admissions.

Targeted literature searches were run in PubMed to source the clinical inputs as shown in FIG. 15F. The baseline risk for severe hypoglycaemic events was also sourced from Heller et al., *Severe Hypoglycaemia in adults with insulin-treated diabetes: impact on healthcare resources*, J Diabetic Medicine, 2016, 33(4): p. 471-477, which is herein incorporated by reference in its entirety. This rate was adjusted to account for a 3-fold higher rate of severe hypoglycaemia reported in real world settings compared to clinical trials. Further adjustments can be applied to account for higher rates of severe hypoglycaemia amongst intensified insulin regimen users with IAH compared with those without IAH.

Efficacy data for both flash glucose monitoring with alarms and rtCGM was sourced from Heinemann et al., which is herein incorporated in its entirety by reference, using the rate ratio of all severe hypoglycaemic events requiring third party assistance. Treatment discontinuation was modelled using the proportion of patients (23.4%) who discontinued using rtCGM in a real-world study after 1 year. No further discontinuation is assumed beyond year 1. In the base case the discontinuation rate is assumed to be the same for rtCGM and flash monitoring with alarms because no flash monitoring with alarms specific data are available.

As embodied herein, one-way sensitivity analysis can be conducted by varying all inputs individually within lower and upper bounds and ranking the results in order of impact. High and low values were selected using a 95% confidence interval, or by varying the input by 50% or to extreme values where there was a first level of uncertainty and 25% when there was a second level of uncertainty. The inputs for the analysis comparing flash glucose monitoring with alarms to routine SMBG and rtCGM are reported in FIGS. 15G and 15H, respectively.

The rate of severe hypoglycaemic events applied in this exemplary model was calculated using data from an RCT in a T1DM diabetes population and applying an adjustment for a real-world setting and an IAH population. To account for uncertainty between these adjustments, the IAH rate ratio, the combined adjustment for real-world setting and IAH population, was varied, while keeping all other model inputs constant.

A second scenario analysis considers the impact if adherence to flash glucose monitoring with optional alarms is higher than adherence to rtCGM. In the base case a conservative assumption was applied, assuming that adherence was equal however flash monitoring with optional alarms is potentially more engaging for users than rtCGM as the notification feature is more flexible.

The base case results over a 3-year time horizon are illustrated in FIG. 15B. Over 3 years, a patient using flash glucose monitoring with optional alarms is expected to realize cost savings of SEK 7,708 when compared to a patient using routine SMBG and SEK 69,908 when compared to rtCGM.

In comparison to rtCGM, the savings accrued by using flash monitoring with optional alarms are largely due to differences in the sensor cost, the fact that there is no need for a transmitter, and a lower reader cost. In contrast, the cost savings when compared to routine SMBG are due to severe hypoglycaemic events avoided because the aggregate cost of treating severe hypoglycaemic events is around 50% lower.

The base-case analysis according to this present embodiment shows that the higher acquisition cost of flash glucose monitoring with optional alarms compared to routine SMBG is offset by cost savings from avoiding severe hypoglycaemic events. In addition to costs avoided, reducing risk of severe hypoglycaemic events has additional health benefits not captured in the model. These include avoiding detriments to patient's quality of life associated with severe hypoglycaemic events and reducing risk of further complications or death. Sensitivity and scenario analyses found some uncertainty regarding this conclusion, where the result was particularly sensitive to varying the severe hypoglycaemic event parameters, most notably the intervention rate ratio.

The results of the one-way sensitivity analysis comparing flash glucose monitoring with optional alarms with routine SMBG are illustrated in a tornado plot in FIG. 15C, ranking the parameters in order of effect. The model is most sensitive to the severe hypoglycaemic event parameters. Changing the intervention incidence rate ratio, the rate ratio to account for IAH, or the base line severe hypoglycaemic event rate to their respective upper and lower bounds can cause the model results to shift over the cost saving threshold or become even more cost saving than the base case.

The results of the one-way sensitivity analysis projecting the cost saving of flash glucose monitoring with optional alarms compared to rtCGM after 3 years are illustrated in FIG. 15D. This shows that the analysis is most sensitive to the unit cost of the rtCGM sensor and the intervention rate ratio for flash glucose monitoring with optional alarms respectively. However, in all scenarios the cost per patient using flash monitoring with optional alarms is substantially lower than with rtCGM.

The results of the scenario analysis varying IAH rate ratio, according to some embodiments, are illustrated in FIG. 15J, and show that flash glucose monitoring with optional alarms is cost-saving compared to SMBG when the IAH severe hypoglycaemic event rate ratio is above 12.72. Flash monitoring with optional alarms is cost-neutral when the IAH ratio is 12.72. The cost-savings compared to rtCGM do not change when this rate is varied as the effect of rtCGM on severe hypoglycaemic events is the same for both flash monitoring with optional alarms and rtCGM. The results of the scenario analysis varying adherence to flash glucose monitoring with optional alarms, according to some embodiments, are illustrated in FIG. 15K and show that the model is not particularly sensitive to this input. Flash monitoring with optional alarms is cost-saving compared to rtCGM or routine SMGB in all variations of adherence to flash monitoring with alarms considered. The relationship between this variable and difference in cost need not be linear because higher adherence ca be associated with both higher consumable costs as well as costs savings from severe hypoglycaemic events avoided.

The comparison with rtCGM suggests that flash monitoring with optional alarms dominates rtCGM because the acquisition costs are substantially lower and both treatment strategies may provide similar efficacy. This conclusion, that cost savings are associated with switching from rtCGM to flash monitoring with optional alarms was consistent across the sensitivity and scenario analyses.

Glucose monitoring can be in people with diabetes and IAH who are using an intensified insulin regimen due to the increased risk of severe hypoglycaemic events. Managing complications with diabetes imposes a high cost burden on health care services in Sweden, with the cost of treating hypoglycaemia projected to be SEK 34 million in 2020.

Two RCTs in populations using an intensified insulin regimen demonstrate high scanning rates and real-world evidence confirms that this is maintained when used as regular, daily diabetes management. Frequent testing is recommended in certain clinical guidelines for effective diabetes management because real-world studies can suggest this is associated with more effective management of both HbA1c levels and reduced risk of hypoglycemia with intensified insulin regimen use. This benefit is expected to be particularly pertinent to IAH populations who are using an intensified insulin regimen given their higher susceptibility to hypoglycaemia.

A further benefit of flash monitoring with optional alarms over routine SMBG can include the additional information captured, making this monitoring strategy more compliant with current international consensus for good practice. Each scan provides more information than a single glucose reading from an SMBG test and flash monitoring with optional alarms can provide a summary ambulatory glucose profile (AGP) and a complete 24-hour glucose record. A recent international consensus statement endorsed by EASD, ADA, AACE, AADE and ISPAD recognizes the importance of time in glucose ranges (TIR) as "appropriate and useful as clinical targets and outcome measurements". The flash monitoring system with optional alarms provides TIR in the AGP report, in contrast with SMBG which does not easily facilitate capturing this metric.

Example 2

In accordance with an embodiment as described herein, a nationwide audit, Deshmukh et. al., *Effect of flash glucose monitoring on glycemic control, hypoglycemia, diabetes-related distress, and resource utilization in the Association of British Clinical Diabetologists (ABCD) nationwide audit* J Diabetes care, 2020, 43(9): p. 2153-2160, which is incorporated herein in its entirety, was set-up to assess the patterns of use of FreeStyle Libre system and to study its effect on glycemic control, hypoglycemia, diabetes-related distress, and hospital admissions due to hypoglycemia and hyperglycemia/diabetic ketoacidosis (DKA). The study commenced in November 2017 and involved clinicians from 102 NHS hospitals in the UK for which they were asked to submit user data collected during routine clinical care.

In this embodiment, the budget impact of more widespread adoption of the FreeStyle Libre system from a local health economy's perspective in the UK by applying the outcome data reported in the ABCD nationwide audit was estimated. The potential cost-effectiveness is also explored in a subsequent simplified cost-utility analysis.

Improved glycemic control, facilitated by effective blood glucose monitoring improves acute outcomes in Type 1 diabetes mellitus (T1DM) by reducing the risk of hypoglycemia and severe hypoglycaemic events ("SHE"), as well longer-term outcomes such as slowing down disease progression of retinopathy, nephropathy and other diabetes end-points. Self-monitoring of blood glucose ("SMBG"), or 'finger-prick' testing, has been the standard of care for people with T1DM. However, the introduction of new technology, such as sensor-based glucose monitoring, is changing the standard approach to glucose monitoring. The FreeStyle Libre system is convenient and easy to use and improves the frequency of glucose monitoring relative to SMBG. Furthermore, it can provide dense data, enabling informed discussion between people with diabetes and their clinicians about glucose management and, with the addition of digital communication tools, it minimizes the need for face-to-face contact. It is indicated for measuring interstitial fluid glucose levels in people age 4 and older with diabetes mellitus, including pregnant women and is designed to replace SMBG testing in the self-management of diabetes.

In this exemplary study, a budget impact model was developed in Microsoft Excel to calculate the net difference in costs per patient and total budget impact over a 3-year time horizon, comparing the FreeStyle Libre system to SMBG. Included in the analysis were the acquisition costs, costs associated with severe hypoglycaemic events ("SHE"), cost of diabetic ketoacidosis and hyperglycemia ("DKA") events, and cost savings from a reduction in HbA1c. The change in resource utilization with the FreeStyle Libre system compared to SMBG was sourced from the ABCD nationwide audit, where the people included in the ABCD audit are a sub-group of all T1DM populations defined by the NHS funding criteria and those able to self-fund. The budget impact analysis can estimate total costs, multiplying uptake by the cost per person using the FreeStyle Libre system and SMBG.

An additional, simplified, cost utility analysis calculated the expected quality adjusted life years ("QALYs") gained and an incremental cost-effectiveness ratio, comparing the FreeStyle Libre system to SMBG over a 1-year time horizon. Due to the short time horizon, only difference in quality of life was captured and mortality was assumed to be the same with both technologies. The incremental cost-effectiveness ratio ("ICER") can be calculated as the net difference in cost per patient divided by the net difference in QALYs gained, where QALYs gained can be estimated by applying a system utility weight to the FreeStyle Libre system use vs SMBG, a utility decrement associated with diabetes related events and a utility increment associated with a change in HbA1c. This approach facilitated the calculation of the utility difference on an incremental basis, reporting the difference in QALYs gained relative to SMBG rather than total QALYs gained for each comparator. No discounting was applied because the cost-utility analysis was conducted over a one-year time horizon.

In the analysis according to this embodiment, a selected cohort included 1,790 people with T1DM, which represents the mean number of people with T1DM across all clinical commissioning groups ("CCGs"), representing local health economies in England. In the base-case, parameters for the rate of SHE events, DKA events and change in HbA1c for the FreeStyle Libre system and SMBG can be sourced using data from ABCD audit, as illustrated in FIG. 21A. For post-FreeStyle Libre system use, 7-month data can be applied and prorated to estimate annual outcomes.

FIG. 21A illustrates unit costs applied in the model according to this embodiment. Acquisition costs for the FreeStyle Libre system can be obtained from a plurality of publicly available databased, for example, the NHS tariff databases. Unit costs for SMBG testing can be averaged from the top ten strips used in the UK calculated from IQVIA prescribing data. The number of tests strips per day with SMBG can sourced from IMPACT, a multi-center randomized control trial of the FreeStyle Libre in T1DM, which is incorporated by reference in its entirety herein. The cost of an ambulance callout and admission for SHE and DKA events can be sourced from the NHS reference cost and tariff data collection.

The cost associated with each incremental reduction in HbA1c was sourced from a study that estimated the costs associated with micro and macrovascular complications with different HbA1c levels using the diabetes CORE model, is incorporated by reference in its entirety herein. It reports the cost avoided from a UK payer perspective in 5 years periods. The costs for the first 5-year period reported were annualized to a one-year basis.

The budget impact analysis according to this embodiment can evaluate a scenario where the FreeStyle Libre system would replace a proportion of SMBG use in T1DM adults within three years from the perspective of a UK local health economy (n=1,790). For example, in year 1, 30% of the T1DM population are assumed to use the FreeStyle Libre system and the remaining 70% use SMBG, reflecting estimated trends in 2020. In years 2 and 3, uptake of the FreeStyle Libre system is assumed to increase to 50% and 70% respectively, with the remaining population using SMBG.

FIG. 21B illustrates Utility gain from using the FreeStyle Libre system compared to SMBG. This gain can reflect the greater convenience as well as intangible benefits of empowering people to monitor and self-manage their glucose levels compared to SMBG. Utility decrements were also applied for SHE and DKA events and a further utility gain was applied per decrease in HbA1c.

One-way sensitivity analysis ("OWSA") can be performed on all model parameters to investigate the sensitivity of the cost effectiveness model result to variations in each of the parameter values. Where confidence intervals are at undesired levels, parameters may by varied by approximately 25%.

In addition, threshold analysis can vary the number SMBG tests per day, for example and not limitation, between 0.5 and 10 to show the impact of this on the ICER. A further scenario analysis can be applied to a set of assumptions for the utility benefits with FreeSyle Libre system. In this exemplary embodiment the utility benefit with the FreeStyle Libre system was reduced from 0.03 to 0.01.

The results from the ABCD nationwide audit found that the reduction in HbA1c was greater amongst people with a higher baseline HbA1c. The impact of this was considered in a sub-group analysis comparing the FreeStyle Libre system with SMBG reporting the cost-per patient treated and cost-effectiveness in people with T1DM with higher baseline HbA1c.

As illustrated in FIG. 21C, the FreeStyle Libre system can be marginally more expensive than SMBG when testing 5.6 times per day because higher acquisition costs can be at least partially offset by cost savings from reduced resource utilization. As embodied herein, the net budget impact of increasing the proportion of people with T1DM using the FreeStyle Libre system from 30% in year 1 to 50% and 70% in year 2 and 3 respectively is illustrated in FIG. 21D. In year 1 the total cost was £1,787,345 increasing to £1,847,618 and £1,907,890 in years 2 and 3 respectively representing 3.4% and 3.3% year on year increase.

As illustrated in FIG. 21E, a cost utility analysis can be used to estimate a net difference in cost as well as a net incremental QALY between a CGM system, such as the FreeStyle Libre system, and SMBG. In a study according to this embodiment, for example, a net difference in cost of £163 and a net incremental QALY of 0.048 can be observed between a FreeStyle Libre System and SMBG over a one-year period. This resulted in an incremental cost effectiveness ratio of £3,516 per QALY gained.

Figure 21F:
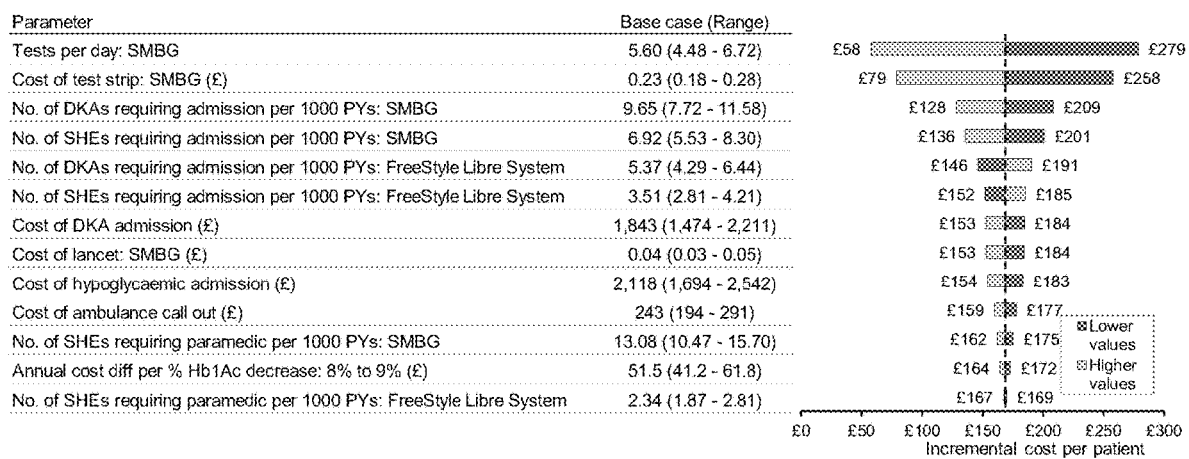
Figure 21G:
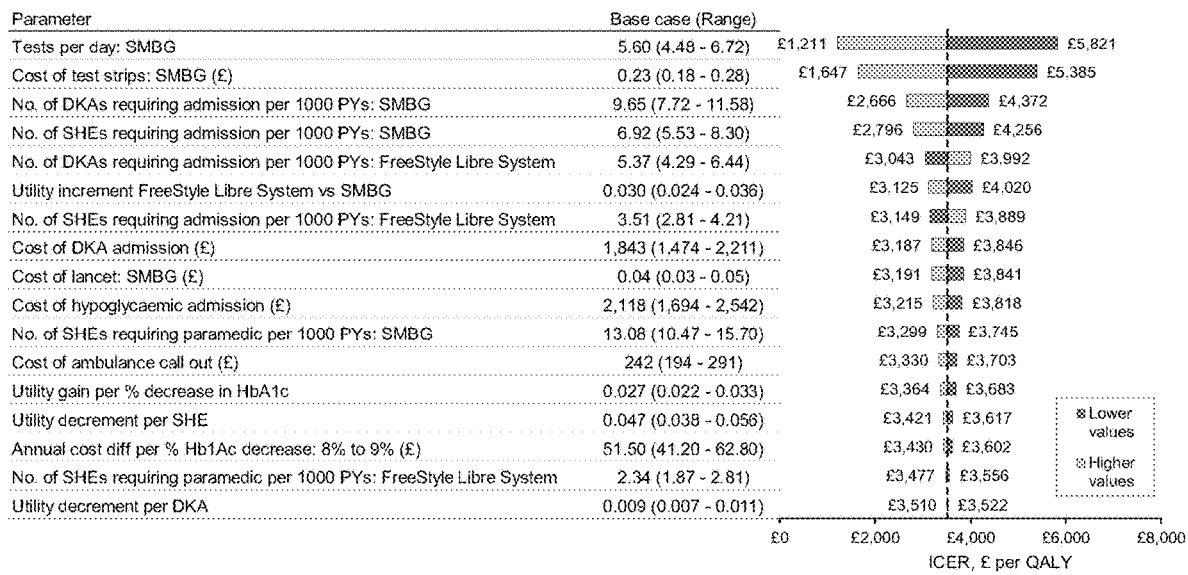
Figure 21H:
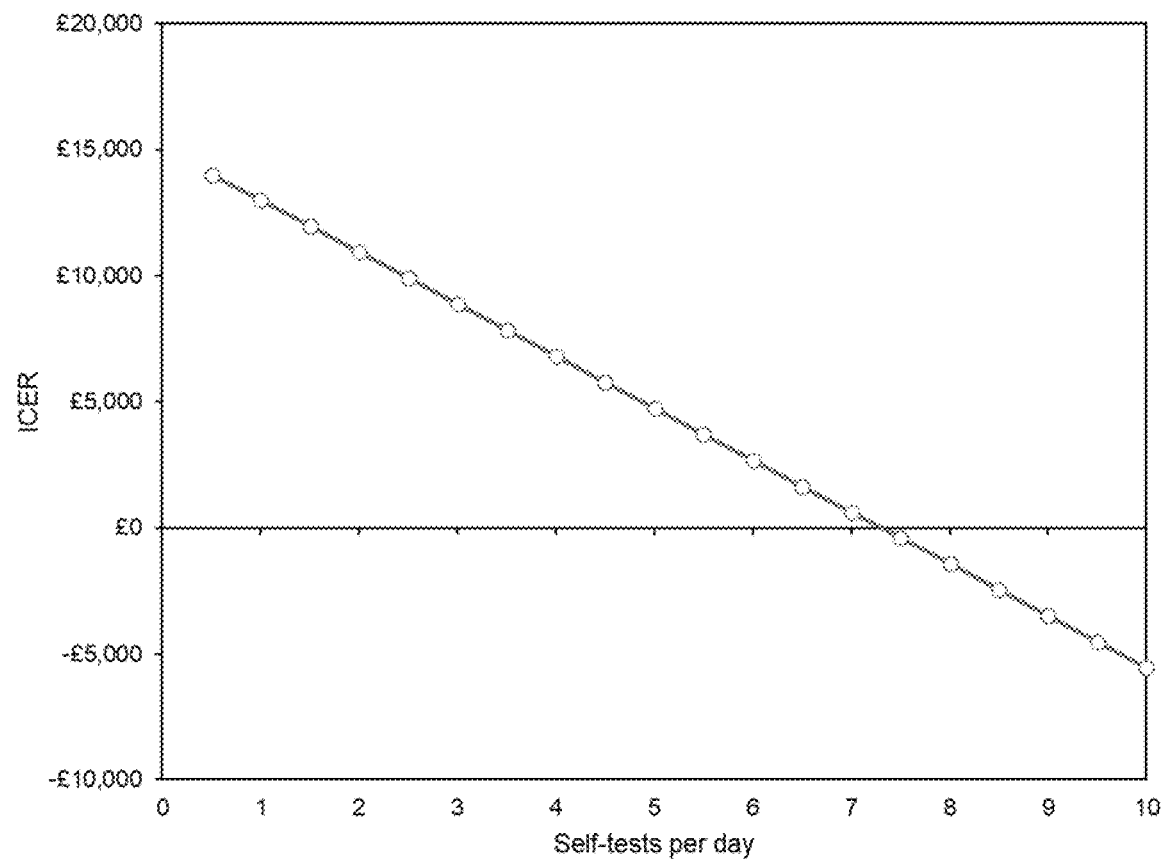

As illustrated in FIGS. 21F and 21G, it can be observed that the model according to this embodiment is sensitive to the number of SMBG tests per day as well as the costs of the strips. For example, when SMBG tests per day is varied between 0.5 and 10 tests per day, it can be observed, in FIG. 21H, that ICER is below £20,000 in all scenarios, and further that the FreeStyle Libre system performs better than SMBG when the strip per day value is 7 or more. A further exemplary analysis can apply conservative assumptions for the utility benefits with FreeStyle Libre system, effectively reducing the incremental utility benefit associated with using FreeStyle Libre system from 0.03 to 0.01; using this assumption the ICER increases to £16,313.

Figure 21J:
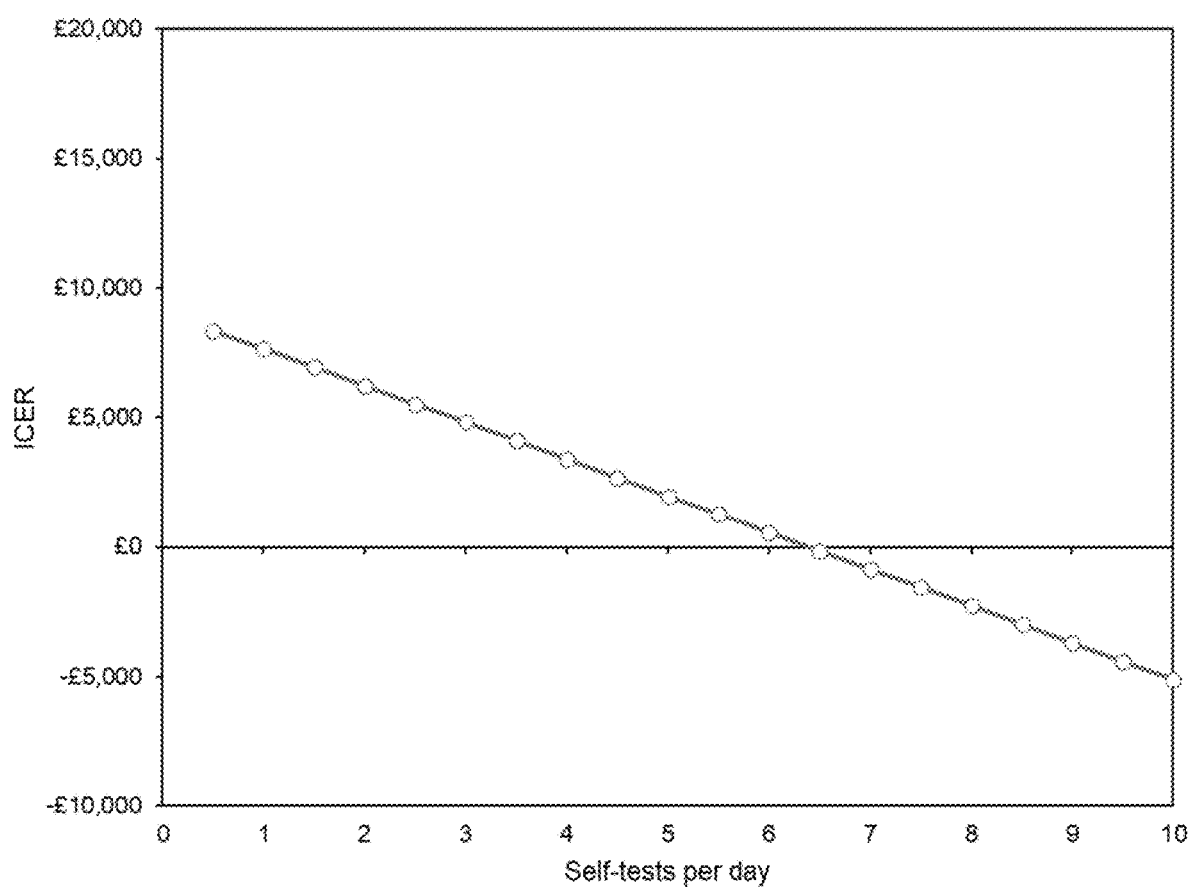

FIG. 21I illustrates the results of a sub-group analysis in people with higher baseline HbA1c. Amongst those with a high HbA1c baseline (>8.5%), the costs savings from reduced HbA1c with the FreeStyle Libre system are projected to be greater relative to the overall population. According to this exemplary analysis, the difference in cost per patient per year with the FreeStyle Libre system compared to SMBG is, £73, compared to £163 in the overall population. Applying this difference in cost to the cost-utility analysis reduces the ICER from £3,516 in the overall population to £1,129 in this sub-group. Threshold analysis of the number of tests per day in the high HbA1c group, as illustrated in FIG. 21J, shows that cost neutrality with SMBG would be achieved when carrying out approximately 6.5 tests per day.

As reflected in the data outlined above, the ABCD nationwide audit demonstrates that the FreeStyle Libre system use is associated with improved outcomes, resulting in reduced diabetes-related resource utilization in T1 DM populations in the real world. In an average sized local health economy in England (population size of 1,790 T1DM), increasing the proportion of people using the FreeStyle Libre system by 30% in year 1 to 50% in year 2 increased costs by 3.4%. Similarly increasing the FreeStyle Libre system uptake to 70% in year 3 increased the budget by a further 3.3%.

This increase in costs can be associated with patient and healthcare system benefits including improved glucose monitoring, reduced hospital admissions and improved quality of life from discreet and easy to use sensing technology. In this embodiment, the cost utility analysis estimated an ICER of £3,516 per QALY gained, below £20,000 the 'willingness to pay' threshold typically applied in the United Kingdom deemed to represent good value. A further benefit of more widespread use of the FreeStyle Libre system is the access to glucose data in the cloud on Libreview which enables physicians to monitor people with diabetes remotely. Furthermore, the data can include time in range and the glucose management indicator which can be used as a substitute for quarterly HbA1c blood tests, further reducing system costs.

As illustrated above, widespread adoption of FreeStyle Libre system in T1DM populations can offer benefits and have a relatively small budget impact compared to the total cost of glucose management to health economies in the United Kingdom. People with T1DM and healthcare systems stand to benefit from the improved glycemic control, reduced diabetes related distress, reduced hospital admissions and the opportunity of virtual reviews which this easy to use monitoring solution provides.

Example 3

In this exemplary review, several studies were examined for evidence related to the flash glucose monitoring system in patients with T2D, although several real-world studies had mixed type 1 diabetes (T1D) and T2D populations. These studies are tabulated in FIGS. 23A-B. Additional details of this embodiment are disclosed in *A review of flash glucose monitoring in type 2 diabetes*, which was originally published in Diabetology & Metabolic Syndrome, Volume 13, Article Number 42, 2021, BMC and can be accessed at the website https://dmsjournal.biomedcentral.com/articles/10.1186/s13098-021-00654-3, and is incorporated by reference herein in its entirety.

To identify clinical trials of the flash glucose monitoring system, searches were conducted of PubMed and Google Scholar from inception to 30 Jun. 2020 using the search terms flash glucose monitoring; continuous and/or intermittent glucose monitoring; and FreeStyle Libre system. No language restrictions were applied. Reference lists of retrieved papers were hand-searched for additional clinical studies and other articles of interest. Relevant abstracts presented at the American Diabetes Association Congress in June 2020 were also considered for inclusion.

The benefits of the flash glucose monitoring system in improving glycemia in T1D were shown in the IMPACT randomized controlled trial (RCT) of 239 randomized patients, and subsequently in a large real-world study (n=1913).

In the IMPACT study, which is incorporated by reference in its entirety herein, of adult patients with well-controlled T1D (glycosylated hemoglobin [HbA1c]≤7.5%), flash glucose monitoring for 6 months significantly reduced the time spent in hypoglycemia compared with SMBG (P<0.0001). The mean change from baseline of −1.39 vs. −0.14 hours/day equated to a 38% reduction. In this 6-month study, the mean±SD number of scans/day recorded by the flash glucose monitoring device was 15.1±6.9, which was almost triple the frequency of blood glucose testing (5.5±2.0 tests/day). A prespecified subgroup analysis of the IMPACT trial showed the benefit of flash glucose monitoring in patients receiving multiple daily insulin injection therapy, as evidenced by a 46% reduction in time spent in hypoglycemia compared with SMBG (mean change from baseline −1.65 vs. 0.00 hours/day; P<0.0001).

A 1-year observational real-world cohort study of adults with T1D treated in specialist Belgian diabetes centers found that flash glucose monitoring improved treatment satisfaction and reduced severe hypoglycemia whilst maintaining HbA1c levels. Compared with the year before the study, flash glucose monitoring reduced admissions for severe hypoglycemia and/or ketoacidosis (3.3 vs. 2.2%; P=0.031), and reduced the incidence of reported severe hypoglycemic events (14.6 vs. 7.8%, P>0.0001) and hypoglycemic coma (2.7 vs. 1.2% P=0.001).

The REPLACE open-label randomized controlled trial (RCT) of adults with T2D, which is incorporated by reference in its entirety herein, compared the efficacy and safety of flash glucose monitoring (n=149) with SMBG (n=75). The study assessed the effect of flash glucose monitoring on glycemic control in patients receiving intensive insulin therapy or continuous subcutaneous insulin infusion. Although no significant difference was observed between flash technology and SMBG in the outcome measure of change in HbA1c at 6 months (mean −0.29 vs. −0.31%, respectively), prespecified subgroup analyses demonstrated several benefits, as shown in FIG. 22A. The 6-month HbA1c level was significantly reduced in patients aged <65 years using the flash system compared with SMBG (mean −0.53 vs. −0.20%; P=0.030) although the trend was reversed in patients aged ≥65 years (mean −0.05 vs. −0.49%; P=0.008). As further demonstrated in FIG. 22A, other glycemic measures significantly reduced with flash glucose monitoring compared with SMBG include time spent in hypoglycemia, frequency of hypoglycemic events and area under the concentration-time curve (AUC) for glucose, with a reduction in each of these measures in inverse proportion to the glucose level. SMBG frequency from baseline to study end was decreased in flash glucose monitoring participants from a mean±standard deviation (SD) of 3.8±1.4 to 0.3±0.7 tests/day. Treatment satisfaction, as assessed by the Diabetes Treatment Satisfaction Questionnaire, was higher in the flash glucose monitoring group compared with the SMBG group (mean±SE 13.1±0.50 vs. 9.0±0.72; P<0.0001). No serious adverse events (SAEs) or severe hypoglycemic events were reported in association with the device.

A total of 139 participants in the flash glucose monitoring group of the REPLACE RCT completed the 6-month treatment phase and continued into a 6-month open-access phase. The mean changes from baseline (start of treatment period) in glycemic parameters measured at 12 months paralleled those measured at 6 months. In FIG. 22A, reductions in sensor measures of time spent in hypoglycemia, number of hypoglycemic events, and glucose AUC were observed for open-access participants at 12 months post-baseline compared with baseline, and the magnitude of change increased as glucose cut-off points decreased.

Time in range (sensor glucose 70-180 mg/dL) remained unchanged between baseline and 12 months post-baseline (14.0±4.4 vs. 14.1±4.0 hours). Mean±SD frequency of SMBG decreased from 3.9±1.2 tests/day at baseline to 0.2±0.6 tests/day at 12 months post-baseline. During 12 months' use of the flash glucose monitoring device there were no reports of diabetic ketoacidosis or a state of hyperosmolar hyperglycemia. No SAEs were attributable to the device. Sixteen device-related adverse events (sensor adhesive or site reactions) were reported in nine participants, which were classified as severe (n=4), moderate (n=9) or mild (n=3). All events resolved after treatment with mainly topical preparations.

Collectively, the 6-month REPLACE RCT and follow-on 6-month open-access study showed that, in individuals with T2D managed by intensive insulin therapy, the flash glucose monitoring system reduces hypoglycemia and is a safe alternative to SMBG. In the initial 6-month phase, the mean±SD number of scans/day recorded by the flash glucose monitoring device was 8.3±4.4 (median 6.8), which was double the frequency of blood glucose testing (median 3.8±1.9 tests/day). Average sensor-scanning frequency during the extension phase was 7.1±3.5 times/day (median 5.7).

A further RCT compared the effect on glycemia of intermittent wearing of the professional flash glucose monitoring sensor with SMBG in insulin-treated T2D patients with a HbA1c level between 7.5 and 12.0%. Patients performed SMBG (n=52, control group A), or SMBG plus flash sensor worn for two 14-day periods during 4.5 months (n=46, intervention group B), or SMBG plus flash sensor worn for four 14-day periods during 7 months (n=50, intervention group C). No significant changes were observed within group C for sensor-derived time in range (70-180 mg/dL) from baseline to penultimate sensor wear (days 172-187; endpoint), with mean±SD values of 15.0±5.0 and 14.1±4.7 hours/day, respectively, or for the difference versus the control group at study end (days 215-230). In group C, HbA1c was reduced significantly during the study period by a mean±SD of 0.44%±0.81% (P=0.0003). At study end, HbA1c was significantly reduced in group C compared with the control group by an adjusted mean±SE of 0.48%±0.16% (P=0.004). In contrast, there was no significant difference in HbA1c between group B and control group at day 144 (P=0.133).

A further open-label RCT compared the effect of 10-week flash glucose monitoring (n=53) or SMBG (n=48) on glycemic control in patients with T2D receiving multiple daily insulin injections. HbA1c was significantly reduced in the flash device group compared with SMBG, with mean changes from baseline of −0.82% and −0.33%, respectively (P=0.005). Non-prespecified post hoc analyses showed that higher proportions of patients in the flash device group, compared with the SMBG group, had HbA1c reductions of ≥0.5% (68.6 vs. 30.2%; P<0.001), or of ≥1.0% (39.2 vs. 18.6%; P=0.0023). No significant differences were found in the mean±SD perceived frequency of hypoglycemic episodes: 1.41±1.29 vs. 0.75±1.57, respectively (P=0.066). There was a trend towards higher treatment satisfaction in the flash device group, with a mean Diabetes Treatment Satisfaction Questionnaire change version score of 2.47±0.77 compared with 2.18±0.83 in the standard care group (P=0.053). Patients found flash glucose monitoring to be significantly more flexible than SMBG (2.28±1.28 vs. 1.61±1.59, P=0.019), and more would recommend it to their counterparts (2.61±0.86 vs. 2.19±1.04, P=0.023).

Further retrospective real-world chart review studies from three European countries examined the effectiveness of flash glucose monitoring on HbA1c in adults with T2D managed by basal bolus insulin therapy. Medical records from centers in Austria (n=92), France (n=88) and Germany (n=183) were evaluated prior to, and following, use of the device for 90 days. Mean±SD changes in HbA1c were −0.9%±0.8% (P<0.0001), −0.8%±1.1% (P<0.0001) and −0.9%±1.1% (P<0.0001), respectively. In a combined analysis of the three studies, the overall effect size was −0.9% (P<0.0001 vs. baseline). There was no significant heterogeneity between studies performed in each country (P=0.711). No significant differences were recorded for changes in HbA1c according to age group, gender, body mass index, or duration of insulin use.

A real-world retrospective, observational study, which analyzed data from the US electronic health record database IBM Explorys, showed that de novo prescription of flash glucose monitoring significantly reduced HbA1c in T2D patients (n=1034) not using bolus insulin. Mean HbA1c levels decreased from 10.1% at baseline to 8.6% within 60-300 days of the flash glucose monitoring prescription (P<0.001). Similarly, another real-world retrospective study which analyzed claims data by the Decision Resources Group, a commercial medical and pharmacy claims database, showed a significant reduction in HbA1c levels in T2D patients on long-acting insulin or non-insulin therapy after 6-month and 12-month use of flash glucose monitoring. Mean HbA1c was reduced by 0.8% (from 8.5% to 7.7%) in the 6-month T2D cohort (n=774), and by 0.6% (from 8.5% to 7.9%) in the 12-month T2D cohort (n=207) (both P<0.0001).

Patient inclusion criteria differed among studies with some patient populations using intensive insulin therapy and others not. The 12-month General Practice Optimising Structured Monitoring To achieve Improved Clinical Outcomes (GP-OSMOTIC) trial, which compared professional-mode (masked) flash glucose monitoring with usual care (non-insulin glucose-lowering drugs, insulin, or both) in 299 adults with T2D in primary care, reported a significant reduction in mean HbA1c with flash monitoring at 6 months (−0.5%; P=0.0001) but not at 12 months (−0.3%; P=0.059), although the mean percentage of time spent in target glucose range at 12 months was 7.9% higher with flash monitoring than usual care (P=0.0060).

Two recent real-world retrospective, observational analyses of the MarketScan database, which contains insurance billing claims for inpatient, outpatient, and pharmacy expenses, have shown benefits for flash glucose monitoring beyond glycemic control. In T2D patients not using bolus insulin (n=7167), de novo flash glucose monitoring use (purchased between Q4 of 2017 and Q4 of 2018) significantly reduced inpatient and outpatient emergency acute diabetes events from 0.071 to 0.052 events/patient-year (hazard ratio [HR]: 0.70; 95% CI: 0.57-0.85; P<0.001), and all-cause hospitalization from 0.180 to 0.161 events/patient-year (HR: 0.87; 95% CI: 0.78-0.98; P=0.025). In T2D patients receiving fast- or short-acting insulin, flash glucose monitoring use (purchased between Q4 of 2017 and Q2 of 2018) significantly reduced acute diabetes events from 0.158 to 0.077 events/patient-year (HR: 0.49; 95% CI: 0.34-0.69; P<0.001) and all-cause hospitalization from 0.345 to 0.247 events/patient-year (HR: 0.72; 95% CI: 0.58-0.88; P=0.002).

Further real-world observational studies from several world regions have assessed the impact of flash glucose monitoring in often large groups of patients with T1D or T2D.

A retrospective nationwide study of reimbursement claims from a French database assessed ketoacidosis rates in T1D (n=33,203) and T2D (n=40,955) patients who initiated flash glucose monitoring use during a 5-month study period in 2017.

Four studies assessed the benefits of flash glucose monitoring mainly on HbA1c. A Dutch prospective nationwide registry study which analyzed data from 1365 participants with T1D (77.2%), T2D (16.4%), Latent Autoimmune Diabetes in Adults (4.6%) or maturity-onset diabetes of the young (0.5%) examined the effect of flash glucose monitoring on HbA1c, disease burden and well-being. A cohort study using data from the Swedish National Diabetes Register (January 2014-June 2019) assessed the effectiveness of the FreeStyle Libre system on HbA1c reduction. A meta-analysis of 29 clinical trials and real-world studies, of which 25 reported longitudinal HbA1c data in 1723 participants with T1D or T2D using the FreeStyle Libre system, examined the impact of flash glucose monitoring on HbA1c. A study from Israel assessed the impact of flash glucose monitoring on HbA1c in T2D (n=25) and T1D (n=6) patients.

Other studies assessed the impact of increased scanning frequency on glycemic measures. A real-world European analysis examined deidentified data from more than 50,000 users worldwide of the FreeStyle Libre system who had performed more than 60 million scans over a 20-month period. To assess the role of flash glucose monitoring in early and late changes of glycemic markers under real-life conditions, a longitudinal study analyzed deidentified glucose results from 6802 flash monitors after stratification into high, medium and low-risk groups based on tertiles of time spent in hypoglycemia (min/day <70 mg/dL) or hyperglycemia (hours/day >240 mg/dL). Another large real-world study analyzed deidentified glucose and user scanning data (250 million glucose readings, 37.1 million glucose scans) collected over a 4-year period from Spanish users (n=22, 949) to determine the relationship between testing frequency and glycemic parameters. An interesting study from Brazil analyzed glucose results captured from launch of the FreeStyle Libre flash glucose monitor in 2016 and compared them with global population data collected between September 2014 and December 2018. Data were analyzed from 688,640 readers and 7,329,052 sensors worldwide, including 17,691 readers and 147,166 sensors from Brazil.

As illustrated in FIG. 22B, four studies show that flash glucose monitoring improved glycemic control, as assessed by HbA1c, compared with prior to its use. In the Dutch prospective registry study, estimated HbA1c decreased from 8.0% before use of flash glucose monitoring to 7.6% after 6 months of use (P<0.001) and remained steady at 7.6% at 12 months (P<0.001). The 12-month difference in estimated HbA1c was more pronounced in patients with T2D (n=223) than T1D (n=1054). Swedish National Diabetes Register data also showed a significant decrease in HbA1c (method of measurement unspecified) before and after incident FreeStyle Libre use, with a mean change of −0.33% for T1D patients (n=8,316) and −0.52% for T2D patients (n=538) at 12 months (both P<0.0001). The meta-analysis of clinical trials and real-world studies of flash glucose monitoring indicated a mean change in laboratory HbA1c of −0.55% at 2-4 months, with a negligible difference (−0.56% and −0.54%, respectively) observed between adults (n=1023) and children and adolescents (n=447). Longitudinal analysis of studies involving adult subjects (n=1276) showed that laboratory HbA1c was reduced within the first 2 months of use, and that changes were sustained for up to 12 months, thus confirming a trend observed in a previous small study of flash glucose monitoring in patients with HbA1c ≥7.5%, in which the majority of change from baseline in mean HbA1c (method of measurement unspecified) occurred by 8 weeks (−1.33%; P<0.0001) and was maintained at 24 weeks (−1.21%; P=0.009).

Additional studies, illustrated in FIG. 22B, show that people who scan more tend to have lower HbA1c. In the European real-world analysis, greater scanning frequency from 4.4 (lowest) to 48.1 (highest) scans/day was associated with a reduction in estimated HbA1c from 8.0% to 6.7% (P<0.001). In the real-world study of Spanish users of the flash glucose monitoring device, estimated HbA1c was significantly lower in the highest (39.6 scans/day) versus lowest (3.9 scans/day) scan frequency group (6.9 vs. 8.0%; P<0.001). Similarly, the Brazilian study found that, in line with worldwide data, increased scanning frequency in Brazil was associated with better glycemic control, as evidenced by a lower estimated HbA1c in the highest (43.1 scans/day) versus lowest (3.6 scans/day) scan rate groups (6.7 vs. 7.6%; P<0.01).

FIG. 22C further illustrates results from four real-world studies showing that increased scanning frequency of the flash monitoring device was associated with benefits on glycemic measures apart from HbA1c.

In a European analysis, greater scanning frequency was inversely correlated with time spent in hypoglycemia and hyperglycemia. For blood glucose levels <70 mg/dL, <56 mg/dL and <45 mg/dL, time in hypoglycemia was lower by 15%, 40% and 49%, respectively (all P<0.001) in the highest (48.1 scans/day) compared with the lowest (4.4 scans/day) scan rate group. Highest versus lowest scanning frequency was also associated with a 44% decrease (P<0.001) in time spent in hyperglycemia and a 40% increase in time in range. Six-month data from the real-world longitudinal study showed that, in the high-risk hypoglycemia group, flash glucose monitoring significantly (P<0.0001) reduced the mean time spent in hypoglycemia (blood glucose ≤70 mg/dL) from the first to last 14-day periods of the study, irrespective of scanning frequency (high, medium, or low). In the high-risk hyperglycemia group, flash glucose monitoring reduced the time spent in hyperglycemia (blood glucose >240 mg/dL) by 0.8 hours/day in higher-frequency scanners (P<0.0001), by 0.3 hours/day in medium-frequency scanners (P=0.02), and had no effect in low-frequency scanners from the first to last 14-day periods of the study.

In a real-world study of Spanish users of the flash glucose monitoring device, glucose parameters progressively improved as average scanning frequency increased from the lowest (3.9 scans/day) to highest (39.6 scans/day) scan rate group. Time in hypoglycemia for blood glucose thresholds of <70 mg/dL and ≤54 mg/dL, respectively, was decreased by 14% and 37% in the highest versus lowest scan rate group. Respective times in hypoglycemia for the highest and lowest scan rate groups were 85.3 and 99.2 min/day (P<0.001) for blood glucose <70 mg/dL; and 29.7 min/day and 46.8 min/day for blood glucose ≤54 mg/dL. Time spent in hyperglycemia (blood glucose >180 mg/dL) was decreased by 37% (P<0.001), and time in range was increased by 36% (P<0.001) and in the highest versus lowest scan rate group. A comparison of sensor data derived from flash glucose monitoring users in Brazil and worldwide showed significant (P<0.01) improvements in time spent in hyperglycemia (blood glucose >180 mg/dL) associated with highest versus lowest scanning frequency: 43.1 and 3.6 scans/day, respectively, in Brazil; 37.8 and 3.4 scans/day, respectively, worldwide. In both populations, greater scanning frequency also increased time in range (blood glucose 70-180 mg/dL).

The retrospective study analyzing reimbursement claims from a French database showed a marked reduction in ketoacidosis rates in patients who initiated flash glucose monitoring during a 5-month study period in 2017. The hospitalization rate for ketoacidosis (excluding incidence for coma) was reduced by 52% (from 5.5 to 2.6 per 100 patient-years) and by 47% (from 1.7 to 0.9 per 100 patient-years) in T1D and T2D patients, respectively.

In a Dutch prospective registry study, 12-month use of flash glucose monitoring significantly reduced the proportion of patients experiencing any hypoglycemic event from 93.5% to 91.0%; the proportion of diabetes-related hospitalization from 13.7% to 4.7%; and work absenteeism from 18.5% to 7.7% (all comparisons P<0.05). In addition, flash glucose monitoring improved 12-month well-being scores, with changes from baseline of 0.03 (95% CI 0.01-0.05) in the EuroQol 5D tariff, 4.4 (95% CI 2.1-6.7) in the EQ-visual analogue scale, and 3.3 (95% CI 2.1-4.4) in the 12-Item Short Form Health Survey v2 mental component score.

While the disclosed subject matter is described herein in terms of certain illustrations and examples, those skilled in the art will recognize that various modifications and improvements may be made to the disclosed subject matter without departing from the scope thereof. Moreover, although individual features of one embodiment of the disclosed subject matter may be discussed herein or shown in the drawings of one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for the purposes of illustration and description. It is not intended to be exhaustive or to limit the disclosed subject matter to those embodiments disclosed.

The description herein merely illustrates the principles of the disclosed subject matter. Various modifications and alterations to the described embodiments will be apparent to those skilled in the art in view of the teachings herein. Accordingly, the disclosure herein is intended to be illustrative, but not limiting, of the scope of the disclosed subject matter.

The invention claimed is:

1. A system to establish and monitor an analyte monitor regimen of a user comprising:
   a sensor control device comprising an analyte sensor coupled with sensor electronics, the sensor control device configured to transmit data indicative of an analyte level; and,
   a reader device comprising a user interface, wireless communication circuitry configured to receive the data indicative of the analyte level and
   one or more processors coupled with a memory, the memory configured to store instructions that, when executed by the one or more processors, cause the one or more processors to:
      output, based on one or more instances of operation of the reader device over a predetermined period of time, at least one measurement of an analyte level on the user interface of the reader device, wherein the at least one measurement of the analyte level is a current analyte level during the one or more instances of the operation of the reader device;
      determine a trending analyte level based on the current analyte level and historical analyte data stored in the memory;
      output the trending analyte level on the user interface of the reader device;
      update and store the historical analyte data in the memory to include the current analyte level;

receive, from the sensor control device, an updated current analyte level;

determine an updated trending analyte level based on the updated current analyte level and the updated historical analyte data stored in the memory;

output the updated trending analyte level on the user interface of the reader device;

quantify at least one of a total number of scans or views for a day or a marker to indicate that a scan or view had occurred at a particular time on the user interface of the reader device;

output a sensor usage indicator including the at least one of a total number of scans or views for a day or a marker to indicate that a scan or view had occurred at a particular time on the user interface of the reader device;

output a notification on the user interface of the reader device that indicates at least one of an alarm condition, the updated current analyte level measurement associated with the alarm condition, and the updated trending analyte level associated with the alarm condition;

determine a determined rate of hospitalization for a predetermined diagnostic category based on collected data of users without a continuous glucose monitoring and having a predetermined comorbidity; and estimate a rate of hospitalization for the user in the predetermined diagnostic category and having the predetermined comorbidity, wherein the rate of hospitalization for the user is at least 12% less than the determined rate of hospitalization for the users without the continuous glucose monitoring and having the predetermined comorbidity;

wherein the analyte monitor regimen is configured to increase the instances of operation of the reader device and actionable engagement with the user interface.

2. The system of claim 1, wherein the predetermined comorbidity is anemia.

3. The system of claim 2, wherein the instructions further comprise causing the one or more processors to receive data about basal-bolus insulin therapy treatment of the user.

4. The system of claim 3, wherein the predetermined period of time is six months and the predetermined diagnostic category is infectious and parasitic diseases, and the rate of hospitalization for the user is 51% less than the determined rate of hospitalization for infectious and parasitic diseases.

5. The system of claim 3, wherein the predetermined period of time is six months and the predetermined diagnostic category is respiratory diseases, and the rate of hospitalization for the user is 38% less than the determined rate of hospitalization for respiratory diseases.

6. The system of claim 3, wherein the predetermined period of time is six months and the predetermined diagnostic category is kidney and urinary tract diseases, and the first rate of hospitalization for the user is 57% less than the determined rate of hospitalization for kidney and urinary tract diseases.

7. The system of claim 3, wherein the predetermined period of time is six months and the predetermined diagnostic category is hepatobiliary and pancreatic diseases, and the rate of hospitalization for the user is 55% less than the determined rate of hospitalization for hepatobiliary and pancreatic diseases.

8. The system of claim 2, wherein the instructions further comprise causing the one or more processors to receive data about non-multiple daily insulin injection therapy treatment of the user.

9. The system of claim 8, wherein the predetermined period of time is six months and the predetermined diagnostic category is infectious and parasitic diseases, and the rate of hospitalization for the user is 48% less than the determined rate of hospitalization for infectious and parasitic diseases.

10. The system of claim 8, wherein the predetermined period of time is six months and the predetermined diagnostic category is respiratory diseases, and the rate of hospitalization for the user is 59% less than the determined rate of hospitalization for respiratory diseases.

11. The system of claim 8, wherein the predetermined period of time is six months and the predetermined diagnostic category is kidney and urinary tract diseases, and the first rate of hospitalization for the user is 51% less than the determined rate of hospitalization for kidney and urinary tract diseases.

12. The system of claim 8, wherein the predetermined period of time is six months and the predetermined diagnostic category is hepatobiliary and pancreatic diseases, and the rate of hospitalization for the user is 44% less than the determined rate of hospitalization for hepatobiliary and pancreatic diseases.

13. The system of claim 2, wherein the predetermined period of time is six months and the predetermined diagnostic category is infectious and parasitic diseases, and the rate of hospitalization for the user is 33% less than the determined rate of hospitalization for infectious and parasitic diseases.

14. The system of claim 1, wherein the instructions further comprise causing the one or more processors to receive data about basal-bolus insulin therapy treatment of the user.

15. The system of claim 14, wherein the predetermined period of time is six months and the predetermined comorbidity is a fluid and electrolyte disorder, and the rate of hospitalization for infectious and parasitic diseases for the user is 59% less than the determined rate of hospitalization for infectious and parasitic diseases.

16. The system of claim 14, wherein the predetermined period of time is six months and the predetermined comorbidity is a valvular disorder, and the rate of hospitalization for infectious and parasitic diseases for the user is 58% less than the determined rate of hospitalization for infectious and parasitic diseases.

17. The system of claim 14, wherein the predetermined period of time is six months and the predetermined comorbidity is liver disease, and the rate of hospitalization for infectious and parasitic diseases for the user is 50% less than the determined rate of hospitalization for infectious and parasitic diseases.

18. The system of claim 1, wherein the instructions further comprise causing the one or more processors to receive data about non-multiple daily insulin injection therapy treatment of the user.

19. The system of claim 18, wherein the predetermined period of time is six months and the predetermined comorbidity is a fluid or electrolyte disorder, and the first rate of hospitalization for infectious and parasitic diseases for the user is 68% less than the determined rate of hospitalization for infectious and parasitic diseases.

20. The system of claim 18, wherein the predetermined period of time is six months and the predetermined comorbidity is a valvular disorder, and the rate of hospitalization for infectious and parasitic diseases for the user is 53% less than the determined rate of hospitalization for infectious and parasitic diseases.

21. The system of claim 18, wherein the predetermined period of time is six months and the predetermined comorbidity is liver disease, and the rate of hospitalization for infectious and parasitic diseases for the user is 54% less than the determined rate of hospitalization for infectious and parasitic diseases.

\* \* \* \* \*